United States Patent
Aznarez

(10) Patent No.: US 12,060,558 B2
(45) Date of Patent: Aug. 13, 2024

(54) METHODS AND COMPOSITIONS FOR TREATMENT OF CHOLESTERYL ESTER STORAGE DISEASE

(71) Applicant: STOKE THERAPEUTICS, Inc., Bedford, MA (US)

(72) Inventor: Isabel Aznarez, Jamaica Plain, MA (US)

(73) Assignee: STOKE THERAPEUTICS, INC., Bedford, MA (US)

( * ) Notice: Subject to any disclaimer, the term of this patent is extended or adjusted under 35 U.S.C. 154(b) by 827 days.

(21) Appl. No.: 17/052,874

(22) PCT Filed: May 3, 2019

(86) PCT No.: PCT/US2019/030605
§ 371 (c)(1),
(2) Date: Nov. 4, 2020

(87) PCT Pub. No.: WO2019/213525
PCT Pub. Date: Nov. 7, 2019

(65) Prior Publication Data
US 2021/0371866 A1    Dec. 2, 2021

Related U.S. Application Data

(60) Provisional application No. 62/667,205, filed on May 4, 2018.

(51) Int. Cl.
*C07H 21/02* (2006.01)
*A61K 38/46* (2006.01)
*C12N 15/113* (2010.01)

(52) U.S. Cl.
CPC ........ *C12N 15/1137* (2013.01); *A61K 38/465* (2013.01); *C12N 2310/11* (2013.01); *C12N 2310/315* (2013.01); *C12N 2310/32* (2013.01); *C12N 2320/11* (2013.01); *C12N 2320/33* (2013.01); *C12Y 301/01013* (2013.01)

(58) Field of Classification Search
CPC .................................................. C12N 15/113
See application file for complete search history.

(56) References Cited

U.S. PATENT DOCUMENTS

| | | | |
|---|---|---|---|
| 4,866,042 A | 9/1989 | Neuwelt | |
| 5,151,510 A | 9/1992 | Stec et al. | |
| 5,656,612 A | 8/1997 | Monia | |
| 5,665,593 A | 9/1997 | Kole et al. | |
| 5,914,396 A | 6/1999 | Cook et al. | |
| 5,916,808 A | 6/1999 | Kole et al. | |
| 5,976,879 A | 11/1999 | Kole et al. | |
| 6,083,482 A | 7/2000 | Wang | |
| 6,166,197 A | 12/2000 | Cook et al. | |
| 6,210,892 B1 | 4/2001 | Bennett et al. | |
| 6,294,520 B1 | 9/2001 | Naito | |
| 6,383,752 B1 | 5/2002 | Agrawal et al. | |
| 6,436,657 B1 | 8/2002 | Famodu et al. | |
| 6,451,991 B1 | 9/2002 | Martin et al. | |
| 6,485,960 B1 | 11/2002 | Harris et al. | |
| 6,531,591 B1 | 3/2003 | Fensholdt | |
| 6,573,073 B2 | 6/2003 | Harris | |
| 6,605,611 B2 | 8/2003 | Simmonds et al. | |
| 6,632,427 B1 | 10/2003 | Finiels et al. | |
| 6,639,059 B1 | 10/2003 | Kochkine et al. | |
| 6,670,461 B1 | 12/2003 | Wengel et al. | |
| 6,677,445 B1 | 1/2004 | Innis et al. | |
| 6,734,291 B2 | 5/2004 | Kochkine et al. | |
| 6,756,523 B1 | 6/2004 | Kahn et al. | |
| 6,770,748 B2 | 8/2004 | Imanishi et al. | |
| 6,794,499 B2 | 9/2004 | Wengel et al. | |
| 6,846,921 B2 | 1/2005 | Innis et al. | |
| 6,936,589 B2 | 8/2005 | Naito | |
| 6,963,589 B1 | 11/2005 | Sugata et al. | |
| 6,998,484 B2 | 2/2006 | Koch et al. | |
| 7,015,315 B1 | 3/2006 | Cook et al. | |
| 7,034,133 B2 | 4/2006 | Wengel et al. | |
| 7,053,199 B2 | 5/2006 | Imanishi et al. | |
| 7,053,207 B2 | 5/2006 | Wengel | |
| 7,060,809 B2 | 6/2006 | Wengel et al. | |
| 7,071,324 B2 | 7/2006 | Preparata et al. | |
| 7,084,125 B2 | 8/2006 | Wengel | |
| 7,101,993 B1 | 9/2006 | Cook et al. | |
| 7,169,594 B2 | 1/2007 | Guan | |
| 7,214,783 B2 | 5/2007 | Jeon et al. | |
| 7,217,805 B2 | 5/2007 | Imanishi et al. | |
| 7,314,923 B2 | 1/2008 | Kaneko et al. | |
| 7,335,765 B2 | 2/2008 | Kaneko et al. | |
| 7,368,549 B2 | 5/2008 | Dempcy et al. | |

(Continued)

FOREIGN PATENT DOCUMENTS

| | | | |
|---|---|---|---|
| AU | 2016334804 B2 | 3/2022 | |
| AU | 2022204606 A1 | 7/2022 | |

(Continued)

OTHER PUBLICATIONS

Dardis et al. (Genes, 2018, 9, 73, 1-16).*
Chora et al. (Journal of Clinical Llipidology, 2017, 11, 477-484).*
Rajamohan et al. (Protein Expression and Purification, 110, 2015, 22-29).*
Aguisanda, F. et al., "Targeting Wolman Disease and Cholesteryl Ester Storage Disease: Disease Pathogenesis and Therapeutic Development," Current Chemical Genomics and Translational Medicine, 2017, vol. 11, No. 1, pp. 1-18.
Ameis, D. et al., "A 5' splice-region mutation and a dinucleotide deletion in the lysosomal acid lipase gene in two patients with cholesteryl ester storage disease," Journal of Lipid Research, 1995, vol. 36, No. 2, pp. 241-250.

(Continued)

*Primary Examiner* — Amy Rose Hudson
(74) *Attorney, Agent, or Firm* — Wilson Sonsini Goodrich & Rosati

(57) ABSTRACT

Provided herein are methods and compositions for treating a subject in need thereof, such as a subject with deficient LAL protein expression or a subject having Cholesteryl Ester Storage Disease.

18 Claims, 10 Drawing Sheets

Specification includes a Sequence Listing.

(56) References Cited

U.S. PATENT DOCUMENTS

| | | |
|---|---|---|
| 7,399,845 B2 | 7/2008 | Seth et al. |
| 7,432,249 B2 | 10/2008 | Crooke |
| 7,432,250 B2 | 10/2008 | Crooke |
| 7,547,684 B2 | 6/2009 | Seth et al. |
| 7,553,644 B2 | 6/2009 | Germino et al. |
| 7,569,575 B2 | 8/2009 | Soerensen et al. |
| 7,569,686 B1 | 8/2009 | Bhat et al. |
| 7,572,582 B2 | 8/2009 | Wengel et al. |
| 7,595,304 B2 | 9/2009 | Zhao et al. |
| 7,615,619 B2 | 11/2009 | Imanishi et al. |
| 7,662,946 B2 | 2/2010 | Ginsburg et al. |
| 7,662,948 B2 | 2/2010 | Kurreck et al. |
| 7,666,854 B2 | 2/2010 | Seth et al. |
| 7,687,617 B2 | 3/2010 | Thrue et al. |
| 7,696,345 B2 | 4/2010 | Allerson et al. |
| 7,741,457 B2 | 6/2010 | Seth et al. |
| 7,750,131 B2 | 7/2010 | Seth et al. |
| 7,816,333 B2 | 10/2010 | Kaneko et al. |
| 7,846,686 B2 | 12/2010 | Kramer |
| 7,951,934 B2 | 5/2011 | Freier |
| 7,994,145 B2 | 8/2011 | Imanishi et al. |
| 8,022,193 B2 | 9/2011 | Seth et al. |
| 8,030,467 B2 | 10/2011 | Seth et al. |
| 8,048,998 B2 | 11/2011 | Rasmussen et al. |
| 8,067,569 B2 | 11/2011 | Iversen et al. |
| 8,084,458 B2 | 12/2011 | Soerensen et al. |
| 8,088,746 B2 | 1/2012 | Seth et al. |
| 8,110,674 B2 | 2/2012 | Manoharan et al. |
| 8,124,745 B2 | 2/2012 | Allerson et al. |
| 8,129,515 B2 | 3/2012 | Esau et al. |
| 8,168,605 B2 | 5/2012 | Zhao et al. |
| 8,258,109 B2 | 9/2012 | Bennett et al. |
| 8,268,980 B2 | 9/2012 | Seth et al. |
| 8,278,036 B2 | 10/2012 | Kariko et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,293,684 B2 | 10/2012 | Mouritzen et al. |
| 8,361,977 B2 * | 1/2013 | Baker .................. C12N 15/111 536/23.1 |
| 8,361,979 B2 | 1/2013 | Aartsma-Rus et al. |
| 8,383,792 B2 | 2/2013 | Okamoto et al. |
| 8,394,947 B2 | 3/2013 | Bhat et al. |
| 8,415,465 B2 | 4/2013 | Freier |
| 8,436,163 B2 | 5/2013 | Iversen et al. |
| 8,450,467 B2 | 5/2013 | Manoharan et al. |
| 8,461,124 B2 | 6/2013 | Chattopadhyaya |
| 8,492,390 B2 | 7/2013 | Detlef et al. |
| 8,501,703 B2 | 8/2013 | Bennett et al. |
| 8,501,805 B2 | 8/2013 | Seth et al. |
| 8,518,908 B2 | 8/2013 | Hrdlicka et al. |
| 8,530,640 B2 | 9/2013 | Seth et al. |
| 8,541,562 B2 | 9/2013 | Obika et al. |
| 8,546,556 B2 | 10/2013 | Seth et al. |
| 8,592,156 B2 | 11/2013 | Liu et al. |
| 8,637,478 B2 | 1/2014 | Bennett |
| RE44,779 E | 2/2014 | Imanishi et al. |
| 8,653,252 B2 | 2/2014 | Elmen et al. |
| 8,673,560 B2 | 3/2014 | Leamon et al. |
| 8,680,254 B2 | 3/2014 | Lutz et al. |
| 8,691,783 B2 | 4/2014 | Thum et al. |
| 8,703,728 B2 | 4/2014 | Swayze et al. |
| 8,710,021 B2 | 4/2014 | Anro et al. |
| 8,735,366 B2 | 5/2014 | Bauer et al. |
| 8,748,089 B2 | 6/2014 | Kariko et al. |
| 8,779,118 B2 | 7/2014 | Allerson et al. |
| 8,796,437 B2 | 8/2014 | Swayze et al. |
| 8,809,516 B2 | 8/2014 | Manoharan et al. |
| 8,846,386 B2 | 9/2014 | Ambati et al. |
| 8,846,637 B2 | 9/2014 | Seth et al. |
| 8,846,639 B2 | 9/2014 | Swayze et al. |
| 8,846,885 B2 | 9/2014 | Hirai et al. |
| 8,895,722 B2 | 11/2014 | Iversen et al. |
| 8,957,040 B2 | 2/2015 | Bennett et al. |
| 8,957,200 B2 | 2/2015 | Seth et al. |
| 8,957,201 B2 | 2/2015 | Kaneko et al. |
| 9,005,906 B2 | 4/2015 | Swayze et al. |
| 9,006,194 B2 | 4/2015 | Katsikis et al. |
| 9,006,415 B2 | 4/2015 | Ren et al. |
| 9,012,139 B2 | 4/2015 | Collard et al. |
| 9,029,335 B2 | 5/2015 | Prakash et al. |
| 9,045,518 B2 | 6/2015 | Christensen et al. |
| 9,045,754 B2 | 6/2015 | Bhanot et al. |
| 9,057,066 B2 | 6/2015 | Hung et al. |
| 9,109,001 B2 | 8/2015 | Parsy et al. |
| 9,127,272 B2 | 9/2015 | Esau et al. |
| 9,127,276 B2 | 9/2015 | Prakash et al. |
| 9,156,873 B2 | 10/2015 | Prakash et al. |
| 9,157,081 B2 | 10/2015 | Bennett et al. |
| 9,181,549 B2 | 11/2015 | Prakash et al. |
| 9,187,515 B2 | 11/2015 | Mayes et al. |
| 9,192,621 B2 | 11/2015 | Mayes et al. |
| 9,193,752 B2 | 11/2015 | Migawa et al. |
| 9,193,969 B2 | 11/2015 | Montefeltro et al. |
| 9,211,300 B2 | 12/2015 | Mayes et al. |
| 9,217,147 B2 | 12/2015 | Singh et al. |
| 9,221,864 B2 | 12/2015 | Seth et al. |
| 9,243,245 B2 | 1/2016 | De Kimpe et al. |
| 9,290,534 B2 | 3/2016 | Seth et al. |
| 9,296,778 B2 | 3/2016 | Parsy et al. |
| 9,309,275 B2 | 4/2016 | Stewart et al. |
| 9,315,535 B2 | 4/2016 | Mitsuoka et al. |
| 9,334,495 B2 | 5/2016 | Khvorova et al. |
| 9,339,541 B2 | 5/2016 | Dousson et al. |
| 9,347,068 B2 | 5/2016 | Dhugga et al. |
| 9,359,445 B2 | 6/2016 | Finkbeiner et al. |
| 9,359,603 B2 | 6/2016 | Lutz et al. |
| 9,359,609 B2 | 6/2016 | Duffield et al. |
| 9,410,155 B2 | 8/2016 | Collard et al. |
| 9,428,534 B2 | 8/2016 | Christensen et al. |
| 9,447,166 B2 | 9/2016 | Ambati et al. |
| 9,453,261 B2 | 9/2016 | Lee et al. |
| 9,464,292 B2 | 10/2016 | Okumura et al. |
| 9,499,818 B2 | 11/2016 | Van Deutekom |
| 9,518,259 B2 | 12/2016 | Rigo et al. |
| 9,534,222 B2 | 1/2017 | Ambati et al. |
| 9,550,988 B2 | 1/2017 | Swayze |
| 9,714,422 B2 | 7/2017 | Vorechovsky et al. |
| 9,745,577 B2 | 8/2017 | Vorechovsky et al. |
| 9,771,579 B2 | 9/2017 | Collard et al. |
| 9,976,143 B2 | 5/2018 | Krainer et al. |
| 10,119,168 B2 | 11/2018 | Vaidya et al. |
| 10,196,639 B2 | 2/2019 | Vorechovsky et al. |
| 10,517,853 B2 | 12/2019 | Welch et al. |
| 10,583,128 B2 | 3/2020 | Collard et al. |
| 10,941,405 B2 | 3/2021 | Vorechovsky et al. |
| 11,702,660 B2 | 7/2023 | Vorechovsky et al. |
| 2003/0148974 A1 | 8/2003 | Monia et al. |
| 2004/0063129 A1 | 4/2004 | Gaarde et al. |
| 2004/0219515 A1 | 11/2004 | Bentwich |
| 2005/0221354 A1 | 10/2005 | Mounts |
| 2005/0233327 A1 | 10/2005 | Welch et al. |
| 2006/0062790 A1 | 3/2006 | Reinhard et al. |
| 2006/0134670 A1 | 6/2006 | Piu |
| 2007/0009899 A1 | 1/2007 | Mounts |
| 2007/0087376 A1 | 4/2007 | Potashkin |
| 2007/0249538 A1 | 10/2007 | Sazani et al. |
| 2008/0269123 A1 | 10/2008 | Li et al. |
| 2009/0186846 A1 | 7/2009 | Chabot et al. |
| 2009/0186946 A1 | 7/2009 | Taketomi et al. |
| 2009/0264353 A1 | 10/2009 | Orum et al. |
| 2009/0270332 A1 | 10/2009 | Bare et al. |
| 2010/0150839 A1 | 6/2010 | Kelleher |
| 2010/0166784 A1 | 7/2010 | Murphy et al. |
| 2011/0124591 A1 | 5/2011 | Bennett |
| 2011/0229891 A1 | 9/2011 | Michaud et al. |
| 2012/0190728 A1 | 7/2012 | Bennett et al. |
| 2012/0252877 A1 | 10/2012 | Lo |
| 2013/0072671 A1 | 3/2013 | Van Deutekom |
| 2013/0096183 A1 | 4/2013 | Collard et al. |
| 2013/0109850 A1 | 5/2013 | Prakash et al. |
| 2013/0136732 A1 | 5/2013 | Wagner et al. |
| 2013/0184223 A1 | 7/2013 | Land et al. |
| 2013/0253036 A1 | 9/2013 | Collard et al. |

(56) References Cited

U.S. PATENT DOCUMENTS

| | | | |
|---|---|---|---|
| 2013/0266560 A1 | 10/2013 | Demopulos et al. |
| 2013/0289092 A1 | 10/2013 | Rigo et al. |
| 2014/0011761 A1 | 1/2014 | Hotamisligil et al. |
| 2014/0128449 A1 | 5/2014 | Liu et al. |
| 2014/0186839 A1 | 7/2014 | Margulies et al. |
| 2014/0194610 A1 | 7/2014 | Verdine et al. |
| 2014/0235605 A1 | 8/2014 | Shiffman et al. |
| 2014/0309181 A1 | 10/2014 | Collard et al. |
| 2014/0336238 A1 | 11/2014 | Collin et al. |
| 2014/0343127 A1 | 11/2014 | Kammler |
| 2014/0349290 A1 | 11/2014 | Watnick et al. |
| 2014/0378526 A1 | 12/2014 | Rossi et al. |
| 2014/0378527 A1 | 12/2014 | Van Deutekom |
| 2014/0378533 A1 | 12/2014 | Freier |
| 2015/0004217 A1 | 1/2015 | Guild et al. |
| 2015/0018540 A1 | 1/2015 | Prakash et al. |
| 2015/0184153 A1 | 7/2015 | Freier et al. |
| 2015/0211006 A1 | 7/2015 | Butler et al. |
| 2015/0211010 A1 | 7/2015 | Kerem et al. |
| 2015/0232845 A1 | 8/2015 | Ozsolak |
| 2015/0232858 A1 | 8/2015 | Ozsolak |
| 2015/0238516 A1 | 8/2015 | Dowdy et al. |
| 2015/0267192 A1 | 9/2015 | Heartlein et al. |
| 2015/0291957 A1 | 10/2015 | Smith |
| 2015/0329918 A1 | 11/2015 | Kang et al. |
| 2015/0337310 A1 | 11/2015 | Walker et al. |
| 2015/0361497 A1 | 12/2015 | Rose |
| 2016/0017322 A1 | 1/2016 | Vorechovsky et al. |
| 2016/0024500 A1 | 1/2016 | Popplewell et al. |
| 2016/0046935 A1 | 2/2016 | Bentwich et al. |
| 2016/0122767 A1 | 5/2016 | Gouya et al. |
| 2016/0201063 A1 | 7/2016 | Ozsolak |
| 2016/0201064 A1 | 7/2016 | Ozsolak |
| 2016/0208264 A1 | 7/2016 | Wilton et al. |
| 2016/0215291 A1 | 7/2016 | Garcia et al. |
| 2016/0244762 A1 | 8/2016 | Vorechovsky et al. |
| 2016/0244767 A1 | 8/2016 | Hastings |
| 2016/0298121 A1 | 10/2016 | Krainer et al. |
| 2017/0159049 A9 | 6/2017 | Krainer et al. |
| 2017/0240904 A1 | 8/2017 | Tallent et al. |
| 2018/0002694 A1 | 1/2018 | Vorechovsky et al. |
| 2018/0296501 A1 | 10/2018 | During |
| 2018/0362987 A1 | 12/2018 | Krainer et al. |
| 2018/0369275 A1 | 12/2018 | Arnarez et al. |
| 2019/0024118 A1 | 1/2019 | Tagliatela et al. |
| 2019/0024119 A1 | 1/2019 | Tagliatela et al. |
| 2019/0024120 A1 | 1/2019 | Tagliatela et al. |
| 2019/0024121 A1 | 1/2019 | Tagliatela et al. |
| 2019/0070213 A1 | 3/2019 | Aznarez et al. |
| 2019/0192691 A1 | 6/2019 | Barrett et al. |
| 2019/0218255 A1 | 7/2019 | Chung et al. |
| 2019/0225939 A1 | 7/2019 | Chambers et al. |
| 2019/0264211 A1 | 8/2019 | Vorechovsky et al. |
| 2020/0085838 A1 | 3/2020 | Martinez Botella et al. |
| 2020/0101174 A1 | 4/2020 | Coller et al. |
| 2021/0371866 A1 | 12/2021 | Aznarez |

FOREIGN PATENT DOCUMENTS

| | | |
|---|---|---|
| CN | 103667438 A | 3/2014 |
| CN | 104131094 A | 11/2014 |
| EP | 0549615 A1 | 7/1993 |
| EP | 1201678 B1 | 9/2004 |
| EP | 1409497 B1 | 1/2005 |
| EP | 1007714 B1 | 12/2005 |
| EP | 1334109 B1 | 5/2006 |
| EP | 1178999 B1 | 3/2007 |
| EP | 1203827 B1 | 5/2007 |
| EP | 1501848 B1 | 8/2007 |
| EP | 1569661 B1 | 9/2009 |
| EP | 1161439 B1 | 4/2010 |
| EP | 1984381 B1 | 9/2010 |
| EP | 1013661 B1 | 1/2012 |
| EP | 2092065 B1 | 1/2012 |
| EP | 2099461 B1 | 3/2012 |
| EP | 2170917 B1 | 6/2012 |
| EP | 2066684 B1 | 7/2012 |
| EP | 2284269 A3 | 8/2012 |
| EP | 2356129 B1 | 4/2013 |
| EP | 2376516 B1 | 4/2013 |
| EP | 2114981 B1 | 5/2013 |
| EP | 2149605 B1 | 7/2013 |
| EP | 2285819 B1 | 10/2013 |
| EP | 2161038 B1 | 12/2013 |
| EP | 1562971 B1 | 2/2014 |
| EP | 2295441 B1 | 5/2014 |
| EP | 2314594 B1 | 7/2014 |
| EP | 2410053 B1 | 10/2014 |
| EP | 2176280 B2 | 6/2015 |
| EP | 2361921 B1 | 6/2015 |
| EP | 2462153 B1 | 7/2015 |
| EP | 1015469 B2 | 11/2015 |
| EP | 2173760 B2 | 11/2015 |
| EP | 1937312 B1 | 6/2016 |
| EP | 2141233 B1 | 10/2016 |
| EP | 2410054 B1 | 1/2017 |
| EP | 3329909 A1 | 6/2018 |
| EP | 3359685 A1 | 8/2018 |
| EP | 2753317 B1 | 2/2020 |
| GB | 1517937 A | 7/1978 |
| GB | 2546719 A | 8/2017 |
| JP | 6923517 B2 | 8/2021 |
| JP | 2021180669 A | 11/2021 |
| WO | WO-9402501 A1 | 2/1994 |
| WO | WO-9426887 A1 | 11/1994 |
| WO | WO-9747772 A2 | 12/1997 |
| WO | WO-0107660 A1 | 2/2001 |
| WO | WO-2005049651 A2 | 6/2005 |
| WO | WO-2006107846 A2 | 10/2006 |
| WO | WO-2007002390 A2 | 1/2007 |
| WO | WO-2007048628 A2 | 5/2007 |
| WO | WO-2007048629 A2 | 5/2007 |
| WO | WO-2007002390 A3 | 11/2007 |
| WO | WO-2009084472 A1 | 7/2009 |
| WO | WO-2010148249 A1 | 12/2010 |
| WO | WO-2011057350 A1 | 5/2011 |
| WO | WO-2012112681 A1 | 8/2012 |
| WO | WO-2012168435 A1 | 12/2012 |
| WO | WO-2012178146 A1 | 12/2012 |
| WO | WO-2013036105 A1 | 3/2013 |
| WO | WO-2013081755 A1 | 6/2013 |
| WO | WO-2013106770 A1 | 7/2013 |
| WO | WO-2013119916 A2 | 8/2013 |
| WO | WO-2014012081 A2 | 1/2014 |
| WO | WO-201428459 A1 | 2/2014 |
| WO | WO-2014028459 A1 | 2/2014 |
| WO | WO-2014031575 A1 | 2/2014 |
| WO | WO-2014049536 A2 | 4/2014 |
| WO | WO-2014121287 A2 | 8/2014 |
| WO | WO-2014172698 A1 | 10/2014 |
| WO | WO-2014201413 A1 | 12/2014 |
| WO | WO-2014209841 A2 | 12/2014 |
| WO | WO-2015035091 A1 | 3/2015 |
| WO | WO-2015024876 A3 | 7/2015 |
| WO | WO-2015190922 A1 | 12/2015 |
| WO | WO-2015193651 A1 | 12/2015 |
| WO | WO-2015198054 A1 | 12/2015 |
| WO | WO-2016027168 A2 | 2/2016 |
| WO | WO-2016054615 A2 | 4/2016 |
| WO | WO-2016061509 A1 | 4/2016 |
| WO | WO-2016077837 A1 | 5/2016 |
| WO | WO-2016087842 A1 | 6/2016 |
| WO | WO-2016118697 A1 | 7/2016 |
| WO | WO-2016128343 A1 | 8/2016 |
| WO | WO-2016138534 A2 | 9/2016 |
| WO | WO-2016161429 A1 | 10/2016 |
| WO | WO-2016196386 A1 | 12/2016 |
| WO | WO-2017053982 A1 | 3/2017 |
| WO | WO-2017060731 A1 | 4/2017 |
| WO | WO-2017106210 A1 | 6/2017 |
| WO | WO-2017106211 A1 | 6/2017 |
| WO | WO-2017106283 A1 | 6/2017 |
| WO | WO-2017106292 A1 | 6/2017 |
| WO | WO-2017106364 A2 | 6/2017 |

(56) References Cited

FOREIGN PATENT DOCUMENTS

| WO | WO-2017106370 A1 | 6/2017 |
|---|---|---|
| WO | WO-2017106375 A1 | 6/2017 |
| WO | WO-2017106377 A1 | 6/2017 |
| WO | WO-2017106382 A1 | 6/2017 |
| WO | WO-2017106364 A3 | 7/2017 |
| WO | WO-2017218926 A1 | 12/2017 |
| WO | WO-2018187363 A1 | 10/2018 |
| WO | WO-2018191482 A2 | 10/2018 |
| WO | WO-2018206924 A1 | 11/2018 |
| WO | WO-2019040923 A1 | 2/2019 |
| WO | WO-2019084050 A1 | 5/2019 |
| WO | WO-2019109051 A1 | 6/2019 |
| WO | WO-2019191341 A1 | 10/2019 |
| WO | WO-2019199867 A1 | 10/2019 |
| WO | WO-2019227096 A1 | 11/2019 |
| WO | WO-2019236750 A2 | 12/2019 |
| WO | WO-2019243430 A1 | 12/2019 |
| WO | WO-2020041348 A1 | 2/2020 |

OTHER PUBLICATIONS

Aslanidis, C. et al., "Genomic Organization of the Human Lysosomal Acid Lipase Gene (LIPA)," Genomics, 1994, vol. 20, No. 2, pp. 329-331.

Du, H. et al., "Molecular and enzymatic analyses of lysosomal acid lipase in cholesteryl ester storage disease," Molecular Genetics and Metabolism, 1998, vol. 64, No. 2, pp. 126-134.

Du, H. et al., "Wolman disease/cholesteryl ester storage disease: efficacy of plant-produced human lysosomal acid lipase in mice," Journal of Lipid Research, 2008, vol. 49, No. 8, pp. 1646-1657.

Godfrey, C. et al., "Delivery is key: lessons learnt from developing splice-switching antisense therapies," EMBO Molecular Medicine, 2017, vol. 9, No. 5, pp. 545-557.

Havens, M. A. et al., "Splice-switching antisense oligonucleotides as therapeutic drugs," Nucleic Acids Research, 2016, vol. 44, No. 14, pp. 6549-6563.

Pagani, F. et al., "New lysosomal acid lipase gene mutants explain the phenotype of Wolman disease and cholesteryl ester storage disease," Journal of Lipid Research, 1998, vol. 39, pp. 1382-1388.

Wood, M. J. A. et al., "Spinal muscular atrophy: antisense oligonucleotide therapy opens the door to an integrated therapeutic landscape," Human Molecular Genetics, 2017, vol. 26, No. R2, pp. R151-159.

Altschul SF et al.Basic local alignment search tool. J. Mol. Biol., vol. 215, No. 3, pp. 403-410, (Oct. 5, 1990).

Berge, SM et al. Pharmaceutical Salts Journal of Pharmaceutical Sciences, vol. 66, No. 1, pp. 1-19 (1977).

"Dardis et al., "Impact Characterization, and Rescue of Pre-mRNA Splicing Mutations in Lysosomal Storage Disorders" Genes, Feb. 6, 2018, vol. 9, No. 73 (pp. 1-16)".

Dias, N. et al. Antisense oligonucleotides: basic concepts and mechanisms Mol. Cancer Ther. vol. 1, pp. 347-355, (Mar. 2002).

EP16781187.6 Office Action dated May 20, 2019.

EP16876499.1 Extended Search Report dated Jun. 14, 2019.

Geary et al. Absolute Bioavailability of 29-O-(2-Methoxyethyl)-Modified Antisense Oligonucleotides following Intraduodenal Instillation in Rats. J Pharmacal Exp Ther. vol. 296, No. 3, pp. 898-904 (Mar. 2001).

"Singh, et al., "A short antisense oligonucleotide masking a unique intronic motif prevents skipping of a critical exon in spinal muscular atrophy" RNA Biology, Jul. 2009, vol. 6, No. 3, pp. 341-350".

"International Search Report and Written Opinion in corresponding PCT Application No. PCT/US2019/030605 dated Oct. 11, 2019".

Jarver, P. et al., A Chemical View of Oligonucleotides for Exon Skipping and Related Drug Applications, Nucleic Acid Therapeutics vol. 24, No. (1), pp. 37-47, (2014).

Kole, et al. RNA therapeutics: beyond RNA interference and antisense oligonucleotides. Nat Rev Drug Discov. Jan. 20, 2012;11(2):125-40. doi: 10.1038/nrd3625.

Kralovicova et al. Exon-centric regulation of ATM expression is population-dependent and amenable to antisense modification by pseudoexon targeting, Scientific Reports, 6:18741, doi:10.1038/srep18741, Jan. 6, 2016, 13 pages.

LaPlanche et al. Phosphorothioate-modified oligodeoxyribonucleotides. III. NMR and UV spectroscoptc studies of thRp-Rp,Sp-Sp, anRp-Sduplexes, [d(GGsAATTCC)]2, derived from diastereomeriO-ethyl phosphorothioates Nucleic Acids Res. vol. 14, No. 22, pp. 9081-9093 (Nov. 25, 1986).

Li et al. JAG1 Mutation Spectrum and Origin in Chinese Children with Clinical Features of Alagille Syndrome. PLoS One 10(6):e0130355 (2015).

Pilia et al. Jagged-1 mutation analysis in Italian Alagille syndrome patients. Hum Mut 14(5):394-400 (1999).

Spinner et al. Jagged1 mutations in alagille syndrome. Hum Mutat 17(1):18-33 (2001).

Stec et al. Automated solid-phase synthesis, separation, and stereochemistry of phosphorothioate analogs of oligodeoxyribonucleotides J. Am. Chem. Soc., 1984, 106 (20), pp. 6077-6079 (1984).

Stein et al. Physicochemical properties of phosphorothioate oligodeoxynucleotides. Nucleic Acids Res. Apr. 25, 1988;16(8):3209-21.

Turnpenny, P. D. et al. Alagille syndrome: pathogenesis, diagnosis and management.European Journal of Human Genetics vol. 20, pp. 251-257 (2012).

Uhlmann, E. et al. Antisense oligonucleotides: a new therapeutic principle. Chemical Reviews vol. 90, No. 4, pp. 543-584 (Jun. 1990).

Wan et al. Synthesis, biophysical properties and biological activity of second generation antisense oligonucleotides containing chiral phosphorothioate linkages.Nucleic Acids Research, vol. 42, No. 22, pp. 13456-13468 (2014).

Yamamoto et al. Mib-Jag1-Notch signalling regulates patterning and structural roles of the notochord by controlling cell-fate decisions. Development 137(15):2527-2537 (2010).

Zhang, J. et al. PowerBlast: A New Network Blast Application for Interactive or Automated Sequence Analysis and Annotation Genome Res., vol. 7, pp. 649-656, (1997).

Zon et al. Phosphorothioate oligonucleotides: chemistry, purification, analysis, scale-up and future directions. Anti Cancer Drug Design vol. 6, No. 6, pp. 539-568 (1991).

Zon G. and Stec, W.J. (1991) In Eckstein, F. (ed.), Oligonucleotides and Analogues: A Practical Approach. Oxford University Press, Oxford, UK, pp. 87-108.

Aartsma-Rus et al.: Antisense-mediated exon skipping: a versatile tool with therapeutic and research applications. RNA 13(10):1609-24 (2007). Epub Aug. 7, 2007.

Aceti et al.: Syngap1 haploinsufficiency damages a postnatal critical period of pyramidal cell structural maturation linked to cortical circuit assembly, Biol Psychiatry 77(9):805-815 (2015).

Aizer et al.: Lack of reduction in racial disparities in cancer-specific mortality over a 20-year period. Cancer 120:1532-9 (2014).

Aly et al.: Extreme genetic risk for type 1A diabetes. Proc Natl Acad Sci U.S.A. 103(38):14074-9 (2006). Epub Sep. 11, 2006.

Amarnath et al.: The PDL1-PD1 Axis Converts Human TH1 Cells into Regulatory T Cells. Science Translational Medicine 3(111):1-13 (2011).

Anders et al.: Detecting differential usage of exons from RNA-seq data. Genome Res. 22(10):2008-17 (2012). Epub Jun. 23, 2012. doi: gr.133744.111 [pii] 10.1101/gr.133744.111. PubMed PMID: 22722343.

Au et al.: Molecular Genetic Basis of Tuberous Sclerosis Complex: From Bench to Bedside. Journal of Child Neurology 19:9 (2004).

Audentes Therapeutics Announces Expansion of AAV Technology Platform and Pipeline with New Development Programs for Duchenne Muscular Dystrophy and Myotonic Dystrophy. PRNewswire Apr. 8, 2019 (7 pgs).

Aznarez et al.: Tango-Targeted augmentation of nuclear gene output—for the treatment of genetic diseases [abstract]. In: 2018 Annual Meeting Abstract of the American Society of Gene and Cell Therapy, May 16-19, 2018, Chicago, IL (2018), Abstract No. 304.

Bakkenist et al.: DNA damage activates ATM through intermolecular autophosphorylation and dimer dissociation. Nature 421(6922):499-506 (2003). doi: 10.1038/nature01368. PubMed PMID: 12556884.

(56) References Cited

OTHER PUBLICATIONS

Balagurumoorthy et al.: Hairpin and parallel quartet structures for telomeric sequences. Nucleic Acids Res. 20(15):4061-7 (1992).
Balkwill et al.: Repression of translation of human estrogen receptor alpha by G-quadruplex formation. Biochemistry 48(48):11487-95 (2009). doi: 10.1021/bi901420k.
Barratt et al.: Remapping the insulin gene/IDDM2 locus in type 1 diabetes. Diabetes 53(7):1884-9 (2004).
Bassi et al.: A novel mutation in the ATP1A2 gene causes alternating hemiplegia of childhood. J. Med. Genet. 41:621-628 (2004).
Battistini et al.: A new CACNA1A gene mutation in acetazolamide-responsive familial hemiplegic migraine and ataxia. Neurology 53(1):38-43 (1999).
Baughan et al.: Delivery of bifunctional RNAs that target an intronic repressor and increase SMN levels in an animal model of spinal muscular atrophy. Hum Mol Genet. 18(9):1600-11 (2009). doi: 10.1093/hmg/ddp076. Epub Feb. 19, 2009.
Bauman et al.: Therapeutic potential of splice-switching oligonucleotides. Oligonucleotides 19.1:1-13 (2009).
Beaudoin et al.: 5'-UTR G-quadruplex structures acting as translational repressors. Nucleic Acids Res. 38(20):7022-36 (2010). doi: 10.1093/nar/gkq557. Epub Jun. 22, 2010.
Beli et al.: Proteomic investigations reveal a role for RNA processing factor THRAP3 in the DNA damage response. Mol Cell. 46(2):212-25 (2012). doi: 10.1016/j.molcel.2012.01.026. PubMed PMID: 22424773; PubMed Central PMCID: PMC3565437.
Berger et al.: The molecular basis of human retinal and vitreoretinal diseases. Progress in Retinal and Eye Research 29:335-375 (2010).
Bethke et al.: Comprehensive analysis of the role of DNA repair gene polymorphisms on risk of glioma. Hum Mol Genet. 17(6):800-5 (2008). Epub Dec. 1, 2007.doi: ddm351 [pii] 10.1093/hmg/ddm351. PubMed PMID: 18048407.
Bicknell et al.: Introns in UTRs: why we should stop ignoring them. Bioessays 34(12):1025-34 (2012). doi: 10.1002/bies.201200073. Epub Oct. 26, 2012.
Blencowe, B: Reflections for the 20th anniversary issue of RNA journal. RNA Journal 21(4):573-575 (2015).
Blencowe BJ: Splicing regulation: the cell cycle connection. Curr. Biol. 13(4):R149-51 (2003). PubMed PMID: 12593819.
Bonnen et al.: Haplotypes at ATM identify coding-sequence variation and indicate a region of extensive linkage disequilibrium. Am J Hum Genet. 67(6):1437-51 (2000). Epub Nov. 15, 2000.doi: S0002-9297(07)63213-3 [pii] 10.1086/316908. PubMed PMID: 11078475.
Boothby et al.: Removal of Retained Introns Regulates Translation in the Rapidly Developing Gametophyte of Marsilea vestita. Developmental Cell 24:517-529 (2013).
Booy et al.: The RNA helicase RHAU (DHX36) unwinds a G4-quadruplex in human telomerase RNA and promotes the formation of the P1 helix template boundary. Nucleic Acids Res. (9):4110-24 (2012). doi: 10.1093/nar/gkr1306. Epub Jan. 11, 2012.
Boutz et al.: Detained introns are a novel, widespread class of post-transcriptionally spliced introns. Genes Dev. 29(1):63-80 (2015). doi: 10.1101/gad.247361.114.
Braunschweig et al.: Widespread intron retention in mammals functionally tunes transcriptomes. Widespread intron retention in mammals functionally tunes transcriptomes. Genome Res. 24(11):1774-86 (2014). doi: 10.1101/gr.177790.114. Epub Sep. 25, 2014.
Bravo-Gil et al.: Improving the management of Inherited Retinal Dystrophies by targeted sequencing of a population-specific gene panel. Scientific Reports 6:23910, 10 pages (2015).
Brooks et al.: A pan-cancer analysis of transcriptome changes associated with somatic mutations in U2AF1 reveals commonly altered splicing events. PLoS One. 9(1):e87361 (2014). Epub Feb. 6, 2014.doi: 10.1371/journal.pone.0087361 PONE-D-13-26905 [pii]. PubMed PMID: 24498085.
Buchman et al.: Comparison of intron-dependent and intron-independent gene expression. Mol Cell Biol. 8(10):4395-405 (1988).
Buckley et al.: Cytoplasmic intron retention, function, splicing, and the sentinel RNA hypothesis. WIREs RNA 5:223-2330 (2014).

Bugaut et al.: 5'-UTR RNA G-quadruplexes: translation regulation and targeting. Nucleic Acids Res. 40(11):4727-41 (2012). doi: 10.1093/nar/gks068. Epub Feb. 20, 2012.
Bugaut et al.: An RNA hairpin to G-quadruplex conformational transition. J Am Chem Soc. 134(49):19953-6 (2012). doi: 10.1021/ja308665g. Epub Nov. 29, 2012.
Buratti et al.: DBASS3 and DBASS5: databases of aberrant 3'-and 5'-splice sites. Nucleic Acids Res. 39(Database issue): D86-91 (2011). doi: 10.1093/nar/gkq887. Epub Oct. 6, 2010.
Buratti et al.: RNA folding affects the recruitment of SR proteins by mouse and human polypurinic enhancer elements in the fibronectin EDA exon. Mol Cell Biol. 24(3):1387-400 (2004).
Burnette et al.: Subdivision of large introns in Drosophila by recursive splicing at non-exonic elements. Genetics (2005).
Burns et al.: Connections between pre-mRNA processing and regulation of the eukaryotic cell cycle. Front Horm Res. 25:59-82 (1999).
Buschmann et al.: Chitosans for delivery of nucleic acids. Advanced drug delivery reviews 65.9:1234-1270 (2013).
Busslinger et al.: β+ Thalassemia: Aberrant splicing results from a single point mutation in an intron. Cell 27.2:289-298 (1981).
Callis et al. Introns increase gene expression in cultured maize cells. Genes Dev. 1(10):1183-200 (1987).
Catterall et al.: Nav1.1 channels and epilepsy. J Physiol. 1; 588(Pt 11):1849-59 (2010).
Cavaloc et al.: The splicing factors 9G8 and SRp20 transactivate splicing through different and specific enhancers. RNA 5(3):468-83 (1999).
Cazzola et al.: Translational pathophysiology: a novel molecular mechanism of human disease. Blood 95(11):3280-8 (2000).
Chambers et al.: The INO80 chromatin remodeling complex prevents polyploidy and maintains normal chromatin structure at centromeres. Genes Dev. 26(23):2590-603 (2012). Epub Dec. 5, 2012.doi: 26/23/2590 [pii] 10.1101/gad.199976.112. PubMed PMID: 23207916.
Chen et al.: A functional single nucleotide polymorphism in promoter of ATM is associated with longevity. Mech Ageing Dev. 131:636-40 (2010).
Chen et al.: Chk1 kinase negatively regulates mitotic function of Cdc25A phosphatase through 14-3-3 binding. Mol Cell Biol. 23(21):7488-97 (2003). PubMed PMID: 14559997; PubMed Central PMCID: PMC207598.
Choi et al.: CHK2 kinase promotes pre-mRNA splicing via phosphorylating CDK11p110. Oncogene 33:108-15 (2014).
Colla et al.: Telomere dysfunction drives aberrant hematopoietic differentiation and myelodysplastic syndrome. Cancer Cell. 27(5):644-57 (2015). doi: 10.1016/j.ccell.2015.04.007. PubMed PMID: 25965571.
Collie et al.: The application of DNA and RNA G-quadruplexes to therapeutic medicines. Chem Soc Rev. 40(12):5867-92 (2011). doi: 10.1039/c1cs15067g. Epub Jul. 25, 2011.
Collin et al.: Antisense Oligonucleotide (AON)-based Therapy for Leber Congenital Amaurosis caused by a Frequent Mutation in CEP290. Molecular Therapy-Nucleic Acids, pp. 1-7 (2012).
Consortium. TGP. An integrated map of genetic variation from 1,092 human genomes. Nature (London). 491:56-65 (2012).
Corey et al.: A non-classical translocation involving 17q12 (retinoic acid receptor alpha) in acute promyelocytic leukemia (APML) with atypical features. Leukemia 8(8):1350-3 (1994). PubMed PMID: 8057672.
Corvelo et al.: Genome-wide association between branch point properties and alternative splicing. PLoS Comput Biol. 6(11):e1001016 (2010). Epub Dec. 3, 2010.doi: 10.1371/journal.pcbi. 1001016. PubMed PMID: 21124863.
Coulombe-Huntington et al.: Fine-Scale Variation and Genetic Determinants of Alternative Splicing across Individuals. PLoS Genet. 5(12):e1000766 (2009). Epub Dec. 17, 2009.doi: 10.1371/journal.pgen. 1000766. PubMed PMID: 20011102.
Coutinho et al.: Functional significance of a deep intronic mutation in the ATM gene and evidence for an alternative exon 28a. Hum Mutat. 25(2):118-24 (2005). Epub Dec. 1, 2005.doi: 10.1002/humu.20170. PubMed PMID: 15643608.
Creacy, et al. G4 resolvase 1 binds both DNA and RNA tetramolecular quadruplex with high affinity and is the major source of tetramolecular

(56) References Cited

OTHER PUBLICATIONS quadruplex G4-DNA and G4-RNA resolving activity in HeLa cell lysates. J Biol Chem. 283(50):34626-34 (2008). doi: 10.1074/jbc. M806277200. Epub Oct. 7, 2008.
Creson et al.: Re-expression of SynGAP Protein in Adulthood Improves Translatable Measures of Brain Function and Behavior in a Model of Neurodevelopmental Disorders. Departments of Neuroscience and Molecular medicine, The Scripps Research Institute (2018).
Culler et al.: Functional selection and systematic analysis of intronic splicing elements identify active sequence motifs and associated splicing factors. Nucleic Acids Res. 38(15):5152-65 (2010). doi: 10.1093/nar/gkq248. Epub Apr. 12, 2010.
Database Geneseq [Online], Nov. 13, 2008 (Nov. 13, 2008), Dual label detection probe, QF probe 1, 5. 3.11, XP055572852, retrieved from EBI Accession No. GSN:ARK21623.
Davies et al.: A genome-wide search for human type 1 diabetes susceptibility genes. Nature 8;371(6493):130-6 (1994).
Decorsiere et al.: Essential role for the interaction between hnRNP H/F and a G quadruplex in maintaining p53 pre-mRNA 3'-end processing and function during DNA damage. Genes Dev. 25(3):220-5 (2011). doi: 10.1101/gad.607011.
Dedic et al.: Alagille Syndrome Mimicking Biliary Atresia in Early Infancy, PLOS OONE, 10(11):e0143939: pp. 1-7 (2015).
Deere et al.: Antisense Phosphorodiamidate Morpholino Oligomer Length and Target Position Effects on Gene-Specific Inhibition in *Escherichia coli*. Antimicrobial Agents Andchemotherapy 49(1):249-255 (2005).
Derecka et al.: Occurrence of a quadruplex motif in a unique insert within exon C of the bovine estrogen receptor alpha gene (ESR1). Biochemistry 49(35):7625-33 (2010). doi: 10.1021/bi100804f.
Didiot et al.: The G-quartet containing FMRP binding site in FMR1 mRNA is a potent exonic splicing enhancer. Nucleic Acids Res. Sep. 2008;36(15):4902-12. doi: 10.1093/nar/gkn472. Epub Jul. 24, 2008.
Ding, H. et al.: DeliveringPD-1 inhibitory signal concomitant with blocking ICOS co-stimulation suppresses lupus-like syndrome in autoimmune BXSB mice. Clinical Immunology, vol. 118, pp. 258-267, (2006).
Divina, P. et al.: Ab initio prediction of cryptic splice-site activation and exon skipping. Eur J Hum Genet. 2009; 17:759-65.
Dominski, et al.: Restoration of correct splicing in thalassemic pre-mRNA by antisense oligonucleotides. Proc Natl Acad Sci U S A. Sep. 15, 1993;90(18):8673-7.
Dredge, et al.: NeuN/Rbfox3 Nuclear and Cytoplasmic Isoforms Differentially Regulate Alternative Splicing and Nonsense-Mediated Decay of Rbfox2. PLoS One. 2011; 6(6): e21585.
Du, et al.: Correction of prototypic ATM splicing mutations and aberrant ATM function with antisense morpholino oligonucleotides. Proc. Natl. Acad. Sci. U S A. Apr. 3, 2007;104(14):6007-12. Epub Mar. 26, 2007.
Ducros et al.: Recurrence of the T666M calcium channel CACNA1A gene mutation in familial hemiplegic migraine with progressive cerebellar ataxia. Am J Hum Genet. vol. 64, No. 1, pp. 89-98 (Jan. 1999).
Duikers, et al.: Antisense Oligonucleotide-Based Splicing Correction in Individuals with Leber Congenital Amaurosis due to Compound Heterozygosity for the c.2991+1655AG Mutation in CEP290. International Journal of Molecular Sciences 19(753):1-12 (2018).
Dulla, et al.: Splice-Modulating Oligonucleotide QR-110 Restores CEP290 mRNA and Function in Human c.2991+1655AG LCA10 Models. (2018) Molecular Therapy: Nucleic Acids pp. 730-740 (2018).
Duryagina R, et al.: Overexpression of Jagged-1 and its intracellular domain in human mesenchymal stromal cells differentially affect the interaction with hematopoietic stem and progenitor cells. Stem Cells Dev. vol. 22, No. 20, pp. 2736-2750 (2013).
Dutertre, M., et al.: DNA damage: RNA-binding proteins protect from near and far. Trends Biochem Sci. 2014; 39(3):141-9. Epub Feb. 19, 2014.doi: S0968-0004(14)00015-2 [pii] 10.1016/j.tibs.2014. 01.003. PubMed PMID: 24534650.

Eddy, et al.: G4 motifs correlate with promoter-proximal transcriptional pausing in human genes. Nucleic Acids Res. Jul. 2011;39(12):4975-83. doi: 10.1093/nar/gkr079. Epub Mar. 3, 2011.
El Bougrini et al.: PML positively regulates interferon gamma signaling. Biochimie. 2011; 93(3):389-98. doi: 10.1016/j.biochi. 2010.11.005. PubMed PMID: 21115099.
Emerick, et al.: Multivariate analysis and visualization of splicing correlations in single-gene transcriptomes. BMC Bioinformatics 8:16 (2007).
EP 15846242.4 Partial Supplementary Search Report and Search Opinion dated May 2, 2018.
EP 16876621.0 Extended European Search Report and Search Opinion dated Mar. 7, 2019.
EP15729929.8 Office Action dated Dec. 22, 2017.
EP15729929.8 Office Action dated Oct. 30, 2018.
EP15846242.4 Extended European Search Report dated Aug. 21, 2018.
EP168766061.1 Extended Search Report dated May 24, 2019.
Fairbrother, W.G., et al. Predictive identification of exonic splicing enhancers in human genes. Science. 2002; 297(5583):1007-13. PubMed PMID: 12114529.
Fededa, et al.: A polar mechanism coordinates different regions of alternative splicing within a single gene. Mol Cell. Aug. 5, 2005;19(3):393-404.
Ferreira, P.G., et al.: Transcriptome characterization by RNA sequencing identifies a major molecular and clinical subdivision in chronic lymphocytic leukemia. Genome Res. 2014; 24:212-26.
Fletcher, Sue et al.: Antisense suppression of donor splice site mutations in the dystrophin gene transcript. Molecular Genetics & Genomic Medicine, vol. 1, No. 3, pp. 162-173, Jun. 13, 2013.
Fred et al.: The human insulin mRNA is partly translated via a cap-and eIF4A-independent mechanism. Biochem Biophys Res Commun. Sep. 9, 2011;412(4):693-8. doi: 10.1016/j.bbrc.2011.08. 030. Epub Aug. 16, 2011.
Friedman, et al.: Correction of Aberrant Splicing of the Cystic Fibrosis Transmembrane Conductance Regulator (CFTR) Gene by Antisense Oligonucleotides. The Journal of Biological Chemistry 274(51):36193-36199 (1999).
Friedman, KJ et al.: Correction of aberrant splicing of the cystic fibrosis transmembrane conductance regulator (CFTR) gene by antisense oligonucleotides. J Biol Chem. Dec. 17, 1999;274(51):36193-36199.
Friend, KL et al. Detection of a novel missense mutation and second recurrent mutation in the CACNA1A gene in individuals with EA-2 and FHM. Hum Genet. vol. 105(3):261-5 (Sep. 1999).
Furukawa & Kish 2008, Gene Reviews, Pagon Ra et al. eds., Univ. of WA Seattle, NCBI Bookshelf ID NBK1437.
Galante, et al.: Detection and evaluation of intron retention events in the human transcriptome. RNA. May 2004;10(5):757-65.
Garanto, et al.: In vitro and in vivo rescue of aberrant splicing in CEP290-associted LCA by antisense oligonucleotide delivery. Human Molecular Genetics 25(12):2552-2563 (2016).
Garner, et al.: Selectivity of small molecule ligands for parallel and anti-parallel DNA G-quadruplex structures. Org Biomol. Chem. Oct. 21, 2009;7(20):4194-200. doi: 10.1039/b910505k. Epub Aug. 14, 2009.
Geary, et al.: Pharmacokinetics, biodistribution and cell uptake of antisense oligonucleotides. Advance Drug Delivery Reviews (2015).
Geary, RS, et al.: Pharmacokinetic properties of 2'-O-(2-methoxyethyl)-modified oligonucleotide analogs in rats. J Pharmacal Exp Ther. vol. 296, No. 3, pp. 890-897 (Mar. 2001).
Gerard, et al., "AON-mediated Exon Skipping Restores ciliation in Fibroblasts Harboring the Common Leber Congenital Amaurosis CEP290 Mutation" (2012) Molecular Therapy-Nucleic Acids, pp. 1-9.
Gianchecchi et al.: Recent insights into the role of the PD-1/PD-L1 pathway in immunological tolerance and autoimmunity. Autoimmunity Reviews 12:1091-1100 (2013).
Gibson, G.: Hints of hidden heritability in GWAS. Nat Genet. 2010; 42(7):558-60. Epub Jun. 29, 2010.doi: ng0710-558 [pii] 10.1038/ ng0710-558. PubMed PMID: 20581876.
Gohring, J. et al.: Imaging of Endogenous Messenger Splice Variants in Living Cells Reveals Nuclear Retention of Transcripts

(56) References Cited

OTHER PUBLICATIONS

Inaccessible to Nonsense-Mediated Decay in *Arabidopsis*. The Plant Cell. vol. 26, pp. 754-764.(Feb. 2014).
Gomes et al.: Translating chitosan to clinical delivery of nucleic acid-based drugs. MRS bulletin 39.1 (2014): 60-70.
Gomez, et al.: Telomerase downregulation induced by the G-quadruplex ligand 12459 in A549 cells is mediated by hTERT RNA alternative splicing. Nucleic Acids Res. Jan. 16, 2004;32(1):371-9. Print 2004.
Goncharova et al.: Tuberin regulates p70 S6 kinase activation and ribosomal protein S6 phosphorylation. A role for the TSC2 tumor suppressor gene in pulmonary lymphangioleiomyomatosis (LAM). J. Biol. Chem. (Aug. 23, 2002) 277(34);30958-67. EPub Jun. 3, 2002.
Gonzalez-Santos, et al.: Mutation in the splicing factor Hprp3p linked to retinitis pigmentosa impairs interactions within the U4/U6 snRNP pigmentosa impairs interactions within the U4/U6 snRNP complex, PubMed Central Canada , Author Manuscript, 29 pages.
Goto, et al.: Targeted skipping of a Single Exon Harboring a Premature termination Codon Mutation: Implications and Potential for Gene Correction Therapy for Selective Dystrophic Epiderolysis Bullosa Patients. Journal of Investigative Dermatology 126: 2614-262 (2006).
Goyenvalie et al.: Therapeutic approaches to muscular dystrophy. Hum Mol Genet. Apr. 15, 2011;20(R1):R69-78. doi: 10.1093/hmg/ddr105. Epub Mar. 24, 2011.
Gozani, O., et al.: A potential role for U2AF-SAP 155 interactions in recruiting U2 snRNP to the branch site. Mol Cell Biol. 1998; 18(8):4752-60. PubMed PMID: 9671485.
Graveley, B.R.: The haplo-spliceo-transcriptome: common variations in alternative splicing in the human population. Trends Genet. 2008; 24(1):5-7. Epub Dec. 7, 2007.doi: S0168-9525(07)00349-6 [pii] 10.1016/j.tig.2007.10.004. PubMed PMID: 18054116.
Gutell, R.R., et al.: A story: unpaired adenosine bases in ribosomal RNAs. J Mol Biol. 2000; 304(3):335-54. Epub Nov. 25, 2000.doi: 10.1006/jmbi.2000.4172 S0022-2836(00)94172-X [pii]. PubMed PMID: 11090278.
Guth, S et al.: Dual function for U2AF(35) in AG-dependent pre-mRNA splicing. Mol Cell Biol. 2001;21(22):7673-81. PubMed PMID: 11604503.
Guy et al.: A mouse Mecp2-null mutation causes neurological symptoms that mimic Rett syndrome. Nat Genet 27:322-326 (2001).
Hai, et al.: A G-tract element in apoptotic agents-induced alternative splicing. Nucleic Acids Res. Jun. 2008;36(10):3320-31. doi: 10.1093/nar/gkn207. Epub Apr. 24, 2008.
Hamdan, F. et al.: Mutations in SYNGAP1 in Autosomal Nonsyndromic Mental Retardation. The New England Journal of Medicine. N.Engl. Med. vol. 360, No. 6, pp. 599, (2009).
Hamdan, F. F. et al.: De Novo SYNGAP1 Mutations in Nonsyndromic Intellectual Disability and Autism, Biol. Psychiatry, 69:898-901 (2011).
Hammond, et al."Genetic therapies for RNA mis-splicing diseases" (2011) Cell Press 10 pages.
Han, et al.: Antisense oligonucleotides increase Scn1a expression and reduce seizures and SUDEP incidence in a mouse model of Dravet syndrome. Science Translational Medicine, 12, pp. 1-14 (2020).
Han, et al.: Tango-Targeted augmentation of nuclear gene output for the treatment of genetic diseases. Poster session presented at the American Society of Gene and Cell Therapy, Chicago, IL. (May 2018).
Hargous, et al.: Molecular basis of RNA recognition and TAP binding by the SR proteins SRp20 and 9G8. EMBO J. Nov. 1, 2006;25(21):5126-37. Epub Oct. 12, 2006.
Harkin, et al.: The spectrum of SCN1A-related infantile epileptic encephalopathies. Brain. Mar. 2007; 130(Pt 3):843-52.
Hastings, M.L.: et al. Control of pre-mRNA splicing by the general splicing factors PUF60 and U2AF. PLoS One. 2007;2:e538. PubMed PMID: 17579712.
Havens, et al.: Targeting RNA Splicing for Disease Therapy. Wiley Interdiscip. Rev RNA 4(3): 247-266 (2013).

He, Y.H., et al.: Association of the insulin-like growth factor binding protein 3 (IGFBP-3) polymorphism with longevity in Chinese nonagenarians and centenarians. Aging (Milano). 2014;6:944-56.
Hegele et al.: Dynamic protein-protein interaction wiring of the human spliceosome. Mol Cell. Feb. 24, 2012;45(4):567-80. doi: 10.1016/j.molcel.2011.12.034.
Hernan, I. et al.: Cellular Expression and siRNA-Mediated Interference of Rhodopsin cis-Acting Splicing Mutants Associated with Autosomal Dominant Retinitis Pigmentosa, Invest Ophthalmol. Vis. Sci. (2011) 52:3723-3729.
Heyn, P. et al.: Introns and gene expression: Cellular constraints, transcriptional regulation, and evolutionary consequences. Bioessays vol. 37, pp. 148-154 (2014).
Hiller et al. Pre-mRNA secondary structures influence exon recognition. PLoS genetics 3.11 (2007): e204.
Hirata et al.: Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand. J. Immunology vol. 174 pp. 1888-1897 (2005).
Hishida, A. et al.: Polymorphisms in PPAR Genes (PPARD, PPARG, and PPARGC1A) and the Risk of Chronic Kidney Disease in Japanese: Cross-Sectional Data from the J-MICC Study. PPAR 2013; 980471 pp. 1-8.
*Homo sapiens* pre-mRNA processing factor 3 (PRPF3), mRNA, NCBI Reference Sequence: NM_004698.2 Accessed Apr. 6, 2017.
Hua, et al.: Antisense correction of SMN2 splicing in the CNS rescues necrosis in a type III SMA mouse model. Genes Dev. Aug. 1, 2010;24(15):1634-44. doi: 10.1101/gad.1941310. Epub Jul. 12, 2010.
Hua et al.: Antisense masking of an hnRNP A1/A2 intronic splicing silencer corrects SMN2 splicing in transgenic mice. Am. J. Hum. Genet. 82:834-848 (Mar. 27, 2008).
Hua, Y., et al.: Enhancement of SMN2 exon 7 inclusion by antisense oligonucleotides targeting the exon. PLoS Biol. 2007;5(4):e73. Epub Mar. 16, 2007.doi: 06-PLBI-RA-1492R3 [pii] 10.1371/journal.pbio.0050073. PubMed PMID: 17355180.
Hunt, et al.: Negligible impact of rare autoimmune-locus coding-region variants on missing heritability. Nature. Jun. 13, 2013;498(7453):232-5. doi: 10.1038/nature12170. Epub May 22, 2013.
Huynh, K.D., et al.: BCoR, a novel corepressor involved in BCL-6 repression. Genes Dev. 2000;14(14):1810-23. PubMed PMID: 10898795; PubMed Central PMCID: PMC316791.
International Application No. PCT/GB2015/051756 International Preliminary Report on Patentability, Dec. 26, 2016.
International Application No. PCT/GB2015/051756 International Search Report and Written Opinion Mailed Nov. 30, 2015.
International Application No. PCT/GB2016/053136 International Search Report and Written Opinion Mailed Mar. 6, 2017.
International Application No. PCT/GB2016/053136 Partial International Search Report Mailed Jan. 19, 2017.
International Application No. PCT/US16/66576 International Search Report and Written Opinion Mailed May 4, 2017.
International Application No. PCT/US16/66691 International Search Report and Written Opinion Mailed May 10, 2017.
International Application No. PCT/US16/66708 International Search Report and Written Opinion Mailed May 8, 2017.
International Application No. PCT/US16/66721 International Search Report and Written Opinion mailed May 1, 2017.
International Application No. PCT/US2015/053896 International Preliminary Report on Patentability Mailed Apr. 4, 2017.
International Application No. PCT/US2015/53896 International Search Report and Written Opinion dated Mar. 3, 2016.
International Application No. PCT/US2016/066414 International Search Report and Written Opinion Mailed Apr. 19, 2017.
International Application No. PCT/US2016/066417 International Search Report and Written Opinion Mailed Apr. 19, 2017.
International Application No. PCT/US2016/066564 International Search Report and Written Opinion Mailed May 4, 2017.
International Application No. PCT/US2016/066705 International Search Report and Written Opinion Mailed Apr. 24, 2017.

(56) References Cited

OTHER PUBLICATIONS

International Application No. PCT/US2018/048031 International Search Report and Written Opinion Mailed Jan. 22, 2019.
International search report and written opinion dated Jun. 5, 2017 for PCT Application No. PCT/US2016/066684.
International Search Report and Written Opinion dated Mar. 28, 2019 for PCT/US2018/057165.
Itoh et al.: Methyl CpG-binding Protein Isoform MeCP2_e2 Is Dispensable for Rett Syndrome Phenotypes but Essential for Embryo Viability and Placenta Development. J Biol Chem 287:13859-13867 (2012).
Iwamoto, et al.: Transcription-dependent nucleolar cap localization and possible nuclear function of DExH RNA helicase RHAU. Exp Cell Res. Apr. 1, 2008;314(6):1378-91. doi: 10.1016/j.yexcr.2008.01.006. Epub Jan. 16, 2008.
Jacob et al.: Intron retention as a component of regulated gene expression programs. Hum Genet 136:1043-1057 (2017).
Jearawiriyapaisarn et al.: Sustained Dystrophin Expression Induced by Peptide-conjugated Morpholino Oligomers in the Muscles of mdx Mice. Mol Ther. 16(9): 1624-1629 (2008).
Jurka et al.: Identification of new medium reiteration frequency repeats in the genomes of Primates, Rodentia and Lagomorpha. Genetica98.3 (1996): 235-247.
Jurkiewicz, D. et al.: Spectrum of JAG1 gene mutations in Polish patients with Alagille syndrome J. Appl. Genetics vol. 55, pp. 329-336, (2014).
Kach et al.: A novel antisense oligonucleotide approach to treat eye diseases by increasing target gene expression. No. 3423-A0194 Arvo Poster Apr. 19, 2019 (1 pg.).
Kaminker, P.G., et al.: A novel form of the telomere-associated protein TIN2 localizes to the nuclear matrix. Cell Cycle. 2009;8(6):931-9. PubMed PMID: 19229133; PubMed Central PMCID: PMC2751576.
Kang et al.: Up-regulation of luciferase gene expression with antisense oligonucleotides: implications and applications in functional assay development. Biochemistry 37.18 (1998): 6235-6239.
Kaplan et al.: Medium reiteration frequency repetitive sequences in the human genome. Nucleic acids research 19.17 (1991): 4731-4738.
Katsani, K.R. et al.: Functional Genomics Evidence Unearths New Moonlighting Roles of Outer Ring Coat Nucleoporins Scientific Reports vol. 4, No. 4655 (Apr. 11, 2014).
Kawamata, N., et al.: Genetic differences between Asian and Caucasian chronic lymphocytic leukemia. Int J Oncol. 2013;43(2):561-5. doi: 10.3892/ijo.2013.1966. PubMed PMID: 23708256; PubMed Central PMCID: PMC3775563.
Ke, et al.: Quantitative evaluation of all hexamers as exonic splicing elements. Genome Res. Aug. 2011;21(8):1360-74. doi: 10.1101/gr.119628.110. Epub Jun. 9, 2011.
Keir, M.E. et al.: PD-1 and Its Ligands in Tolerance and Immunity. Annu. Rev. Immunol. vol. 26, pp. 677-704 (2008).
Kervestin et al.: NMD: a multifaceted response to premature translational termination. Nature reviews Molecular cell biology13.11 (2012): 700.
Kikin, et al.: QGRS Mapper: a web-based server for predicting G-quadruplexes in nucleotide sequences. Nucleic Acids Res. Jul. 1, 2006;34(Web Server issue):W676-82.
Kim, E., et al.: SRSF2 Mutations Contribute to Myelodysplasia by Mutant-Specific Effects on Exon Recognition. Cancer Cell. 2015;27(5):617-30. doi: 10.1016/j.ccell.2015.04.006. PubMed PMID: 25965569; PubMed Central PMCID: PMC4429920.
Kim et al.: ChimerDB 2.0—a knowledgebase for fusion genes updated. Nucleic Acids Res. 2009;38(Database issue): D81-5. Epub Nov. 13, 2009.doi: gkp982 [pii] 10.1093/nar/gkp982. PubMed PMID: 19906715.
Kim et al.: The role of synaptic GTPase-activating protein in neuronal development and synaptic plasticity. J. Neurosci. 23(4):1119-1124 (Feb. 15, 2003).

Kim et al.: The splicing factor U2AF65 stabilizes TRF1 protein by inhibiting its ubiquitin-dependent proteolysis. Biochem Biophys Res Commun. 2014;443(3):1124-30. doi: 10.1016/j.bbrc.2013.12.118. PubMed PMID: 24389012.
Knudsen et al.: Increased skewing of X chromosome inactivation in Rett syndrome patients and their mothers. Eur J Hum Genet 14:1189-1194 (2006).
Kralovicova, et al.: Allele-specific recognition of the 3' splice site of INS intron 1. Hum Genet. Oct. 2010;128(4):383-400. doi: 10.1007/s00439-010-0860-1. Epub Jul. 14, 2010.
Kralovicova, et al.: Compensatory signals associated with the activation of human GC 5' splice sites. Nucleic Acids Res. Sep. 1, 2011;39(16):7077-91. doi: 10.1093/nar/gkr306. Epub May 23, 2011.
Kralovicova, et al.: Global control of aberrant splice-site activation by auxiliary splicing sequences: evidence for a gradient in exon and intron definition. Nucleic Acids Res. Oct. 2007; 35(19): 6399-6413.
Kralovicova, et al.: Identification of U2AF(35)-dependent exons by RNA-Seq reveals a link between 3' splice-site organization and activity of U2AF-related proteins. Nucleic Acids Res. Apr. 20, 2015;43(7):3747-63. doi: 10.1093/nar/gkv194. Epub Mar. 16, 2015.
Kralovicova, et al.: Optimal antisense target reducing INS intron 1 retention is adjacent to a parallel G quadruplex. Nucleic Acids Res. Jul. 2014;42(12):8161-73. doi: 10.1093/nar/gku507. Epub Jun. 17, 2014.
Kralovicova, et al.: Phenotypic consequences of branch point substitutions. Hum Mutat. Aug. 2006;27(8):803-13.
Kralovicova, et al.: Position-dependent repression and promotion of DQB1 intron 3 splicing by GGGG motifs. J Immunol. Feb. 15, 2006;176(4):2381-8.
Kralovicova, et al.: Variants in the human insulin gene that affect pre-mRNA splicing: is-23Hphl a functional single nucleotide polymorphism at IDDM2? Diabetes. Jan. 2006;55(1):260-4.
Kralovicova, et al.: Antisense Oligonucleotides Modulating Activation of a Nonsense-Mediated RNA Decay Switch Exon in the ATM Gene. Nucleic Acid Ther. Dec. 1, 2016; 26(6): 392-400.
Kralovicova, J. et al.: Branch sites haplotypes that control alternative splicing. Hum Mol Genet. 2004;13:3189-202.
Kralovicova, J. et al.: The role of short RNA loops in recognition of a single-hairpin exon derived from a mammalian-wide interspersed repeat. RNA Biol. 2015;12(1):54-69. doi: 10.1080/15476286.2015.1017207. PubMed PMID: 25826413.
Kriaucionis et al.: The major form of MeCP2 has a novel N-terminus generated by alternative splicing. Nucleic Acids Res 32:1818-1823 (2004).
Krishnaraj et al.: RettBASE: Rett syndrome database update. Hum Mutat 38:922-931 (2017).
Laceerra, et al.: Restoration of hemoglobin A synthesis in erythroid cells from peripheral blood of thalassemic patients. PNAS 97(17): 9591-9596 (2000).
Lander, et al.: Initial sequencing and analysis of the human genome. Nature 409:860-921 (Feb. 15, 2001).
Le Hir, et al.: How introns influence and enhance eukaryotic gene expression. Trends Biochem Sci. Apr. 2003;28(4):215-20.
Lee et al.: The Consensus 5' Splice Site Motif Inhibits mRNA Nuclear Export. PLoS One vol. 10, No. 3, p. e0122743 (Mar. 31, 2015).
Lee, J., et al.: Metastasis of neuroendocrine tumors are characterized by increased cell proliferation and reduced expression of the ATM gene. PLoS One. 2012;7:e34456.
Lefave, et al.: Splicing factor hnRNPH drives an oncogenic splicing switch in gliomas. The EMBO Journal 30(19): 4084-4097 (2011).
Lehir, H. et al.: 5'-End RET Splicing: Absence of Variants in Normal Tissues and Intron Retention in Pheochromocytomas, Oncology 63:84-91 (2002).
Lei et al.: Exonization of Alu Ya5 in the human ACE gene requires mutations in both 3' and 5' splice sites and is facilitated by a conserved splicing enhancer. Nucleic acids research 33.12 (2005): 3897-3906.
Lei, et al.: Identification of splicing silencers and enhancers in sense Alus: a role for pseudoacceptors in splice site repression. Mol Cell Biol. Aug. 2005;25(16):6912-20.
Lemaire, M., et al. CDC25B phosphorylation by p38 and MK-2. Cell Cycle. 2006;5(15):1649-53. PubMed PMID: 16861915.

(56) References Cited

OTHER PUBLICATIONS

Levin, et al.: Treating Disease at the RNA Level with Oligonucleotides. The New England Journal of Medicine 380:57-70 (2019).
Lev-Maor et al.: Intronic Alus influence alternative splicing. PLoS genetics 4.9 (2008): e1000204.
Lev-Maor et al.: The birth of an alternatively spliced exon: 3'splice-site selection in Alu exons. Science 300.5623: 1288-1291 (2003).
Levy et al.: TranspoGene and micro TranspoGene: transposed elements influence on the transcriptome of seven vertebrates and invertebrates. Nucleic acids research 36.suppl_1 (2007): D47-D52.
Li et al.: PD-L1-Driven Tolerance Protects Neurogenin3-Induced Islet Neogenesis to Reverse Established Type 1 Diabetes in NOD Mice. Diabetes vol. 64, pp. 529-540 (Feb. 2015; epub Oct. 20, 2014).
Liang, et al.: Short Intronic Repeat Sequences Facilitate Circular RNA Production. Genes & Development 28(20):2233-47 (2014).
Liang, Xue-Hai et al.: Translation efficiency of mRNAs is increased by antisense oligonucleotides targeting upstream open reading frames, Nature Biotechnology, 34(8):875-882 (2016).
Lianoglou, S., et al.: Ubiquitously transcribed genes use alternative polyadenylation to achieve tissue-specific expression. Genes Dev. 2013;27(21):2380-96. Epub Oct. 23, 2013.doi: gad.229328.113 [pii] 10.1101/gad.229328.113. PubMed PMID: 24145798.
Lim et al.: A computational analysis of sequence features involved in recognition of short introns. Proceedings of the National Academy of Sciences98.20 (2001): 11193-11198.
Lim, et al.: Antisense oligonucleotide modulation of non-productive alternative splicing upregulates gene expression. Nature Communication (2020).
Litchfield, D.W., et al.: Pin1: Intimate involvement with the regulatory protein kinase networks in the global phosphorylation landscape. Biochem Biophys Acta. 2015. doi: 10.1016/j.bbagen.2015.02.018. PubMed PMID: 25766872.
Liu et al.: Alternative splicing and retinal degeneration. Clinical Genetics 84(2):142-149 (2013).
Llorian et al.: Position-dependent alternative splicing activity revealed by global profiling of alternative splicing events regulated by PTB. Nature structural & molecular biology 17.9 (2010): 1114.
Lo, Yl et al.: ATM Polymorphisms and risk of lung cancer among never smokers, Lung Cancer 69(2):148-154 (2010).
Long et al.: Correction of diverse muscular dystrophy mutations in human engineered heart muscle by single-site genome editing. Sci Adv 4:eaap9004 (2018).
Lorenz, et al.: 2D meets 4G: G-Quadruplexes in RNA Secondary Structure Prediction. IEEE/ACM Trans Comput Biol Bioinform. Jul.-Aug. 2013;10(4):832-44. doi: 10.1109/TCBB.2013.7.
Lu, F.: Conditional JAG1 Mutation Shows the Developing Heart is More Sensitive Than Developing Liver to JAG1 Dosage. Am. J. Hum. Genet. vol. 72, pp. 1065-1070 (2003).
Ludecke et al.: Recessively inherited L-DOPA-responsive parkinsonism in infancy caused by a point mutation (L205P) in the tyrosine hydroxylase gene Hum. Mol. Genet. vol 5, pp. 1023-1028, (1996).
Luo et al.: Palmitic Acid Suppresses Apolipoprotein M Gene Expression via the Pathway of PPARb/d in HepG2 Cells. Biochemical and Biophysical Research Communications, 445(1):203-207 (Feb. 2014).
Magi-Galuzzi, C. et al.: TMPRSS2-ERG gene fusion prevalence and class are significantly difference in prostate cancer of Caucasian, African-American and Japanese patients. The Prostate. 2011;71:489-97.
Makishima, et al.: Mutations in the spliceosome machinery, a novel and ubiquitous pathway in leukemogenesis. Blood. Apr. 5, 2012;119(14):3203-10. doi: 10.1182/blood-2011-12-399774. Epub Feb. 9, 2012.
Maniatis et al.: An extensive network of coupling among gene expression machines. Nature 416.6880 (2002): 499.
Mansouri, S. et al.: Epstein-Barr Virus EBNA1 Protein Regulates Viral Latency through Effects on let-7 MicroRNA and Dicer. Journal of Virology, vol. 88, No. 19, pp. 11166-11177, (Oct. 2014).

Marcel, et al.: G-quadruplex structures in TP53 intron 3: role in alternative splicing and in production of p53 mRNA isoforms. Carcinogenesis. Mar. 2011;32(3):271-8. doi: 10.1093/carcin/bgq253. Epub Nov. 26, 2010.
Marquez, Y. et al.: Unmasking alternative splicing inside protein-coding exons defines exitrons and their role in proteome plasticity. Genome vol. 25, pp. 995-1007 (2015).
Matsuoka et al.: ATM and ATR substrate analysis reveals extensive protein networks responsive to DNA damage. Science 316(5828):1160-1166 (2007).
Matsuoka, S., et al.: Ataxia telangiectasia-mutated phosphorylates Chk2 in vivo and in vitro. Proc Natl Acad Sci USA. 2000;97:10389-94.
Mayeda, et al.: Surveying cis-acting sequences of pre-mRNA by adding antisense 2'-O-methyl oligoribonucleotides to a splicing reaction. J Biochem. Sep. 1990;108(3):399-405.
Mckie et al.: Mutations in the pre-mRNA splicing factor gene PRPC8 in autosomal dominant retinitis pigmentosa (RP13). Human Molecular Genetics 10(15):1555-1562 (2001).
Melhuish, et al.: The Tgif2 gene contains a retained intron within the coding sequence, BMC Molecular Biology 7(2);1-10 (2006).
Melko, et al.: Functional characterization of the AFF (AF4/FMR2) family of RNA-binding proteins: insights into the molecular pathology of FRAXE intellectual disability. Hum Mol Genet. May 15, 2011;20(10):1873-85. doi: 10.1093/hmg/ddr069. Epub Feb. 17, 2011.
Mendell, J.T.: ap Rhys CM, Dietz HC. Separable roles for rent1/hUpf1 in altered splicing and decay of nonsense transcripts. Science. 2002;298(5592):419-22. Epub Sep. 14, 2002.doi: 10.1126/science. 1074428 1074428 [pii]. PubMed PMID: 12228722.
Merendino, L., et al.: Inhibition of msl-2 splicing by Sex-lethal reveals interaction between U2AF35 and the 3' splice site AG. Nature. 1999;402(6763):838-41. PubMed PMID: 10617208.
Michael, et al.: Mfold web server for nucleic acid folding and hybridization prediction. Nucleic Acids Research. 31 (2003): 3406-3415.
Miller at al .: GeneReviews Eds. Pagon RA et al. Seattle (WA); University of WA, Seattle Bookshelf ID NBK1318 1993-2015.
Millevoi, et al.: G-quadruplexes in RNA biology. Wiley Interdiscip Rev RNA. Jul.-Aug. 2012;3(4):495-507. doi: 10.1002/wrna.1113. Epub Apr. 4, 2012.
Min et al.: Optimization of a novel series of ataxia-telangiectasia mutated kinase inhibitors as potential radiosensitizing agents. Journal of medicinal chemistry 59.2 (2016): 559-577.
Mirey, G., et al. CDC25B phosphorylated by pEg3 localizes to the centrosome and the spindle poles at mitosis. Cell Cycle. 2005;4(6):806-11. PubMed PMID: 15908796.
Mitelman, F., et al.: The impact of translocations and gene fusions on cancer causation. Nat Rev Cancer. 2007;7(4):233-45. Epub Mar. 16, 2007.
Mnatzakanian et al.: A previously unidentified MECP2 open reading frame defines a new protein isoform relevant to Rett syndrome. Nat Genet 36:339-341 (2004).
Mochizuki, T. et al.: PKD2, a gene for polycystic kidney disease that encodes an integral membrane protein. Science vol. 272, pp. 1339-1342 (1996).
Montecucco, A., et al.: Pre-mRNA processing factors meet the DNA damage response. Front Genet. 2013;4:102. doi: 10.3389/fgene.2013.00102. PubMed PMID: 23761808; PubMed Central PMCID: PMC3674313.
Moreno et al.: Delivery of splice switching oligonucleotides by amphiphilic chitosan-based nanoparticles. Molecular pharmaceutics13.2 (2016): 344-356.
Morris, et al.: An RNA G-quadruplex is essential for cap-independent translation initiation in human VEGF IRES. J Am Chem Soc. Dec. 22, 2010;132(50):17831-9. doi: 10.1021/ja106287x. Epub Nov. 24, 2010.
Morrison, A.J., et al.: Mec1/Tel1 phosphorylation of the INO80 chromatin remodeling complex influences DNA damage checkpoint responses. Cell. 2007;130(3):499-511. doi: 10.1016/j.cell.2007.06.010. PubMed PMID: 17693258.

(56) References Cited

OTHER PUBLICATIONS

Moskowitz, et al.: Mutation in Scheie syndrome (MPS IS): a G→A transition creates new splice site in intron 5 of one IDUA allele, Hum. Mutat. 2(2):141-144 (1993).
Mulley et al.: A new molecular mechanism for severe myoclonic epilepsy of infancy: Exonic deletions in SCN1A.Neurol. vol. 67, pp. 1094-1095 (2006).
Mulley et al.: SCN1A mutations and epilepsy. Hum. Muta. vol. 25, pp. 535-542 (2005).
Murray, S.F. et al.: Allele-Specific Inhibition of Rhodopsin with an Antisense Oligonucleotide Slows Photoreceptor Cell Degeneration, Invest Ophthalmol. Vis. Sci. 56:6362-6375 (Oct. 2015).
Neidle, S. and Balasubramanian, S. (2006) Quadruplex Nucleic Acids. RSC Biomolecular Sciences, Cambridge, UK.
Nemeroff et al.: Identification of cis-acting intron and exon regions in influenza virus NS1 mRNA that inhibit splicing and cause the formation of aberrantly sedimenting presplicing complexes. Molecular and cellular biology 12.3 (1992): 962-970.
Nguyen, L.A., et al.: Physical and functional link of the leukemia-associated factors AML1 and PML. Blood. 2005;105(1):292-300. doi: 10.1182/blood-2004-03-1185. PubMed PMID: 15331439.
Nishi, M. et al.: Insulin gene mutations and diabetes. Journal of Diabetes Investigation vol. 2 Issue 2 (Apr. 2011).
Nishida, A. et al.: Tissue-and Case-specific retention of intron 40 in mature dystrophin mRNA, Journal of Human Genetic 60;327-333 (2015).
Nisole, S., et al.: Differential Roles of PML Isoforms. Front Oncol. 2013;3:125. doi: 10.3389/fonc.2013.00125. PubMed PMID: 23734343; PubMed Central PMCID: PMC3660695.
Nomakuchi et al.: Antisense-oligonucleotide-directed inhibition of nonsense-mediated mRNA decay. Nat. Biotechnol. 34(2):164-166 (Feb. 2016).
Nozu et al.: Alport syndrome caused by a COL4A5 deletion and exonization of an adjacent AluY. Molecular genetics & genomic medicine 2.5 (2014): 451-453.
Nussinov. Conserved quartets near 5' intron junctions in primate nuclear pre-mRNA. J Theor Biol. Jul. 8, 1988;133(1):73-84.
Oda, T. et al.: Identification and cloning of the human homolog (JAG) of the rat Jagged1 gene from the Alagille syndrome critical region at 20p12.Genomics vol. 43, No. 3, pp. 376-379 (1997).
Okazaki, T. et al.: PD-1 and PD-1 ligands: from discovery to clinical application. International Immunology(The Japanese Society for Immunology), vol. 19, No. 7, pp. 813-824, (2007).
Oustric, V. et al.: Antisense oligonucleotide-based therapy in human erythropoietic protoporphyria. Am J Hum Genet. 2014;94(4):611-7. doi: 10.1016/j.ajhg.2014.02.010. PubMed PMID: 24680888; PubMed Central PMCID: PMC3980518.
Pacheco, et al.: Diversity of vertebrate splicing factor U2AF35: identification of alternatively spliced U2AF1 mRNAS. J Biol Chem. Jun. 25, 2004;279(26):27039-49. Epub Apr. 19, 2004.
Pacheco, et al.: RNA interference knockdown of hU2AF35 impairs cell cycle progression and modulates alternative splicing of Cdc25 transcripts. Mol Biol Cell. Oct. 2006;17(10):4187-99. Epub Jul. 19, 2006.
Page-McCaw, P.S., et al.: PUF60: a novel U2AF65-related splicing activity. RNA. 1999;5(12):1548-60. PubMed PMID: 10606266.
Palazzo et al.: Non-coding RNA: what is functional and what is junk?. Frontiers in genetics 6 (2015): 2.
Pandit et al.: Genome-wide analysis reveals SR protein cooperation and competition in regulated splicing. Molecular cell 50.2 (2013): 223-235.
Papaemmanuil, et al.: Clinical and biological implications of driver mutations in myelodysplastic syndromes. Blood. Nov. 21, 2013;122(22):3616-27; quiz 3699. doi: 10.1182/blood-2013-08-518886. Epub Sep. 12, 2013.
Passamonti, C. et al.: A novel inherited SCN1A mutation associated with different neuropsychological phenotypes: Is there a common core deficit? Epilepsy & Behavior 43:89-92 (2015).

Pastor, et al.: Interaction of hnRNPA1/A2 and DAZAP1 with an Alu-derived intronic splicing enhancer regulates ATM aberrant splicing. PLoS One. 2011;6(8):e23349. doi: 10.1371/journal.pone.0023349. Epub Aug. 8, 2011.
Pastor, F., et al.: Induction of tumour immunity by targeted inhibition of nonsense-mediated mRNA decay. Nature. 2010;465(7295):227-30. doi: 10.1038/nature08999. PubMed PMID: 20463739; PubMed Central PMCID: PMC3107067.
Paz, A., et al.: Spike: a database of highly curated human signaling pathways. Nucleic Acids Res. 2011;39(Database issue):D793-9. doi: 10.1093/nar/gkq1167. PubMed PMID: 21097778; PubMed Central PMCID: PMC3014840.
Pear, Warren S.: New roles for Notch in tuberous sclerosis, Journal of Clinical Investigation, 120(1):84-87 (Jan. 4, 2010).
Pecarelli et al.: Regulation of natural mRNAs by the nonsense-mediated mRNA decay pathway. Eukaryotic cell(2014): EC-00090.
Pellagatti, A., et al.: Deregulated gene expression pathways in myelodysplastic syndrome hematopoietic stem cells. Leukemia. 2010;24(4):756-64. doi: 10.1038/leu.2010.31. PubMed PMID: 20220779.
Peng, et al.: Functional importance of different patterns of correlation between adjacent cassette exons in human and mouse. BMC Genomics. Apr. 26, 2008;9:191. doi: 10.1186/1471-2164-9-191.
Penton, A.L.: Notch signaling in human development and disease. Seminars in Cell & Developmental Biology 23:450-457 (2012).
Perdiguero, E., et al.: Regulation of Cdc25C activity during the meiotic G2/M transition. Cell Cycle. 2004;3(6):733-7. PubMed PMID: 15136768.
Piaceri, I., et al.: Ataxia-telangiectasia mutated (ATM) genetic variant in Italian centenarians. Neurophysiology. 2013;34:573-5.
Pomentel et al.: A dynamic intron retention program enriched in RNA processing genes regulates gene expression during terminal erythropoiesis. Nucleic acids research 44.2 (2015): 838-851.
Precursor mRNA-Processing Factor 3, S. Cerevisiae, Homolog of; PRPF3m, 3 pages.
Przychodzen, B., et al.: Patterns of missplicing due to somatic U2AF1 mutations in myeloid neoplasms. Blood. 2013;122:999-1006. Epub Jun. 19, 2013.doi: blood-2013-01-480970 [pii] 10.1182/blood-2013-01-480970. PubMed PMID: 23775717.
Pugliese, et al.: The insulin gene is transcribed in the human thymus and transcription levels correlated with allelic variation at the INS VNTR-IDDM2 susceptibility locus for type 1 diabetes. Nat Genet. Mar. 1997;15(3):293-7.
Rainey et al.: Transient inhibition of ATM kinase is sufficient to enhance cellular sensitivity to ionizing radiation. Cancer research68. 18 (2008): 7466-7474.
Ramocki et al.: The MECP2 duplication syndrome. Am J Med Genet A 152A:1079-1088 (2010).
Rangasamy et al.: Reduced neuronal size and mTOR pathway activity in the Mecp2 A140V Rett syndrome mouse model. F1000research 5:2269 (2016).
Ray, D. et al.: A compendium of RNA-binding motifs for decoding gene regulation. Nature 499(7457):172-177 (2013).
Reineke, E.L., et al.: Degradation of the tumor suppressor PML by Pin1 contributes to the cancer phenotype of breast cancer MDA-MB-231 cells. Mol Cell Biol. 2008;28(3):997-1006. doi: 10.1128/MCB.01848-07. PubMed PMID: 18039859; PubMed Central PMCID: PMC2223389.
Rendu, J. et al.: Hum Gene Ther. Exon skipping as a therapeutic strategy applied to an RYR1 mutation with pseudo-exon inclusion causing a severe core myopathy. Jul. 2013;24(7):702-13. doi: 10.1089/hum.2013.052.
Reynolds, DM et al.: Aberrant Splicing in the PKD2 Gene as a Cause of Polycystic Kidney Disease. Am. Soc. Nephrol. vol. 10, pp. 2342-2351 (1999).
Ritprajak et al.: Keratinocyte-Associated B7-H1 Directly Regulates Cutaneous Effector CD8+ T Cell Responses. J Immunology vol. 184, pp. 4918-4925 (2010).
RNA 2-14 The Nineteenth Annual Meeting of the RNA Society. Quebec City, Canada. (Jun. 3-8, 2014).
Roberts, Jennifer et al.: Efficient and Persistent Splice Switching by Systemically Delivered LNA Oligonucleotides in Mice. Molecular Therapy, Nature Publishing 14(4):471-475 (2006).

(56) References Cited

OTHER PUBLICATIONS

Romero, P.R., et al.: Alternative splicing in concert with protein intrinsic disorder enables increased functional diversity in multicellular organisms. Proc Natl Acad Sci USA. 2006;103(22):8390-5. Epub May 24, 2006.doi: 0507916103 [pii] 10.1073/pnas. 0507916103. PubMed PMID: 16717195.

Rosenbloom et al.: The UCSC Genome Browser database: 2015 Update. Nucleic Acids Research 43, Database Issue doi:101093/nar/gku1177.

Ruchlemer, R. et al.: Geography, ethnicity and "roots" in chronic lymphocytic leukemia. Leuk Lymphoma. 2013;54(6):1142-50. doi: 10.3109/10428194.2012.740670. PubMed PMID: 23121522.

Rudd, M.F., et al.: Variants in the ATM-BRCA2-CHEK2 axis predispose to chronic lymphocytic leukemia. Blood. 2006;108(2):638-44. Epub Apr. 1, 2006.doi: 2005-12-5022 [pii] 10.1182/blood-2005-12-5022. PubMed PMID: 16574953.

Ruskin, et al.: A factor, U2AF, is required for U2 snRNP binding and splicing complex assembly. Cell. Jan. 29, 1988;52(2):207-19.

Sadleir, et al.: Not all SCN1A epileptic encephalopathies are Dravet syndrome. Neurology. Sep. 5, 2017; 89(10): 1-8.

Sahashi et al.: Pathological impact of SMN2 mis-splicing in adult SMA mice. EMBO Mol. Med. 5(10):1586-601 (2013).

Sahashi et al.: Tsunami: an antisense method to phenocopy splicing-associated diseases in animals. Genes Dev. 26(16):1874-1884 (Aug. 15, 2012).

Sakabe, et al.: Sequence features responsible for intron retention in human. BMC Genomics. Feb. 26, 2007;8:59.

Samatanga, et al.: The high kinetic stability of a G-quadruplex limits hnRNP F qRRM3 binding to G-tract RNA. Nucleic Acids Res. Feb. 1, 2013;41(4):2505-16. doi: 10.1093/nar/gks1289. Epub Dec. 28, 2012.

Sazani, et al.: Therapeutic potential of antisense oligonucleotides as modulators of alternative splicing. The Journal of clinical Investigation 112(4):481-486 (2003).

Schanen et al.: A Severely Affected Male Born into a Rett Syndrome Kindred Supports X-Linked Inheritance and Allows Extension of the Exclusion Map. Am J Hum Genetics 63:267-269 (1998).

Schwarze, et al.: Redefinition of exon 7 in the COL1A1 gene of type I collagen by an intron 8 splice-donor-site mutation in a form of osteogenesis imperfecta: influence of intron splice order on outcome of splice-site mutation. Am J Hum Genet. Aug. 1999;65(2):336-44.

Scott, S.P., et al.: Missense mutations but not allelic variants alter the function of ATM by dominant interference in patients with breast cancer. Proc Natl Acad Sci USA. 2002;99:925-30.

SG 11201702682P Search Report and Written Opinion dated Apr. 9, 2018.

Shao, C., et al.: Mechanisms for U2AF to define 3' splice sites and regulate alternative splicing in the human genome. Nat Struct Mol Biol. 2014;doi: 10.1038/nsmb.2906.

Shcherbakova, I., et al.: Alternative spliceosome assembly pathways revealed by single-molecule fluorescence microscopy. Cell Rep. 2013;5(1):151-65. Epub Oct. 1, 2013.doi: S2211-1247(13)00467-1 [pii] 10.1016/j.celrep.2013.08.026. PubMed PMID: 24075986.

Shen, M., et al.: Characterization and cell cycle regulation of the related human telomeric proteins Pin2 and TRF1 suggest a role in mitosis. Proc Natl Acad Sci USA. 1997;94(25):13618-23. PubMed PMID: 9391075; PubMed Central PMCID: PMC28355.

Shiloh, Y., et al.: The ATM protein kinase: regulating the cellular response to genotoxic stress, and more. Nat Rev Mol Cell Biol. 2013;14(4):197-210. doi: 10.1038/nrm3546. PubMed PMID: 23486281.

Shiria, C.L. et al.: Mutant U2AF1 Expression Alters Hematopoiesis and Pre-mRNA Splicing In Vivo. Cancer Cell. 2015;27(5):631-43. doi: 10.1016/j.ccell.2015.04.008. PubMed PMID: 25965570; PubMed Central PMCID: PMC4430854.

Shirley, M.H., et al.: Incidence of haematological malignancies by ethnic group in England, 2001-7. Br J Haematol. 2013;163(4):465-77. doi: 10.1111/bjh.12562. PubMed PMID: 24033296.

Sierakowska, H et al.: Repair of thalassemic human beta-globin mRNA in mammalian cells by antisense oligonucleotides. Proc Natl Acad Sci U S A. Nov. 12, 1996;93(23):12840-4.

Singh, et al.: An antisense microwalk reveals critical role of an intronic position linked to a unique long-distance interaction in pre-mRNA splicing. RNA. Jun. 2010;16(6):1167-81. doi: 10.1261/rna.2154310. Epub Apr. 22, 2010.

Sirand-Pugnet, et al.: An intronic (A/U)GGG repeat enhances the splicing of an alternative intron of the chicken beta-tropomyosin pre-mRNA. Nucleic Acids Res. Sep. 11, 1995;23(17):3501-7.

Skjevik et al.: The N-Terminal Sequence of Tyrosine Hydroxylase is a Conformationally Versatile Motif That Binds 14-3-3 Proteins and Membranes. J. Mol. Bio. vol. 426, pp. 150-168 (2014).

Smith, C.W., et al.: Scanning and competition between AGs are involved in 3' splice site selection in mammalian introns. Mol Cell Biol. 1993;13(8):4939-52. PubMed PMID: 8336728.

Smith, et al.: Alternative pre-mRNA splicing: the logic of combinatorial control. Trends Biochem Sci. 25(8):381-8 (2000).

Smith, et al.: Nonsense-mediated RNA decay-a switch and dial for regulating gene expression. Bioessays 37(6): 612-623 (2015).

Smith, P.J., et al.: An increased specificity score matrix for the prediction of SF2/ASF-specific exonic splicing enhancers. Hum Mol Genet. 2006;15(16):2490-508. PubMed PMID: 16825284.

Soo, R.A., et al.: Ethnic differences in survival outcome in patients with advanced stage non-small cell lung cancer. J Thorac Oncol. 2011;6:1030-8.

Sorek et al.: Minimal conditions for exonization of intronic sequences: 5' splice site formation in alu exons. Molecular cell 14.2 (2004): 221-231.

Spellman et al.: Regulation of alternative splicing by PTB and associated factors. (2005): 457-460.

Stamm, S.: Regulation of alternative splicing by reversible protein phosphorylation. J Biol Chem. 2008;283(3):1223-7. PubMed PMID: 18024427.

Stankovic, T., et al.: Inactivation of ataxia telangiectasia mutated gene in B-cell chronic lymphocytic leukaemia. Lancet. 1999;353(9146):26-9. doi: 10.1016/S0140-6736(98)10117-4. PubMed PMID: 10023947.

Staropoli et al.: Rescue of gene-expression changes in an induced mouse model of spinal muscular atrophy by an antisense oligonucleotide that promotes inclusion of SMN2 exon 7. Genomics 105:220-228 (2015).

Stead, et al.: Global haplotype diversity in the human insulin gene region. Genome Res. Sep. 2003;13(9):2101-11.

Stein et al.: FDA-Approved Oligonucleotide Therapies in 2017. Mol Ther 25:1069-1075 (2017).

Story, M.D. et al.: ATM has a major role in the double-stand break repair pathway dysregulation in sporadic breast carcinomas and is an independent prognostic marker at both mRNA and protein levels, Breast Diseases: A Yearbook Quarterly, 26(4);297-299 (Mar. 17, 2015).

Strausfeld, U., et al.: Activation of p34cdc2 protein kinase by microinjection of human cdc25C into mammalian cells. Requirement for prior phosphorylation of cdc25C by p34cdc2 on sites phosphorylated at mitosis. J Biol Chem. 1994;269(8):5989-6000. PubMed PMID: 8119945.

Suarez, F. et al.: Incidence, presentation, and prognosis of malignancies in ataxia-telangiectasia: a report from the French national registry of primary immune deficiencies. J Clin Oncol. 2015;33(2):202-8. doi: 10.1200/JCO.2014.56.5101. PubMed PMID: 25488969.

Summerton, James: Morpholino Antisense Oligos: Applications in Biopharmaceutical Research Morpholinos constitute a radical re-design of DNA, providing decisive advantages over the more conventional oligo types used for modulating gene expression. Innovations in Pharmaceutical Technology Issue No. 17 (2005).

Sun, H., et al.: Multiple splicing defects in an intronic false exon. Mol Cell Biol. 2000;20(17):6414-25. PubMed PMID: 10938119.

Supplementary European Search Report dated Apr. 18, 2019 for EP16876615.2.

Svasti, et al.: RNA repair restores hemoglobin expression in IVS2-654 thalassemic mice. Proc Natl Acad Sci U S A. Jan. 27, 2009; 106(4): 1205-1210.

(56) References Cited

OTHER PUBLICATIONS

Swaans, Rjm et al.: Four novel mutations in the Tyrosine Hydroxylase gene in patients with infantile parkinsonism Annals of Human Genetic, vol. 64, No. 1, pp. 25-31, (Jan. 2000).
Tabrez, S. et al.: A Synopsis of the Role of Tyrosine Hydroxylase in Parkinson's Disease. CNS & Neurological Disorders—Drug Targets vol. 11, No. 4 (2012).
Takahashi et al.: Skewed X chromosome inactivation failed to explain the normal phenotype of a carrier female with MECP2 mutation resulting in Rett syndrome. Clin Genet 73:257-261 (2008).
Tavanez, J.P., et al.: hnRNP A1 proofreads 3' splice site recognition by U2AF. Mol Cell. 2012;45(3):314-29. Epub Feb. 14, 2012. doi: S1097-2765(12)00032-9 [pii] 10.1016/j.molcel.2011.11.033. PubMed PMID: 22325350.
Taylor, A.M., et al.: Ataxia telangiectasia: more variation at clinical and cellular levels. Clin Genet. 2015;87(3):199-208. doi: 10.1111/cge.12453. PubMed PMID: 25040471.
Taylor, A.M., et al.: Leukemia and lymphoma in ataxia telangiectasia. Blood. 1996;87(2):423-38. PubMed PMID: 8555463.
Thisted, et al.: Optimized RNA targets of two closely related triple KH domain proteins, heterogeneous nuclear ribonucleoprotein K and alphaCP-2KL, suggest Distinct modes of RNA recognition. J Biol Chem. May 18, 2001;276(20):17484-96. Epub Feb. 2, 2001.
Tilgner et al.: Deep Sequencing of subcellular RNA factions shows splicing to be predominantly co-transcriptional in the human genome but inefficient for IncRNAs. Genome Research vol. 22, No. 9, pp. 1616-1625 (2012).
Tillotson et al.: Radically truncated MeCP2 rescues Rett syndrome-like neurological defects. Nature 550:398 (2017).
Torres, V.E. et al.: Autosomal dominant polycystic kidney disease: the last 3 years. Kidney International 76:149-168 (2009).
Trabattoni et al.: Costimulatory Pathways in Multiple Disease Sclerosis: Distinctive Expression of PD-1 and PD-L1 in Patients with Different Patterns of Disease. J. Immunol. vol. 183, pp. 4984-4993 (2009).
Trapnell, C. et al.: Differential gene and transcript expression analysis of RNA-seq experiments with Top Hat and Cufflinks. Nat Protoc. 2012;7(3):562-78. Epub Mar. 3, 2012.doi: nprot.2012.016 [pii] 10.1038/nprot.2012.016. PubMed PMID: 22383036.
U.S. Appl. No. 14/741,071 Non-Final Office Action mailed Dec. 1, 2016.
U.S. Appl. No. 14/874,420 Non-Final Office Action Mailed Mar. 21, 2017.
U.S. Appl. No. 14/874,420 Office Action dated Oct. 24, 2017 .
U.S. Appl. No. 15/619,984 Office Action dated Dec. 17, 2018.
U.S. Appl. No. 15/949,902 Office Action dated Mar. 1, 2019.
U.S. Appl. No. 15/288,415 Office Action dated Jun. 26, 2018.
Vafiadis, et al. Insulin expression in human thymus is modulated by INS VNTR alleles at the IDDM2 locus. Nat Genet. Mar. 1997;15(3):289-92.
Van Nostrand et al. Robust transcriptome-wide discovery of RNA-binding protein binding sites with enhanced CLIP (eCLIP). Nature methods 13.6 (2016): 508.
Verhaart, I.E.C.: AON-Mediated Exon Skipping for Duchenne Muscular Dystrophy. Chapter 3. pp. 1-26 (Aug. 1, 2012).
Verret et al.: Inhibitory Interneuron Deficit Links Altered Network Activity and Cognitive Dysfunction in Alzheimer Model, Cell, 149(3):708-721 (2012).
Vieira, N. et al.: Jagged 1Rescues the Duchenne Muscular Dystrophy Phenotype. Cell vol. 163, pp. 1204-1213 (2015).
Voelker, et al.: A comprehensive computational characterization of conserved mammalian intronic sequences reveals conserved motifs associated with constitutive and alternative splicing. Genome Res. Jul. 2007;17(7):1023-33. Epub May 24, 2007.
Vorechovsky: Correspondence Pediatric Research 2010.
Vorechovsky, I.: Letter to the Editor: MER91B-assisted cryptic exon activation in Gitelman syndrome. Pediatric research 67.4 (2010): 444-445.
Vorechovsky: Transposable elements in disease-associated cryptic exons. Human genetics 127.2 (2010): 135-154.
Wahl, et al.: The spliceosome: design principles of a dynamic RNP machine. Cell. Feb. 20, 2009;136(4):701-18. doi: 10.1016/j.cell.2009.02.009.
Wang, et al.: A complex network of factors with overlapping affinities represses splicing through intronic elements. Nat Struct Mol Biol. Jan. 2013;20(1):36-45. doi: 10.1038/nsmb.2459. Epub Dec. 16, 2012.
Wang et al.: Alternative isoform regulation in human tissue transcriptomes. Nature. 2008;456(Nov.):470-476.
Wang et al.: Human Adenovirus Type 36 Enhances Glucose Uptake in Diabetic and Nondiabetic Human Skeletal Muscle Cells Independent of Insulin Signaling. Diabetes vol. 57, pp. 1861-1869 (2008).
Wang, et al.: Intronic splicing enhancers, cognate splicing factors and context-dependent regulation rules. Nat Struct Mol Biol. Oct. 2012;19(10):1044-52. doi: 10.1038/nsmb.2377. Epub Sep. 16, 2012.
Wang, et al.: Regulation of insulin preRNA splicing by glucose. Proc Natl Acad Sci U S A. Apr. 29, 1997;94(9):4360-5.
Wang, Z. et al.: Systematic identification and analysis of exonic splicing silencers. Cell. 2004;119(6):831-45. PubMed PMID: 15607979.
Warf, M.B., et al.: Role of RNA structure in regulating pre-mRNA splicing. Trends Biochem Sci. 2010;35(3):169-78. Epub Dec. 5, 2009.doi: S0968-0004(09)00196-0 [pii].
Wieland, et al.: RNA quadruplex-based modulation of gene expression. Chem Biol. Jul. 2007;14(7):757-63.
Wilton, et al.: Splice modification to restore functional dystrophin synthesis in Duchenne muscular dystrophy. Current pharmaceutical design 16.8 (2010): 988-1001.
Wong et al.: Orchestrated intron retention regulates normal granulocyte differentiation. Cell 154.3 (2013): 583-595.
Wu et al.: AT-AC Pre-mRNA Splicing Mechanisms and Conservation of Minor Introns in Voltage-Gated Ion Channel Genes. Molecular and Cellular Biology 19(5): 3225-3236 (May 1999).
Wu et al.: Functional recognition of the 3' splice site AG by the splicing factor U2AF35.Nature. 1999;402(6763):832-5. PubMed PMID: 10617206.
Wu et al.: MRE11-RAD50-NBS1 and ATM function as co-mediators of TRF1 in telomere length control. Nat Struct Mol Biol. 2007;14(9):832-40. doi: 10.1038/nsmb1286. PubMed PMID: 17694070.
Wu, J.Y., et al.: Specific interactions between proteins implicated in splice site selection and regulated alternative splicing. Cell. 1993;75(6):1061-70. Epub Dec. 17, 1993.doi: 0092-8674(93)90316-1 [pii]. PubMed PMID: 8261509.
Xia, Y. et al.: Frequencies of SF3B1, NOTCH1, MYD88, BIRC3 and IGHV mutations and TP53 disruptions in Chinese with chronic lymphocytic leukemia: disparities with Europeans. Oncotarget. 2015;6(7):5426-34. PubMed PMID: 25605254.
Xing, et al.: The multiassembly problem: reconstructing multiple transcript isoforms from EST fragment mixtures. Genome Res. Mar. 2004;14(3):426-41. Epub Feb. 12, 2004.
Yamamoto, Y., et al. BCOR as a novel fusion partner of retinoic acid receptor alpha in a t(X;17)(p11;q12) variant of acute promyelocytic leukemia. Blood. 2010;116(20):4274-83. doi: 10.1182/blood-2010-01-264432. PubMed PMID: 20807888.
Yan, et al.: Systematic discovery of regulated and conserved alternative exons in the mammalian brain reveals NMD modulating chromatin regulators. Proc Natl Acad Sci U S A. Mar. 17, 2015; 112(11): 3445-3450.
Yang et al.: Biophysical analysis and small-angle X-ray scattering-derived structures of MeCP2-nucleosome complexes. Nucleic Acids Res 39:4122-4135 (2011).
Yang, S. et al.: PML-dependent apoptosis after DNA damage is regulated by the checkpoint kinase hCds1/Chk2. Nat Cell Biol. 2002;4(11):865-70. doi: 10.1038/ncb869. PubMed PMID: 12402044.
Yang, S., et al.: Promyelocytic leukemia activates Chk2 by mediating Chk2 autophosphorylation. J Biol Chem. 2006;281(36):26645-54. doi: 10.1074/jbc.M604391200. PubMed PMID: 16835227.
Yang, Y. et al.: Oligomerization of the polycystin-2 C-terminal tail and effects on its Ca2+binding properties. J. Bio. Chem. vol. 290, No. 16, pp. 10544-10554 (2015).
Yeo, et al.: Discovery and analysis of evolutionarily conserved intronic splicing regulatory elements. PLoS Genet. May 25, 2007;3(5):e85. Epub Apr. 13, 2007.

(56) References Cited

OTHER PUBLICATIONS

Yoshida, et al.: Frequent pathway mutations of splicing machinery in myelodysplasia. Nature. Sep. 11, 2011;478(7367):64-9. doi: 10.1038/nature10496.

Yoshida, K., et al.: Splicing factor mutations and cancer. Wiley Interdiscip Rev RNA. 2014;5(4):445-59. doi: 10.1002/wrna.1222. PubMed PMID: 24523246.

Young et al.: 915—a GABA-Selective AAV Vector-Based Approach to Up-Regulate Endogenous Scn1a Expression reverses key Phenotypes in a Mouse Model of Dravet Syndrome. 22nd Annual Meeting American Society of Gene & Cell Therapy. Washington, D.C. Apr. 29-May 2, 2019 (Abstract).

Yu, E.Y., et al.: Regulation of telomere structure and functions by subunits of the INO80 chromatin remodeling complex. Mol Cell Biol. 2007;27(16):5639-49. doi: 10.1128/MCB.00418-07. PubMed PMID: 17562861; PubMed Central PMCID: PMC1952117.

Yuan et al.: Brain localization and neurotoxicity evaluation of polysorbate 80-modified chitosan nanoparticles in rats. PloS one 10.8 (2015): e0134722.

Yuan X., et al.: Nuclear protein profiling of Jurkat cells during heat stress-induced apoptosis by 2-DE and MS/MS. Electrophoresis. 2007;28(12):2018-26. doi: 10.1002/elps.200600821. PubMed PMID: 17523140.

Zammarchi, et al.: Antitumorigenic potential of STAT3 alternative splicing modulation. PNAS 108(43):17779-17784 (2011).

Zamore, P.D., et al.: Identification, purification, and biochemical characterization of U2 small nuclear ribonucleoprotein auxiliary factor. Proc Natl Acad. Sci USA. 1989;86(23):9243-7. PubMed PMID: 2531895.

Zarnack K., et al.: Direct competition between hnRNP C and U2AF65 protects the transcriptome from the exonization of Alu elements. Cell. 2013;152(3):453-66. Epub Feb. 5, 2013.doi: S0092-8674(12)01545-0 [pii] 10.1016/j.cell.2012.12.023. PubMed PMID: 23374342.

Zhang C., et al.: RNA landscape of evolution for optimal exon and intron discrimination. Proc Natl Acad Sci USA. 2008;105(15):5797-802. Epub Apr. 9, 2008.doi: 0801692105 [pii] 10.1073/pnas.0801692105. PubMed PMID: 18391195.

Zhang et al.: Computational definition of sequence motifs governing constitutive exon splicing. Genes Dev. 2004; 18:1241-50. PubMed PMID: 15145827.

Zhang, et al.: Insulin as an autoantigen in NOD/human diabetes. Curr. Opin. Immunol. Feb. 2008;20(1):111-8. doi: 10.1016/j.coi.2007.11.005.

Zhang, et al.: The kinetics and folding pathways of intramolecular G-quadruplex nucleic acids. J Am Chem Soc. Nov. 21, 2012;134(46):19297-308. doi: 10.1021/ja309851t. Epub Nov. 12, 2012.

Zimrin et al.: An Antisense Oligonucleotide to the Notch Ligand Jagged Enhances Firbroblast Growth Factor-induced Angiogenesis in Vitro. J. Biol. Chem. 271(51):32499-502 (Dec. 20, 1996).

Zorio, D.A., et al.: Both subunits of U2AF recognize the 3' splice site in Caenorhabditis elegans. Nature 402(6763):835-8 (1999). PubMed PMID: 10617207.

Zuker, M.: Mfold web server for nucleic acid folding and hybridization prediction. Nucleic Acids Res. 31, 3406-3415 (2003).

\* cited by examiner

FIG. 3

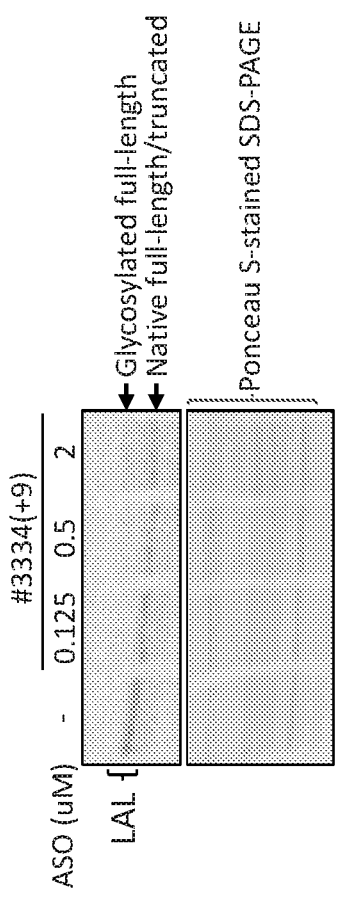
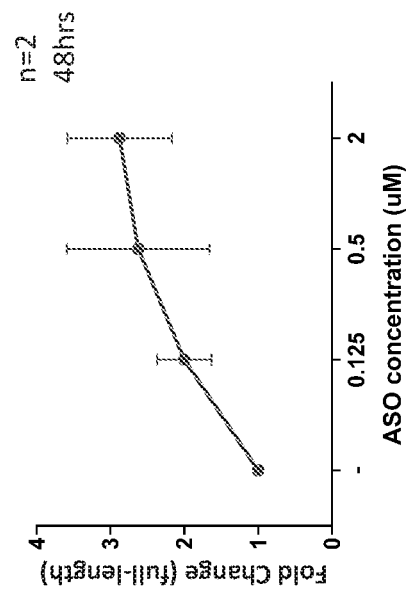

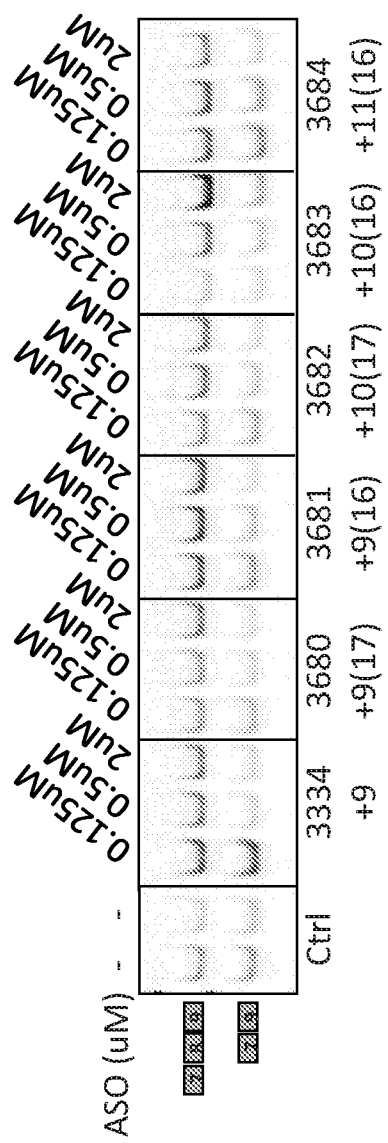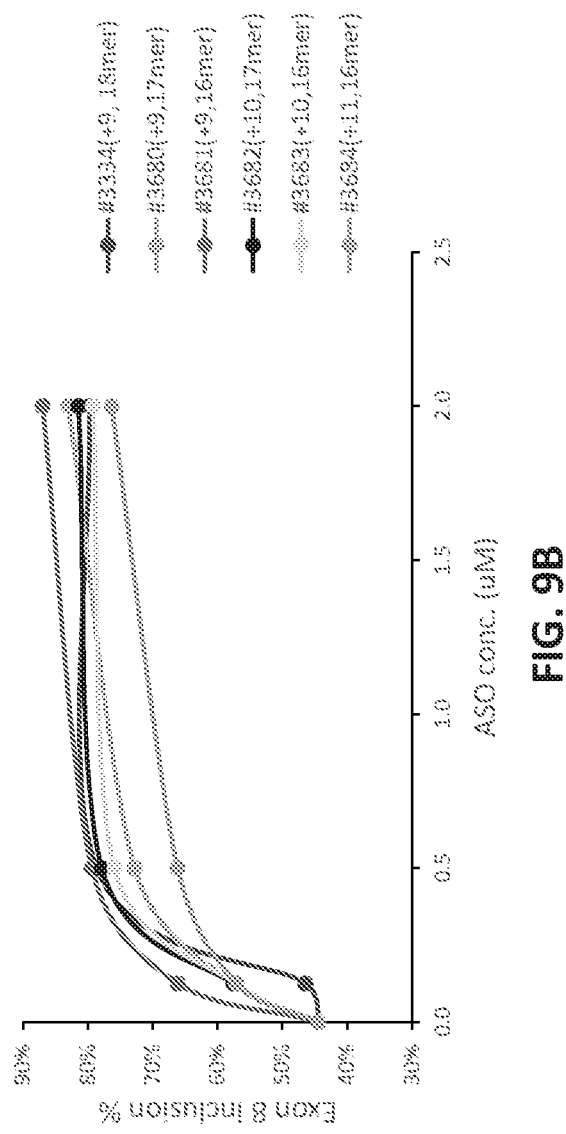
FIG. 9A
FIG. 9B

SEQUENCE LISTING

<160> NUMBER OF SEQ ID NOS: 64

<210> SEQ ID NO 1
<211> LENGTH: 38490
<212> TYPE: DNA

<213> ORGANISM: Homo sapiens

<400> SEQUENCE: 1

| | | | | | |
|---|---|---|---|---|---|
| gcgtaggcga | cgcgctggta | gagctgtgga | cctgccagcc | tgcgaggcgg | aggacgggct | 60 |
| ccatctctta | gaaacgccta | cggcgcatgc | tctatgggt | caactggggg | gctggcaagc | 120 |
| ggcagcgctg | gtctggggcg | gagtctccga | ggcacttccc | ggtggctggc | tgctctgatt | 180 |
| ggctgaacaa | atagtccgag | ggtggtgggc | atccgccctc | ccgacaaggc | agaccaggcc | 240 |
| ccctgcaggt | cccctatccg | cacccggcc | cctgagagct | ggcactgcga | ctcgagacag | 300 |
| cggcccggca | ggacagctcc | aggtgagagt | gccggcgccg | cggcgctgcc | aggtgcgggt | 360 |
| gcggcgtgga | agctggtgcc | ttcagcaagg | ggagggtcgc | gccccgaggc | tctgccggcc | 420 |
| ggcaagaccc | tctgcgtttg | gacccagcga | gtcttgcctg | gggtgcctgc | gggtgctttt | 480 |
| tctgcgggcg | ttggctcaag | gcatctgcca | atcaaccagg | gcaacttcag | agagcaactt | 540 |
| cagagagaag | cccactctct | tccctgggcg | ctgtccactt | tcctggacag | gcgcggtctc | 600 |
| cggtcagtga | agctgcccag | tgctcctgga | ccgcgaggac | agcagggatg | tctgattcct | 660 |
| ctctctgcat | cctcgtgctc | tccccttagc | tcctccaggc | atcccatcct | acctctcttg | 720 |
| ttagccaacg | gcgtggtcga | aagcagactt | gggcatcaat | cctggttaaa | gtcccagcga | 780 |
| tactgctttt | taaacagctg | acactttgct | tccagtactt | cagctgggtg | aacctcagat | 840 |
| tcctgaaaaa | tggaattaat | ggtactgcca | tagggtcggt | ggaggagtaa | ttgacagtag | 900 |
| atcagaagcg | ctgcctgcgg | tggctggcgc | ctcgcaagag | cttaaatggg | agtcgtaata | 960 |
| attgttgtta | ttagaaagtt | aaatagcatg | ctgcgttggg | gccttttctt | ctgccactga | 1020 |
| actgttggac | tgctcttatc | ttttttcaga | atctgtacta | tgcatctaat | atatacgtgg | 1080 |
| cactttgctt | ggtcctgggg | gtacaaagct | gagtcagatt | gttacaaagt | ctaaataact | 1140 |
| gagataaagg | tgttaataca | gcccagaaaa | gcacacttaa | ttcagcctgg | aaggtttttt | 1200 |
| ttccccctc | cttcgagatt | ttcagagtat | ctccttctta | gtaagaattg | cttggcttag | 1260 |
| tatgttgaga | aaaacatact | aagtatgtag | tgttgtgttg | gaaggaaaac | ttaactgggt | 1320 |
| gagattttca | gctgagtagc | tttagctgtt | actctcatgg | accttcctct | gggcggttga | 1380 |
| tacaggttct | gtaggaaaac | cgctgaatga | aagcagctcc | tgcagatgct | attctgtttt | 1440 |
| caattgtggt | aattccttta | atttttttccc | tttcaattta | ctccttattc | tctagtaata | 1500 |
| atggactttt | gggaggttgc | atttatgata | aaaaatagcc | tggggctgta | caatccttcc | 1560 |
| tatcatgaag | aagtacaaag | ttgtaagtag | aagcagtggc | cttgctttgc | caatgcacac | 1620 |
| tgaaggggat | aacgtttgct | cctgttcaga | gttcacggtc | gggcgcggtg | gctcacgcct | 1680 |
| gtaatcctag | cacttttgga | ggccgaggcc | ggcggatcac | gaggtcagga | gatcgagacc | 1740 |
| atcctggcta | acacggtgaa | accctgtttc | tactaaaaat | acaaaacaa | aattagccag | 1800 |
| gcgtggtggt | gggcgcctgt | agtcccagct | acttgggagg | ctgaggcggg | agaatggcct | 1860 |
| gaacccagga | ggtggagctt | gcagtgagcc | aagatctcgc | cactgtactc | cagcctgggg | 1920 |
| gacagagcaa | gactgtctca | aaaaaaaaaa | agaagaaaa | gaaagaaaa | agaaaaagaa | 1980 |
| aaagaaaaa | agaaagaat | tcagagttc | actacttctt | ggaaaaaaat | aatcccagga | 2040 |
| ggaattccat | caacagaagg | gagtcagttc | acttttgcaa | tctcctgaga | atcaatttct | 2100 |
| taagacttgt | ggaatattca | gtttaaacac | aaaactaaaa | acaaacagct | gtattggagt | 2160 |
| attattgaca | tacaatagca | tggcatattt | caattgtaca | attgtataag | ttttttgcatg | 2220 |
| tgtacacacc | tgtgaaacca | tcagtacatt | caatattatg | aacctgtaca | tcacctccaa | 2280 |

```
aatattattt gtgcataccc ctttgtgatc ctttcttact gccccttctc tccaggaaac   2340
cactgatctg ctttctgtga atatagatta gactgcattt tgtggagttt tatatgaatg   2400
ggatcagaca gtactttttt ttttccttat tttgatctgg cttcttttgg cataattatt   2460
ttgagattaa tctatatttt tttgtgttcc ttcccttta tagctgagta gtaggtatat    2520
accataattt atccaatcat ccatttaaag catttgggtt tttccagttt tgtctatta    2580 cacccaaagc tgttataaac atttatgtac aagtctttgt atgggcatac atgcctgcat   2640 cttttttaagt gattctattt attttttaaa aatgtagaag ttctgggatc tagtcctagg  2700 ttttctctg accacttgcg tgatcttagg agaggcattt aactttgcct tcagcatcct    2760 caaggtctttt gctgtgattt tgagtcatca ctgccagaaa ccaagatggt ctttgttgat  2820
ttgatggtta gagaatttca gaaggagaga gacgggtcaa attttccctt tctgtttctt   2880
ttgaaagctc tattttcttt catttcactt ttttcccatg aatgacaaat ttaaatgctg   2940
acgtataatt tggggcaaga acagaagtgg ttagataagt aggaggaaga gctaatagtg   3000
gttagataag taggaggaag agctaatagt ggctgaactt aaacatgtct aaatcatagg   3060
tggaaggcaa gaggtgggaa ataagcaagc tcagaaattt tgtgtctctt tcttttttctc 3120 aaactatcct cttctaagtc ttgccttttg ttatttctcc atgaccaatt tgttttaaac   3180
tttggggtta ggaggtgaat gggtatgctg gactccaaag gtcatatatc aactggaggt   3240
ggtgggtggg aggtttctta gttaaaagta attccttttgg gccgggcgcg gtggctcacg  3300
cctgtcatcc cagcactttg ggaggccgag gcgtgatcac gaggttagga gatcgagacc   3360
atcctggcta acacagtgaa accccgtctc tactaaaaaa aaaaaaatac aaaaaaattt   3420
gccgggcgtg gtggcgggcg cctgtagtcc cagctacctg ggagtctgag gcaggagaat   3480
ggcctgaacc tgggaggcgg agcttgcagt gagccaagat tgcgccactg cactccagcc   3540
tgggcgacag agcgagactc agcctcaaaa taaataaata aataaataaa taaataaata   3600
aataaataaa taaatataaa ataataataa taataattcc tttgggaggc ggaggcgggc   3660
aggtcacgaa gtcatctgag accagccttg ccaatatagt gaaaccctgt ctctactaaa   3720
aatacaaaaa ttagccgggc atggtggcct gcacctgtag tcccagctac tctggaggct   3780
gaggcaggag aaccgcttga acctgggagg cggaggttgt ggtgagccga gattgtgcca   3840
ctgcactcca gcctgggcaa cagagcgaga ctccgaaaaa aaaaaaaaat tcctgggcag   3900
gcgcggtggc tcacgcctgt aatcccagca ctttgagagg ccgaggtggg cgaatcacga   3960
agccaggagt tcgagaccag cctagccaat atggtgaaag cccatcgcta caaaaataca   4020
aaaattagcc aggcgtggtg gtgcgtgcct gttgtcccag ctacttggga ggctgaggca   4080
gaagaattgc ttgaaccagg aggcagaggt tgcagtgagc tgagattgca ccactgcact   4140
ccagcctggg tgacagagca agactccatc tcaacataaa taaataaata aataaataaa   4200
taaataaata aaataaaaat aaataaataa aatttaaaaa ttccttattc tcctttcaga   4260
tatggctgga gtcatttgtt tcatattttc ctttcacctt ttacttgccc taaatctggt   4320
tcagaacttt ttgtgggagc attaagttac cagaatattt ttgtgtagta aaattcaagc   4380
aaataataat agactgtttt attatacaga atgaaaatgc ggttcttggg gttggtggtc   4440
tgtttggttc tctggaccct gcattctgag gggtctggag ggaaactgac agctgtggat   4500
cctgaaacaa acatgaatgt ggtaagtttc tcaaagttat gtactttttaa aatgcatcta  4560 tttccccgat ccagttatgt gagctacatg aagccatacc catacattca tctctttata   4620
```

```
actcctttgc ttttcaattt ctctgaattt tttttttttt tttttttttt tttttttttg    4680
aggcagagtc ttactctgtc acctgcccgc ccaggctgga gtgcagtggt gtgatctcgg    4740
ctcattgcga cctccgcctc aggggctcaa gtgattctcg agcctcagcc tcccaagtag    4800
ctgggactac aggcatgcac caccatgcct ggctaatttt ttttgtattt agtagataca    4860
gggtttcacc atgttgccca ggtggtctt gaactcctga gctcaggtga tctgtccacc    4920
tcagcctccc aaagtcctgg gattacaggc gtgagccacc gtgccagcc caatttctct    4980 gaatcttaga ttcaatttgc taggcttttc tcaccaggta atatgtagcc aacaaacctc    5040
agtttaatgt tatatatact tcttaataag ataaattatg attttttatt aattcatttc    5100 attttaagt ctcactaagt ttgtttaaac tataaaaaag tatttaaact ttgcaagaac    5160
attaccgcta ttgagagctg gttttagaat acattgaaca aaggttgtga ttaagaatgt    5220
ccagggaaca tatttctata cagaagtcaa agtatctgag ctaaattttg ttagaaaaaa    5280
tatgcaaaaa taaccactcg actaattaaa acatctgaaa gttattaatc gtaagtaaac    5340
aataaaatct ggaaatacct catttaggca caaaatatca gtaaagtaca aattattaaa    5400 gaaacagca actttaaaat agatgttgca gtgacccagc tgaagaatca ggcaagctta    5460
gggactcgca gagaaattca cagtgagcca ggagagtatg acctgataac agggtcttaa    5520
agttaagttt tacttcttag ctcaaagctt ttcttttgcc tcccaatttt tccaactttt    5580
aaaataattt tttaaataag aatgataaaa ttaaattctt tcaagtactt atggtagaga    5640
gggtatgtgc acttatttac attaaatccc ctggataatt gaattatcca tatcccactg    5700
agctcctgat taacaattgt cccatgaatc cttccttata gaaagtgaa tgtgaccata    5760 attccctatt ttgttcaact tttcttccat cccaccttga cattctatgt aattatttta    5820
gtccattgat aaaaacaagt taatattttt tatactttat tggccagcag gggatctctc    5880
aaaacaaaga aagtgtttta tacattgaca gttctagctg ggatatttag aaaagaaaga    5940
aatgagcatt tatttgtgcc cggtaggcag gatggaaaca aagaggccca agatgtggta    6000
aagttaggca aatttggtat aaaacatgct agaatgatga aactgaagtt taaccagaca    6060
ccggtaggtg gaacacaagc gtgaaacaag ggaggattta ctcttgtgat gagaagttgg    6120
ctactagatt tagcagacta aaatttcaat gacaaatgct ttcttaaagc ctggagaaca    6180
tagtttatct gctcctttgc ttgttaatgt gggagactgt ttcagattct gtccacccaa    6240
tttccatcgt cctttttctc tacagagtga aattatctct tactggggat tccctagtga    6300
ggaataccta gttgagacag aagatggata tattctgtgc cttaaccgaa ttcctcatgg    6360
gaggaagaac cattctgaca aaggtatggg aaggctctta aaagtaaaaa ccagaattct    6420
tctgggtttt gtgttagtaa ccaagttcag atttaactta aaaacattga atgggatta    6480 ttttagacg aaagcactaa ctgtgttgag gtttgcaagg caagaaaaa taattttctt    6540 ttaaagaagt aaggacaaga gtcatctaat tttttgttca aaggccagat tcatttgagg    6600
atatgctaaa atctctgagg ctttgttttt ttaaggaagt gtatttaatg aaatgttttg    6660
agcattaaat agatggcttt tgctatttaa aaattattta atttttttga attcacataa    6720
tctaaaaatc agagaattag aagacataca gtgaaatgcc tcccttctct ctcactccct    6780
acttcctgct ttttgtgta tcttttgaa ataacttcat tttaaaatct tttatttcc    6840 aaaaatctca ttagaaacaa atacacacac agattcttat ttttcccttg cctccatttg    6900
aatgcaaaag atggcactat tttgttcttt gaattttta cttaatatct tggagatctt    6960
tccatacaat acataaagca catcttccag aagtgcatga tatttcacta tatgactgta    7020
```

```
tcattattta tttaccaagt gtcctattaa tgcatatttg tgctatttca gtcttctgtt    7080
aacaaatatt gctgctgtaa ataagctttt gtgtgtgcaa gtttatttac atgatacatg    7140
tccagaagta gaatttttgg atcacaggat atatgcattt gtgattttga tatatattgc    7200
caagctgatt ttcatgtgca tgtgtcctga taattactat cactatgaat atatgaaagt    7260
tcttgtagct ttggcttaaa aagtatatat atacatatat atgtatatct tttttctctc    7320
tctcatttta taactcaagc aaaactgcag tttccagtgc agataaagga atttctagac    7380
agactgattg aaattattaa gcagttatca gaagaaggat ctaatcttta ttcaattatc    7440
tctccagatg tagcttattt atttatttat tttttgaga cggattttcg gtcttgttgc    7500
ccaggctgga atgcaatggt gcaatcttgg ctcactgcaa cctccgcctc ccaggttcaa    7560
gtaagatgta gcttattctc taacattttt ttgtttctgg agacttttct tggggaaatt    7620
aaggtttaga ttaaggtagt tagatagcta tttattcttc aatttaagtg ttatacgggc    7680
aaaagagcca cctttgcctc aattcctgcc caaattgtta ttcaaagcaa acttaaacac    7740
cctttgtgtt aatgtgagca ttgtattatt atttgctttg ttttttctta atttatccta    7800
gtttaacttt ttcttccat gtgttctagc tgtaataaga ttttaataat gtttaggtgg    7860
ccacgacaac catttttttt gaaatttgat ttctaactct tgagattttt atgctttaca    7920
gatatatgcc attaagcttc cttttttataa atatgttata aaatgagtga tgagtttatag    7980 tgagagcttt tagttttttcc tgtgctcaaa acactcaaaa catatatttt atgctagagc    8040
gagcatatga tcttggtttc cttccttttt tttcccccaa agaataaccc ctgtatactg    8100
atttcagaca ctgtataaag aaaaatgctt tatattattt ttcttaaaat tatagttgat    8160
taattagtaa cgtgaatcac tgttaaatga tggtaagcat ctcagtaaaa cttgctgaga    8220
gctctcctcc tatatccagc ttcagacttc tctctccata cagtggttaa aacactcaga    8280
gtcacatgcc ctacctgtgt gtatcacact gttgcagggg aaggtgcagt gccctggaat    8340
atgaagaaag tgagcatgag tcttgatatg ctcccaggta atagaaagga gacttatggg    8400
accttggtgc tacacctggg tttgcccctg acttcttgtg tgctttgttt tttcttttt    8460 tttttttaacc tctgtgggat atattatata tactttattt tattttttggc aagagggttg    8520 gggattggga gagtggagag tctaggtctt tagaatgggg gaatatagac tgaaagtatt    8580
tactctaagc taaatctgtt catagcattt ggtcctcatg ttctttctct attctgagag    8640
gccctccctg tagggatca ctgatgtgta tgtcatacct gctatgagct aacctcagtg    8700
gggagtcttc aaggaagtct acagtgaaca actcagttct ctaaaggaat tgtgattttc    8760
ctaagaactg cataggcgct ttcctgatgg tttgcatttc cacattctaa aacagagcat    8820
ggacagaggc tctttactgt ccttcactcc tattcaagag caaggttgtt gccactggtg    8880
ttatttccgg tgtttaaagg caaatagata aaagaatgg agaaggcctt tcacacccaa    8940
agtgaaacgc gtcctcttct catgcatccc gcttccctcc ctgacttcct cctctattat    9000
taatagcacc agcatcctcc taatgaccta gcctggaatc tgcagaatca ttcttgacca    9060
cgggtcctct ctaggccacc cacgttaaat tgcttcagtt catcttttc ttctgtttcc    9120 ctgaccacca gcctacatta ggctcttgtt accacttaac tgggcgcctg aaataagctc    9180
agcagctgag agagtcttga gccatttcca ttttcaaggc tcctcgtata ctaacagaaa    9240
gaaagaattt caagacagga ttatggaaat tcagtttgct tatatagttt aagaaattaa    9300
tgcttttaat acacacaaaa atactgctat acattcatac tatttacaag taattacaaa    9360
```

```
atgtattaaa acattattca tttttggta ccacattcct tgtggaacct gagtctacag   9420
ctgaatggtg agcatctttc agtcctgttg ccatgggcct cttgactga ctgtgtagcc   9480 tcacttggag atcaggtttt ttatgaac acagggcttg ccacatggc ttctctgctc   9540 atgtttgctt aaaggcttta cctaactgct cttttctctg ccaggcttcc tgttctcatt   9600
catcctatgt ggttttgcag gattaagttt cttaaagctt agctataatg atgtgaaatt   9660
gccattcagc aatctttagg ggtctcagaa atgaagatac acactgttcc ttaaatattc   9720
tgtccagctg gtatttgtac cttcacctc cattctgcac agtagtagcc cttggctact   9780
cgtgcagtat gtgcatgctg ttcccacca ttaagcaacc ttcttaggaa gtgttgagca   9840
atgctttgct cctgaaggga attgaaattc agaaattaca cttcataggg aagtggctct   9900
gttttcatct gctcagcctt atttcagaaa gtcatgggga gttagcactg gagggatctc   9960
agattcctgc ctgggctagg gatttttgtt ttttttaaa cacacttcac tggtggattc  10020
caaggtagaa ttcttggttt tgcaacctg tgttctagac taacatcctc attttgttgg  10080
ataagacagc caggttcaaa tagggaaatg aatttgtctc agggcagagg gtcatgtcct  10140
gacctgtctg actacagatt cagtgatctt tgaactggag aatgtggcct tacataataa  10200
atattaacca agttgatgcc atgataggca caatatatat tttatatata tatacacaca  10260
ccaagagtgg cacatttgta tctgaaagtt atgcatctga ttgccgagtg ggtgaagtgg  10320
cactctagac tgtgaaagcc tggaatgact gccttcagca tgcagaaaca ggcttttcaa  10380
ctgtggcctc agcaaagatt ccccaggggt tgtccattga gctattagag tcatagctga  10440
aaattcacag cgtggcttgt gagttaagtc tttagaagga gaccatcagc ttgtatttg   10500 ctttgattgt ttattttaga attctggttg atttctagat ttttcttcc ttatagaaaa   10560 atccttcact tctaaagaaa ctattttttg aatcactgca gtgctctaac gggctacaca  10620
taggcgttgg taatctggga tgtaattcct caccccctggt ggtgccgaac agacatggtt  10680
tcattaatca atgcctgagc ttggtgactt gggctgagct caggctcatg tagcactctg  10740
atggcgcatt gggtagggga ttgcattcag aaccttttgcc taatggagca gcataagtga  10800
ggtcagctgt acagcttatc tcatagaccc aggttgggat cagagcagaa agccaagtgg  10860
aaaggaagat agtgctctgc cctgtcccct tccctcctct tcctcctggt taaccgctct  10920
gacctgtcct ctgttctcaa cctaattttc acatcttcag ggaggatttc ctcagcctct  10980
cacaccaggt caggcccctg gctacatatt cttatagtcc tctgtgttt tctccatcgc  11040 aattaagaca ataaacaata tattattatg taggtgatga tgtgtgtgac ctctgtcatc  11100
cccaccagac tctgcgggga tgaagacttt tctgattctc tttacttggt aaattgcttt  11160
agctccaggc tgcagtctac ccaagcatgc tcctgcagcc ctcctgtgac attgcgattt  11220
aatagtgtcc cctgctcaag ggcacactgc atgaaggatt tcctactcct gggctcctag  11280
gagtccacga acacaactta aatgcttcct gtggtgggta aaacttgaag ctgtattgcc  11340
tcatgattaa gctgagcatg tgaagagcca ccagtcatgg gtgtaagttc tggctctact  11400
atttaactgg ctgtgtgacc ttggcaattt tctttacctc ttgaagtttt gacttattca  11460
attattaaac aggaagaata atactggcta cttcgtaggc tgttgtgaaa atttgataag  11520
gcctgtgaaa tatatgcagt atagtaagtg caggtgatac aatttcttt acaacattta   11580 tttatttaaa atattaatga ataaatacat aaatattta aaagtctcac cgtgtctccc   11640
aggctagaat gcagtggtac aatcatagct tactacagct tcaaatgatc ctccctcagc  11700
ctcccaaagg gctgggataa caggcatgaa ccatggtgcc cagcctctgt ttttaatttt  11760
```

```
gaaatgtcaa catggatttg atggtggtct ctgatattga cttcttcagg attaagccct    11820
ccatgacagg gatgtattct aaactgtgtg gacaggagga agatgcattt gtttacaatg    11880
gacagaagta agaaaagtaa gaaatgtcat agaactatgt ctgggggtca ggtgacaagc    11940
actgtgtcat ttctagccct gtgtcccctg caggtgcttt cttctgtgga ccctctgctc    12000
cttctgttga gggagaattt tggatgagag ctggataatt tcccaaaatt cgctcaactg    12060
tgaagctctg gaactcaagt tgctgtgctg caaagctgtc tgaggacagg ccgtggtggc    12120 agagagggc agggaagaca ggcaatttgg catggagatg atgggcacat tgtcacatg     12180 acctgggttt gattcccagc tgcatcgtat actaattgtg tgtcctaggg caaatgattt    12240
agtctctcta agcctcagag gccccaaagg aggaagaatg atgtaaatgg cccagcacca    12300
tcctgggtgc gtggaaaact ctaattatga taatgtcctg gaacgttctg cagtgaacaa    12360
gacagaccac attactgcct tcgtgttgcc tggtgatcag agtgattatt gctggttttg    12420
gggaaaacag cattctgagg catggaacgg ttttcttccc tgctctgtga tgcagggtgc    12480
tcttgttgtg ttcactcctg caggtcacct gctccccagc agggtgacag tgaagtgtga    12540
gtgcagtgga ctgcacagtg gcaaaggcca catgactcct gaatgcatcc tgtggacagg    12600
ccaagcgctg tgccctgtgt gaatcatcag gtgaactctc atacaattct agggtgtaag    12660
aactcctatt acctcctgtt ttacagatga ggaaaccaag gtttataggg ttaattaact    12720
tgcccaagat aaagcagctg atgggtagtg aaggcaggag tcacacagcc cgtgactgtt    12780
tctgcccact tggccctctt ctcaggctag agaacagcta tgatgtccct gataaagtca    12840
cactgtggaa agtggaaagt atctgactta gatgtcctgc atctgctaga tgtcctgctt    12900
gtgcctacta cagcaactca gagagctgtt aggtgactta tctgagataa tgcgtgtaaa    12960
gtgcttaagt gcttagcatg gtgcctgtca cattgtcaac acttagtatg cgcttgctgt    13020
tactatgatt atattacctg ggccaaagaa tgccacttca ctctatcctt cttcatagtg    13080
gttatgttct aataatattt tattacattt acagttaact ctttaacaac atgggggtta    13140
ggggtgctgt cccccagagt tattgaaaac tgcatataac ttttgcattc cccaaaattt    13200
aactaatagc ctactgttga ccagagggct tacctgtaac gtacatagcc aattaacaaa    13260
tattttatat gttatatgta ttatattcca tatatacaat aagtaagcta gagaaaagaa    13320
aatgttataa ggaaatcata aggaaaatag gatgtatta ctattcatta agtggaagtg     13380
gatcatcata aaggtcttca ttcttatgtt ggaacaggct aaggaagagg aggaagagga    13440
ggagttggtc ttgctgttgt aggagtagca gaggtggaag aggggagga agtggaaggg     13500 gagacaggag aagtgggcac attcagggta actttatgaa aatacattgt aatttctgtc    13560
cttttttcat ttccctagaa atgtttctat agaatagcaa ttcttccatc atttgcttta    13620
gtttcagtgc ctgtgtcata gaagcgtcag tgttgtaaag gaagtcttga ataattgcaa    13680
ttgccaccct tctcctgaat tgtctaatat cagtttgttt tctagcactg catctcccat    13740
gtcttctttc ccatcgtctg gtgctgtttt agaagcactc gtctccatca aatcatcttc    13800
tgttaattcc tctggtgtgt ctattagctc ttgactttat ttaagatgca tatattgaaa    13860
ctatttacct gctcccaccc tccacctttt tgccatatcc acaatctttt tcttgatttc    13920
cttgattggc taagtcatgg atatggatac tgtgaagtca tgcacaacat ctggatacac    13980
ttttctccag caggaattta ttgtttcagg cttgataact ttcacagctt tttctgtaac    14040
aacaatggca tcttcagtgg tgtaattctt ccagaccttc atgatgttct ctctgttggg    14100
```

```
gttctcttcc aattcaatcc tttccatagt gtatgtgtgt aatgagcctt aaaggtcctt    14160
atgacctcct gatttagaga ctgaattaaa gatgtgtttg ggggcaagta gaccacttcg    14220
atgcctttgg tattgaattc atggggttct gggtggccag aggcattttc ctatatcaaa    14280
agaactttga aaggcagtcc cttactggca aagcacttcc tgacttcagg aaaaaagcat    14340
caatggaacc aatctggaaa aatagttctc attgtccagt ccttcttatt gtacagccaa    14400
aagactgaca gctgatgtct atattttccc tttaaggctc agggattagc agatttatag    14460
gtaagggcag acctgaccat caaccctact gcatttgcac agaacagtag agttagccta    14520
tcccttcttg ccttaaatcc tggtgcttgt ttctcttcct tactaataaa cgtcctttgt    14580
gggatatata tatatatttt tttttgttag aatggaacac tttcatctgc attaaaaacc    14640
tgttcaggca gatacatttt cctctaggaa tttatatgca gcctcttggt tggcaggagc    14700
tgcttcttct gttatcttga catatttta aagttttaa aatttttaat tcttaaaatt    14760
aattaatttt tggttttta gagacagcat cttgctctgt caccaagctg gagtacagtg    14820
gcaccattat agctcactgt aacctcaaac tccttggctc aaccagtctt ctcacctcag    14880
ccttctaagt agctaggact acagacatgt gccaaccata ctcggctaat ttttaaaaca    14940 attttgata gagatgggga tctcactgtg tttttcagac tggtttcgaa cacctggcct    15000
caagaggtcc tcccactttg gcctcccaaa atgctgggat tacaaacata agccaccgtg    15060
cctggtctat attggcattt taaaagccaa acctctttgt aaaattatca aagcatcttc    15120
tattggcatt aaattctcca actttagatt cttcaccttc tttttctctt aagttgtcat    15180
ataatgactt tgcttttctt tgaatctag agtctagaat ctattcttgc tttatcttga    15240
atattagagt ctagaatcat attagagcaa tcctgcaccc acataaaagc tgcattttca    15300
atatgagata aaaggtattt cggaaaaagt gcaaggtttt ggcacttgct gtcatagctg    15360
caatgacaaa tggcttcaca aatttctttt ccctttttt ttaacagtca tctttatgtg    15420
tcatttatct tgaaatgaag ataattgaag ctgcagacct caatctatga cacatatcaa    15480
gcaattcaac tttttcttgt ctggactttt ctctgctttt tgggagcact cccagatcac    15540
tattagttct ttgtatgggt ccaatggtgt tattcaaggt ttatgatatc gtgctaaaca    15600
tgatgaaaaa catatgagaa ctgcaagaga tcacttttta ctgcaatgtg caatttactg    15660
gagaaactgc ttacgtggag atgattagtg tcatgagaaa tttaagcaga tatttacaat    15720
acttgagcaa caggaggcgg ctacaaaatt attacagtag tacacaataa actctagtta    15780
attttatgca gttatgattt aataccacat ctttacattt gtttacattt ctcttaactg    15840
tcaatggcac catgtttggt ctgtaagtgt gtgtctaagt tttgaaaatg ttaacttttt    15900
atactttgtg tatatttatg gtaataaata aaaaaggcca atatctaaat atattttatg    15960
cattcatgac atacttaacc ttttagtaac tttttattat ttccagacta cagagttggt    16020
ctgttagttt ttctcaaatt gttgcaaatc tccaacaaat ttttcaatgt ttattgaaaa    16080
aaaatccatg tatgagtgga cctgtgcagt tcaaacctgt gttgtttaag gaccaactgt    16140
atagatttat tattgttact atcagggacc attatttatt cagctttact atgtattaac    16200
tacttcgtca ttctcacttt agaaaaggac acctatactt cagagagagt tgagcaaatc    16260
ctacaaagtt ttgtagccag taagaactga ggtctgcttc atgctaacgc cctggtgtct    16320
gaccacctcc ttgttctctg ttttggttct gccctggccc tcagctgatt tctcacatgt    16380
gttttggagt gtgacggagt cctgtccgga ctcagcatcc tggcagagaa ggccagtgcc    16440
ttgggaggca ggaggaactt ccccaccctac ccggtcatct tcctcctgcg ggactgtggg    16500
```

```
ctcagcacat tcagtttcgg agcttgagta atcgcctcct ggcttccacc cacactggga    16560
aggcagcgtt gtcgtggact gccactgggc tgcttctttg tcagctttgt cctatttagg    16620
gccataatga aatcacttgc catctccagg ctgagaaatg gtcctttagt ctttccctt     16680 aatccccagc cctcctaggg cttctttttc ttcaagttgc atttgcacag aactcccaga    16740
gccacccgta gggcatagct ggggaaggca gcccttgacc tgtcatgctg gtttgtcact    16800
ctgacaaaca gggcttcagg gtgcctgagt gcattgagca ggctgggcct tggaggagct    16860
gcctgaccag gcgaggctga gtgggtgccc ctcctttcat tccctatccc cctccatcta    16920
ctagagatta ctttcttcaa gcactttgtc cacatccttt caaaaatagc tttctgcctt    16980
cagccggaag gcctcagtgt gttctagaga cttctctctt gttaaccttc tttccctagc    17040
aaagcactga aaagcatggc ctgtggtgtc agacacacct ggttagactc caaccctcac    17100
gcttcctagc tctcgttcag ccttgggcaa gttacttgac ttctttacca caattccctg    17160
ttctgttaaa tggcagtagt gccaacttca aaggattttc agtacagtac ctacagcata    17220
caagcgtgca atcggcgcta gctatcattt caatcagctg ttctcagcaa ggtgaagtga    17280
aatctgaaat agttcactgg aagatgtgaa cagcaatagg ttttaccttc ccagagagaa    17340
acatcctttg ccagtcaatc cttaaatcct tctttggtgg tgggatggga aagaaccaca    17400
ttgtaccttc ctttcttccc cctggtggga gcaggtgaga gaagctggca acagttggct    17460
gggcctgctt ccagcgtcca gtcttttcca ttcccttttg tattcaccca atgccagagg    17520
gaaggggcaa gaggtttgga agccattttt aaaggttttt cacccgagga ttcgatacta    17580
ttttctttgc tgaggatccg tcatgcctaa tggaactgcc atctctagaa gttcagtaag    17640
ttatatcctc tgcatctccc tcctcagaag agacttttttt gttctgggat gaaaggaaac    17700
tggcccagcc tggaaagatg tgcaccccat gaagtccttc ctattccctg tgtccccagg    17760
tcagacaagg cactggactt ttcctagtgg ttccccagcc tggctgcgcg tcagaatcag    17820
gcagggaggc tttcatgtgc acactggtcc catctggcca aggcctgggt gcagtgtcag    17880
ctctttattc atctggctcc tatgtttcct ccagaaccct ttgtggaaac atctgtctct    17940
tacttagaat ccaggtcaaa tgtttgtccc actggccaag taactttctc cttcttctgg    18000
gacttcctga gtggtgttct agccttcttc ttgctgggtt agacagtcat cgtgtgtctg    18060
actccctcga ggatggagct ccctgtggga gggagtgtgg gttacccatc tttgcattcc    18120
tagcatctat tagtttgggg caaaagtaat tgtggttttt gccattgctt ttttattttg    18180 tgggggggtgg gggtaaatgg aatccctctc tgtcacccag gctagagtcc agtggtgcga    18240
tcttggctga ccacaacttc tacctcttgg gttcaaacaa ttctcctgcc tcagcctcct    18300
gagtaactgg gattacaggc acccaccacg agggtttcac catgctggcc aggctggcct    18360
caaactcttg acctcaggtg atccacccgc ctcggcctcc caaaatgctg ggattacagg    18420
cgtgagccac cgtgcccggc ctgccattgc tttttaaggg caaaaaccac aatgactttt    18480
gcaacaacct aatagcagtg gctggtactc agtaggcacc actaaaggtt tgcacgaaac    18540
gtaatgtatg ttttcaaatc acttcttgat attttacctt ctagtgcact gcttaagata    18600
cagcagattt ccattaaaaa cttttcacct gaatgtggag gacacagctg agtggcctcc    18660
attctctaaa gccatgccat ttgtcagacg tttacccttc ttcatcagcc ctttcctca    18720 tctgccagca tttcccatga gaaaacagtg tggtctgcag tacccttgc agtgcttggc    18780 ccagattctc cagatttgaa aacatttagc ttgtaaagaa tagattcact gtttccttcc    18840
```

-continued

```
catctgctgc atcttttgtg cctgttgttc attgagcttt tgtattcagc ttgaagtagg   18900
ggatggaaga accctaacaa acaaaaaagg acaattagaa aaatagtgtc tttgacttat   18960
tctctggaag cctccttcaa aggataaagt aattccctga gaaaagcgtt gtgcaggtgt   19020
gaattcggtc tgggtggaac aagggtattt accgatgttc ttagaagctg cacagccacc   19080
ttaggcgtgg tctcctgggt agcacatgct ccagctgtcc acaggccatt cctttcttca   19140
cactcacctc ccaggaaaac tgcagcagct cctcattgcc cttgggaatc caggagttat   19200
ttattgggga tgtttaaaga cttccctgat gtatcttcaa cttgtcagct tccacatttc   19260
cccattcaaa gctctagagg ttacagaggg aagtacagag actttaggga aattttaaac   19320
attctccatc gagagaaggt ggggagctga gtcctggtcc catgtgctgg ccaacatctc   19380
cccttccagc ctctgtcctg gcctggctgc cacatatcac cctccttctc ctctctcaat   19440
tatccttgcc ccagggccct ctttggtttc aaaccattcc tgcctttctc tggacactct   19500
cccctgagga gtagactagg cagtcccatg ttttccgtgt taactacaga ggcacagatt   19560
ggaacaagtg ccaaggaatt aggccaccta ccgagccttc ctcttgcctc tctctgactc   19620
tccatcctga gggaagacga ttgcagtcgt ttttgttgga aatgacctga cctgtgggag   19680
cagcccgttc ctggcctttc aaagtcaagt caccttactc atggcctagc tcctgatcac   19740
tcctggtggg tgaaaagtgc ctcaacatac ctaaagagct gtgacatgag caggaaagcc   19800
cctctttcta gaaagtgttg ggcaccatca gtacagcaga gccactgcat cgtacagcgc   19860
ccggtcacca ttctcacgta cagttaccat gagatgatga tggtgcctgt agttacacat   19920
ttttcaacta taatttaatg ataaattaat tttggtaatt ataattgtca cttacactgc   19980
agtttataat tttggatttt taatgatcaa ttttcatatt ttcccagctg gattatcatc   20040
ctcttcattg aagccaagaa gcctgtgcat aagacgctgt atctaccaca atgccttcca   20100
cttacatttt tcgtagtaaa tttagtcttg ttaatattgc attaaaatga acctttgaag   20160
gcaaagatga gcacataaag cagccctaat cttgtccagt ttgctttcta ttttctcccc   20220
atgggtagaa gttcacctgc atggccctgg catttctatt ttgtgattag aaaatcacac   20280
cagccataca tgatgtttca cttctgtaat ccccgcactt tgagaggcca aggcgagaga   20340
atcacttgag gccaggagtt tgagaccagc ctgggcaaca tagtaagacc tcatctctat   20400
gaaaagtttt ttaaaaaatt ggctggatgt tgtggtacac acctgtaatc ccagttcttc   20460
aggggcctga ggtgggagga tcacttgagt ccaggagttt gaggctgcag tgagcagtca   20520
tgccactgca ctccagtcta ggtgatagaa tgagaccttt tctctcttaa aaaaaaaaa   20580 gttatgggaa tcattttata ctcttggcct ggggtcctgc tattttaaca acacgagggt   20640
atagcacccc caggttgtac aactccaggg agtaccatgt atattttcat gtatgtgagc   20700
agtgccttcc ggagtagtct acggaagcta ccttgcagca gaactgtcat ttaaaaacaa   20760
tttgctagtt atcaaatcta tattaggaca ttagcagaaa tgaacatttg tcaattcact   20820
tatagtctta tcatctggac aaatcattct tctcattttt ccttggtatt ttacactcct   20880
ctttggtgta cattaatttt gcacagctgt aatttagagt agtctataat tttgtatttt   20940 gcttttttt cctttgcaag gtataagctt ttctatgctg tcactgtcct tgtcatggtt   21000
gatggataat tattatacca agtggatttc aatgaattat ttgaccactt gacaattagc   21060
ttatttccag ttttttcactg ttataaagaa tgagcagagg gcaaaggaag ctctcatttg   21120
ttcactgtga cccgtgtgtc agtcactata ctggatactt acctcactta ttcctcttaa   21180
caattatttt tggaactgag acgcagactg gttaagcaac ttaatagtat gagttgatat   21240
```

```
atagtgaact cttactgtgt gtcagactct ttgctaccta cttttcatat aatatctcat   21300
atctcactgt gtcctataaa atgtgtatta tcatttctac tcttcaggga attatattaa   21360
ttttaggaga tgtttcccca aggtgtcatg ttagaacttg gagaggacag agttgagcct   21420
aggtttgttt gagctgtcta aaactcatga tcgggctggg cgtggtggct cacacctgta   21480
aaccccgcac tttgggaagc cgaggtgggt ggatcgcttg agtccaggag tttgagacca   21540
gcctgggaac atggtgaaac actgtctcta caaaaacac aaaaattagc tgggtgtgtt    21600
ggtgcacgcc tgaaatccca actactcagg aggttgagat ggaaggatca cttgagccca   21660
gaaggtggag gttgctgtga gcagagatca cgccactgca ctccatcctg ggtcacagag   21720
caacatccta tctcaatcaa tcaatcaatc aaatagtgg ataaaactca tggtcagtat    21780
aatgtcagct ccatggaggt acttttttc ctcttgtttt tgttctctgc tgtgttctca    21840
gtgctgagaa gaaggcctgg cacatagttg gtactcaata aaggcttgtt tcatgaataa   21900
ctgaatggtc tcagcgttag gtaagcagct tgaggtcagg tttctttggc tcccacatct   21960
ttgttttttc tgctatatca ctgtctcggg tacaggtgag tagaaaataa attctcacag   22020
gcagacacag acacatatat ttatgaattt gtgtgtgtga gccttttat ctatttaact     22080 tttattcagc tttaaaaatt tttattaaat tttattttt aaagcagttt taagttcata    22140
gcaaaattga gtggaaggta cagagatttc ccatacaccc tctgccccca cactccctg    22200 ttatgaacat ccctcacaga gtggaattgt aattgttaca gctgatgaac ctacattcac   22260
acaaagtccg tagtttacat tagggttccc tttttttttt tttttgaga ctgagtctcc    22320 ctctgtcccc taggctggag tgcagcagtg caatcttggc tcactgcaac ctctgcctcc   22380
cgggttcaag caattctcct gcctcagctt cctgaatagc tgggattaca ggtgtggggc   22440
accacaccca gctacctttt tgtattttt agtagagaca gggtttcgcc atgttggcca    22500
ggctagtctc gaactactga cctcaagtga tccactcgcc tcagcctccc aaagtgctgg   22560
gattgcaggc atgaaccacc acaccggcc actacagttc actcttgatg ttgtatattc    22620
tatagttttg acaaatgta tgatggcatg tgtctacctc tatagtatca tgcagagtag     22680
tcttactgcc ctgaaaaatc ctctttactc tgtctatgaa ttccttcctc cctcctaacc    22740
cctggcaacc aggatctttt ttactctctc tatagttttg tcttttccag catgtcatat    22800
agaatgcagc ctttacagat cttggtaata tgtatttaag gttcctctac atctttttgt   22860
ggcttgatag ctcatttcct tttagggctg agtaatactc cattgtctgg atgtagcaca   22920
gtttagttat gcattcattt actggagcac atcttggttg cttctaaatt ttggcaatta   22980
tgagtaaaac tactatagac atctgtatgc aggttttgt gtagatgtaa gttttcaact    23040
cctttgggta aaataccaag gaatgtgatt gctggattat atggtaagag tatgtttagt   23100
tttgtaagaa actgccaaac ttttccagtg tggtgctacc agtttgcatt tccaccagca   23160
atgaatgaga gttcctgttc ctccacatcc tcttcagcag ttggtgtttt cagcgttttt   23220
ggatgttgct cattctgata cgtgtatagt gatgtctcat tatgtgtgat cttttctttt   23280
ccttttgttt attttgttag gaattattgt gagaaatgca attacgaaag caaattgtaa    23340
aaacatttta taagaaaaaa attgtaaaaa cattttataa tttcttaaaa atatattgat    23400
ttttgttttt gctgcttaca taagtgtgtc ttgttagtgg acatgcaaaa aatggtccag   23460
tttcactgct accttgccag tgctgtttta aaaaaattct ttactaacat tatatgtgag   23520
tacatcacta tgtcaatctt tcaatttatt tctagttcat tatttgctta tggatctttt   23580
```

```
acgaatgttc tatttagcaa gatatcatat ttgttttgaa gcttggtgct actgcctcct   23640
aaacaatgaa tgttttttcag gtcccaaacc agttgtcttc ctgcaacatg gcttgctggc   23700
agattctagt aactgggtca caaaccttgc caacagcagc ctgggcttca ttcttgctga   23760
tgctggtttt gacgtgtgga tgggcaacag cagaggaaat acctggtctc ggaaacataa   23820
gacactctca gtttctcagg atgaattctg ggctttcagg tatatatgaa ttgataatgg   23880
catggatgta tttccttagt actcttaaag cagacaacag gcttccagca gaagaggtag   23940
ataggtggta actctgaagt tgtatgagag gggaagttag tgtcttttga aaggttttaa   24000
atgttgctag gaatttaatg actagcagta aggtaaatta taagtaaatg attacattaa   24060
gatttacatt tagttaggaa ttcttaagtt acttcggcat ttctggtggt gtgggtgctg   24120
ctgggtaaac gttattccat aactttcctc ctttctccat aaatatgtaa tccagatgtt   24180 cactttttctt ctttccagaa attatccttt cctccctctt ccttctggct ccaccagtta   24240
attgctgtat gacattggac atcttacata agcctcctgt gtctcggttt ccttatttgt   24300
aaaatggagc gtaataaaca cctacctcat aaggtcactg ggggcttaaa ggagagggtg   24360
cagagaagga acctccacag aacctggcac cttgtatgaa ctggctaggg gttggctctt   24420
ctcctgccag tggcaacatg cgcatgcata tacccatacg cacactttggg ttttggtcta   24480 tgttttggta ccaggtatta gagaaagtca gcagcactat agcagcctcc gggcttgctt   24540 cccatttttta aaaccagagg cacctctaag gacatgaaac acaagaatga gagctttttaa  24600 caaaaggcat atacaagaat tggtttattg tcacgctatt tgtaacaacg gaaaacagga   24660
aactacccaa atgcatgtca gcagtgaatg gataaagtgt tgtatattta tagtagaaa    24720 taagaatgaa caacttacaa ttatatgcag caaaaaatgg attaagccag atacaggaga   24780
atacacattg tataattcta cttacagaaa tatttaaaaa caggcgaaac taatttctgg   24840
tgtgaaaaat gaggacaata gttacttttg ggagacacaa ctggaagaga gcccaagggg   24900
gcttctgcag tcctgctggt gttgtttcct ggactcactg ctggttttcc cagctgtgtt   24960
tagtttgtga taactcatca aactgcatac tcagtatgtg tgtgctctat tttatgtact   25020
atttcaatga aagagttcct ttcttggatt acagttatga tgagatggca aaatatgacc   25080
taccagcttc cattaacttc attctgaata aaactggcca agaacaagtg tattatgtgg   25140
gtcattctca aggcaccact ataggtatgt atgtaaataa gatcagaagt tgatataaat   25200
tcttcattac agagtttgta ctttttcttaa aagtgaaata taaaaagatg ttagttcaaa   25260
ttccatttat tttttaaatgc caaacagaaa taatgaataa gataaggaat gttggtaaca   25320
tttagtcttc tatgaaaatt catgtatatg gttgaaattg aagaaattaa tgtaagccac   25380
aatatattac atgtttttcct agatgaagca agatagggat gtgagagagt agaaaacaag   25440
tagtttctaa gttcagagac ttacataaag aaaacaagaa aatatactgc cttctgaagt   25500
taagtggaat ataactaact acaggtacat ttggtttaca aaaaattttg aaaagttata   25560
tgcattttaa tttatgctga ttatataagt aatgcatgtt cactgtagaa aaacagaaga   25620
acagaagatt tagcaaaatt aaagaaaata aaaattgccc ataattctag tcagcaagag   25680 ttttttgtaat tagggactag gaacctgtcc tataatttat ttaattctcc cttttaatgt   25740
ttactatgac taacaccttaa gtgttcccat cacatgcttt ccttacaata tattcctaga   25800
aggagcctta ctatatgaaa ggtatgaatg ttttgaaggg tctcaaaaca tgtggttata   25860
ttgccaggaa aaaaatggag ttaggcattt ttcttttattt atatttcttc tttcatgact   25920
tgcctgcttg ggacctttgc cccactgctt cctaaagtga cattctgggg ccaggtggca   25980
```

```
agacgtcaga gagggttgta ttaattcgtt ttcatgccac tactaaagac atacccgaga   26040
ctgggcaatt tataaagaaa aagaggttta atggactcac agtttaatgg attgtgagct   26100
agggaggcct tacaataatg acggaagagc aaggaacatc ttacatggtg gcagacaaga   26160
gagagtgaga gccaagtgag ggagtttccc cttataaaac catcaaatct caagagactt   26220
actcactacc acaagaacag tatggggga accgcctccg tgattcaatt atctcccacc    26280
aggtccctcc cacaacacat gggaattatg ggaactacaa ttaaagatga gatttgggtg   26340
ggaacacacc caaaccatat caagggttaa aatatatttt aaagctaggg gattctaaat   26400
gtgtgagttc ctttgaaatc attggtggtt tatttcaacg tggtgtctgt aaattgttct   26460 ttggggagg ggcatggggg agataaaggt gatgggtga ggctcttgga aatagtctgt      26520
tatttacatt gtaaaaggaa ctgggaagat tttctgattc tcccagactg gatttcttcc   26580
agtgcttatc taggttgaga tttggagcaa gcattaacaa atgcttgatt tactagttta   26640
accaaattca gtgttagggc acacggaagt tcagagtgcc ccatgtcaag tgttttggct   26700
cctgctggtg gtattgtttg cgtgggtctc aggcctccgc gagagggcgt cgcgagtgac   26760
ggcctttgtg ttttctgaga aggaaatccc agatgatgga attcctgttt tctgtccttt   26820
gttctcacag gttttatagc attttcacag atccctgagc tggctaaaag gattaaaatg   26880
ttttttgccc tgggtcctgt ggcttccgtc gccttctgta ctagccctat ggccaaatta   26940
ggacgattac cagatcatct cattaaggta cttggaccc tcccatccct ctcctctccc    27000
cgcagatttc ctcctgagat ctgaagaaat ggcaagggga gggataatct gtgccttcct   27060
cccctgcgtt ttgatatcag tggagcagtg ggcttttctt tttccgttta ccctccttc    27120 cagacccagg ggtggccggg gacgcctgtc gtttcctgca cactggtgcc acgtgtactc   27180
atggttagca tgtgtcagta cagctctgcc cacctcacag ggagagcaag gagagtctgg   27240
gagaaaataa tttaagcatt tgtggagttg cccttatcc catgaggtga gcctgtgcac    27300
agaggatgta ggagatggga gataggaaat gttcccaaaa gcccatccct agctacactg   27360
agggtgacct aacaacgcta tcattattgt attttataat atggctccta aacacagcca   27420
gtagcttcat cagggctctg ccctaaagct gtggcacccg aacctctgtt cagggaggaa   27480
atagatttca tgaaaagag ttttaagcta ggtaagacca gatgttctat tatgcatgca    27540
ttatatgtct tttatgaaat atatgttcac acacacacat atgaaatcct gtatagaaat   27600
atatacatga aatgaggtat aacgtctctc atgggccatt tagaagactt aaataggaaa   27660
gatggaatct cctaggctta ggcagtcctt ctgccttggc ctctcaaagt gctgggatta   27720
caggcatgag ctaccatgcc tggccaataa aaaaatttt aaaaaacaaa ataaaaaagc    27780
aagcgatggg ctgatttgg cctgctggcc agtagcattg aattagatgg gcacacctct    27840
ggcagacatt actgatcaat cacagccttg actgtttctt agaagtaacc accgatccat   27900
cagagtcaga tgaaaattac ttgggatgg ccctgggagg ggtgatcatt aaggccctt     27960 cccactgtag aagtccgctg aaaacttatt tgattttctg cctccttctc ttcatttgga   28020
gaatttaaat acacctctgt agtgtgtgat ttttgctttg gtaaacttgt gcaaaagcat   28080
cctgatttga tgtccactgg ttgccattct ctcctgaggc cattcgtgga gacattgggt   28140
acttgtctct gcttctgagg tgagtcacgg agacttatgc accagagtga aatgctgaga   28200
tgttcttggg tttctttta ttttgtagga cttatttgga gacaaagaat tcttccccca    28260
gagtgcgttt ttgaagtggc tgggtaccca cgtttgcact catgtcatac tgaaggagct   28320
```

```
ctgtggaaat ctctgttttc ttctgtgtgg atttaatgag agaaatttaa atatggtatg    28380
catgtttata gtaagatttg attttttttt ttatctgtga atgtgcttat ttgtgttgaa    28440
tgatatggga gaggtgggaa tgacctcatc agaactctaa agagtctttc atttgagagg    28500
cacaagcatg aactttggcc aatgcctaga atacggtacc acctgctgcc atcctcaggc    28560
tgactgtggt caccttctta tgttgtacct agatggagat tattgaatga ggagatctgt    28620
cacaaattaa gctgtaatat ttataattac tctagtgatt tgtttctttt agaaatcatt    28680
ataagtataa acataaagat gggaacaata gacagtgggg actccaaaag gaaggaggga    28740
gagggacaag ggctgaagcc tgttgagtac tatagccaat attgagtact gtggttatgg    28800
gatcaataga agcccgcatc tcagcatcat gcaatccacc cttgtaacaa acctgcacat    28860
ggaccccccg aatctaaaat acacaaattt tcaaaaatta ctataagtat ttaaatttgg    28920
aacggccatt tacatacaca taagtgtatg cttgcagtgt gtgtgtattt ataaaagtac    28980
attttataaa atgtaaaccc attttatttt ataaaatata aacccttggc caatactatg    29040
cccgtgtttc taaatatgtt tgttagtttg tcatgtggca ttttgaaaaa aagggttaaa    29100
atcctggaat aaaggcccta aggaatttca gtgccatttt tcttttgtct gataattaaa    29160
gcaaggtgtg attgttatat gaaatttggg aaattcagga aagcatgaag aacaaaatga    29220
aaatgccctg taaacgaaac ccacacagtc ccgtgcttac catgttgttg cacctccttc    29280
atatggactt tgtatgtggt tgtatgtatt tttataggc agattttag tcaataatt     29340 tttttctacc tctcatctca catacttgag attatggctc tagtttttag tgctttgaag    29400
ggcaaaatac aatgtttatt atcaatgcca ccttaatgct gttttcattc ttcatttcaa    29460
tgtatttatt ttgcagtcta gagtggatgt atatacaaca cattctcctg ctggaacttc    29520
tgtgcaaaac atgttacact ggagccaggt aggcattcca ggagtgcatt tggggttcat    29580
gtaaaatcaa catcagaaag gtctgggcat gcaaaccctt tccaaataga aagacaacct    29640
gcttacaaat ctgatctggt tttcttcccc agagtcctgg gttttgtca tcgtgcttgt     29700 gttgcttttg atacctgtgg tggggcacac tgtgttatac gtgggttcac aaacagctac    29760
tggggttgac attttctttt tccctcctct cccttcctca agtctcaggt taatatattc    29820
tctccctttc cttctccccc agctttcttt tcctcctcct gtttcctccc ctccatctgc    29880
ttctcattga gtcctagatt ttttttattt ctgtgttgct tcataaagag tgattttaag    29940
tccgttttgg agatagaaac cgctgtttca acactaaccc ctgatcacaa tatgcttgga    30000
atagcagtga ataaactgga gctaaaccaa tgatagatgt gaatgggggc ccctgacttt    30060
tgaaatacag ttttgattat tttatcatgt aaataagtca tgttcattct agaaaattta    30120
gaaactacat ctagaaaaaa attatcttaa atgaaaata aaatcattct ataaccctag    30180
acagagagga aatgcatatc catagatatt gaatgtctct gcattctatt ctatacctct    30240
tttcaaaaag atgctgttaa agacatggat agaaatagta gatgtagaaa tagattgatt    30300
tttctcctgc ttactgtttt acagcttgct tttcttttt cacctgacaa tatgtcaggg     30360
acttctttct acctcaggac ataattttgt gccatttatt tttcagctaa cttcatttt      30420 aatatgaaac aactcaccat ttaagcccta aaccaagaca ctgtaggtgt cttgaatagt    30480
aatttccaaa cacctggcag tcactgcttg catcagaatc accaaattgc tttaaaaagt    30540 acactatttta ataatcatt gcattaaaaa agtaatgaga gttggaatta tagtggaatt    30600
cttggattgg ctaccatcca ggcttataaa acaaatactc ctgtgtccca atcatttgga    30660
ctagagaatc tgtacttta ttttttcgtt ttattttatt ttttgagat ggactctcac     30720
```

```
tctgttgcca ggctggagtg tagtggtgcg atcttggctc actgcaacct ccgcctccca   30780
gcttcatgtg attctcctgc ctcagcctcc cgagtcgttt tattatttta aaaaaaaatt   30840
ttttattgag gtataagtga catagaatat ttaaagtata caatttgata tatttcagtg   30900
tttgtataca cctgtgaaac catcaccata atcgacacag caaatatatc atcatcctaa   30960
aaggtccctg ctgccccttt gtgatacctc cccccatccc tcccctcaat cccactgatc   31020
tgcttcctgt cattgtagct tagtttgcat tttctagagc ttgcatgaga acagtcatgc   31080
agtttatact tgttttttgtc tggcttcttc cactcagaat acttgttttg aaattttcct   31140
atgttgtgta tgtcagtagt tcattccttt ttatttctga ggatctgcat ttttaaaaaa   31200
tctgcctggt agattctttt gctccaccag gtttgggagc agacctgttc gggacatcct   31260
gatactttca tctccttctt cagttgcccc aggaactcta acagtgctat agttctcctt   31320
tccctggggc tcgtctctaa ggaactagga agagcctggc ctgaggctcc tggtcctttta  31380 tagtaactag aaggctgaga gttaaatgtc agttcctcag gggcagagtt tgttgtggcc   31440
taaaagaggg gcatctggaa tgcaaatagt tcatgacgtg ctgaacagca catgcttacc   31500
acttaaggaa tgccccaaa ccttcaaaaa tcctcaaatt cacaaagatt gaggattttc   31560
gttcttggtt caggtctctg cttttctcct tggtcacatt tatgcttata gtcacttgtt   31620
ttcttcatat accctgtcac tagaattccc ctacattttt gaggatgcct aggacctctt   31680
acctaatgga cattttccta aaaggcccaa tgtctgtcac ctcatcagtt attgcacccc   31740
cagagatgat ggagggtgac tgagctggct ggaggcagat cctgagcttt cccaccagct   31800
tagtgactgc cagcagccca cacacagtac acgccaggcc tcagcaaagt acaaatggcc   31860
accagacctg ggatgtcaga ggcccttggg aatgttgaaa ccaaggctgt cctaggccaa   31920
ctctatttta tattacagac ctgtgttgct tcacccttct gtgtcttggg cctccactgg   31980
gcatggggtt tgcagtagag acattggatc ggctatcatc taggctactg gtcttgttcc   32040
agccctctta tccagcagct tgccagggtc aaaggctgca gggtgagggc cagagcactg   32100
ctctgtgccc catttgtgac ctggtgactt tagattctaa ctaccctgga atatacctcc   32160
agaatatttg caaagcccag atttgctgta caaggcagcc tgggcctttg ctcttctacc   32220
cgctgtacca tcttttgtca gtaaaatggt tggttgcttt gtgcagccat tgtatcggat   32280 cttcccttttg gctttccctc ctctgggctg ttggccaggg gctgccactg gtgcaggctg   32340
caggctccaa gaggcagtgc aggaaaaggc ttctgtggaa gctgggcagg cctggatgcc   32400
gggcaggctg gggctagaat tcaggtgtgg cattagaggg ctcttatggt atgagtttgg   32460
ggttgacctt aaaggccatt tgtttacag tccattcaga agtttacttt tgtttaaat   32520 aattaggatt aacttgttaa taaattccat accttgttct ttagcgggat tttaaatata   32580
gcatactcat ctttccattc tccttataaa cctgatgaat ttcggagctc cccagagcca   32640
agacttgata ttacttctca ctttctcact ggccctgccc agagcccagg tactctcacc   32700
tgtttgaaga aggccatccc agtgtagttt tccagtgttg ttctgaccta cctaaggtgc   32760
tattaaaaat actggttctt gggcctgtct gagacctgtg gagactctga attcctaggg   32820
ctgtgaccct gggatctatg tttgagttaa gtgccttaga tgattacgat gtgctctttt   32880
tttttctttt aaaggaaaaa acatacttttt ggtaggcttt taaagaacac tgtaaaaagg   32940
atattcagta taattttttgt taaacatgta atatgtttta tgaaattttta gaaaatacat   33000 gagtgaaaga aaaatgactt gtatgtctag cacccagcaa tagccactat taatattttg   33060
```

```
gtataatctt acagttttgt aatataatca tttccattac aaaagtcaga tcatactaca    33120
tctgctttta tgtaaatttt catttaaaga aatgccatta tatttgttag atacaagtta    33180
agctgttgta ttagagaccc caaaatacag ctgctaaata aagagtttat ttctttctca    33240
taataaagtt cagagagagg tggcccagac tgatgataga gggggttttg gctgtgttcc    33300
atgaggccat gcagggaccc agttccctcc atactatagc tctgccatcc tcggggtgtt    33360
gtcctcttct gcctggttgc agcccggtca cctccatgtc tcttccaact cacaggaagg    33420
caggggagag ggagctcagg gcaagtgact ttgtgcgaag gagatagctt agaagtgagc    33480
ggtatggcca tagcctggct gctcgcagga ggatgaggat gtggtttcta tcttggcagc    33540
catgtactta gggaaagctt tagggattct gttactgaaa ggaagaaggc aagaatggga    33600
atgggtggca gtctctgcca taattaaaaa tgcctttccg ggtcagtaac taagttttta    33660
aaatatttgt cataaagggc agtttctgtt gcttgaattt tattatcatt ttgttttttg    33720
cagtgatagt tgttttgcag tcataaatca tctgtcctta tatgttagag tgttttctta    33780
ggatgataca tttatagcag tagacttagt aagggagagg gtaggcatag ctttaagact    33840
tctaatacat attgtacttt agaaaagttg aacccgttta catttttatt accattcaag    33900
acctaaatat aattttttaaa tgtcatttta aaacggttta tcctaatact ataggcattt    33960
cctcctgatc attatctaca tatactctgt gatatgatta tcacagaagt ataaccttag    34020
tgtatatttg gtttcattt tttccactta gtattattta tgagattatc tgtaagccat    34080
tttctgtttg tattttattt atatttatga cagtggcata cccccttgtgt atatttatgt    34140 aacatattta cccaaatatc tattatttga aatggtaagt tttggccaca aggtggcgcc    34200
cggtaaaaag aaatgcccag acattctctt caaaactgct tttggtttat gtgaagtctg    34260
ttcttatcaa ctgcatacaa ttctactgtt tgatgtaata aaacacagag cgagatgata    34320
tactacaagg gattgttact tattaaaatt gggctttagc ttatttccag gttttgtta    34380 ctggaaatca tcttaatact tttctttga aatatccttt caagtggata gcttgaagtc    34440
ctaagtgact tagcacaaag tcaaatttag aacttcagtc tgagctatag gcaagtttca    34500
cctttgtatt ctgtgctcac gctggtgctt catatgaatg ctgaaggaca tgtgacaaag    34560
tgatgaactg ctgtctgtgt tcagtggcag aatagtttgc atcaatatat tttcactgac    34620
aaagatgggg aacagatgta ccaacaggtg ctgtgaatcc aaattttgtt ttgcttgtta    34680
aatatgccac aggtatttaa tatcagtcat ttgcaacggc aaaaacagat gccaaatatt    34740
tctcctgtaa caatcccta tagtatatca tctcactctg tcttttatta catcaaacag    34800
tagaattgta tgcagttgat tagaacagac ttcacataaa tcaaaagcag ttttgacaaa    34860
gaatgtctga gcatttctt ttaccaggcg ccaccttgtg gccaaaactt accatttcaa    34920
attcatttgg cttgccaatt ttgtgtttaa tttttgacat acatttaatt tgagagtgta    34980 gaggaaaatat ggatttgcac tattttgaat tttaaaaata agtgacattt tgctaatatt    35040
ttatattata ctattttaaa tatgaataaa tgtaaattc aatacaattt caatttcatg    35100
gctctagtat ccctaactag ttagaattgt gctggcatgc agtactactt ggtgattata    35160
ctgataccag tactcaagaa aaagtgttta atcaatacca tcattaaaat ttgactaata    35220
taactagaca agtagaatgg gtaaatagaa aatatacagt catccctcaa gtatctttgg    35280
ggactggctg cagacatcat ccccaaacca aaattcacag atactcaagt cccttatata    35340
aaatgatgta gtatttgcat atagcctatg catatccttt catatgcttt aaatcatctc    35400
tagattactt atgatgctta atacaatgta aacgctatgt aagtaggtgt tacactgttt    35460
```

```
taaaatttgt attttttatt gttttattat cttttattgt tttttttccaa atattttcca    35520 tctgcaaaat atcacttggc tgaatccaca gatacaaaac tggatatgga gggccaattg    35580
tatattataa ttattttatc tatatatatc catctctctc tctctctctc tattatatat    35640
atatatatgt atatatatat gtagctacct atctgtctac ctttatttcc caagtaaaat    35700
gactaactct ttgaaaaagc ttaggatgca aatttcagca gaaaatgtca gcataaagtt    35760
ccgctagcag gagcaactgt tgatctagta taattgacag catatgtgca tagctgcttt    35820
cttgtgtcag gtggtagctg cttaacaatc atacaatgag aaattgagtc attcagtaaa    35880
gcaggacaaa accatgccat ctcatttaaa ataatgcctt ggaaatgaag agtaaatctg    35940
gatattggta taaagttgat ttccgaggtt gtggctagct ccagcaacct atgatgttat    36000
ctctaacttt ggtgtcagat aactcttttc caaattatct tctttttagg ctgttaaatt    36060
ccaaaagttt caagcctttg actggggaag cagtgccaag aattattttc attacaacca    36120
ggtaaagttt ttagtctttt cattaaaggg ggccctgaaa actcatcaag aaagccagcc    36180
tggcctatca ggattctggc caggctcagg tgctgtggga aatgtttgca ggagttgact    36240
agtgtttgtt ttccatcagt ccattcagaa caatccaagc tttgtagctg gtgttgtgga    36300
ctgggcctcc tctctttgtc cttttcccag ctctaaataa gaatcatcac tgttatgcat    36360
tactcagagt aatcacgaac atagcctgta gagtcagaca gtcctatgtc tgttatctgg    36420
tagctatggg gccttggcca gattacattg cttaagcctc ttccctgcac taataaaatt    36480
agcatttttg agcatgctaa atgcactgaa gtgtgaggca ctttgctctg tttttttaaat   36540 ttaattccca gagcatctct gtgatgtaaa cgtgattatc tctgacttaa acatgaggac   36600
agtgaggctt agagaatttc tgtgacttgt cttcacccca aagggaagaa gtaggagggc    36660 atgacccccaa actctttcca gccactattg ccttgagtgt actacctatg gagtacaaca   36720
ccttccttgc cggggattaa acattcattt tggtgcccag cctacggcag cagctccaca   36780
gctagtggcg attataatta gcattctctc atttggggtt agatttcttt ttttgtgccg    36840
gtaatggcaa cttgaaaaga tactcaaaga gattttaaaa atttagtctg ttagtcaaac   36900
ttactagaca atgtttaatg gagattgcgc ttattgtgat tttgaaaatt aaaacaacaa   36960
caacaacgag gctttctctg gttccttttc attgtagagt tatcctccca catacaatgt    37020
gaaggacatg cttgtgccga ctgcagtctg gagcgggggt cacgactggc ttgcagatgt   37080
ctacgacgtc aatatcttac tgactcagat caccaacttg gtgttccatg agagcattcc    37140
ggaatgggag catcttgact tcatttgggg cctggatgcc ccttggaggc tttataataa    37200
aattattaat ctaatgagga aatatcagtg aaagctggac ttgagctgtg taccaccaag   37260
tcaatgatta tgtcatgtga aaatgtgttt gcttcatttc tgtaaaacac ttgttttttct    37320 ttcccaggtc ttttgttttt ttatatccaa gaaaatgata actttgaaga tgcccagttc    37380
actctagttt caattagaaa catactagct attttttctt taattagggc tggaatagga    37440
agccagtgtc tcaaccatag tattgtctct ttaagtcttt taaatatcac tgatgtgtaa    37500
aaaggtcatt atatccattc tgttttttaaa atttaaaata tattgacttt ttgcccttca    37560
taggacaaag taatatatgt gttggaattt taaaattgtg ttgtcattgg taaatctgtc    37620
actgacttaa gcgaggtata aaagtacgca gttttcatgt ccttgcctta aagagctctc    37680
tagtctaacg gtcttgtagt tagagatcta aatgacattt tatcatgttt tcctgcagca    37740
ggtgcatagt caaatccaga aatatcacag ctgtgccagt aataaggatg ctaacaatta    37800
```

| | |
|---|---|
| attttatcaa acctaactgt gacagctgtg atttgacacg ttttaattgc tcaggttaaa | 37860 |
| tgaaatagtt ttccggcgtc ttcaaaaaca aattgcactg ataaaacaaa acaaaagta | 37920 |
| tgttttaaat gctttgaaga ctgatacact caaccatcta tattcatgag ctctcaattt | 37980 |
| catggcaggc catagttcta cttatctgag aagcaaatcc ctgtggagac tataccacta | 38040 |
| tttttctga gattaatgta ctcttggagc ccgctactgt cgttattgat cacatctgtg | 38100 |
| tgaagccaaa gccccgtggt tgcccatgag aagtgtcctt gttcattttc acccaaatga | 38160 |
| agtgtgaacg tgatgttttc ggatgcaaac tcagctcagg gattcatttt gtgtcttagt | 38220 |
| tttatatgca tccttatttt taatacacct gcttcacgtc cctatgttgg gaagtccata | 38280 |
| tttgtctgct tttcttgcag catcatttcc ttacaatact gtccggtgga caaaatgaca | 38340 |
| attgatatgt ttttctgata taattacttt agctgcacta acagtacaat gcttgttaat | 38400 |
| ggttaatata ggcagggcga atactacttt gtaacttttta aagtcttaaa cttttcaata | 38460 |
| aaattgagtg agacttatag gcccaaagaa | 38490 |

<210> SEQ ID NO 2
<211> LENGTH: 6501
<212> TYPE: DNA
<213> ORGANISM: Homo sapiens

<400> SEQUENCE: 2

| | |
|---|---|
| gtaggcattc caggagtgca tttggggttc atgtaaaatc aacatcagaa aggtctgggc | 60 |
| atgcaaaccc tttccaaata gaaagacaac ctgcttacaa atctgatctg gttttcttcc | 120 |
| ccagagtcct gggttttttgt catcgtgctt gtgttgcttt tgatacctgt ggtggggcac | 180 |
| actgtgttat acgtgggttc acaaacagct actggggttg acatttttct tttccctcct | 240 |
| ctcccttcct caagtctcag gttaatatat tctctccctt tccttctccc ccagcttttct | 300 |
| tttcctcctc ctgtttcctc ccctccatct gcttctcatt gagtcctaga ttttttttat | 360 |
| ttctgtgttg cttcataaag agtgatttta agtccgtttt ggagatagaa accgctgttt | 420 |
| caacactaac ccctgatcac aatatgcttg gaatagcagt gaataaactg gagctaaacc | 480 |
| aatgatagat gtgaatgggg gcccctgact tttgaaatac agttttgatt attttatcat | 540 |
| gtaaataagt catgttcatt ctagaaaatt tagaaactac atctagaaaa aaattatctt | 600 |
| aaaatgaaaa taaatcatt ctataaccct agacagagag gaaatgcata tccatagata | 660 |
| ttgaatgtct ctgcattcta ttctatacct cttttcaaaa agatgctgtt aaagacatgg | 720 |
| atagaaatag tagatgtaga aatagattga ttttttctcct gcttactgtt ttacagcttg | 780 |
| cttttctttt ttcacctgac aatatgtcag ggacttcttt ctacctcagg acataatttt | 840 |
| gtgccattta ttttttcagct aacttcattt ttaatatgaa acaactcacc atttaagccc | 900 |
| taaaccaaga cactgtaggt gtcttgaata gtaatttcca aacacctggc agtcactgct | 960 |
| tgcatcagaa tcaccaaatt gctttaaaaa gtacactatt taataaatca ttgcattaaa | 1020 |
| aaagtaatga gagttggaat tatagtggaa ttcttggatt ggctaccatc caggcttata | 1080 |
| aaacaaatac tcctgtgtcc caatcatttg gactagagaa tctgtacttt tattttttcg | 1140 |
| ttttatttta ttttttttgag atggactctc actctgttgc caggctggag tgtagtggtg | 1200 |
| cgatcttggc tcactgcaac ctccgcctcc cagcttcatg tgattctcct gcctcagcct | 1260 |
| cccgagtcgt tttattattt taaaaaaaaa ttttttattg aggtataagt gacatagaat | 1320 |
| atttaaagta tacaatttga tatatttcag tgtttgtata cacctgtgaa accatcacca | 1380 |
| taatcgacac agcaaatata tcatcatcct aaaaggtccc tgctgccccct tgtgatacc | 1440 |

```
tcccccatc cctccctca atcccactga tctgcttcct gtcattgtag cttagtttgc    1500
attttctaga gcttgcatga gaacagtcat gcagtttata cttgtttttg tctggcttct    1560
tccactcaga atacttgttt tgaaattttc ctatgttgtg tatgtcagta gttcattcct    1620
ttttatttct gaggatctgc attttaaaa aatctgcctg gtagattctt ttgctccacc    1680
aggtttggga gcagacctgt tcgggacatc ctgatacttt catctccttc ttcagttgcc    1740
ccaggaactc taacagtgct atagttctcc tttccctggg gctcgtctct aaggaactag    1800
gaagagcctg gcctgaggct cctggtcctt tatagtaact agaaggctga gagttaaatg    1860
tcagttcctc aggggcagag tttgttgtgg cctaaaagag gggcatctgg aatgcaaata    1920
gttcatgacg tgctgaacag cacatgctta ccacttaagg aatgccccca aaccttcaaa    1980
aatcctcaaa ttcacaaaga ttgaggattt tcgttcttgg ttcaggtctc tgcttttctc    2040
cttggtcaca tttatgctta tagtcacttg ttttcttcat atacccgtgtc actagaattc    2100 ccctacattt tgaggatgc ctaggacctc ttacctaatg gacattttcc taaaaggccc    2160
aatgtctgtc acctcatcag ttattgcacc cccagagatg atggagggtg actgagctgg    2220
ctggaggcag atcctgagct ttcccaccag cttagtgact gccagcagcc cacacacagt    2280
acacgccagg cctcagcaaa gtacaaatgg ccaccagacc tgggatgtca gaggcccttg    2340
ggaatgttga aaccaaggct gtcctaggcc aactctattt tatattacag acctgtgttg    2400 cttcacccctt ctgtgtcttg ggcctccact gggcatgggg tttgcagtag agacattgga    2460
tcggctatca tctaggctac tggtcttgtt ccagccctct tatccagcag cttgccaggg    2520
tcaaaggctg cagggtgagg gccagagcac tgctctgtgc cccatttgtg acctggtgac    2580
tttagattct aactaccctg gaatatacct ccagaatatt tgcaaagccc agatttgctg    2640
tacaaggcag cctgggcctt tgctcttcta cccgctgtac catcttttgt cagtaaaatg    2700
gttggttgct ttgtgcagcc attgtatcgg atcttccctt tggctttccc tcctctgggc    2760
tgttggccag gggctgccac tggtgcaggc tgcaggctcc aagaggcagt gcaggaaaag    2820
gcttctgtgg aagctgggca ggcctggatg ccgggcaggc tggggctaga attcaggtgt    2880
ggcattagag ggctcttatg gtatgagttt ggggttgacc ttaaaggcca ttttgtttac    2940
agtccattca gaagtttact ttttgtttaa ataattagga ttaacttgtt aataaattcc    3000
ataccttgtt ctttagcggg atttttaaata tagcatactc atcttttccat tctccttata    3060 aacctgatga atttcggagc tccccagagc caagacttga tattacttct cactttctca    3120
ctggccctgc ccagagccca ggtactctca cctgtttgaa gaaggccatc ccagtgtagt    3180
tttccagtgt tgttctgacc tacctaaggt gctattaaaa atactggttc ttgggcctgt    3240
ctgagacctg tggagactct gaattcctag ggctgtgacc ctgggatcta tgtttgagtt    3300
aagtgcctta gatgattacg atgtgctctt tttttttct ttaaaggaaa aaacatactt    3360
ttggtaggct tttaaagaac actgtaaaaa ggatattcag tataattttt gttaaacatg    3420
taatatgttt tatgaaattt tagaaaatac atgagtgaaa gaaaaatgac ttgtatgtct    3480
agcacccagc aatagccact attaatattt tggtataatc ttacagtttt gtaatataat    3540
catttccatt acaaaagtca gatcatacta catctgcttt tatgtaaatt tcatttaaa    3600 gaaatgccat tatatttgtt agatacaagt taagctgttg tattagagac cccaaaatac    3660
agctgctaaa taaagagttt attttctttct cataataaag ttcagagaga ggtggcccag    3720
actgatgata gaggggtttt tggctgtgtt ccatgaggcc atgcagggac ccagttccct    3780
```

```
ccatactata gctctgccat cctcggggtg ttgtcctctt ctgcctggtt gcagcccggt    3840
cacctccatg tctcttccaa ctcacaggaa ggcaggggag agggagctca gggcaagtga    3900 cttttgtgcga aggagatagc ttagaagtga gcggtatggc catagcctgg ctgctcgcag   3960
gaggatgagg atgtggtttc tatcttggca gccatgtact tagggaaagc tttagggatt    4020
ctgttactga aaggaagaag gcaagaatgg gaatgggtgg cagtctctgc cataattaaa    4080
aatgcctttc cgggtcagta actaaagttt taaaatattt gtcataaagg gcagtttctg    4140
ttgcttgaat tttattatca ttttgttttt tgcagtgata gttgttttgc agtcataaat    4200
catctgtcct tatatgttag agtgttttct taggatgata catttatagc agtagactta    4260
gtaagggaga gggtaggcat agcttttaaga cttctaatac atattgtact ttagaaaagt   4320
tgaacccgtt tacatttta ttaccattca agacctaaat ataattttta aatgtcattt     4380
taaaacggtt tatcctaata ctataggcat ttcctcctga tcattatcta catatactct    4440
gtgatatgat tatcacagaa gtataacctt agtgtatatt tggtttcatt ttttccact    4500 tagtattatt tatgagatta tctgtaagcc attttctgtt tgtattttat ttatatttat    4560
gacagtggca taccccttgt gtatatttat gtaacatatt tacccaaata tctattattt    4620
gaaatggtaa gttttggcca caaggtggcg cccggtaaaa agaaatgccc agacattctc    4680
ttcaaaactg cttttggttt atgtgaagtc tgttcttatc aactgcatac aattctactg    4740
tttgatgtaa taaaacacag agcgagatga tatactacaa gggattgtta cttattaaaa   4800
ttgggcttta gcttatttcc aggttttgt tactggaaat catcttaata cttttctttt     4860
gaaatatcct ttcaagtgga tagcttgaag tcctaagtga cttagcacaa agtcaaattt    4920
agaacttcag tctgagctat aggcaagttt cacctttgta ttctgtgctc acgctggtgc    4980
ttcatatgaa tgctgaagga catgtgacaa agtgatgaac tgctgtctgt gttcagtggc    5040
agaatagttt gcatcaatat attttcactg acaaagatgg ggaacagatg taccaacagg    5100
tgctgtgaat ccaaattttg ttttgcttgt taaatatgcc acaggtattt aatatcagtc    5160
atttgcaacg gcaaaaacag atgccaaata tttctcctgt aacaatcccc tatagtatat    5220
catctcactc tgtctttat tacatcaaac agtagaattg tatgcagttg attagaacag     5280
acttcacata aatcaaaagc agttttgaca aagaatgtct gagcatttct ttttaccagg    5340
cgccaccttg tggccaaaac ttaccatttc aaattcattt ggcttgccaa ttttgtgttt    5400 aattttttgac atacatttaa tttgagagtg tagaggaaat atggatttgc actattttga   5460
attttaaaaa taagtgacat tttgctaata ttttatatta tactatttta aatatgaata    5520
aatgtaaatt tcaatacaat ttcaatttca tggctctagt atccctaact agttagaatt    5580
gtgctggcat gcagtactac ttggtgatta tactgatacc agtactcaag aaaaagtgtt    5640
taatcaatac catcattaaa atttgactaa tataactaga caagtagaat gggtaaatag    5700
aaaatataca gtcatccctc aagtatcttt ggggactggc tgcagacatc atccccaaac    5760
caaaattcac agatactcaa gtcccttata taaaatgatg tagtatttgc atatagccta    5820
tgcatatcct ttcatatgct ttaaatcatc tctagattac ttatgatgct taatacaatg    5880
taaacgctat gtaagtaggt gttacactgt tttaaaattt gtattttta ttgtttttatt    5940 atctttatt gttttttcc aaatattttc catctgcaaa atatcacttg gctgaatcca      6000
cagatacaaa actggatatg gagggccaat tgtatattat aattattta tctatatata    6060 tccatctctc tctctctctc tctattatat atatatatat gtatatatat atgtagctac    6120
ctatctgtct acctttatt cccaagtaaa atgactaact cttttgaaaaa gcttaggatg    6180
```

```
caaatttcag cagaaaatgt cagcataaag ttccgctagc aggagcaact gttgatctag    6240
tataattgac agcatatgtg catagctgct ttcttgtgtc aggtggtagc tgcttaacaa    6300
tcatacaatg agaaattgag tcattcagta aagcaggaca aaaccatgcc atctcattta    6360
aaataatgcc ttggaaatga agagtaaatc tggatattgg tataaagttg atttccgagg    6420
ttgtggctag ctccagcaac ctatgatgtt atctctaact ttggtgtcag ataactcttt    6480
tccaaattat cttcttttta g                                              6501
```

<210> SEQ ID NO 3
<211> LENGTH: 1101
<212> TYPE: DNA
<213> ORGANISM: Homo sapiens

<400> SEQUENCE: 3

```
gtatgcatgt ttatagtaag atttgatttt ttttttatc tgtgaatgtg cttatttgtg     60
ttgaatgata tgggagaggt gggaatgacc tcatcagaac tctaaagagt ctttcatttg    120
agaggcacaa gcatgaactt tggccaatgc ctagaatacg gtaccacctg ctgccatcct    180
caggctgact gtggtcacct tcttatgttg tacctagatg gagattattg aatgaggaga    240
tctgtcacaa attaagctgt aatatttata attactctag tgatttgttt cttttagaaa    300
tcattataag tataaacata aagatgggaa caatagacag tggggactcc aaaaggaagg    360
agggagaggg acaagggctg aagcctgttg agtactatag ccaatattga gtactgtggt    420
tatgggatca atagaagccc gcatctcagc atcatgcaat ccaccccttgt aacaaacctg    480 cacatggacc ccccgaatct aaaatacaca aattttcaaa aattactata agtatttaaa    540 tttgaacgg ccatttacat acacataagt gtatgcttgc agtgtgtgtg tatttataaa     600
agtacatttt ataaaatgta aacccatttt attttataaa atataaaccc ttggccaata    660
ctatgcccgt gtttctaaat atgtttgtta gtttgtcatg tggcattttg aaaaaaaggg    720
ttaaaatcct ggaataaagg ccctaaggaa tttcagtgcc attttctttt tgtctgataa    780
ttaaagcaag gtgtgattgt tatatgaaat tgggaaatt caggaaagca tgaagaacaa     840
aatgaaaatg ccctgtaaac gaaacccaca cagtcccgtg cttaccatgt tgttgcacct    900
ccttcatatg gactttgtat gtggttgtat gtattttat agggcagatt tttagtcaaa    960
taattttttt ctacctctca tctcacatac ttgagattat ggctctagtt tttagtgctt   1020
tgaagggcaa aatacaatgt ttattatcaa tgccacctta atgctgtttt cattcttcat   1080
ttcaatgtat ttattttgca g                                              1101
```

<210> SEQ ID NO 4
<211> LENGTH: 72
<212> TYPE: DNA
<213> ORGANISM: Homo sapiens

<400> SEQUENCE: 4

```
tctagagtgg atgtatatac aacacattct cctgctggaa cttctgtgca aaacatgtta     60
cactggagcc ag                                                         72
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
aaatgcactc ctggaatg                                               18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caaatgcact cctggaat                                               18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccaaatgcac tcctggaa                                               18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cccaaatgca ctcctgga                                               18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccccaaatgc actcctgg                                               18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
accccaaatg cactcctg                                               18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 11
catgaacccc aaatgcac                                                        18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttttacatga accccaaa                                                        18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gttgatttta catgaacc                                                        18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctgatgttga ttttacat                                                        18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cctttctgat gttgattt                                                        18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccagaccttt ctgatgtt                                                        18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
```
catgcccaga cctttctg                                                 18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtttgcatgc ccagacct                                                 18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaagggtttg catgccca                                                 18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tttggaaagg gtttgcat                                                 18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atttggaaag ggtttgca                                                 18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tatttggaaa gggtttgc                                                 18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ctatttggaa agggtttg                                              18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tctatttgga aagggttt                                              18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttctatttgg aaagggtt                                              18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tttctatttg gaaagggt                                              18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctttctattt ggaaaggg                                              18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tctttctatt tggaaagg                                              18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gtctttctat ttggaaag                                              18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tgtctttcta tttggaaa                                                18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
caggttgtct ttctattt                                                18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtaagcaggt tgtctttc                                                18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gatttgtaag caggttgt                                                18

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccaaatgcac tcctgga                                                 17

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
caaatgcact cctgga                                                  16

```
<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cccaaatgca ctcctgg                                                       17

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ccaaatgcac tcctgg                                                        16

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cccaaatgca ctcctg                                                        16

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
actaaaaact agagccat                                                      18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aaagcactaa aaactaga                                                      18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ccttcaaagc actaaaaa                                                      18
```

```
<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tttgcccttc aaagcact                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tgtattttgc ccttcaaa                                                 18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aacattgtat tttgccct                                                 18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
taataaacat tgtatttt                                                 18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
attgataata aacattgt                                                 18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gtggcattga taataaac                                                 18

<210> SEQ ID NO 48
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttaaggtggc attgataa                                                       18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cagcattaag gtggcatt                                                       18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gaaaacagca ttaaggtg                                                       18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agaatgaaaa cagcatta                                                       18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aatgaagaat gaaaacag                                                       18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
attgaaatga agaatgaa                                                       18

<210> SEQ ID NO 54
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tatatacatc cactctag                                                 18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tgttgtatat acatccac                                                 18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gaatgtgttg tatataca                                                 18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
caggagaatg tgttgtat                                                 18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tccagcagga gaatgtgt                                                 18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gcacagaagt tccagcag                                                 18

<210> SEQ ID NO 60
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 60
gttttgcaca gaagttcc                                                    18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
aacatgtttt gcacagaa                                                    18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
agtgtaacat gttttgca                                                    18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gctccagtgt aacatgtt                                                    18

<210> SEQ ID NO 64
<211> LENGTH: 112
<212> TYPE: DNA
<213> ORGANISM: Homo sapiens

<400> SEQUENCE: 64
ggagccaggt aggcattcca ggagtgcatt tggggttcat gtaaaatcaa catcagaaag      60
gtctgggcat gcaaaccctt tccaaataga aagacaacct gcttacaaat ct             112
```

METHODS AND COMPOSITIONS FOR TREATMENT OF CHOLESTERYL ESTER STORAGE DISEASE

CROSS-REFERENCE

This application is a national phase entry of International Application No. PCT/US2019/030605, filed May 3, 2019, which claims the benefit of U.S. Provisional Application No. 62/667,205, filed May 4, 2018, which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 7, 2019, is named 47991-720_601_SL.txt and is 74.883 bytes in size.

BACKGROUND

Cholesteryl ester storage disease (CESD) (also sometimes referred to as lysosomal acid lipase (LAL) deficiency) is an autosomal recessive chronic liver disease caused by functional LAL enzyme deficiency. CESD is a rare but serious disease and happens when the body is not producing enough LAL. The LAL enzyme (also referred to as cholesteryl ester hydrolase) is an enzyme that breaks down fatty material and is essential for metabolizing cholesteryl esters and triglycerides. A point mutation on the LIPA gene results in the production of truncated proteins with deficient enzymatic activity leading to accumulation of cholesteryl ester in organs and tissues. Reduced LAL enzyme activity typically results in a massive build-up of fatty material in various tissues including liver, spleen, gut, blood vessel walls and other important organs. As a result. CESD is typically associated with significant morbidity and mortality and can affect individuals from infancy through adulthood.

SUMMARY

According to one aspect of the present disclosure, provided herein is a method of treating Cholesteryl Ester Storage Disease (CESD) in a subject in need thereof by modulating the expression of a target protein or functional RNA by cells of the subject, wherein the cells have a skippable-exon-containing pre-mRNA (SEC pre-mRNA), the SEC pre-mRNA comprising the skippable exon, an intron flanking the 5' splice site of the skippable exon, and an intron flanking the 3' splice site of the skippable exon, and wherein the SEC pre-mRNA encodes the target protein or functional RNA, the method comprising contacting the cells of the subject with an antisense oligomer (ASO) complementary to a targeted portion of the SEC pre-mRNA encoding the target protein or functional RNA, whereby the skippable exon is retained in an mRNA processed from the SEC pre-mRNA encoding the target protein or functional RNA, thereby modulating a level of mRNA encoding the target protein or functional RNA and modulating the expression of the target protein or functional RNA in the cells of the subject.

According to another aspect of the present disclosure, provided herein is a method of modulating expression of a target protein, wherein the target protein is lysosomal acid lipase (LAL), by cells having a skippable-exon-containing pre-mRNA (SEC pre-mRNA), the SEC pre-mRNA comprising the skippable exon, an intron flanking the 5' splice site of the skippable exon, an intron flanking the 3' splice site of the skippable exon, and wherein the SEC pre-mRNA encodes LAL protein, the method comprising contacting the cells with an antisense oligomer (ASO) complementary to a targeted portion of the SEC pre-mRNA encoding LAL protein, whereby the skippable exon is retained in an mRNA processed from the SEC pre-mRNA encoding LAL protein, thereby modulating the level of mRNA encoding LAL protein and modulating the expression of LAL protein in the cells.

In some embodiments, modulating expression or level of the target protein or mRNA encoding the target protein increases the expression or level of the target protein or mRNA encoding the target protein. In some embodiments, modulating expression or level of LAL protein or mRNA encoding LAL protein increases the expression or level of LAL protein or mRNA encoding LAL protein. In some embodiments, the target protein is LAL. In some embodiments, the cells are in or from a subject having a condition caused by a deficient amount or activity of LAL protein. In some embodiments, at least one nucleotide of the 9 nucleotides at +1 to +6 of the intron flanking the 5' splice site and −3e to −1e of the skippable exon comprises at least one mutation. In some embodiments, the mutation is a substitution. In some embodiments, the mutation is at −1e. In some embodiments, the mutation is c.894G>A. In some embodiments, the deficient amount of the target protein is caused by autosomal recessive inheritance. In some embodiments, the subject has a first allele encoding a functional target protein and (a) a second allele encoding a functional target protein, wherein the antisense oligomer binds to a targeted portion of a SEC pre-mRNA transcribed from the first or second allele; or (b) a second allele, wherein the antisense oligomer binds to a targeted portion of a SEC pre-mRNA transcribed from the first allele. In some embodiments, the subject has a condition caused by a disorder resulting from a deficiency in the amount or function of the target protein, wherein the subject has a first allele comprising a first mutation from which the target protein is produced at a reduced level compared to production from a wild-type allele, the target protein is produced in a form having reduced function compared to an equivalent wild-type protein, or the target protein is not produced, and a second allele comprising a second mutation from which the target protein is produced at a reduced level compared to production from a wild-type allele, the target protein is produced in a form having reduced function compared to an equivalent wild-type protein, or the target protein is not produced, and wherein the first and second mutation are the same or different. In some embodiments, the target protein is produced in a form having reduced function compared to the equivalent wild-type protein. In some embodiments, the target protein is produced in a form that is fully-functional compared to the equivalent wild-type protein. In some embodiments, the targeted portion of the SEC pre-mRNA is in the skippable exon within the region −4e relative to the 5' splice site of the skippable exon to +2e relative to the 3' splice site of the skippable exon. In some embodiments, the targeted portion of the SEC pre-mRNA is within: the region +6 to +500 in the intron flanking the 5' splice site of the skippable exon; or the region −16 to −500 in the intron flanking the 3" splice site of the skippable exon. In some embodiments, the targeted portion of the SEC pre-mRNA is within: the region −4e to −500e relative to the 5' splice site of the skippable exon: the region +6 to +500 relative to the 5' splice site of the skippable exon: the region −16 to −500 relative to the 3' splice site of the skippable exon; or the region +2e to +500e relative to the 3' splice site of the skippable exon. In some embodiments, the SEC pre-mRNA comprises a sequence with at least about 80%, 85%, 90%, 95%, 97%, or 100% sequence identity to any one of SEQ ID NOs: 1 or a complement thereof. In some embodiments, the SEC pre-mRNA is encoded by a genetic sequence with at least about 80%, 85%, 90%, 95%, 97%, or 100% sequence identity to SEQ ID NO: 1 or a complement thereof. In some embodiments, the targeted portion of the SEC pre-mRNA comprises a sequence with at least 80%, 85%, 90%, 95%, 97%, or 100% sequence identity to a region comprising at least 8 contiguous nucleic acids of SEQ ID NOs: 2-4 or complements thereof. In some embodiments, the ASO comprises a sequence that is at least about 80%, 85%, 90%, 95%, 97%, or 100% identical to any one of SEQ ID NOs: 5-63 or complements thereof. In some embodiments, the targeted portion of the SEC pre-mRNA is within the region −4e relative to the 5' splice site of the skippable exon to +2e relative to the 3' splice site of the skippable exon, wherein the skippable exon is exon 8. In some embodiments, the ASO comprises a sequence that is at least about 80%, 85%, 90%, 95%, 97%, or 100% identical to any one of SEQ ID NOs: 54-63 or complements thereof. In some embodiments, the targeted portion of the SEC pre-mRNA is within the region +6 to +500 relative to the 5' splice site of the skippable exon, wherein the skippable exon is exon 8. In some embodiments, the ASO comprises a sequence that is at least about 80%, 85%, 90%, 95%, 97%, or 100% identical to any one of SEQ ID NOs: 5-38 or complements thereof. In some embodiments, the targeted portion of the SEC pre-mRNA is within the region −16 to −500 relative to the 3' splice site of the skippable exon, wherein the skippable exon is exon 8. In some embodiments, the ASO comprises a sequence that is at least about 80%, 85%, 90%, 95%, 97%, or 100% identical to any one of SEQ ID NOs: 39-53 or complements thereof. In some embodiments, the SEC pre-mRNA is a partially spliced pre-mRNA of a full-length pre-mRNA or is a partially spliced pre-mRNA of a wild-type pre-mRNA. In some embodiments, the mRNA encoding the target protein or functional RNA is a full-length mature mRNA, or a wild-type mature mRNA. In some embodiments, the target protein produced is full-length protein, or wild-type protein, or a combination thereof.

In some embodiments, the total amount of the mRNA encoding the target protein or functional RNA produced in the cell contacted with the antisense oligomer is increased about 1.1 to about 10-fold, about 1.5 to about 10-fold, about 2 to about 10)-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of the mRNA encoding the target protein or functional RNA produced in a control cell.

In some embodiments, the total amount of the mRNA encoding the target protein or functional RNA produced in the cell contacted with the antisense oligomer is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150)%, about 100% to about 200%, about 100% to about 250%, about 150% to about 200%, about 150% to about 250)%, about 200% to about 250%, at least about 10%, at least about 20%, at least about 50%, at least about 100%, at least about 150%, at least about 200%, at least about 250%, or at least about 300%, compared to the total amount of the mRNA encoding the target protein or functional RNA produced in a control cell.

In some embodiments, the total amount of target protein produced by the cell contacted with the antisense oligomer is increased about 1.1 to about 10-fold, about 1.5 to about 10-fold, about 2 to about 10-fold, about 3 to about 10)-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of target protein produced by a control cell.

In some embodiments, the total amount of target protein produced by the cell contacted with the antisense oligomer is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250)%, about 100% to about 150%, about 100% to about 200%, about 100% to about 250%, about 150% to about 200%, about 150% to about 250%, about 200% to about 250)%, at least about 10%, at least about 20%, at least about 50%, at least about 100%, at least about 150%, at least about 200%, at least about 250%, or at least about 300%, compared to the total amount of target protein produced by a control cell.

In some embodiments, the antisense oligomer comprises a backbone modification comprising a phosphorothioate linkage or a phosphorodiamidate linkage. In some embodiments, the antisense oligomer comprises a phosphorodiamidate morpholino, a locked nucleic acid, a peptide nucleic acid, a 2'-O-methyl, a 2'-Fluoro, or a 2'-O-methoxyethyl moiety. In some embodiments, the antisense oligomer comprises at least one modified sugar moiety. In some embodiments, each sugar moiety is a modified sugar moiety.

In some embodiments, the antisense oligomer consists of from 8 to 50 nucleobases, 8 to 40) nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases. 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

In some embodiments, the antisense oligomer is at least 80%, at least 85%, at least 90%, at least 95%, at least 98%, at least 99%, or 100%, complementary to the targeted portion of the SEC pre-mRNA encoding the protein. In some embodiments, the method further comprises assessing LIPA protein expression. In some embodiments. CESD is treated and wherein the antisense oligomer binds to a targeted portion of a LIPA SEC pre-mRNA, wherein the targeted portion comprises at least 8 contiguous nucleic acids of SEQ ID NO: 2-4 or complements thereof. In some embodiments, the subject is a human. In some embodiments, the subject is a non-human animal. In some embodiments, the subject is a fetus, an embryo, or a child. In some embodiments, the cells are contacted ex vivo. In some embodiments, the antisense oligomer is administered by intrathecal injection, intracerebroventricular injection, intraperitoneal injection, intramuscular injection, subcutaneous injection, or intravenous injection of the subject.

In some embodiments, the 16 nucleotides at −15 to −1 of the intron and +1e of the skippable exon flanking the 3' splice site are identical to the corresponding wild-type sequence, wherein the intron is intron 7 and wherein the skippable exon is exon 8.

According to another aspect of the present disclosure, provided herein is an antisense oligomer as used in any one of the methods provided herein.

According to another aspect of the present disclosure, provided herein is an antisense oligomer comprising a sequence with at least about 80%, 85%, 90%, 95%, 97%, or 100% sequence identity to any one of SEQ ID NOs: 5-63 or complements thereof.

According to another aspect of the present disclosure, provided herein is a pharmaceutical composition comprising the antisense oligomer and a pharmaceutically acceptable excipient, diluent, or carrier.

A method of treating a subject in need thereof, by administering the pharmaceutical composition of claim 52 by intrathecal injection, intracerebroventricular injection, intraperitoneal injection, intramuscular injection, subcutaneous injection, or intravenous injection.

According to another aspect of the present disclosure, provided herein is a composition comprising an antisense oligomer for use in a method of modulating expression of a target protein or a functional RNA by cells to treat Cholesteryl Ester Storage Disease (CESD) in a subject in need thereof, associated with a deficient protein or deficient functional RNA, wherein the deficient protein or deficient functional RNA is deficient in amount or activity in the subject, wherein the antisense oligomer reduces exclusion of an exon from a skippable-exon-containing pre-mRNA (SEC pre-mRNA) encoding the target protein or the functional RNA, wherein the target protein is the deficient protein, wherein the functional RNA is the deficient RNA and wherein the SEC pre-mRNA comprises the skippable exon, an intron flanking the 5' splice site of the skippable exon and an intron flanking the 3' splice site of the skippable exon, and wherein the skippable exon is retained in an mRNA processed from the SEC pre-mRNA encoding the target protein or the functional RNA, thereby modulating production or activity of the target protein or the functional RNA in the subject. Also provided herein is a composition comprising an antisense oligomer for use in a method of treating a condition associated with lysosomal acid lipase (LAL) protein in a subject in need thereof, the method comprising the step of modulating expression of LAL protein by cells of the subject, wherein the cells have a skippable-exon-containing pre-mRNA (SEC pre-mRNA) comprising the skippable exon, an intron flanking the 5' splice site of the skippable exon, an intron flanking the 3' splice site of the skippable exon, and wherein the SEC pre-mRNA encodes the LAL protein, the method comprising contacting the cells with the antisense oligomer, whereby the skippable exon is retained in an mRNA processed from the SEC pre-mRNA transcripts encoding LAL protein, thereby modulating the level of mRNA encoding LAL protein, and modulating the expression of LAL protein, in the cells of the subject.

In some embodiments, modulating the activity, expression and/or production of the target protein or mRNA encoding the target protein increases the activity, expression and/or production of the target protein or mRNA encoding the target protein. In some embodiments, modulating the activity, expression and/or production of LAL protein or mRNA encoding LAL protein increases the activity, expression and/or production of LAL protein or mRNA encoding LAL protein. In some embodiments, the target protein is LAL. In some embodiments, the condition is a disease or disorder. In some embodiments, the disease or disorder is CESD. In some embodiments, the target protein and SEC pre-mRNA are encoded by the LIPA gene. In some embodiments, the ASO targets a portion of the SEC pre-mRNA that is in the skippable exon within the region −4e relative to the 5' splice site of the skippable exon to +2e relative to the 3' splice site of the skippable exon. In some embodiments, the antisense oligomer targets a portion of the SEC pre-mRNA that is in the skippable exon within: the region +6 to +500 relative to the 5' splice site of the skippable exon; or the region −16 to −500 relative to the 3' splice site of the skippable exon. In some embodiments, the antisense oligomer targets a portion of the SEC pre-mRNA that is within the region about 100 nucleotides downstream of the 5' splice site of the skippable exon, to about 100 nucleotides upstream of the 3' splice site of the skippable exon. In some embodiments, the targeted portion of the SEC pre-mRNA is within: the region +6 to +500 in the intron flanking the 5' splice site of the skippable exon; or the region −16 to −500 in the exon flanking the 3' splice site of the skippable exon. In some embodiments, the targeted portion of the SEC pre-mRNA is within: the region −4e to −500c relative to the 5' splice site of the skippable exon: the region +6 to +500 relative to the 5' splice site of the skippable exon: the region −16 to −500 relative to the 3' splice site of the skippable exon; or the region +2c to +500e relative to the 3' splice site of the skippable exon. In some embodiments, the target protein is LAL. In some embodiments, the SEC pre-mRNA comprises a sequence with at least about 80%, 85%, 90%, 95%, 97%, or 100% sequence identity to any one of SEQ ID NOs: 1 or a complement thereof. In some embodiments, the SEC pre-mRNA is encoded by a genetic sequence with at least about 80%, 85%, 90%, 95%, 97%, or 100% sequence identity to SEQ ID NO: 1 or a complement thereof. In some embodiments, the targeted portion of the SEC pre-mRNA comprises a sequence with at least 80%, 85%, 90%, 95%, 97%, or 100% sequence identity to a region comprising at least 8 contiguous nucleic acids of SEQ ID NO: 2-4 or complements thereof. In some embodiments, the ASO comprises a sequence that is at least about 80%, 85%, 90%, 95%, 97%, or 100% identical to any one of SEQ ID NOs: 5-63 or complements thereof. In some embodiments, the targeted portion of the SEC pre-mRNA is within the region −4e relative to the 5' splice site of the skippable exon to +2e relative to the 3' splice site of the skippable exon, wherein the skippable exon is exon 8. In some embodiments, the ASO comprises a sequence that is at least about 80%, 85%, 90%, 95%, 97%, or 100% identical to any one of SEQ ID NOs: 54-63 or complements thereof. In some embodiments, the targeted portion of the SEC pre-mRNA is within the region −16 to −500 relative to the 3' splice site of the skippable exon, wherein the skippable exon is exon 8. In some embodiments, the ASO comprises a sequence that is at least about 80%, 85%, 90%, 95%, 97%, or 100% identical to any one of SEQ ID NOs: 5-38 or complements thereof. In some embodiments, the targeted portion of the SEC pre-mRNA is within the region +6 to +500 relative to the 5' splice site of the skippable exon, wherein the skippable exon is exon 8. In some embodiments, the ASO comprises a sequence that is at least about 80%, 85%, 90%, 95%, 97%, or 100% identical to any one of SEQ ID NOs: 39-53 or complements thereof. In some embodiments, the SEC pre-mRNA was produced by partial splicing from a full-length pre-mRNA or a wild-type pre-mRNA. In some embodiments, the mRNA encoding the target protein or functional RNA is a full-length mature mRNA, or a wild-type mature mRNA. In some embodiments, the target protein produced is full-length protein, or wild-type protein. In some embodiments, the antisense oligomer comprises a backbone modification comprising a phosphorothioate linkage or a phosphorodiamidate linkage. In some embodiments, said antisense oligomer is an antisense oligonucleotide. In some embodiments, the antisense oligomer comprises a phosphorodiamidate morpholino, a locked nucleic acid, a peptide nucleic acid, a 2'-O-methyl, a 2'-Fluoro, or a 2'-O-methoxyethyl moiety. In some embodiments, the antisense oligomer comprises at least one modified sugar moiety. In some embodiments, each sugar moiety is a modified sugar moiety. In some embodiments, the antisense oligomer consists of from 8 to 50 nucleobases, 8 to 40) nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases. 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Also provided herein is a pharmaceutical composition comprising the antisense oligomer of any of the compositions of claims 54 to 86, and a pharmaceutically acceptable excipient, diluent, or carrier.

According to another aspect of the present disclosure, provided herein is a method of treating a subject in need thereof, by administering the pharmaceutical composition of claim 87 by intrathecal injection, intracerebroventricular injection, intraperitoneal injection, intramuscular injection, subcutaneous injection, or intravenous injection.

According to another aspect of the present disclosure, provided herein is a pharmaceutical composition comprising: an antisense oligomer that hybridizes to a target sequence of a LIPA mRNA transcript, wherein the LIPA mRNA transcript comprises a skipped exon, wherein the antisense oligomer induces retention of the skipped exon from the LIPA mRNA transcript; and a pharmaceutically acceptable excipient, diluent, or carrier. In some embodiments, the LIPA mRNA transcript is a LIPA SEC pre-mRNA transcript. In some embodiments, the targeted portion of the LIPA SEC pre-mRNA transcript is in the skippable exon within the region −4e relative to the 5' splice site of the skippable exon to +2e relative to the 3' spliced site of the skippable exon. In some embodiments, the LIPA SEC pre-mRNA transcript is encoded by a genetic sequence with at least about 80%, 85%, 90%, 95%, 96%, 97%, 98%, 99% or 100% sequence identity to any one of SEQ ID NOs: 1 or a complement thereof. In some embodiments, the LIPA SEC pre-mRNA transcript comprises a sequence with at least about 80%, 85%, 90%, 95%, 96%, 97%, 98%, 99% or 100% sequence identity to any one of SEQ ID NOs: 1 or a complement thereof. In some embodiments, the antisense oligomer comprises a backbone modification comprising a phosphorothioate linkage or a phosphorodiamidate linkage. In some embodiments, the antisense oligomer is an antisense oligonucleotide. In some embodiments, the antisense oligomer comprises a phosphorodiamidate morpholino, a locked nucleic acid, a peptide nucleic acid, a 2'-O-methyl, a 2'-Fluoro, or a 2'-O-methoxyethyl moiety. In some embodiments, the antisense oligomer comprises at least one modified sugar moiety. In some embodiments, the antisense oligomer comprises from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases. In some embodiments, the antisense oligomer is at least 80%, at least 85%, at least 90%, at least 95%, at least 98%, at least 99%, or is 100% complementary to a targeted portion of the LIPA SEC pre-mRNA transcript. In some embodiments, the targeted portion of the LIPA SEC pre-mRNA transcript is within a sequence selected from SEQ ID NOs: 2-4 or complements thereof.

In some embodiments, the antisense oligomer comprises a nucleotide sequence that is at least about 80%, 85%, 90%, 91%, 92%, 93%, 94%, 95%, 96%, 97%, 98%, or 99% sequence identity to any one of SEQ ID NOs: 5-63 or complements thereof.

In some embodiments, the antisense oligomer comprises a nucleotide sequence selected from SEQ ID NOs: 5-63 or complements thereof.

In some embodiments, the pharmaceutical composition is formulated for intrathecal injection, intracerebroventricular injection, intraperitoneal injection, intramuscular injection, subcutaneous injection, or intravenous injection.

According to yet another aspect of the present disclosure, provided herein is Aa method of treating a subject having a condition caused by a deficient amount or activity of LAL protein comprising administering to the subject an antisense oligomer comprising a nucleotide sequence with at least about 80%, 85%, 90%, 91%, 92%, 93%, 94%, 95%, 96%, 97%, 98%, or 99% sequence identity to any one of SEQ ID NOs: 5-63 or complements thereof. In some embodiments, the subject is a human.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 3 depicts an exemplary LIPA intron 8 5' splice site region antisense oligonucleotide (ASO) walk. A graphic representation of an ASO walk performed for LIPA intron 8 5' splice site region targeting sequences downstream of the 5' splice site using 2'-O-methoxyethyl (2'-MOE) ASOs with a phosphorothioate (PS) backbone is shown. ASOs were designed to cover this region by shifting 1 nucleotide at a time from position +6 to +11 and 5 nucleotides at a time thereafter. FIG. 3 discloses SEQ ID NO: 64.

FIG. 7A depicts exemplary dose-dependent effect of selected ASO in CESD patient fibroblast cells. A representative sodium dodecylsulfate-polyacrylamide gel electrophoresis (SDS-PAGE) showing lysosomal acid lipase (LAL) protein from mock-treated cells (−), or treated with A-3334 (+9) 2'-MOE ASO targeting intron 8 at 0.125-µM, 0.5-µM, and 2-µM concentrations in CESD patient fibroblast carrying the c.894G>A mutation via electroporation is shown. A product corresponding to glycosylated full-length protein was quantified and normalized to Ponceau S-stained blot.

FIG. 7B depicts a graph plotting the fold-change in glycosylated full-length protein with respect to mock from the data in FIG. 7A.

FIG. 9A depicts exemplary dose-dependent effect of selected ASOs of different lengths targeting the intron 8+9 region in CESD patient fibroblast cells. A representative PAGE showing SYBR-safe-stained RT-PCR products of LIPA mock-treated (Ctrl), or treated with A-3334 (+9), A-3680) (+9(17)), A-3681 (+9(16)), A-3682 (+10(17)), A-3683 (+10(16)), A-3684 (+11(16)) 2'-MOE ASOs targeting intron 8 at 0.125-µM, 0.5-µM, and 2-µM concentrations in CESD patient fibroblast carrying the c.894G>A mutation via electroporation is shown. Two products corresponding to exon 8 inclusion (full-length, top band) and exon 8 skipping (bottom band) were quantified.

FIG. 9B depicts a graph plotting the percent full-length (exon 8 inclusion) from the data in FIG. 9A.

DETAILED DESCRIPTION

Figure 1:
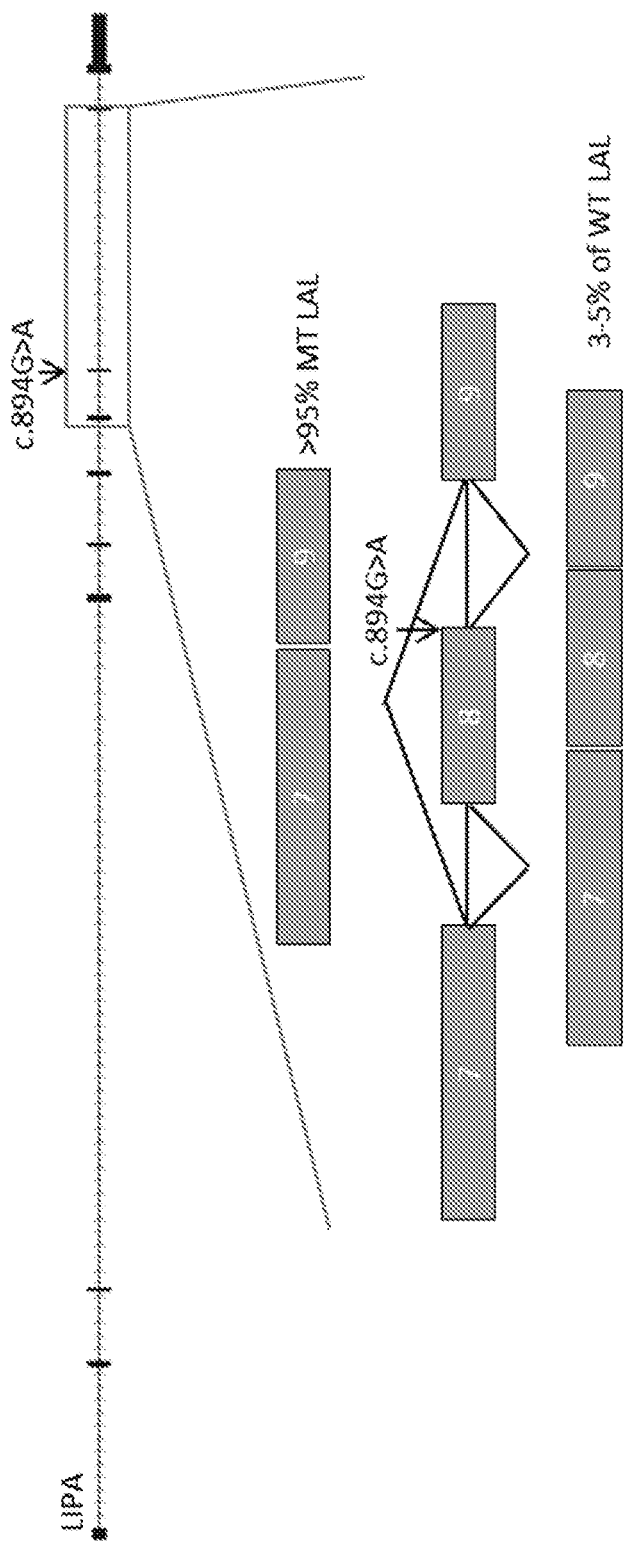
FIG. 1 depicts a schematic representation of the LIPA pre-mRNA. The LIPA mutation c.894G>A that leads to skipping of exon 8 and ultimately Cholesteryl ester storage disease (CESD) is depicted. Also depicted are schematic representations of the wild-type (WT) and mutant (MT) spliced mRNA transcripts resulting from the LIPA mutation. As shown, the CESD mutation results in about 95% of the mRNA transcripts in a truncated form leading to a non-functional LAL protein and only 3-5% of the functional (full length) mRNA leading to a functional LAL protein.
Figure 2:
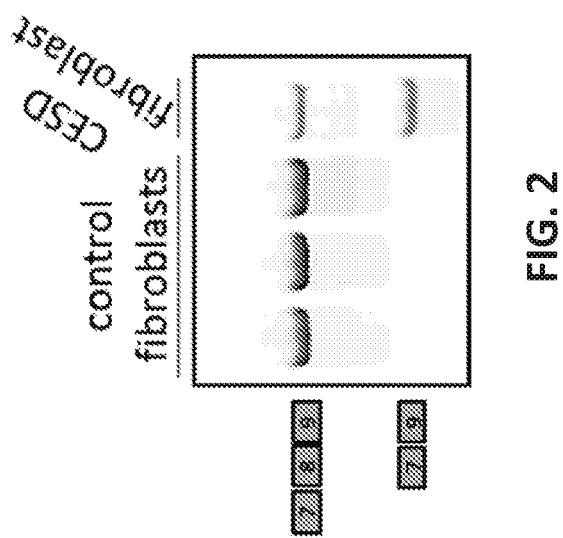
FIG. 2 depicts an example Polyacrylamide gel electrophoresis (PAGE) showing confirmation of exon 8 skipping in CESD patient fibroblast cells carrying the LIPA c.894G>A mutation. RT-PCR analysis using control and CESD patient fibroblast cells and primers in exon 7 and exon 9 confirmed the presence of a band corresponding to the skipping of exon 8 caused by the c.894G>A mutation. The identity of the products was confirmed by sequencing.

Certain specific details of this description are set forth in order to provide a thorough understanding of various embodiments. However, one skilled in the art will understand that the present disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below.

Cholesteryl Ester Storage Disease and LIPA Gene

Cholesteryl ester storage disease (CESD) is an autosomal recessive chronic liver disease caused by functional lysosomal acid lipase (LAL) enzyme deficiency. The LAL enzyme is essential for metabolizing cholesteryl esters and, to a lesser extent, triglycerides. Deficient LAL activity predominantly results in accumulation of cholesteryl ester in the organs and tissues, particularly in the liver, spleen and macrophages. The disease is characterized by hypercholesterolemia, hypertriglyceridemia. HDL deficiency, and abnormal lipid deposition in many organs. In the liver this results in hepatomegaly caused by hepatic steatosis and fibrosis that can lead to micronodular cirrhosis. The life expectancy of patients is often less than 30 years of age. CESD onset typically occurs during childhood or adolescence: however symptoms may not be detected until adulthood and is about equally prevalent in females and males.

Mutations in the LIPA gene encoding the LAL protein are the underlying cause of CESD. Unlike Wolman disease in which LIPA gene mutations result in an enzyme with no residual activity or no enzyme at all. CESD causing mutations encode for LAL which retains some enzyme activity. A previous study of LAL activity in cultured skin fibroblasts of a CESD patient identified a G→A mutation at position −1 of the exon 8 5' splice site (E8SJM. Exon 8 Splice Junction Mutation, c.894G>A) leading to a 72 base pair (bp) in-frame deletion from the resulting mRNA. This 72 bp deletion was subsequently shown to correspond to the full exon 8. The G→A mutation causes aberrant splicing of the LIPA pre-mRNA and skipping of exon 8. Deletion of exon 8 from the mRNA results in the loss of the codons for amino acids 254-277 of LAL protein. The shorter protein has no residual LAL activity: however E8SJM does not cause Wolman Disease because 2% to 5% of normally spliced LIPA is present in homozygote carriers. The vast majority of CESD patients described to date are E8SJM carriers.

The present disclosure provides compositions and methods for modulating aberrant splicing caused by the LIPA c.894G>A mutation to increase the production of functional protein-coding mature mRNA, and thus, translated functional LAL protein. These compositions and methods include antisense oligomers (ASOs) that can promote exon inclusion and constitutive splicing of LIPA pre-mRNA. In various embodiments, functional LAL protein can be increased using the methods of the disclosure to treat a condition caused by LAL protein deficiency. In some embodiments, the condition is CESD.

In some embodiments, the methods of the invention are used to increase functional LAL protein production to treat a condition in a subject in need thereof. In some embodiments, the subject has a condition in which LAL is not necessarily deficient relative to wild-type, but where an increase in LAL mitigates the condition nonetheless. In some embodiments. CESD is caused by autosomal recessive inheritance.

Splicing

Intervening sequences or introns are removed by a large and highly dynamic RNA-protein complex termed the spliceosome, which orchestrates complex interactions between primary transcripts, small nuclear RNAs (snRNAs) and a large number of proteins. Spliceosomes assemble ad hoc on each intron in an ordered manner, starting with recognition of the 5' splice site (5'ss) by U1 snRNA or the 3'splice site (3'ss), which involves binding of the U2 auxiliary factor (U2AF) to the 3'ss region to facilitate U2 snRNA binding to the branch point sequence (BPS). U2AF is a stable heterodimer composed of a U2AF2-encoded 65-KD subunit (U2AF65), which binds the polypyrimidine tract (PPT), and a U2AF1-encoded 35-kD subunit (U2AF35), which interacts with highly conserved AG dinucleotides at 3'ss and stabilizes U2AF65 binding. In addition to the BPS/PPT unit and 3 ss/5'ss, accurate splicing requires auxiliary sequences or structures that activate or repress splice site recognition, known as intronic or exonic splicing enhancers or silencers. These elements allow genuine splice sites to be recognized among a vast excess of cryptic or pseudo-sites in the genome of higher eukaryotes, which have the same sequences but outnumber authentic sites by an order of magnitude. Although they often have a regulatory function, the exact mechanisms of their activation or repression are poorly understood.

The decision as to whether splicing occurs can be typically modeled as a stochastic rather than deterministic process, such that even the most defined splicing signals can sometimes splice incorrectly. However, under normal conditions, pre-mRNA splicing proceeds with surprisingly high accuracy. This may be attributed in part to the activity of adjacent cis-acting auxiliary exonic and intronic splicing regulatory elements (ESRs or ISRs). Typically, these functional elements are classified as either exonic or intronic splicing enhancers (ESEs or ISEs) or silencers (ESSs or ISSs) based on their ability to stimulate or inhibit splicing, respectively. Although there is now evidence to suggest that some auxiliary cis-acting elements may act by influencing the kinetics of spliceosome assembly, such as the arrangement of the complex between U1 snRNP and the 5'ss, it seems highly likely that multiple elements function in a coordinated manner with trans-acting RNA-binding proteins (RBPs). For example, the serine- and arginine-rich family of RBPs (SR proteins) is a conserved family of proteins that play a key role in defining exons. SR proteins promote exon recognition by recruiting components of the pre-spliceosome to adjacent splice sites or by antagonizing the effects of ESSs in the vicinity. The repressive effects of ESSs and ISSs can be mediated by members of the heterogeneous nuclear ribonucleoprotein (hnRNP) family and can alter recruitment of core splicing factors to adjacent splice sites. In addition to their roles in splicing regulation, silencer elements have been suggested to play a role in the repression of pseudo-exons, which are sets of decoy intronic splice sites with the typical spacing of an exon but without a functional open reading frame. ISEs. ISSs. ESEs and ESSs, in cooperation with their related trans-acting RBPs, represent important components in a set of splicing controls that specify how, where and when mRNAs are assembled from their precursors.

The sequences marking the exon-intron boundaries are degenerate signals of varying strengths that can occur at high frequency within human genes. In multi-exon genes, different pairs of splice sites can be linked together in many different combinations, creating a diverse array of transcripts from a single gene. This is commonly referred to as alternative pre-mRNA splicing. Although most mRNA isoforms produced by alternative splicing can be exported from the nucleus and translated into functional polypeptides, different mRNA isoforms from a single gene can vary greatly in their translation efficiency. Those mRNA isoforms with premature termination codons (PTCs) at least 50 bp upstream of an exon junction complex are likely to be targeted for degradation by the nonsense-mediated mRNA decay (NMD) pathway. Mutations in traditional (BPS/PPT/3'ss/5'ss) and auxiliary splicing motifs may cause aberrant splicing, such as exon skipping or cryptic (or pseudo-) exon inclusion or splice-site activation, and contribute significantly to human morbidity and mortality. Both aberrant and alternative splicing patterns can be influenced by natural DNA variants in exons and introns.

ESEs may be very prevalent, being present in the majority, if not all, exons, including constitutive exons. Although some exons may have redundant ESEs, and are therefore resistant to point mutations, in certain cases (e.g., exon 8 of LIPA), single point mutations may disrupt a critical ESE, resulting in partial or complete inappropriate exon skipping.

Target Transcripts

In some embodiments, the methods of the present disclosure exploit the presence of skippable-exon-containing pre-mRNA (SEC pre-mRNA) transcribed from the LIPA gene. Splicing of the identified LIPA SEC pre-mRNA transcripts to produce functional, mature LIPA mRNA can be induced using a therapeutic agent, such as an ASO, that promotes exon inclusion and constitutive splicing of LIPA SEC pre-mRNA. In some embodiments, the resulting functional, mature LIPA mRNA can be translated normally, thereby increasing the amount of functional LAL protein in the patient's cells and alleviating symptoms of CESD.

In various embodiments, the present disclosure provides a therapeutic agent that can target LIPA SEC pre-mRNA to modulate splicing or protein expression level. The therapeutic agent can be a small molecule, polynucleotide, or polypeptide. In some embodiments, the therapeutic agent is an ASO. Various regions or sequences on the LIPA SEC pre-mRNA can be targeted by a therapeutic agent, such as an ASO. In some embodiments, the ASO targets a LIPA SEC pre-mRNA transcribed from the LIPA gene. In some embodiments, the ASO targets a LIPA SEC pre-mRNA transcribed from the LIPA gene comprising a skippable exon. In some embodiments, the skippable exon is exon 8 of a LIPA SEC pre-mRNA transcript. In some embodiments, the skippable exon is spliced out of a LIPA SEC pre-mRNA transcript due to aberrant splicing. In some embodiments, the aberrant splicing is caused by a mutation in the LIPA gene. In some embodiments, the mutation is a G→A mutation at position −1 of the exon 8 splice donor (E8SJM. Exon 8 Splice Junction Mutation, c.894G>A). In some embodiments, the ASO targets a sequence within a skippable exon of a LIPA SEC pre-mRNA transcript. In some embodiments, the skippable exon is exon 8 of a LIPA SEC pre-mRNA transcript. In some embodiments, the ASO targets a sequence within exon 8 of a LIPA SEC pre-mRNA transcript. In some embodiments, the ASO targets an exon sequence upstream (or 5') from the 5' splice site of exon 8 of a LIPA SEC pre-mRNA transcript. In some embodiments, the ASO targets an exon sequence downstream (or 3") from the 3' splice site of exon 8 of a LIPA pre-mRNA transcript. In some embodiments, the ASO targets a sequence within an intron flanking the 3' splice site of a skippable exon of a LIPA SEC pre-mRNA transcript. In some embodiments, the ASO targets a sequence within intron 7 of a LIPA SEC pre-mRNA transcript. In some embodiments, the ASO targets an intron sequence upstream (or 5') from the 3' splice site of intron 7 of a LIPA SEC pre-mRNA transcript. In some embodiments, the ASO targets an intron sequence downstream (or 3') from the 5' splice site of intron 7 of a LIPA pre-mRNA transcript. In some embodiments, the ASO targets a sequence within an intron flanking the 5' splice site of a skippable exon of a LIPA SEC pre-mRNA transcript. In some embodiments, the ASO targets a sequence within intron 8 of a LIPA SEC pre-mRNA transcript. In some embodiments, the ASO targets an intron sequence upstream (or 5') from the 3' splice site of intron 8 of a LIPA SEC pre-mRNA transcript. In some embodiments, the ASO targets an intron sequence downstream (or 3') from the 5' splice site of intron 8 of a LIPA pre-mRNA transcript. In some embodiments, the ASO targets a sequence comprising an exon-intron boundary of a LIPA SEC pre-mRNA transcript. In some embodiments, the exon is a skippable exon. An exon-intron boundary can refer to the junction of an exon sequence and an intron sequence. In some embodiments, the intron sequence can flank the 5' end of the skippable exon, or the 3' end of the exon. In some embodiments, the ASO targets a sequence comprising an exon 8-intron 8 boundary of a LIPA SEC pre-mRNA transcript. In some embodiments, the ASO targets a sequence comprising an intron 7-exon 8 boundary of a LIPA SEC pre-mRNA transcript. In some embodiments, the ASO targets a sequence comprising both a portion of an intron and a portion of an exon.

In some embodiments, the ASO targets a sequence about 4 to about 300 nucleotides upstream (or 5') from the 3' splice site of a skippable exon of a LIPA SEC pre-mRNA transcript. In some embodiments, the ASO targets a sequence about 1 to about 20 nucleotides, about 20 to about 50 nucleotides, about 50) to about 100 nucleotides, about 100 to about 150 nucleotides, about 150 to about 200 nucleotides, about 200 to about 250 nucleotides, or about 250 to about 300 nucleotides upstream (or 5') from the 3' splice site of the skippable exon of a LIPA SEC pre-mRNA transcript. In some embodiments, the ASO may target a sequence more than 300 nucleotides upstream from the 3' splice site of the skippable exon of a LIPA SEC pre-mRNA transcript. In some embodiments, the ASO targets a sequence about 4 to about 300 nucleotides downstream (or 3') from the 3' splice site of a skippable exon of a LIPA SEC pre-mRNA transcript. In some embodiments, the ASO targets a sequence about 1 to about 20 nucleotides, about 20 to about 50 nucleotides, about 50 to about 100 nucleotides, about 100 to about 150 nucleotides, about 150) to about 200 nucleotides, about 200 to about 250 nucleotides, or about 250 to about 300 nucleotides downstream (or 3') from the 3' splice site of the skippable exon of a LIPA SEC pre-mRNA transcript. In some embodiments, the ASO may target a sequence more than 300 nucleotides downstream from the 3' splice site of the skippable exon of a LIPA SEC pre-mRNA transcript. In some embodiments, the ASO targets a sequence about 4 to about 300 nucleotides downstream (or 3') from the 5' splice site of the skippable exon of a LIPA SEC pre-mRNA transcript. In some embodiments, the ASO targets a sequence about 1 to about 20 nucleotides, about 20 to about 50 nucleotides, about 50 to about 100 nucleotides, about 100 to about 150 nucleotides, about 150) to about 200 nucleotides, about 200 to about 250 nucleotides, or about 250) to about 300 nucleotides downstream from the 5' splice site of the skippable exon of a LIPA SEC pre-mRNA transcript. In some embodiments, the ASO targets a sequence more than 300 nucleotides downstream from the 5' splice site of the skippable exon of a LIPA SEC pre-mRNA transcript. In some embodiments, the ASO targets a sequence about 4 to about 300 nucleotides upstream (or 5') from the 5' splice site of the skippable exon of a LIPA SEC pre-mRNA transcript. In some embodiments, the ASO targets a sequence about 1 to about 20 nucleotides, about 20 to about 50) nucleotides, about 50) to about 100 nucleotides, about 100) to about 150 nucleotides, about 150 to about 200 nucleotides, about 200) to about 250 nucleotides, or about 250) to about 300 nucleotides upstream from the 5' splice site of the skippable exon of a LIPA SEC pre-mRNA transcript. In some embodiments, the ASO targets a sequence more than 300 nucleotides upstream from the 5' splice site of the skippable exon of a LIPA SEC pre-mRNA transcript.

As described herein in the Examples, the LIPA gene (SEQ ID NO. 1) was analyzed for exon-skipping events and exclusion of exon 8 from a mRNA processed from the SEC pre-mRNA was observed. In some embodiments, the ASOs disclosed herein target a SEC pre-mRNA transcribed from a LIPA genomic sequence. In some embodiments, the ASO targets a SEC pre-mRNA transcript from a LIPA genomic sequence comprising a skippable exon. In some embodiments the skippable exon is exon 8. In some embodiments, the ASO targets a SEC pre-mRNA transcript from a LIPA genomic sequence comprising exon 8. In some embodiments, the ASO targets a SEC pre-mRNA transcript from a LIPA genomic sequence comprising an intron flanking the 3' splice site of the skippable exon and an intron flanking the 5' splice site of a skippable exon. In some embodiments, the intron flanking the 3' splice site of the skippable exon is intron 7 and the intron flanking the 5' splice site of a skippable exon is intron 8. In some embodiments, the ASO targets a SEC pre-mRNA transcript from a LIPA genomic sequence comprising intron 7, exon 8 and intron 8. In some embodiments, the ASO targets a SEC pre-mRNA transcript of SEQ ID NO: 1. In some embodiments, the ASO targets a SEC pre-mRNA transcript of SEQ ID NO: 1 comprising exon 8. In some embodiments, the ASO targets a SEC pre-mRNA transcript of SEQ ID NO: 1 comprising intron 7. In some embodiments, the ASO targets a SEC pre-mRNA transcript of SEQ ID NO: 1 comprising intron 8. In some embodiments, the ASO targets a SEC pre-mRNA transcript of SEQ ID NO: 1 comprising intron 7, exon 8 and intron 8. In some embodiments, the ASOs disclosed herein target a LIPA SEC pre-mRNA sequence (SEQ ID NO: 1). In some embodiments, the ASO targets a LIPA SEC pre-mRNA sequence comprising a skippable exon. In some embodiments, the ASO targets a LIPA SEC pre-mRNA sequence comprising exon 8. (SEQ ID NO: 4). In some embodiments, the ASO targets a LIPA SEC pre-mRNA sequence comprising an intron flanking the 3' splice site of the skippable exon. In some embodiments, the ASO targets a LIPA SEC pre-mRNA sequence comprising intron 7 (SEQ ID NO: 3). In some embodiments, the ASO targets a LIPA SEC pre-mRNA sequence comprising an intron flanking the 5' splice site of the skippable exon. In some embodiments, the ASO targets a LIPA SEC pre-mRNA sequence comprising intron 8 (SEQ ID NO: 2). In some embodiments, the ASO targets a LIPA SEC pre-mRNA sequence according to any one of SEQ ID NOs: 2-4. In some embodiments, the ASO has a sequence according to any one of SEQ ID NOs: 5-63.

In some embodiments, the LIPA SEC pre-mRNA transcript is encoded by a genetic sequence with at least about 80%, 85%, 90%, 95%, 96%, 97%, 98%, 99% or 100% sequence identity to SEQ ID NO. 1 or a complement thereof. In some embodiments, the LIPA SEC pre-mRNA transcript comprises a sequence with at least about 80%, 85%, 90%, 95%, 96%, 97%, 98%, 99% or 100% sequence identity to any one of SEQ ID NO. 1 or a complement thereof.

In some embodiments, the targeted portion of the LIPA SEC pre-mRNA comprises a sequence with at least 80%, 85%, 90%, 95%, 97%, or 100% sequence identity to a region comprising at least 8 contiguous nucleic acids of SEQ ID NOs: 2-4 or complements thereof. In some embodiments, the ASO comprises a sequence that is at least about 80%, 85%, 90%, 95%, 97%, or 100% identical to any one of SEQ ID Nos: 5-64 or complements thereof.

In some embodiments, the ASO targets exon 8 of a LIPA SEC pre-mRNA comprising a skippable exon. In some embodiments, the ASO targets a sequence about 2 nucleotides downstream (or 3") from the 3' splice site of exon 8 to about 4 nucleotides upstream (or 5') from the 5' splice site of exon 8. In some embodiments, the ASO has a sequence according to any one of SEQ ID NOs: 54-63 or complements thereof.

In some embodiments, the ASO targets intron 7 of a LIPA SEC pre-mRNA comprising a skippable exon. In some embodiments, the ASO targets a sequence about 4 to about 300 nucleotides upstream (or 5') from the 3' splice site of intron 7. In some embodiments, the ASO targets a sequence about 16 to about 100 nucleotides upstream (or 5') from the 3' splice site of intron 7. In some embodiments, the ASO targets a sequence about 4 to about 300 nucleotides downstream (or 3') from the 5' splice site of intron 7. In some embodiments, the ASO has a sequence according to any one of SEQ ID NOs: 39-53 or complements thereof.

In some embodiments, the ASO targets intron 8 of a LIPA SEC pre-mRNA comprising a skippable exon. In some embodiments, the ASO targets a sequence about 4 to about 300 nucleotides upstream (or 5') from the 3' splice site of intron 8. In some embodiments, the ASO targets a sequence about 4 to about 300 nucleotides downstream (or 3") from the 5' splice site of intron 8. In some ASO targets a sequence about 6 to about 100 nucleotides downstream (or 5') from the 5' splice site of intron 8. In some embodiments, the ASO has a sequence according to any one of SEQ ID NOs: 5-38 or complements thereof.

In some embodiments, the targeted portion of the LIPA SEC pre-mRNA is in intron 1, 2, 3, 4, 5, 6, 7, 8, or 9. In some embodiments, the targeted portion of the LIPA SEC pre-mRNA is in exon 1, 2, 3, 4, 5, 6, 7, 8, 9, or 10. In some embodiments, hybridization of an ASO to the targeted portion of the SEC pre-mRNA results in inclusion of exon 8, and subsequently increases LAL protein production. In some embodiments, the targeted portion of the LIPA SEC pre-mRNA is in exon 8. In some embodiments, the targeted portion of the LIPA SEC pre-mRNA is in intron 7. In some embodiments, the targeted portion of the LIPA SEC pre-mRNA is in intron 8.

LAL Protein

Also described above, the most common LIPA mutation in CESD occurs in exon 8 (e.g., E8SJM. Exon 8 Splice Junction Mutation, c.894G>A). In some embodiments, the c.894G>A mutation occurs in both alleles. In some embodiments, the c.894G>A mutation occurs in one of the two alleles. In some embodiments, additional mutation occurs in one of the two alleles. In some embodiments, the additional mutation occurs in the same allele as the c.894G>A mutation. In other embodiments, the additional mutation occurs is a trans mutation.

In some embodiments, the methods described herein are used to increase the production of a functional LAL protein. As used herein, the term "functional" refers to the amount of activity or function of a LAL protein that is necessary to eliminate any one or more symptoms of a treated disease or condition, e.g., CESD. In some embodiments, the methods are used to increase the production of a partially functional LAL protein. As used herein, the term "partially functional" refers to any amount of activity or function of the LAL protein that is less than the amount of activity or function that is necessary to eliminate or prevent any one or more symptoms of a disease or condition, e.g., CESD. In some embodiments, a partially functional protein or RNA will have at least 10%, at least 20%, at least 30%, at least 40%, at least 50%, at least 60%, at least 70%, at least 75%, at least 80%, at least 85%, at least 90%, or at least 95% less activity relative to the fully functional protein or RNA.

In some embodiments, the method is a method of increasing the expression of the LAL protein by cells of a subject having a SEC pre-mRNA encoding the LAL protein, wherein the subject has CESD caused by a deficient amount of activity of LAL protein, and wherein the deficient amount of the LAL protein is caused by autosomal recessive inheritance. In such an embodiment, the subject has a first allele carrying the c.984G>A mutation and a second allele from which the LAL protein is not produced. In another such embodiment, the subject has a first allele carrying the c.984G>A mutation and a second allele encoding a non-functional LAL protein. In another such embodiment, the subject has a first allele carrying the c.984G>A mutation and a second allele encoding a partially functional LAL protein. In another such an embodiment, the subject has a first allele carrying the c.984G>A mutation and a second allele carrying the c.984G>A mutation. In any of these embodiments, the antisense oligomer binds to a targeted portion of the SEC pre-mRNA transcribed from the allele carrying the c.984G>A mutation, thereby prevent exon skipping of the skippable exon from the pre-mRNA, and causing an increase in the level of mature mRNA encoding functional LAL protein, and an increase in the expression of the LAL protein in the cells of the subject.

In related embodiments, the method is a method of using an ASO to increase the expression of a functional protein or functional RNA. In some embodiments, an ASO is used to increase the expression of LIPA protein in cells of a subject having a SEC pre-mRNA encoding LAL protein, wherein the subject has a deficiency, e.g., CESD, in the amount or function of LAL protein.

In some embodiments, the SEC pre-mRNA transcript that encodes the protein that is causative of the disease or condition is targeted by the ASOs described herein. In some embodiments, a SEC pre-mRNA transcript that encodes a protein that is not causative of the disease is targeted by the ASOs. For example, a disease that is the result of a mutation or deficiency of a first protein in a particular pathway may be ameliorated by targeting a NIE containing pre-mRNA that encodes a second protein, thereby increasing production of the second protein. In some embodiments, the function of the second protein is able to compensate for the mutation or deficiency of the first protein (which is causative of the disease or condition).

In some embodiments, the subject has:
(a) a first mutant allele carrying the c.984G>A mutation from which the LAL protein is produced at a reduced level compared to production from a wild-type allele, and
(b) a second mutant allele from which
    (i) the LAL protein is produced at a reduced level compared to production from a wild-type allele dut to the c.984G>A mutation
    (ii) the LAL protein is produced at a reduced level compared to production from a wild-type allele.
    (iii) the LAL protein is produced in a form having reduced function compared to an equivalent wild-type protein, or
    (iv) the LAL protein is not produced, and
wherein the SEC pre-mRNA is transcribed from the first allele and/or the second allele carrying the c.984G>A mutation. In these embodiments, the ASO binds to a targeted portion of the SEC pre-mRNA transcribed from the first allele or the second allele, thereby promoting exon inclusion from the SEC pre-mRNA, and causing an increase in the level of full-length mRNA encoding LAL protein and an increase in the expression of the target protein or functional RNA in the cells of the subject. In these embodiments, the target protein or functional RNA having an increase in expression level resulting from exon inclusion from the SEC pre-mRNA has full function compared to the equivalent wild-type protein (fully-functional).

In some embodiments, contacting cells with an ASO that is complementary to a targeted portion of a LIPA SEC pre-mRNA transcript results in an increase in the amount of LAL protein produced by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of LAL protein produced by the cell to which the antisense oligomer is contacted is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150)% to about 200%, about 150% to about 250%, about 200% to about 250%, at least about 10%, at least about 20%, at least about 50%, at least about 100%, at least about 150%, at least about 200%, at least about 250)%, or at least about 300%, compared to the amount of target protein produced by a control compound. In some embodiments, the total amount of LAL protein produced by the cell to which the antisense oligomer is contacted is increased about 1.1 to about 10-fold, about 1.5 to about 10-fold, about 2 to about 10)-fold, about 3 to about 10-fold, about 4 to about 10)-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the amount of target protein produced by a control compound. A control compound can be, for example, an oligonucleotide that is not complementary to a targeted portion of the pre-mRNA.

In some embodiments, the level of mRNA encoding LAL protein is increased 1.1 to 10-fold, when compared to the amount of mRNA encoding LAL protein that is produced in a control cell, e.g., one that is not treated with the antisense oligomer or one that is treated with an antisense oligomer that does not bind to the targeted portion of the LIPA SEC containing pre-mRNA.

In some embodiments, the level of mRNA encoding LAL protein is increased 1.1 to 10-fold, when compared to the amount of mRNA encoding LAL protein that is produced in a control cell, e.g., one that is not treated with the antisense oligomer or one that is treated with an antisense oligomer that does not bind to the targeted portion of the LIPA SEC pre-mRNA.

In some embodiments of the present invention, a subject can have a mutation in LIPA. A variety of pathogenic variants have been reported to cause LAL deficiency, including missense variants, nonsense variants, single- and double-nucleotide insertions and deletions, complex insertion/deletions, and splice site variants. The most common pathogenic variant resulting in CESD, c.894G>A, involves a G-to-A transition at −1e of exon 8 relative to the 5′ splice site, disrupting the normal donor splice consensus sequence. Typically, this results in alternative splicing and subsequent skipping of exon 8. In the presence of this pathogenic variant approximately 2%-5% of transcripts are correctly spliced, allowing for residual enzyme activity. The catalytic active site of LAL is composed of amino acid residues Ser153. Asp324, and His353. The active-site serine is part of a lipase consensus sequence connecting a β-strand to an α-helix, known as the nucleophilic elbow, which facilitates interaction between the nucleophile and the histidine and ester carbon in the appropriately oriented complex. Disease results from loss of function of LAL caused by LIPA pathogenic variants that generate truncated proteins or proteins with altered conformations or reduced activity.

In some embodiments, a subject having any LIPA mutation known in the art and described as above can be treated using the methods and compositions described herein. In some embodiments, the mutation is within any LIPA intron or exon. In some embodiments, the mutation is within LIPA exon 8.

Exon Skipping

As used herein, a "skippable exon containing" or "SEC pre-mRNA" is a pre-mRNA transcript that contains at least one skippable exon. Alternative or aberrant splicing of the SEC pre-mRNA can result in the skipping of the at least one skippable exon in the mature mRNA transcripts. The terms "mature mRNA." and "fully-spliced mRNA." are used interchangeably herein to describe a fully processed mRNA. Skipping of the at least one skippable exon can result in non-productive mRNA. Mature mRNA may sometimes lead to aberrant protein expression.

The degree of exon skipping can be expressed as percent exon skipping, e.g., the percentage of transcripts in which a given exon is skipped. In brief, percent exon skipping can be calculated as the percentage of the amount of RNA transcripts with the exon skipped, over the sum of the average of the amount of RNA transcripts with exon skipping plus the average of the amount of RNA transcripts with exon inclusion.

In some embodiments, a skipped exon is an exon that is identified as a skipped exon based on a determination of at least about 5%, at least about 10%, at least about 15%, at least about 20%, at least about 25%, at least about 30%, at least about 35%, at least about 40)%, at least about 45%, or at least about 50%, exclusion from the RNA transcript. In some embodiments, a skipped exon is an exon that is identified as a skipped exon based on a determination of about 5% to about 100%, about 5% to about 95%, about 5% to about 90%, about 5% to about 85%, about 5% to about 80%, about 5% to about 75%, about 5% to about 70)%, about 5% to about 65%, about 5% to about 60%, about 5% to about 55%, about 5% to about 50%, about 5% to about 45%, about 5% to about 40%, about 5% to about 35%, about 5% to about 30)%, about 5% to about 25%, about 5% to about 20%, about 5% to about 15%, about 10% to about 100%, about 10% to about 95%, about 10% to about 90%, about 10% to about 85%, about 10% to about 80%, about 10% to about 75%, about 10% to about 70)%, about 10% to about 65%, about 10% to about 60%, about 10% to about 55%, about 10% to about 50%, about 10% to about 45%, about 10% to about 40)%, about 10% to about 35%, about 10% to about 30%, about 10% to about 25%, about 10% to about 20%, about 15% to about 100%, about 15% to about 95%, about 15% to about 90%, about 15% to about 85%, about 15% to about 80%, about 15% to about 75%, about 15% to about 70)%, about 15% to about 65%, about 15% to about 60)%, about 15% to about 55%, about 15% to about 50%, about 15% to about 45%, about 15% to about 40)%, about 15% to about 35%, about 15% to about 30)%, about 15% to about 25%, about 20% to about 100%, about 20% to about 95%, about 20% to about 90%, about 20% to about 85%, about 20% to about 80)%, about 20% to about 75%, about 20% to about 70%, about 20% to about 65%, about 20% to about 60)%, about 20% to about 55%, about 20% to about 50%, about 20% to about 45%, about 20% to about 40)%, about 20% to about 35%, about 20% to about 30)%, about 25% to about 100%, about 25% to about 95%, about 25% to about 90%, about 25% to about 85%, about 25% to about 80%, about 25% to about 75%, about 25% to about 70)%, about 25% to about 65%, about 25% to about 60%, about 25% to about 55%, about 25% to about 50%, about 25% to about 45%, about 25% to about 40)%, or about 25% to about 35%, exclusion from the RNA transcript. ENCODE data (described by, e.g., Tilgner, et al., 2012. "Deep sequencing of subcellular RNA fractions shows splicing to be predominantly co-transcriptional in the human genome but inefficient for lncRNAs." Genome Research 22(9): 1616-25) can be used to aid in identifying exon skipping.

In some embodiments, contacting cells with an ASO that is complementary to a targeted portion of a LIPA pre-mRNA transcript results in an increase in the amount of LAL protein produced by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of LAL protein produced by the cell to which the antisense oligomer is contacted is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250)%, about 150)% to about 200%, about 150% to about 250%, about 200% to about 250%, at least about 10%, at least about 20%, at least about 50%, at least about 100%, at least about 150%, at least about 200%, at least about 250%, or at least about 300%, compared to the amount of target protein produced by a control compound. In some embodiments, the total amount of LAL protein produced by the cell to which the antisense oligomer is contacted is increased about 1.1 to about 10-fold, about 1.5 to about 10-fold, about 2 to about 10-fold, about 3 to about 10)-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the amount of target protein produced by a control compound. A control compound can be, for example, an oligonucleotide that is not complementary to a targeted portion of the pre-mRNA.

In some embodiments, contacting cells with an ASO that is complementary to a targeted portion of a LIPA pre-mRNA transcript results in an increase in the amount of mRNA encoding LAL, including the mature mRNA encoding the target protein. In some embodiments, the amount of mRNA encoding LAL protein, or the mature mRNA encoding the LAL protein, is increased by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of the mRNA encoding LAL protein, or the mature mRNA encoding LAL protein produced in the cell to which the antisense oligomer is contacted is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250)%, at least about 10%, at least about 20%, at least about 50%, at least about 100%, at least about 150%, at least about 200%, at least about 250%, or at least about 300%, compared to the amount of mature RNA produced in an untreated cell. e.g., an untreated cell or a cell treated with a control compound. In some embodiments, the total amount of the mRNA encoding LAL protein, or the mature mRNA encoding LAL protein produced in the cell to which the antisense oligomer is contacted is increased about 1.1 to about 10-fold, about 1.5 to about 10)-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold compared to the amount of mature RNA produced in an untreated cell, e.g., an untreated cell or a cell treated with a control compound. A control compound can be, for example, an oligonucleotide that is not complementary to a targeted portion of the LIPA SEC pre-mRNA.

Therapeutic Agents

In various embodiments of the present disclosure, compositions and methods comprising a therapeutic agent are provided to modulate protein expression level of LAL. In some embodiments, provided herein are compositions and methods to modulate alternative splicing of LIPA pre-mRNA. In some embodiments, provided herein are compositions and methods to prevent exon skipping in the splicing of LIPA pre-mRNA, e.g., to prevent skipping of an exon during splicing of LIPA pre-mRNA.

A therapeutic agent disclosed herein can be an exon skipping repressor agent. In some embodiments, a therapeutic agent may comprise a polynucleic acid polymer.

According to one aspect of the present disclosure, provided herein is a method of treatment or prevention of a condition associated with a functional-LAL protein deficiency, comprising administering a exon skipping repressor agent to a subject to increase levels of functional LAL protein, wherein the agent binds to a region of the pre-mRNA transcript to decrease skipping of the exon in the mature transcript. For example, provided herein is a method of treatment or prevention of a condition associated with a functional-LAL protein deficiency, comprising administering a exon skipping repressor agent to a subject to increase levels of functional LAL protein, wherein the agent binds to a region of an exon or an intron (e.g., exon 8, intron 7 or intron 8 in human LIPA gene) of the pre-mRNA transcript.

Where reference is made to reducing exon skipping in the mature mRNA, the reduction may be complete, e.g., 100%, or may be partial. The reduction may be clinically significant. The reduction/correction may be relative to the level of exon skipping in the subject without treatment, or relative to the amount of exon skipping in a population of similar subjects. The reduction/correction may be at least 10% less exon skipping relative to the average subject, or the subject prior to treatment. The reduction may be at least 20% less exon skipping relative to an average subject, or the subject prior to treatment. The reduction may be at least 40% less exon skipping relative to an average subject, or the subject prior to treatment. The reduction may be at least 50% less exon skipping relative to an average subject, or the subject prior to treatment. The reduction may be at least 60% less exon skipping relative to an average subject, or the subject prior to treatment. The reduction may be at least 80% less exon skipping relative to an average subject, or the subject prior to treatment. The reduction may be at least 90% less exon skipping relative to an average subject, or the subject prior to treatment.

Where reference is made to increasing functional-LAL protein levels, the increase may be clinically significant. The increase may be relative to the level of functional-LAL protein in the subject without treatment, or relative to the amount of functional-LAL protein in a population of similar subjects. The increase may be at least 10% more functional-LAL protein relative to the average subject, or the subject prior to treatment. The increase may be at least 20% more functional-LAL protein relative to the average subject, or the subject prior to treatment. The increase may be at least 40% more functional-LAL protein relative to the average subject, or the subject prior to treatment. The increase may be at least 50% more functional-LAL protein relative to the average subject, or the subject prior to treatment. The increase may be at least 80% more functional-LAL protein relative to the average subject, or the subject prior to treatment. The increase may be at least 100% more functional-LAL protein relative to the average subject, or the subject prior to treatment. The increase may be at least 200% more functional-LAL protein relative to the average subject, or the subject prior to treatment. The increase may be at least 500% more functional-LAL protein relative to the average subject, or the subject prior to treatment.

In embodiments wherein the exon skipping repressor agent comprises a polynucleic acid polymer, the polynucleic acid polymer may be about 50 nucleotides in length. The polynucleic acid polymer may be about 45 nucleotides in length. The polynucleic acid polymer may be about 40) nucleotides in length. The polynucleic acid polymer may be about 35 nucleotides in length. The polynucleic acid polymer may be about 30 nucleotides in length. The polynucleic acid polymer may be about 24 nucleotides in length. The polynucleic acid polymer may be about 25 nucleotides in length. The polynucleic acid polymer may be about 20 nucleotides in length. The polynucleic acid polymer may be about 19 nucleotides in length. The polynucleic acid polymer may be about 18 nucleotides in length. The polynucleic acid polymer may be about 17 nucleotides in length. The polynucleic acid polymer may be about 16 nucleotides in length. The polynucleic acid polymer may be about 15 nucleotides in length. The polynucleic acid polymer may be about 14 nucleotides in length. The polynucleic acid polymer may be about 13 nucleotides in length. The polynucleic acid polymer may be about 12 nucleotides in length. The polynucleic acid polymer may be about 11 nucleotides in length. The polynucleic acid polymer may be about 10 nucleotides in length. The polynucleic acid polymer may be between about 10 and about 50 nucleotides in length. The polynucleic acid polymer may be between about 10 and about 45 nucleotides in length. The polynucleic acid polymer may be between about 10 and about 40 nucleotides in length. The polynucleic acid polymer may be between about 10 and about 35 nucleotides in length. The polynucleic acid polymer may be between about 10 and about 30 nucleotides in length. The polynucleic acid polymer may be between about 10 and about 25 nucleotides in length. The polynucleic acid polymer may be between about 10) and about 20 nucleotides in length. The polynucleic acid polymer may be between about 15 and about 25 nucleotides in length. The polynucleic acid polymer may be between about 15 and about 30 nucleotides in length. The polynucleic acid polymer may be between about 12 and about 30 nucleotides in length.

The sequence of the polynucleic acid polymer may be at least 50%, 55%, 60%, 65%, 70%, 75%, 80%, 85%, 90%, 91%, 92%, 93%, 94%, 95%, 96%, 97%, 98%, 99%, or 99.5% complementary to a target sequence of an mRNA transcript, e.g., a partially processed mRNA transcript. The sequence of the polynucleic acid polymer may be 100% complementary to a target sequence of a pre-mRNA transcript.

The sequence of the polynucleic acid polymer may have 4 or fewer mismatches to a target sequence of the pre-mRNA transcript. The sequence of the polynucleic acid polymer may have 3 or fewer mismatches to a target sequence of the pre-mRNA transcript. The sequence of the polynucleic acid polymer may have 2 or fewer mismatches to a target sequence of the pre-mRNA transcript. The sequence of the polynucleic acid polymer may have 1 or fewer mismatches to a target sequence of the pre-mRNA transcript. The sequence of the polynucleic acid polymer may have no mismatches to a target sequence of the pre-mRNA transcript.

In some embodiments, the polynucleic acid polymer may specifically hybridize to a target sequence of the pre-mRNA transcript. For example, the polynucleic acid polymer may have 91%, 92%. 93%, 94%, 95%, 96%, 97%, 98%, 99%, 99.5% or 100% sequence complementarity to a target sequence of the pre-mRNA transcript. The hybridization may be under high stringent hybridization conditions.

The polynucleic acid polymer may have a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from the group consisting of SEQ ID NOs: 5-63. The polynucleic acid polymer may have a sequence with 100% sequence identity to a sequence selected from the group consisting of SEQ ID NOs: 5-63.

Where reference is made to a polynucleic acid polymer sequence, the skilled person will understand that one or more substitutions may be tolerated, optionally two substitutions may be tolerated in the sequence, such that it maintains the ability to hybridize to the target sequence; or where the substitution is in a target sequence, the ability to be recognized as the target sequence. References to sequence identity may be determined by BLAST sequence alignment using standard/default parameters. For example, the sequence may have 99% identity and still function according to the present disclosure. In other embodiments, the sequence may have 98% identity and still function according to the present disclosure. In another embodiment, the sequence may have 95% identity and still function according to the present disclosure. In another embodiment, the sequence may have 90% identity and still function according to the present disclosure.

Antisense Oligomers

Provided herein is a composition comprising an antisense oligomer that prevents exon skipping by binding to a targeted portion of a LIPA SEC pre-mRNA. As used herein, the terms "ASO" and "antisense oligomer" are used interchangeably and refer to an oligomer such as a polynucleotide, comprising nucleobases that hybridizes to a target nucleic acid (e.g., a LIPA SEC pre-mRNA) sequence by Watson-Crick base pairing or wobble base pairing (G-U). The ASO may have exact sequence complementary to the target sequence or near complementarity (e.g., sufficient complementarity to bind the target sequence and enhancing splicing at a splice site). ASOs are designed so that they bind (hybridize) to a target nucleic acid (e.g., a targeted portion of a pre-mRNA transcript) and remain hybridized under physiological conditions. Typically, if they hybridize to a site other than the intended (targeted) nucleic acid sequence, they hybridize to a limited number of sequences that are not a target nucleic acid (to a few sites other than a target nucleic acid). Design of an ASO can take into consideration the occurrence of the nucleic acid sequence of the targeted portion of the pre-mRNA transcript or a sufficiently similar nucleic acid sequence in other locations in the genome or cellular pre-mRNA or transcriptome, such that the likelihood the ASO will bind other sites and cause "off-target" effects is limited. Any antisense oligomers known in the art, for example in PCT Application No. PCT/US2014/054151, published as WO 2015/035091, titled "Reducing Nonsense-Mediated mRNA Decay." incorporated by reference herein, can be used to practice the methods described herein.

In some embodiments. ASOs "specifically hybridize" to or are "specific" to a target nucleic acid or a targeted portion of a RIC pre-mRNA. Typically such hybridization occurs with a $T_m$ substantially greater than 37° C., preferably at least 50° ° C., and typically between 60° C., to approximately 90° C. Such hybridization preferably corresponds to stringent hybridization conditions. At a given ionic strength and pH, the $T_m$ is the temperature at which 50% of a target sequence hybridizes to a complementary oligonucleotide.

Oligomers, such as oligonucleotides, are "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree to which one polynucleotide is complementary with another) is quantifiable in terms of the proportion (e.g., the percentage) of bases in opposing strands that are expected to form hydrogen bonds with each other, according to generally accepted base-pairing rules. The sequence of an antisense oligomer (ASO) need not be 100% complementary to that of its target nucleic acid to hybridize. In certain embodiments. ASOs can comprise at least 70%, at least 75%, at least 80%, at least 85%, at least 90%, at least 95%, at least 96%, at least 97%, at least 98%, or at least 99% sequence complementarity to a target region within the target nucleic acid sequence to which they are targeted. For example, an ASO in which 18 of 20 nucleobases of the oligomeric compound are complementary to a target region, and would therefore specifically hybridize, would represent 90 percent complementarity. In this example, the remaining non-complementary nucleobases may be clustered together or interspersed with complementary nucleobases and need not be contiguous to each other or to complementary nucleobases. Percent complementarity of an ASO with a region of a target nucleic acid can be determined routinely using BLAST programs (basic local alignment search tools) and PowerBLAST programs known in the art (Altschul, et al., J. Mol. Biol., 1990, 215, 403-410; Zhang and Madden. Genome Res., 1997, 7, 649-656).

An ASO need not hybridize to all nucleobases in a target sequence and the nucleobases to which it does hybridize may be contiguous or noncontiguous. ASOs may hybridize over one or more segments of a pre-mRNA transcript, such that intervening or adjacent segments are not involved in the hybridization event (e.g., a loop structure or hairpin structure may be formed). In certain embodiments, an ASO hybridizes to noncontiguous nucleobases in a target pre-mRNA transcript. For example, an ASO can hybridize to nucleobases in a pre-mRNA transcript that are separated by one or more nucleobase(s) to which the ASO does not hybridize.

The ASOs described herein comprise nucleobases that are complementary to nucleobases present in a target portion of a SEC pre-mRNA. The term ASO embodies oligonucleotides and any other oligomeric molecule that comprises nucleobases capable of hybridizing to a complementary nucleobase on a target mRNA but does not comprise a sugar moiety, such as a peptide nucleic acid (PNA). The ASOs may comprise naturally-occurring nucleotides, nucleotide analogs, modified nucleotides, or any combination of two or three of the preceding. The term "naturally occurring nucleotides" includes deoxyribonucleotides and ribonucleotides. The term "modified nucleotides" includes nucleotides with modified or substituted sugar groups and/or having a modified backbone. In some embodiments, all of the nucleotides of the ASO are modified nucleotides. Chemical modifications of ASOs or components of ASOs that are compatible with the methods and compositions described herein will be evident to one of skill in the art and can be found, for example, in U.S. Pat. No. 8,258,109 B2, U.S. Pat. No. 5,656,612, U.S. Patent Publication No. 2012/0190728, and Dias and Stein, Mol. Cancer Ther. 2002, 347-355, herein incorporated by reference in their entirety.

One or more nucleobases of an ASO may be any naturally occurring, unmodified nucleobase such as adenine, guanine, cytosine, thymine and uracil, or any synthetic or modified nucleobase that is sufficiently similar to an unmodified nucleobase such that it is capable of hydrogen bonding with a nucleobase present on a target pre-mRNA. Examples of modified nucleobases include, without limitation, hypoxanthine, xanthine, 7-methylguanine, 5, 6-dihydrouracil, 5-methylcytosine, and 5-hydroxymethoylcytosine.

The ASOs described herein also comprise a backbone structure that connects the components of an oligomer. The term "backbone structure" and "oligomer linkages" may be used interchangeably and refer to the connection between monomers of the ASO. In naturally occurring oligonucleotides, the backbone comprises a 3'-5' phosphodiester linkage connecting sugar moieties of the oligomer. The backbone structure or oligomer linkages of the ASOs described herein may include (but are not limited to) phosphorothioate, phosphorodithioate, phosphoroselenoate, phosphorodiselenoate, phosphoroanilothioate, phosphoraniladate, phosphoramidate, and the like. Sec, e.g., LaPlanche, et al., Nucleic Acids Res. 14:9081 (1986); Stec, et al., J. Am. Chem. Soc. 106:6077 (1984), Stein, et al., Nucleic Acids Res. 16:3209 (1988), Zon, et al., Anti Cancer Drug Design 6:539 (1991); Zon, et al., Oligonucleotides and Analogues: A Practical Approach, pp. 87-108 (F. Eckstein. Ed., Oxford University Press. Oxford England (1991)); Stec, et al., U.S. Pat. No. 5,151,510; Uhlmann and Peyman. Chemical Reviews 90:543 (1990). In some embodiments, the backbone structure of the ASO does not contain phosphorous but rather contains peptide bonds, for example in a peptide nucleic acid (PNA), or linking groups including carbamate, amides, and linear and cyclic hydrocarbon groups. In some embodiments, the backbone modification is a phosphothioate linkage. In some embodiments, the backbone modification is a phosphoramidate linkage.

In some embodiments, the stereochemistry at each of the phosphorus internucleotide linkages of the ASO backbone is random. In some embodiments, the stereochemistry at each of the phosphorus internucleotide linkages of the ASO backbone is controlled and is not random. For example, U.S. Pat. App. Pub. No. 2014/0194610. "Methods for the Synthesis of Functionalized Nucleic Acids." incorporated herein by reference, describes methods for independently selecting the handedness of chirality at each phosphorous atom in a nucleic acid oligomer. In some embodiments, an ASO used in the methods of the invention, including, but not limited to, any of the ASOs set forth herein in Table 3, comprises an ASO having phosphorus internucleotide linkages that are not random. In some embodiments, a composition used in the methods of the invention comprises a pure diastereomeric ASO. In some embodiments, a composition used in the methods of the invention comprises an ASO that has diastereomeric purity of at least about 90%, at least about 91%, at least about 92%, at least about 93%, at least about 94%, at least about 95%, at least about 96%, at least about 97%, at least about 98%, at least about 99%, about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, or about 99% to about 100%.

In some embodiments, the ASO has a nonrandom mixture of Rp and Sp configurations at its phosphorus internucleotide linkages. For example, it has been suggested that a mix of Rp and Sp is required in antisense oligonucleotides to achieve a balance between good activity and nuclease stability (Wan, et al., 2014. "Synthesis, biophysical properties and biological activity of second generation antisense oligonucleotides containing chiral phosphorothioate linkages." Nucleic Acids Research 42(22): 13456-13468, incorporated herein by reference). In some embodiments, an ASO used in the methods of the invention, including, but not limited to, any of the ASOs set forth herein in Table 3, comprises about 5-100% Rp, at least about 5% Rp, at least about 10% Rp, at least about 15% Rp, at least about 20% Rp, at least about 25% Rp, at least about 30% Rp, at least about 35% Rp, at least about 40% Rp, at least about 45% Rp, at least about 50% Rp, at least about 55% Rp, at least about 60% Rp, at least about 65% Rp, at least about 70% Rp, at least about 75% Rp, at least about 80% Rp, at least about 85% Rp, at least about 90% Rp, or at least about 95% Rp, with the remainder Sp, or about 100% Rp. In some embodiments, an ASO used in the methods of the invention, including, but not limited to, any of the ASOs set forth herein in Table 3, comprises about 10% to about 100% Rp, about 15% to about 100% Rp, about 20% to about 100% Rp, about 25% to about 100% Rp, about 30% to about 100% Rp, about 35% to about 100% Rp, about 40% to about 100% Rp, about 45% to about 100% Rp, about 50% to about 100% Rp, about 55% to about 100% Rp, about 60% to about 100% Rp, about 65% to about 100% Rp, about 70% to about 100% Rp, about 75% to about 100% Rp, about 80% to about 100% Rp, about 85% to about 100% Rp, about 90% to about 100% Rp, or about 95% to about 100% Rp, about 20% to about 80% Rp, about 25% to about 75% Rp, about 30% to about 70% Rp, about 40% to about 60% Rp, or about 45% to about 55% Rp, with the remainder Sp.

In embodiments, an ASO used in the methods of the invention, including, but not limited to, any of the ASOs set forth herein in Table 3, comprises about 5-100% Sp, at least about 5% Sp, at least about 10% Sp, at least about 15% Sp, at least about 20% Sp, at least about 25% Sp, at least about 30% Sp, at least about 35% Sp, at least about 40% Sp, at least about 45% Sp, at least about 50% Sp, at least about 55% Sp, at least about 60% Sp, at least about 65% Sp, at least about 70% Sp, at least about 75% Sp, at least about 80% Sp, at least about 85% Sp, at least about 90% Sp, or at least about 95% Sp, with the remainder Rp, or about 100% Sp. In some embodiments, an ASO used in the methods of the invention, including, but not limited to, any of the ASOs set forth herein in Table 3, comprises about 10% to about 100% Sp, about 15% to about 100% Sp, about 20% to about 100% Sp, about 25% to about 100% Sp, about 30% to about 100% Sp, about 35% to about 100% Sp, about 40% to about 100% Sp, about 45% to about 100% Sp, about 50% to about 100% Sp, about 55% to about 100% Sp, about 60% to about 100% Sp, about 65% to about 100% Sp, about 70% to about 100% Sp, about 75% to about 100% Sp, about 80% to about 100% Sp, about 85% to about 100% Sp, about 90% to about 100% Sp, or about 95% to about 100% Sp, about 20% to about 80% Sp, about 25% to about 75% Sp, about 30% to about 70% Sp, about 40% to about 60% Sp, or about 45% to about 55% Sp, with the remainder Rp.

Any of the ASOs described herein may contain a sugar moiety that comprises ribose or deoxyribose, as present in naturally occurring nucleotides, or a modified sugar moiety or sugar analog, including a morpholine ring. Non-limiting examples of modified sugar moieties include 2' substitutions such as 2'-O-methyl (2'-O-Me), 2'-O-methoxyethyl (2'MOE), 2'-O-aminoethyl, 2'F; N3'→P5' phosphoramidate, 2 dimethylaminooxyethoxy, 2'dimethylaminoethoxyethoxy, 2-guanidinidium, 2'-O-guanidinium ethyl, carbamate modified sugars, and bicyclic modified sugars. In some embodiments, the sugar moiety modification is selected from 2'-O-Me, 2'F, and 2'MOE. In some embodiments, the sugar moiety modification is an extra bridge bond, such as in a locked nucleic acid (LNA). In some embodiments the sugar analog contains a morpholine ring, such as phosphorodiamidate morpholino (PMO). In some embodiments, the sugar moiety comprises a ribofuransyl or 2'deoxyribofuranosyl modification. In some embodiments, the sugar moiety comprises 2'4'-constrained 2'O-methyloxyethyl (cMOE) modifications. In some embodiments, the sugar moiety comprises cEt 2', 4' constrained 2'-O ethyl BNA modifications. In some embodiments, the sugar moiety comprises tricycloDNA (tcDNA) modifications. In some embodiments, the sugar moiety comprises ethylene nucleic acid (ENA) modifications. In some embodiments, the sugar moiety comprises MCE modifications. Modifications are known in the art and described in the literature, e.g., by Jarver, et al., 2014. "A Chemical View of Oligonucleotides for Exon Skipping and Related Drug Applications." Nucleic Acid Therapeutics 24(1): 37-47, incorporated by reference for this purpose herein.

In some embodiments, each monomer of the ASO is modified in the same way, for example each linkage of the backbone of the ASO comprises a phosphorothioate linkage or each ribose sugar moiety comprises a 2'O-methyl modification. Such modifications that are present on each of the monomer components of an ASO are referred to as "uniform modifications." In some embodiments, a combination of different modifications may be desired, for example, an ASO may comprise a combination of phosphorodiamidate linkages and sugar moieties comprising morpholine rings (morpholinos). Combinations of different modifications to an ASO are referred to as "mixed modifications" or "mixed chemistries."

In some embodiments, the ASO comprises one or more backbone modification. In some embodiments, the ASO comprises one or more sugar moiety modification. In some embodiments, the ASO comprises one or more backbone modification and one or more sugar moiety modification. In some embodiments, the ASO comprises 2'MOE modifications and a phosphorothioate backbone. In some embodiments, the ASO comprises a phosphorodiamidate morpholino (PMO). In some embodiments, the ASO comprises a peptide nucleic acid (PNA). Any of the ASOs or any component of an ASO (e.g., a nucleobase, sugar moiety, backbone) described herein may be modified in order to achieve desired properties or activities of the ASO or reduce undesired properties or activities of the ASO. In some embodiments, an ASO or one or more component of any ASO may be modified to enhance binding affinity to a target sequence on a pre-mRNA transcript; reduce binding to any non-target sequence; reduce degradation by cellular nucleases (i.e., RNase H); improve uptake of the ASO into a cell and/or into the nucleus of a cell; alter the pharmacokinetics or pharmacodynamics of the ASO; and modulate the half-life of the ASO.

In some embodiments, the ASOs are comprised of 2'-O-(2-methoxyethyl) (MOE) phosphorothioate-modified nucleotides. ASOs comprised of such nucleotides are especially well-suited to the methods disclosed herein; oligomers having such modifications have been shown to have significantly enhanced resistance to nuclease degradation and increased bioavailability, making them suitable, for example, for oral delivery in some embodiments described herein. Sec e.g., Geary, et al., J Pharmacol Exp Ther. 2001: 296(3): 890-7: Geary, et al., J Pharmacol Exp Ther. 2001: 296(3): 898-904.

Methods of synthesizing ASOs will be known to one of skill in the art. Alternatively or in addition. ASOs may be obtained from a commercial source.

Unless specified otherwise, the left-hand end of single-stranded nucleic acid (e.g., pre-mRNA transcript, oligonucleotide. ASO, etc.) sequences is the 5' end and the left-hand direction of single or double-stranded nucleic acid sequences is referred to as the 5' direction. Similarly, the right-hand end or direction of a nucleic acid sequence (single or double stranded) is the 3' end or direction. Generally, a region or sequence that is 5' to a reference point in a nucleic acid is referred to as "upstream." and a region or sequence that is 3' to a reference point in a nucleic acid is referred to as "downstream." Generally, the 5' direction or end of an mRNA is where the initiation or start codon is located, while the 3' end or direction is where the termination codon is located. In some embodiments, nucleotides that are upstream of a reference point in a nucleic acid may be designated by a negative number, while nucleotides that are downstream of a reference point may be designated by a positive number. For example, a reference point (e.g., an exon-exon junction in mRNA) may be designated as the "zero" site, and a nucleotide that is directly adjacent and upstream of the reference point is designated "minus one." e.g., "−1." while a nucleotide that is directly adjacent and downstream of the reference point is designated "plus one." e.g., "+1."

In some embodiments, the ASOs are complementary to (and bind to) a targeted portion of a LIPA SEC pre-mRNA that is downstream (in the 3' direction) of the 5' splice site of the skippable exon in a LIPA SEC pre-mRNA (e.g., the direction designated by positive numbers relative to the 5' splice site). In some embodiments, the ASOs are complementary to a targeted portion of the LIPA SEC pre-mRNA that is within the region about +6 to about +500 relative to the 5' splice site of the skippable exon. In some embodiments, the ASO is not complementary to nucleotides +1 to +5 relative to the 5' splice site (the first five nucleotides located downstream of the 5' splice site). In some embodiments, the ASOs may be complementary to a targeted portion of a LIPA SEC pre-mRNA that is within the region between nucleotides +6 and +100 relative to the 5' splice site of the skippable exon. In some aspects, the ASOs are complementary to a targeted portion that is within the region about +6 to about +500, about +6 to about +490, about +6 to about +480, about +6 to about +470, about +6 to about +460, about +6 to about +450, about +6 to about +440, about +6 to about +430, about +6 to about +420, about +6 to about +410, about +6 to about +4000, about +6 to about +390, about +6 to about +380, about +6 to about +370, about +6 to about +360, about +6 to about +350, about +6 to about +340, about +6 to about +330, about +6 to about +320, about +6 to about +310, about +6 to about +300, about +6 to about +290, about +6 to about +280, about +6 to about +270, about +6 to about +260, about +6 to about +250, about +6 to about +240, about +6 to about +230, about +6 to about +220, about +6 to about +210, about +6 to about +200, about +6 to about +190, about +6 to about +180, about +6 to about +170, about +6 to about +160, about +6 to about +150, about +6 to about +140, about +6 to about +130, about +6 to about +120, about +6 to about +110, about +6 to about +100, about +6 to about +90, about +6 to about +80, about +6 to about +70, about +6 to about +60, about +6 to about +50, about +6 to about +40, about +6 to about +30, or about +6 to about +20 relative to 5' splice site of the skippable exon.

In some embodiments, the ASOs are complementary to (and bind to) a targeted portion of a LIPA SEC pre-mRNA that is upstream (in the 5' direction) of the 3' splice site of the skippable exon in a LIPA SEC pre-mRNA (e.g., the direction designated by negative numbers relative to the 3' splice site). In some embodiments, the ASOs are complementary to a targeted portion of the LIPA SEC pre-mRNA that is within the region about −16 to about −500 relative to the 3' splice site of the skippable exon. In some embodiments, the ASO is not complementary to nucleotides −1 to −15 relative to the 5' splice site (the first five nucleotides located downstream of the 5' splice site). In some embodiments, the ASOs may be complementary to a targeted portion of a LIPA SEC pre-mRNA that is within the region between nucleotides −16 and −100 relative to the 3' splice site of the skippable exon. In some aspects, the ASOs are complementary to a targeted portion that is within the region about +6 to about +500, about +6 to about +490, about +6 to about +480, about +6 to about +470, about +6 to about +460, about +6 to about +450, about +6 to about +440, about +6 to about +430, about +6 to about +420, about +6 to about +410, about +6 to about +400, about +6 to about +390, about +6 to about +380, about +6 to about +370, about +6 to about +360, about +6 to about +350, about +6 to about +340, about +6 to about +330, about +6 to about +320, about +6 to about +310, about +6 to about +300, about +6 to about +290, about +6 to about +280, about +6 to about +270, about +6 to about +260, about +6 to about +250, about +6 to about +240, about +6 to about +230, about +6 to about +220, about +6 to about +210, about +6 to about +200, about +6 to about +190, about +6 to about +180, about +6 to about +170, about +6 to about +160, about +6 to about +150, about +6 to about +140, about +6 to about +130, about +6 to about +120, about +6 to about +110, about +6 to about +100, about +6 to about +90, about +6 to about +80, about +6 to about +70, about +6 to about +60, about +6 to about +50, about +6 to about +40, about +6 to about +30, or about +6 to about +20 relative to 3' splice site of the skippable exon.

In some embodiments, the targeted portion of the LIPA SEC pre-mRNA is within the region −4c relative to the 3' splice site (5' end) of the skippable exon to +2e relative to the 5' splice site (3' end) of the skippable exon.

The ASOs may be of any length suitable for specific binding and effective enhancement of splicing. In some embodiments, the ASOs consist of 8 to 50 nucleobases. For example, the ASO may be 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, or 50 nucleobases in length. In some embodiments, the ASOs consist of more than 50 nucleobases. In some embodiments, the ASO is from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases. 10 to 25 nucleobases, 10 to 20 nucleobases, 10 to 15 nucleobases, 11 to 50 nucleobases, 11 to 40) nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30) nucleobases, 12 to 25 nucleobases, 12 to 20 nucleobases, 12 to 15 nucleobases, 13 to 50 nucleobases, 13 to 40 nucleobases, 13 to 35 nucleobases, 13 to 30 nucleobases, 13 to 25 nucleobases, 13 to 20 nucleobases, 14 to 50 nucleobases, 14 to 40 nucleobases, 14 to 35 nucleobases, 14 to 30 nucleobases, 14 to 25 nucleobases, 14 to 20 nucleobases, 15 to 50 nucleobases, 15 to 40 nucleobases, 15 to 35 nucleobases, 15 to 30 nucleobases, 15 to 25 nucleobases, 15 to 20 nucleobases, 20 to 50 nucleobases, 20 to 40 nucleobases, 20 to 35 nucleobases, 20 to 30 nucleobases, 20 to 25 nucleobases, 25 to 50) nucleobases, 25 to 40 nucleobases, 25 to 35 nucleobases, or 25 to 30 nucleobases in length. In some embodiments, the ASOs are 15 nucleotides in length. In some embodiments, the ASOs are 16 nucleotides in length. In some embodiments, the ASOs are 17 nucleotides in length. In some embodiments, the ASOs are 18 nucleotides in length. In some embodiments, the ASOs are 25 nucleotides in length.

In some embodiments, two or more ASOs with different chemistries but complementary to the same targeted portion of the SEC pre-mRNA are used. In some embodiments, two or more ASOs that are complementary to different targeted portions of the SEC pre-mRNA are used.

In some embodiments, the antisense oligonucleotides of the invention are chemically linked to one or more moieties or conjugates, e.g., a targeting moiety or other conjugate that enhances the activity or cellular uptake of the oligonucleotide. Such moieties include, but are not limited to, a lipid moiety, e.g., as a cholesterol moiety, a cholesteryl moiety, an aliphatic chain, e.g., dodecandiol or undecyl residues, a polyamine or a polyethylene glycol chain, or adamantane acetic acid. Oligonucleotides comprising lipophilic moieties and preparation methods have been described in the published literature. In embodiments, the antisense oligonucleotide is conjugated with a moiety including, but not limited to, an abasic nucleotide, a polyether, a polyamine, a polyamide, a peptides, a carbohydrate, e.g., N-acetylgalactosamine (GalNAc). N—Ac-Glucosamine (GluNAc), or mannose (e.g., mannose-6-phosphate), a lipid, or a polyhydrocarbon compound. Conjugates can be linked to one or more of any nucleotides comprising the antisense oligonucleotide at any of several positions on the sugar, base or phosphate group, as understood in the art and described in the literature, e.g., using a linker. Linkers can include a bivalent or trivalent branched linker. In embodiments, the conjugate is attached to the 3' end of the antisense oligonucleotide. Methods of preparing oligonucleotide conjugates are described, e.g., in U.S. Pat. No. 8,450,467. "Carbohydrate conjugates as delivery agents for oligonucleotides." incorporated by reference herein.

In some embodiments, the nucleic acid to be targeted by an ASO is a LIPA SEC pre-mRNA expressed in a cell, such as a eukaryotic cell. In some embodiments, the term "cell" may refer to a population of cells. In some embodiments, the cell is in a subject. In some embodiments, the cell is isolated from a subject. In some embodiments, the cell is ex vivo. In some embodiments, the cell is a condition or disease-relevant cell or a cell line. In some embodiments, the cell is in vitro (e.g., in cell culture).

Pharmaceutical Compositions

Pharmaceutical compositions or formulations comprising the agent, e.g., antisense oligonucleotide, of the described compositions and for use in any of the described methods can be prepared according to conventional techniques well known in the pharmaceutical industry and described in the published literature. In embodiments, a pharmaceutical composition or formulation for treating a subject comprises an effective amount of any antisense oligomer as described herein, or a pharmaceutically acceptable salt, solvate, hydrate or ester thereof. The pharmaceutical formulation comprising an antisense oligomer may further comprise a pharmaceutically acceptable excipient, diluent or carrier.

Pharmaceutically acceptable salts are suitable for use in contact with the tissues of humans and lower animals without undue toxicity, irritation, allergic response, etc., and are commensurate with a reasonable benefit/risk ratio. (See, e.g., S. M. Berge, et al., J. Pharmaceutical Sciences, 66: 1-19 (1977), incorporated herein by reference for this purpose. The salts can be prepared in situ during the final isolation and purification of the compounds, or separately by reaction between the free base and a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other documented methodologies such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In some embodiments, the compositions are formulated into any of many possible dosage forms such as, but not limited to, tablets, capsules, gel capsules, liquid syrups, soft gels, suppositories, and enemas. In some embodiments, the compositions are formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers. In some embodiments, a pharmaceutical formulation or composition of the present invention includes, but is not limited to, a solution, emulsion, microemulsion, foam or liposome-containing formulation (e.g., cationic or noncationic liposomes).

The pharmaceutical composition or formulation of the present invention may comprise one or more penetration enhancer, carrier, excipients or other active or inactive ingredients as appropriate and well known to those of skill in the art or described in the published literature. In some embodiments, liposomes also include sterically stabilized liposomes, e.g., liposomes comprising one or more specialized lipids. These specialized lipids result in liposomes with enhanced circulation lifetimes. In some embodiments, a sterically stabilized liposome comprises one or more glycolipids or is derivatized with one or more hydrophilic polymers, such as a polyethylene glycol (PEG) moiety. In some embodiments, a surfactant is included in the pharmaceutical formulation or compositions. The use of surfactants in drug products, formulations and emulsions is well known in the art. In some embodiments, the present invention employs a penetration enhancer to effect the efficient delivery of the antisense oligonucleotide, e.g., to aid diffusion across cell membranes and/or enhance the permeability of a lipophilic drug. In some embodiments, the penetration enhancers are a surfactant, fatty acid, bile salt, chelating agent, or non-chelating nonsurfactant.

In some embodiments, the pharmaceutical formulation comprises multiple antisense oligonucleotides. In some embodiments, the antisense oligonucleotide is administered in combination with another drug or therapeutic agent.

Treatment of Subjects

Any of the compositions provided herein may be administered to an individual. "Individual" may be used interchangeably with "subject" or "patient." An individual may be a mammal, for example a human or animal such as a non-human primate, a rodent, a rabbit, a rat, a mouse, a horse, a donkey, a goat, a cat, a dog, a cow, a pig, or a sheep. In some embodiments, the individual is a human. In some embodiments, the individual is a fetus, an embryo, or a child. In other embodiments, the individual may be another eukaryotic organism, such as a plant. In some embodiments, the compositions provided herein are administered to a cell ex vivo.

In some embodiments, the compositions provided herein are administered to an individual as a method of treating a disease or disorder. In some embodiments, the individual has a genetic disease, such as any of the diseases described herein. In some embodiments, the individual is at risk of having the disease, such as any of the diseases described herein. In some embodiments, the individual is at increased risk of having a disease or disorder caused by insufficient amount of a protein or insufficient activity of a protein. In some embodiments, if an individual is "at an increased risk" of having a disease or disorder caused by insufficient amount of a protein or insufficient activity of a protein, the method involves preventative or prophylactic treatment. For example, an individual may be at an increased risk of having such a disease or disorder because of family history of the disease. Typically, individuals at an increased risk of having such a disease or disorder benefit from prophylactic treatment (e.g., by preventing or delaying the onset or progression of the disease or disorder). In some embodiments, a fetus is treated in utero, e.g., by administering the ASO composition to the fetus directly or indirectly (e.g., via the mother).

Suitable routes for administration of ASOs of the present invention may vary depending on cell type to which delivery of the ASOs is desired. Multiple tissues and organs can be affected by CESD. In some embodiments, the liver can be the most significantly affected tissue. The ASOs of the present invention may be administered to patients parenterally, for example, by intrathecal injection, intracerebroventricular injection, intraperitoneal injection, intramuscular injection, subcutaneous injection, or intravenous injection.

Methods of Identifying Additional ASOs that Prevent Exon Skipping

Also within the scope of the present disclosure are methods for identifying or determining ASOs that prevent exon skipping of a LIPA SEC pre-mRNA. For example, a method can comprise identifying or determining ASOs that prevent exon skipping of a LIPA SEC pre-mRNA. ASOs that specifically hybridize to different nucleotides within the target region of the pre-mRNA may be screened to identify or determine ASOs that improve the extent of retention of the skippable exon. In some embodiments, the ASO may block or interfere with the binding site(s) of a splicing silencer. Any method known in the art may be used to identify (determine) an ASO that when hybridized to the target region of the skippable exon results in the desired effect (e.g., exon inclusion, protein or functional RNA production). These methods also can be used for identifying ASOs that prevent exon skipping of the skippable exon by binding to a targeted region in an intron flanking the skippable exon. An example of a method that may be used is provided below.

A round of screening, referred to as an ASO "walk" may be performed using ASOs that have been designed to hybridize to a target region of a pre-mRNA. For example, the ASOs used in the ASO walk can be tiled every 5 nucleotides from approximately 100 nucleotides upstream of the 3' splice site of the skippable exon (e.g., a portion of sequence of the intron located upstream of the target/skippable exon) to approximately 100 nucleotides downstream of the 3' splice site of the target/skippable exon and/or from approximately 100 nucleotides upstream of the 5' splice site of the skippable exon to approximately 100 nucleotides downstream of the 5' splice site of the target/skippable exon (e.g., a portion of sequence of the intron located downstream of the target/skippable exon). For example, a first ASO of 18 nucleotides in length may be designed to specifically hybridize to nucleotides +6 to +23 relative to the 5' splice site of the target/skippable exon. A second ASO is designed to specifically hybridize to nucleotides +11 to +28 relative to the 5' splice site of the target/skippable exon. ASOs are designed as such spanning the target region of the pre-mRNA. In some embodiments, the ASOs can be tiled more closely, e.g., every 1, 2, 3, or 4 nucleotides. Further, the ASOs can be tiled from 100) nucleotides downstream of the 5' splice site, to 100 nucleotides upstream of the 3' splice site. In some embodiments, the ASOs can be tiled from about 572 nucleotides upstream of the 3' splice site, to about 500 nucleotides downstream of the 5' splice site. In some embodiments, the ASOs can be tiled from about 500 nucleotides upstream of the 3' splice site, to about 572 nucleotides downstream of the 3' splice site.

One or more ASOs, or a control ASO (an ASO with a scrambled sequence, sequence that is not expected to hybridize to the target region) are delivered, for example by transfection, into a disease-relevant cell line that expresses the target pre-mRNA (e.g., a SEC pre-mRNA described herein). The exon retention effects of each of the ASOs may be assessed by any method known in the art, for example by reverse transcriptase (RT)-PCR using primers that span the splice junction, as described in Example XX. An increase or presence of a longer RT-PCR product produced using the primers spanning the region containing the skippable exon in ASO-treated cells as compared to in control ASO-treated cells indicates that retention of the skippable exon has been enhanced. In some embodiments, the exon retention efficiency or the ratio of retained skippable exon containing mRNA to skipped exon mRNA may be improved using the ASOs described herein. The amount of protein or functional RNA that is encoded by the target pre-mRNA can also be assessed to determine whether each ASO achieved the desired effect (e.g., enhanced functional protein production). Any method known in the art for assessing and/or quantifying protein production, such as Western blotting, flow cytometry, immunofluorescence microscopy, and ELISA, can be used.

A second round of screening, referred to as an ASO "micro-walk" may be performed using ASOs that have been designed to hybridize to a target region of a pre-mRNA. The ASOs used in the ASO micro-walk are tiled every 1 nucleotide to further refine the nucleotide acid sequence of the pre-mRNA that when hybridized with an ASO results in exon retention.

Regions defined by ASOs that promote inclusion target skippable exon are explored in greater detail by means of an ASO "micro-walk", involving ASOs spaced in 1-nt steps, as well as longer ASOs, typically 15-25 nt.

As described for the ASO walk above, the ASO micro-walk is performed by delivering one or more ASOs, or a control ASO (an ASO with a scrambled sequence, sequence that is not expected to hybridize to the target region), for example by transfection, into a disease-relevant cell line that expresses the target pre-mRNA. The splicing-inducing effects of each of the ASOs may be assessed by any method known in the art, for example by reverse transcriptase (RT)-PCR using primers that span the skippable exon, as described herein (see, e.g., Example XX). An increase or presence of a longer RT-PCR product produced using the primers spanning the region containing the skippable exon in ASO-treated cells as compared to in control ASO-treated cells indicates that retention of the skippable exon has been enhanced. In some embodiments, the exon retention efficiency or the ratio of retained skippable exon containing mRNA to skipped exon mRNA may be improved using the ASOs described herein. The amount of protein or functional RNA that is encoded by the target pre-mRNA can also be assessed to determine whether each ASO achieved the desired effect (e.g., enhanced functional protein production). Any method known in the art for assessing and/or quantifying protein production, such as Western blotting, flow cytometry, immunofluorescence microscopy, and ELISA, can be used.

ASOs that when hybridized to a region of a pre-mRNA result in exon inclusion and increased protein production may be tested in vivo using animal models, for example transgenic mouse models in which the full-length human gene has been knocked-in or in humanized mouse models of disease. Suitable routes for administration of ASOs may vary depending on the disease and/or the cell types to which delivery of the ASOs is desired. ASOs may be administered, for example, by intrathecal injection, intracerebroventricular injection, intraperitoneal injection, intramuscular injection, subcutaneous injection, or intravenous injection. Following administration, the cells, tissues, and/or organs of the model animals may be assessed to determine the effect of the ASO treatment by for example evaluating splicing (efficiency, rate, extent) and protein production by methods known in the art and described herein. The animal models may also be any phenotypic or behavioral indication of the disease or disease severity.

EXAMPLES

The present invention will be more specifically illustrated by the following Examples. However, it should be understood that the present invention is not limited by these examples in any manner.

Example 1: Identification of Exon Skipping Events in LIPA Transcripts by RT-PCR RT-PCR was carried out to reveal the difference in transcript lengths produced from the LIPA gene in fibroblasts obtained from healthy donors and from donors with Cholesteryl ester storage disease (CESD). Normal cells produce mRNA transcripts of the LIPA gene that retain exon 8, resulting in the full-length active form of LAL protein. CESD results when exon 8 is skipped, due to mutation (c.894G>A) in the LIPA gene, and a non-functional form of LAL protein is expressed predominantly. mRNA transcripts from normal and CESD fibroblasts were amplified using primers that flank exons 7 and 9 in order to detect the presence or absence of exon 8 in the LIPA transcripts produced. Polyacrylamide gel electrophoresis (PAGE) was then used to show the sizes of the resulting RT-PCR products. Control (normal) fibroblasts generated the longer PCR product containing exon 7, 8 and 9, whereas PCR products amplified from CESD patient fibroblasts were shorter in length, consistent with the presence of only exons 7 and 9 being retained in the transcripts and providing confirmation of exon 8 skipping in CESD patient fibroblast cells. From this analysis it was shown that about 95% of the mRNA transcripts from the CESD patients resulted in a truncated form (exon 8 skipped) leading to a non-functional LAL protein and about 5% of the full-length mRNA in which exon 8 is retained being produced. The identity of the products was confirmed by sequencing.

Example 2: Design of ASO-Walk Targeting Exon 8 of LIPA

An ASO walk was designed to target exon 8 (Table 2. SEQ ID NO: 4) of LIPA (Table 1. SEQ ID NO: 1) using the method described herein (Table 3. SEQ ID NOs: 54-63), A region immediately downstream of the exon 8 3' splice site and upstream of the exon 8 5' splice site spanning nucleotides +2e to −4c was utilized to design ASOs to target skippable exon LIPA SEC pre-mRNAs. Table 3 lists exemplary ASOs that were designed and their target sequences. From this design. 2'-MOE. PS backbone. 18-mer ASOs shifted by 5-nucleotide intervals were produced and will be utilized to target LIPA SEC pre-mRNAs to increase LAL protein production.

TABLE 1

LIPA gene/SEC pre-mRNA sequence

LIPA Gene/Pre-mRNA Sequence (SEQ ID NO: 1)

GCGTAGGCGACGCGCTGGTAGAGCTGTGGACCT

GCCAGCCTGCGAGGCGGAGGACGGGCTCCATCTCTTAGAAACGCCTACGGCGCATGCTCTATGGGGTCAACTGGGGGGCTGGCAAGCGGC

AGCGCTGGTCTGGGGCGGAGTCTCCGAGGCACTTCCCGGTGGCTGGCTGCTCTGATTGGCTGAACAAATAGTCCGAGGGTGGTGGGCATC

CGCCCTCCCGACAAGGCAGACCAGGCCCCCTGCAGGTCCCCTATCCGCACCCCGGCCCCTGAGAGCTGGCACTGCGACTCGAGACAGCGG

CCCGGCAGGACAGCTCCAGgtgagagtgccggcgccgcggcgctgccaggtgcgggtgcggcgtggaagctggtgccttcagcaagggga TABLE 1-continued LIPA gene/SEC pre-mRNA sequence gggtcgcgccccgaggctctgccggccggcaagaccctctgcgtttggacccagcgagtcttgcctggggtgcctgcgggtgcttttttct
gcgggcgttggctcaaggcatctgccaatcaaccagggcaacttcagagagcaacttcagagagaagcccactctcttccctgggcgctg
tccactttcctggacaggcgcggtctccggtcagtgaagctgcccagtgctcctggaccgcgaggacagcagggatgtctgattcctctc
tctgcatcctcgtgctctccccttagctcctccaggcatccatcctacctctcttgttagccaacggcgtggtcgaaagcagacttggg
catcaatcctggttaaagtcccagcgatactgcttttttaaacagctgacactttgcttccagtacttcagctgggtgaacctcagattcc
tgaaaaatggaattaatggtactgccatagggtcggtggaggagtaattgacagtagatcagaagcgctgcctgcggtggctggcgcctc
gcaagagcttaaatgggagtcgtaataattgttgttattagaaagttaaatagcatgctgcgttggggccttttcttctgccactgaact
gttggactgctcttatctttttcagaatctgtactatgcatctaatatatacgtggcactttgcttggtcctgggggtacaaagctgag
tcagattgttacaaagtctaaataactgagataaaggtgttaatacagcccagaaaagcacacttaattcagcctggaaggttttttttc
cccctccttcgagattttcagagtatctccttcttagtaagaattgcttggcttagtatgttgagaaaaacatactaagtatgtagtgt
tgtgttggaaggaaaacttaactgggtgagattttcagctgagtagctttagctgttactctcatggaccttcctctgggcggttgatac
aggttctgtaggaaaaccgctgaatgaaagcagctcctgcagatgctattctgttttcaattgtggtaattccttttaattttttccctt
caatttactccttattctctagtaataatggacttttgggaggttgcatttatgataaaaaatagcctggggctgtacaatccttcctat
catgaagaagtacaaagttgtaagtagaagcagtggccttgctttgccaatgcacactgaaggggataacgtttgctcctgttcagagtt
cacggtcgggcgcggtggctcacgcctgtaatcctagcacttttggaggccgaggccggcggatcacgaggtcaggagatcgagaccatc
ctggctaacacggtgaaaccctgtttctactaaaaatacaaaaacaaaattagccaggcgtggtggtgggcgcctgtagtcccagctact
tgggaggctgaggcgggagaatggcctgaacccaggaggtggagcttgcagtgagccaagatctcgccactgtactccagcctgggggac
agagcaagactgtctcaaaaaaaaaagaaagaaagaaagaaaagaaaagaaaagaaaaagaaaagaatttcagagttcact
atttcttggaaaaaaataatcccaggaggaattccatcaacagaagggagtcagttcacttttgcaatctcctgagaatcaatttcttaa
gacttgtggaatattcagtttaaacacaaaactaaaaacaaacagctgtattggagtattattgacatacaatagcatggcatatttcaa
ttgtacaattgtataagttttgcatgtgtacacacctgtgaaaccatcagtacattcaatattatgaacctgtacatcacctccaaaat
attatttgtgcataccctttgtgatcctttcttactgccccttctctccaggaaaccactgatctgctttctgtgaatatagattagac
tgcattttgtggagttttatatgaatgggatcagacagtactttttttttttccttattttgatctggcttcttttggcataattattttg
agattaatctatatttttttgtgttccttcccttttatagctgagtagtaggtatataccataatttatccaatcatccatttaaagcat
ttgggttttccagtttttgtctattacacccaaagctgttataaacatttatgtacaagtctttgtatgggcatacatgcctgcatctt
tttaagtgattctatttatttttaaaaatgtagaagttctgggatctagtcctaggttttctctgaccacttgcgtgatcttaggaga
ggcatttaactttgccttcagcatcctcaaggtctttgctgtgattttgagtcatcactgccagaaaccaagatggtctttgttgatttg
atggttagagaattcagaaggagagagacgggtcaaattttttccttttctgtttcttttgaaagctctatttttctttcatttcactttt
tcccatgaatgacaaatttaaatgctgacgtataatttggggcaagaacagaagtggttagataagtaggaggaagagctaatagtggtt
agataagtaggaggaagagctaatagtggctgaacttaaacatgtctaaatcataggtggaaggcaagaggtgggaaataagcaagctca
gaaattttgtgtctcttttctttttctcaaactatcctcttctaagtcttgccttttgttattctccatgaccaatttgttttaactttt
ggggttaggaggtgaatgggtatgctggactccaaaggtcatatatcaactggaggtggtgggtgggaggtttcttagttaaaagtaatt
cctttgggccgggcgcggtggctcacgcctgtcatcccagcactttgggaggccgaggcgtgatcacgaggttaggagatcgagaccatc
ctggctaacacagtgaaaccccgtctctactaaaaaaaaaaaatacaaaaaaatttgccgggcgtggtggcgggcgcctgtagtcccag
ctacctgggagtctgaggcaggagaatggcctgaacctgggaggcggagcttgcagtgagccaagattgcgccactgcactccagcctgg
gcgacagagcgagactcagcctcaaaataaataaataaataaataaataaataaataaataaataaatataaaataataataataa
taattcctttggggaggcggaggcgggcaggtcacgaagtcatctgagaccagccttgccaatatagtgaaaccctgtctctactaaaaat
acaaaaattagccgggcatggtggcctgcacctgtagtcccagctactctggaggctgaggcaggagaaccgcttgaacctgggaggtgg
ctcacgcctgtaatcccagcactttgagaggccgaggtgggcgaatcacgaagccaggagttcgagaccagcctagccaatatggtgaaa TABLE 1-continued LIPA gene/SEC pre-mRNA sequence gcccatcgctacaaaaatacaaaaattagccaggcgtggtggtgcgtgcctgttgtcccagctacttgggaggctgaggcagaagaattg
cttgaaccaggaggcagaggttgcagtgagctgagattgcaccactgcactccagcctgggtgacagagcaagactccatctcaacataa
ataaataaataaataaataaataaataaaataaataaataaaatttaaaaattccttattctcctttcagatatggctgg
agtcatttgtttcatattttccttttcacctttttacttgccctaaatctggttcagaacttttttgtgggagcattaagttaccagaatatt
tttgtgtagtaaaattcaagcaaataataatagactgttttattatacagAATGAAAATGCGGTTCTTGGGGTTGGTGGTCTGTTTGGTT
CTCTGGACCCTGCATTCTGAGGGGTCTGGAGGGAAACTGACAGCTGTGGATCCTGAAACAAACATGAATGTGgtaagtttctcaaagtta
tgtacttttaaaatgcatctatttccccgatccagttatgtgagctacatgaagccatacccatacattcatctctttataactcctttg
cttttcaatttctctgaattttttttttttttttttttttttttttgaggcagagtcttactctgtcacctgcccgcccaggctgg
agtgcagtggtgtgatctcggctcattgcgacctccgcctcaggggctcaagtgattctcgagcctcagcctcccaagtagctgggacta
caggcatgcaccaccatgcctggctaatttttttgtatttagtagatacagggtttcaccatgttgcccagggtggtcttgaactcctg
agctcaggtgatctgtccacctcagcctcccaaagtcctgggattacaggcgtgagccaccgtgcccagcccaatttctctgaatcttag
attcaatttgctaggcttttctcaccaggtaatatgtagccaacaaacctcagtttaatgttatatacttcttaataagataaattat
gattttttattaattcatttcattttttaagtctcactaagtttgtttaaactataaaaaagtatttaaactttgcaagaacattaccgct
attgagagctggttttagaatacattgaacaaaggttgtgattaagaatgtccagggaacatatttctatacagaagtcaaagtatctga
gctaaattttgttagaaaaaatatgcaaaaataaccactcgactaattaaaacatctgaaagttattaatcgtaagtaaacaataaaatc
tggaaatacctcatttaggcacaaaatatcagtaaagtacaaattattaaagaaaacagcaactttaaaatagatgttgcagtgacccag
ctgaagaatcaggcaagcttagggactcgcagagaaattcacagtgagccaggagagtatgacctgataacagggtcttaaagttaagtt
ttacttcttagctcaaagcttttcttttgcctcccaattttttccaacttttaaaataattttttaaataagaatgataaaattaaattct
ttcaagtacttatggtagagagggtatgtgcacttatttacattaaatcccctggataattgaattatccatatcccactgagctcctga
ttaacaattgtcccatgaatccttccttatagaaaagtgaatgtgaccataattccctattttgttcaacttttcttccatcccaccttg
acattctatgtaattattttagtccattgataaaaacaagttaatatttttatactttattggccagcaggggatctctcaaaacaaag
aaagtgttttatacattgacagttctagctgggatatttagaaaagaaagaaatgagcatttatttgtgcccggtaggcaggatggaaac
aaagaggcccaagatgtggtaaagttaggcaaatttggtataaaacatgctagaatgatgaaactgaagtttaaccagacaccggtaggt
ggaacacaagcgtgaaacaagggaggatttactcttgtgatgagaagttggctactagatttagcagactaaaatttcaatgacaaatgc
tttcttaaagcctggagaacatagtttatctgctccttgcttgttaatgtgggagactgtttcagattctgtccacccaatttccatcg
tcctttttctctacagAGTGAAATTATCTCTTACTGGGGATTCCCTAGTGAGGAATACCTAGTTGAGACAGAAGATGGATATATTCTGTG
CCTTAACCGAATTCCTCATGGGAGGAAGAACCATTCTGACAAAGgtatgggaaggctcttaaaagtaaaaaccagaattcttctgggttt
tgtgttagtaaccaagttcagatttaacttaaaaacattgaaatgggattatttttagacgaaagcactaactgtgttgaggtttgcaag
gcaaagaaaaataattttctttttaaagaagtaaggacaagagtcatctaattttttgttcaaaggccagattcatttgaggatatgctaa
aatctctgaggcttgttttttaaggaagtgtatttaatgaaatgttttgagcattaaatagatggcttttgctatttaaaaattattt
aatttttttgaattcacataatctaaaaatcagagaattagaagacatacagtgaaatgcctcccttctctctcactcccacttcctgc
ttttttgtgtatcttttgaaataacttcatttaaaatctttttatttccaaaaatctcattagaaacaaatacacacacagattctta
ttttcccttgcctccatttgaatgcaaaagatggcactattttgttctttgaattttttacttaatatcttggagatcttccatacaa
tacataaagcacatcttccagaagtgcatgatatttcactatatgactgtatcattatttatttaccaagtgtcctattaatgcatattt
gtgctatttcagtcttctgttaacaaatattgctgctgtaaataagcttttgtgtgtgcaagtttatttacatgatacatgtccagaagt
agaattttggatcacaggatatgcatttgtgattttgatatatattgccaagctgattttcatgtgcatgtgtcctgataattacta
tcactatgaatatatgaaagttcttgtagctttggcttaaaaagtatatatatacatatatatgtatatctttttctctctctcattttt
ataactcaagcaaaactgcagtttccagtgcagataaaggaatttctagacagactgattgaaattattaagcagttatcagaagaagga
tctaatctttattcaattatctctccagatgtagcttatttatttattttttttgagacggattttcggtcttgttgcccaggctgg TABLE 1-continued LIPA gene/SEC pre-mRNA sequence aatgcaatggtgcaatcttggctcactgcaacctccgcctcccaggttcaagtaagatgtagcttattctctaacatttttttgtttctg gagacttttcttggggaaattaaggtttagattaaggtagttagatagctatttattcttcaatttaagtgttatacgggcaaaagagcc acctttgcctcaattcctgcccaaattgttattcaaagcaaacttaaacacccttttgtgttaatgtgagcattgtattattatttgcttt gttttttcttaatttatcctagtttaactttttttcttccatgtgttctagctgtaataagattttaataatgtttaggtggccacgacaa ccattttttttgaaatttgatttctaactcttgagattttatgcttacagatatatgccattaagcttccttttatataaatatgttat aaaatgagtgatgagttatagtgagagcttttagttttcctgtgctcaaaacactcaaaacatatattttatgctagagcgagcatatg atcttggtttccttcctttttttttcccccaaagaataaccctgtatactgatttcagacactgtataaagaaaaatgctttatattatt tttcttaaaattatagttgattaattagtaacgtgaatcactgttaaatgatggtaagcatctcagtaaaacttgctgagagctctcctc ctatatccagcttcagacttctctctccatacagtggttaaaacactcagagtcacatgccctacctgtgtgtatcacactgttgcaggg gaaggtgcagtgccctggaatatgaagaaagtgagcatgagtcttgatatgctcccaggtaatagaaaggagacttatgggaccttggtg ctacacctgggtttgcccctgacttcttgtgtgctttgttttttctttttttttttaacctctgtgggatatattatatatactttatt ttattttggcaagaggggttggggattgggagagtggagagtctaggtctttagaatggggaatatagactgaaagtatttactctaag ctaaatctgttcatagcatttggtcctcatgttctttctctattctgagaggccctccctgtaggggatcactgatgtgtatgtcatacc tgctatgagctaacctcagtggggagtcttcaaggaagtctacagtgaacaactcagttctctaaaggaattgtgattttcctaagaact gcataggcgcttcctgatggtttgcatttccacattctaaaacagagcatggacagaggctctttactgtccttcactcctattcaaga gcaaggttgttgccactggtgttatttccggtgtttaaaggcaaatagataaaaagaatggagaaggcctttcacacccaaagtgaaacg cgtcctcttctcatgcatcccgcttcccctcctgacttcctcctctattattaatagcaccagcatcctcctaatgacctagcctggaat ctgcagaatcattcttgaccacgggtcctctctaggccacccacgttaaattgcttcagttcatcttttttcttctgtttccctgaccacc agcctacattaggctcttgttaccacttaactgggcgcctgaaataagctcagcagctgagagagtcttgagccatttccattttcaagg ctcctcgtatactaacagaaagaaagaatttcaagacaggattatggaaattcagtttgcttatatagtttaagaaattaatgcttttaa tacacacaaaaatactgctatacattcatactatttacaagtaattacaaaatgtattaaaacattattcatttttggtaccacattcc ttgtggaacctgagtctacagctgaatggtgagcatctttcagtcctgttgccatgggcctctttgactgactgtgtagcctcacttgga gatcaggttttttttatgaacacagggcttggccacatggcttctctgctcatgtttgcttaaaggcttacctaactgctctttctct gccaggcttcctgttctcattcatcctatgtggttttgcaggattaagtttcttaaagcttagctataatgatgtgaaattgccattcag caatctttaggggtctcagaaatgaagatacacactgttccttaaatattctgtccagctggtatttgtacctttcacctccattctgca cagtagtagcccttggctactcgtgcagtatgtgcatgctgtttccaccattaagcaacctcttaggaagtgttgagcaatgctttgc tcctgaagggaattgaaattcagaaattacacttcataggaagtggctctgttttcatctgctcagccttatttcagaaagtcatgggg agttagcactggagggatctcagattcctgcctgggctagggattttttgttttttttaaacacacttcactggtggattccaaggtaga attcttggttttggcaacctgtgttctagactaacatcctcatttgttggataagacagccaggttcaaatagggaaatgaatttgtct cagggcagagggtcatgtcctgacctgtctgactacagattcagtgatctttgaactggagaatgtggccttacataataaatattaacc aagttgatgccatgataggcacaatatatattttatatatatacacacaccaagagtggcacatttgtatctgaaagttatgcatctg attgccgagtgggtgaagtggcactctagactgtgaaagcctggaatgactgccttcagcatgcagaaacaggcttttcaactgtggcct cagcaaagattccccaggggttgtccattgagctattagagtcatagctgaaaattcacagcgtggcttgtgagttaagtctttagaagg agaccatcagcttgtatttgctttgattgtttatttttagaattctggttgatttctagatttttctttccttatagaaaaatccttcac ttctaaagaaactatttttttgaatcactgcagtgctctaacgggctacacataggcgttggtaatctgggatgtaattcctcacccctgg tggtgccgaacagacatggtttcattaatcaatgcctgagcttggtgacttgggctgagctcaggctcatgtagcactctgatggcgcat tgggtaggggattgcattcagaacctttgcctaatggagcagcataagtgaggtcagctgtacagcttatctcatagacccaggttgggga tcagagcagaaagccaagtggaaggaagatagtgctctgccctgtccccttccctcctcttcctcctggttaaccgctctgacctgtcc tctgttctcaacctaattttcacatcttcagggaggatttcctcagcctctcacaccaggtcaggcccctggctacatattcttatagtc TABLE 1-continued LIPA gene/SEC pre-mRNA sequence

```
ctctgtgtttttctccatcgcaattaagacaataaacaatatattattatgtaggtgatgatgtgtgtgacctctgtcatccccaccaga
ctctgcggggatgaagacttttctgattctctttacttggtaaattgctttagctccaggctgcagtctacccaagcatgctcctgcagc
cctcctgtgacattgcgatttaatagtgtcccctgctcaagggcacactgcatgaaggatttcctactcctgggctcctaggagtccacg
aacacaacttaaatgcttcctgtggtgggtaaaacttgaagctgtattgcctcatgattaagctgagcatgtgaagagccaccagtcatg
ggtgtaagttctggctctactatttaactggctgtgtgaccttggcaattttctttacctcttgaagttttgacttattcaattattaaa
caggaagaataatactggctacttcgtaggctgttgtgaaaatttgataaggcctgtgaaatatatgcagtatagtaagtgcaggtgata
caatttcttttacaacatttatttatttaaaatattaatgaataaatacataaatattttaaaagtctcaccgtgtctcccaggctagaa
tgcagtggtacaatcatagcttactacagcttcaaatgatcctccctcagcctcccaaagggctgggataacaggcatgaaccatggtgc
ccagcctctgttttaatttgaaatgtcaacatggatttgatggtggtctctgatattgacttcttcaggattaagccctccatgacag
ggatgtattctaaactgtgtggacaggaggaagatgcatttgtttacaatggacagaagtaagaaaagtaagaaatgtcatagaactatg
tctgggggtcaggtgacaagcactgtgtcatttctagccctgtgtcccctgcaggtgctttcttctgtgaccctctgctccttctgttg
agggagaattttggatgagagctggataatttcccaaaattcgctcaactgtgaagctctggaactcaagttgctgtgctgcaaagctgt
ctgaggacaggccgtggtggcagagaggggcagggaagacaggcaatttggcatggagatgatgggcacatttgtcacatgacctgggtt
tgattcccagctgcatcgtatactaattgtgtgtcctagggcaaatgatttagtctctctaagcctcagaggccccaaaggaggaagaat
gatgtaaatggcccagcaccatcctgggtgcgtggaaaactctaattatgataatgtcctggaacgttctgcagtgaacaagacagacca
cattactgccttcgtgttgcctggtgatcagagtgattattgctggttttggggaaaacagcattctgaggcatggaacggttttcttcc
ctgctctgtgatgcagggtgctcttgttgtgttcactcctgcaggtcacctgctccccagcagggtgacagtgaagtgtgagtgcagtgg
actgcacagtggcaaaggccacatgactcctgaatgcatcctgtggacaggccaagcgctgtgccctgtgtgaatcatcaggtgaactct
catacaattctagggtgtaagaactcctattacctcctgttttacagatgaggaaaccaaggtttataggttaattaacttgcccaaga
taaagcagctgatgggtagtgaaggcaggagtcacacagcccgtgactgtttctgcccacttggccctcttctcaggctagagaacagct
atgatgtccctgataaagtcacactgtggaaagtggaaagtatctgacttagatgtcctgcatctgctagatgtcctgcttgtgcctact
acagcaactcagagagctgttaggtgacttatctgagataatgcgtgtaaagtgcttaagtgcttagcatggtgcctgtcacattgtcaa
cacttagtatgcgcttgctgttactatgattatattacctgggccaaagaatgccacttcactctatccttcttcatagtggttatgttc
taataatattttattacatttacagttaactcttttaacaacatgggggttaggggtgctgtcccccagagttattgaaaactgcatataa
cttttgcattccccaaaatttaactaatagcctactgttgaccagagggcttacctgtaacgtacatagccaattaacaaatattttata
tgttatatgtattatattccatatatacaataagtaagctagagaaaagaaaatgttataaggaaatcataaggaaataggatgtatttt
actattcattaagtggaagtggatcatcataaaggtcttcattcttatgttggaacaggctaaggaagaggaggaagaggaggagttggt
cttgctgttgtaggagtagcagaggtggaagaggggaggaagtggaagggagacaggagaagtgggcacattcagggtaactttatga
aaatacattgtaatttctgtccttttttcatttccctagaaatgtttctatagaatagcaattcttccatcatttgctttagtttcagtg
cctgtgtcatagaagcgtcagtgttgtaaaggaagtcttgaataattgcaattgccaccttctcctgaattgtctaatatcagtttgtt
ttctagcactgcatctcccatgtcttctttcccatcgtctggtgctgttttagaagcactcgtctccatcaaatcatcttctgttaattc
ctctggtgtgtctattagctcttgactttatttaagatgcatatattgaaactatttacctgctcccaccctccaccttttttgccatatc
cacaatcttttcttgatttccttgattggctaagtcatggatatggatactgtgaagtcatgcacaacatctggatacacttttctcca
gcaggaatttattgtttcaggcttgataacttcacagcttttctgtaacaacaatggcatcttcagtggtgtaattcttccagacctt
catgatgttctctctgttggggttctcttccaattcaatcctttccatagtgtatgtgtgtaatgagccttaaaggtccttatgacctcc
tgatttagagactgaattaaagatgtgtttggggcaagtagaccacttcgatgcctttggtattgaattcatgggttctgggtggcca
gaggcattttcctatatcaaaagaactttgaaaggcagtcccttactggcaaagcacttcctgacttcaggaaaaaagcatcaatggaac
caatctggaaaaatagttctcattgtccagtccttcttattgtacagccaaaagactgacagctgatgtctatattttccctttaaggct
cagggattagcagatttataggtaagggcagacctgaccatcaaccctactgcatttgcacagaacagtagagttagcctatcccttctt
```

TABLE 1-continued

LIPA gene/SEC pre-mRNA sequence gccttaaatcctggtgcttgtttctcttccttactaataaacgtcctttgtgggatatatatatatattttttttttgttagaatggaaca
ctttcatctgcattaaaaacctgttcaggcagatacatttcctctaggaatttatatgcagcctcttggttggcaggagctgcttcttc
tgttatcttgacatatttttaaagttttaaaattttttaattcttaaaattaattaattttggttttttagagacagcatcttgctctg
tcaccaagctggagtacagtggcaccattatagctcactgtaacctcaaactccttggctcaaccagtcttctcacctcagccttctaag
tagctaggactacagacatgtgccaaccatactcggctaattttaaaacaattttgatagagatggggatctcactgtgttttcaga
ctggtttcgaacacctggcctcaagaggtcctcccactttggcctcccaaaatgctgggattacaaacataagccaccgtgcctggtcta
tattggcattttaaaagccaaacctctttgtaaaattatcaaagcatcttttattggcattaaattctccaactttagattcttcaccttt
ctttttctttaagttgtcatataatgactttgcttttcttgaatcttagagtctagaatctattcttgctttatcttgaatattagag
tctagaatcatattagagcaatcctgcacccacataaaagctgcatttcaatatgagataaaaggtatttcggaaaaagtgcaaggttt
tggcacttgctgtcatagctgcaatgacaaatggcttcacaaattttctttccctttttttttaacagtcatctttatgtgtcatttatc
ttgaaatgaagataattgaagctgcagacctcaatctatgacacatatcaagcaattcaactttttcttgtctggacttttctctgcttt
ttgggagcactcccagatcactattagttctttgtatgggtccaatggtgttattcaaggtttatgatatcgtgctaaacatgatgaaaa
acatatgagaactgcaagagatcactttttactgcaatgtgcaatttactggagaaactgcttacgtggagatgattagtgtcatgagaa
atttaagcagatatttacaatacttgagcaacaggaggcggctacaaaattattacagtagtacacaataaaactctagttaattttatgc
agttatgatttaataccacatctttacatttgtttacatttctcttaactgtcaatggcaccatgtttggtctgtaagtgtgtgtctaag
ttttgaaaatgttaacttttatactttgtgtatatttatggtaatagatttattattgttactatcagggaccattatttattcagctt
tactatgtattaactacttcgtcattctcactttagaaaaggacacctatacttcagagagagttgagcaaatcctacaaagttttgtag
ccagtaagaactgaggtctgcttcatgctaacgccctggtgtctgaccacctccttgttctctgttttggttctgccctggccctcagct
gatttctcacatgtgttttggagtgtgacggagtcctgtccggactcagcatcctggcagagaaggccagtgccttgggaggcaggagga
acttccccacctacccggtcatcttcctcctgcgggactgtgggctcagcacattcagtttcggagcttgagtaatcgcctcctggcttc
cacccacactgggaaggcagcgttgtcgtggactgccactgggctgcttctttgtcagctttgtcctatttagggccataatgaaatcac
ttgccatctccaggctgagaaatggtcctttagtcttttcccttaatccccagccctcctagggcttcttttttcttcaagttgcatttgc
acagaactcccagagccacccgtagggcatagctggggaaggcagcccttgacctgtcatgctggtttgtcactctgacaaacagggctt
cagggtgcctgagtgcattgagcaggctgggccttggaggagctgcctgaccaggcgaggctgagtgggtgcccctcctttcattcccta
tccccctccatctactagagattactttcttcaagcactttgtccacatccttcaaaaatagctttctgccttcagccggaaggcctca
gtgtgttctagagacttctctcttgttaaccttctttccctagcaaagcactgaaaagcatggcctgtggtgtcagacacacctggttag
actccaaccctcacgcttcctagctctcgttcagccttgggcaagttacttgacttctttaccacaattccctgttctgttaaatggcag
tagtgccaacttcaaaggattttcagtacagtacctacagcatacaagcgtgcaatcggcgctagctatcatttcaatcagctgttctca
gcaaggtgaagtgaaatctgaaatagttcactggaagatgtgaacagcaataggttttaccttcccagagagaaacatcctttgccagtc
aatccttaaatcctttcttggtggtgggatggaaagaaccacattgtaccttcctttcttcccctggtgggagcaggtgagagaagct
ggcaacagttggctgggcctgcttccagcgtccagtctttccattcccttttgtattcacccaatgccagagggaagggcaagaggtt
tggaagccattttaaaggttttcacccgaggattcgatactattttctttgctgaggatccgtcatgcctaatggaactgccatctct
agaagttcagtaagttatatcctctgcatctccctcctcagaagagacttttttgttctgggatgaaaggaaactggcccagcctggaaa
gatgtgcacccatgaagtccttcctattccctgtgtccccaggtcagacaaggcactggacttttcctagtggttcccagcctggctg
cgcgtcagaatcaggcagggaggctttcatgtgcacactggtcccatctggccaaggcctgggtgcagtgtcagctctttattcatctgg
ctcctatgttttctccagaaccctttgtggaaacatctgtctcttacttagaatccaggtcaaatgtttgtcccactggccaagtaactt
tctccttcttctgggacttcctgagtggtgttctagccttcttcttgctgggttagacagtcatcgtgtgtctgactcctcgaggatgg
agctccctgtgggagggagtgtgggttacccatctttgcattcctagcatctattagtttggggcaaaagtaattgtggttttttgccatt
gcttttttattttgtgggggtgggggtaaatggaatccctctctgtcacccaggctagagtccagtggtgcgatcttggctgaccacaa TABLE 1-continued LIPA gene/SEC pre-mRNA sequence cttctacctcttgggttcaaacaattctcctgcctcagcctcctgagtaactgggattacaggcacccaccacgagggtttcaccatgct
ggccaggctggcctcaaactcttgacctcaggtgatccaccgcctcggcctcccaaaatgctgggattacaggcgtgagccaccgtgcc
cggcctgccattgcttttaagggcaaaaaccacaatgacttttgcaacaacctaatagcagtggctggtactcagtaggcaccactaaa
ggtttgcacgaaacgtaatgtatgttttcaaatcacttcttgatattttaccttctagtgcactgcttaagatacagcagatttccatta
aaaacttttcacctgaatgtggaggacacagctgagtggcctccattctctaaagccatgccatttgtcagacgtttacctttcttcatc
agcccttttcctcatctgccagcatttcccatgagaaaacagtgtggtctgcagtacccttttgcagtgcttggcccagattctccagatt
tgaaaacatttagcttgtaaagaatagattcactgtttccttcccatctctttgacttattctctggaagcctccttcaaaggataaagt
aattccctgagaaaagcgttgtgcaggtgtgaattcggtctgggtggaacaagggtatttaccgatgttcttagaagctgcacagccacc
ttaggcgtggtctcctgggtagcacatgctccagctgtccacaggccattcctttcttcacactcacctcccaggaaaactgcagcagct
cctcattgcccttgggaatccaggagttatttattggggatgtttaaagactttcctgatgtatcttcaacttgtcagcttccacatttc
cccattcaaagctctagaggttacagagggaagtacagagactttagggaaattttaaacattctccatcgagagaaggtggggagctga
gtcctggtcccatgtgctggccaacatctccccttccagcctctgtcctggcctggctgccacatatcaccctccttctcctctctcaat
tatccttgccccagggccctctttggtttcaaaccattcctgcctttctctggacactctccctgaggagtagactaggcagtcccatg
ttttccgtgttaactacagaggcacagattggaacaagtgccaaggaattaggccacctaccgagccttcctcttgcctctctctgactc
tccatcctgagggaagacgattgcagtcgtttttgttggaaatgacctgacctgtgggagcagcccgttcctggcctttcaaagtcaagt
caccttactcatggcctagctcctgatcactcctggtgggtgaaaagtgcctcaacatacctaaagagctgtgacatgagcaggaaagcc
cctcttctagaaagtgttgggcaccatcagtacagcagagccactgcatcgtacagcgcccggtcaccattctcacgtacagttaccat
gagatgatgatggtgcctgtagttacacatttttcaactataatttaatgataaattaattttggtaattataattgtcacttacactgc
agtttataattttggatttttaatgatcaattttcatattttcccagctggattatcatcctcttcattgaagccaagaagcctgtgcat
aagacgctgtatctaccacaatgccttccacttacatttttcgtagtaaatttagtcttgttaatattgcattaaaatgaacctttgaag
gcaaagatgagcacataaagcagccctaatcttgtccagtttgctttctattttctccccatgggtagaagttcacctgcatggccctgg
catttctattttgtgattagaaaatcacaccagccatacatgatgtttcacttctgtaatccccgcacttttgagaggccaaggcgagaga
atcacttgaggccaggagtttgagaccagcctgggcaacatagtaagacctcatctctatgaaaagttttttaaaaaattggctggatgt
tgtggtacacacctgtaatcccagttcttcaggggcctgaggtgggaggatcacttgagtccaggagtttgaggctggggtcctgctatt
ttaacaacacgagggtatagcaccccaggttgtacaactccagggagtaccatgtatattttcatgtatgtgagcagtgccttccggag
tagtctacggaagctaccttgcagcagaactgtcatttaaaaacaatttgctagttatcaaatctatattaggacattagcagaaatgaa
catttgtcaattcacttatagtcttatcatctggacaaatcattcttctcatttttccttggtattttacactcctctttggtgtacatt
aattttgcacagctgtaatttagagtagtctataattttgtattttgcttttttttccttgcaaggtataagctttttctatgctgtcac
tgtccttgtcatggttgatggataattattataccaagtggatttcaatgaattatttgaccacttgacaattagcttatttccagtttt
tcactgttataaagaatgagcagagggcaaaggaagctctcatttgttcactgtgacccgtgtgtcagtcactatactggatacttacct
cacttattcctcttaacaattattttggaactgagacgcagactggttaagcaacttaatagtatgagttgatatatagtgaactctta
ctgtgtgtcagactctttgctacctacttttcatataatatctcatatctcactgtgtcctataaaatgtgtattatcatttctactctt
cagggaattatattaattttaggagatgtttccccaaggtgtcatgttagaacttggagaggacagagttgagcctaggtttgtttgagc
tgtctaaaactcatgatcgggctgggcgtggtggctcacacctgtaaacccgcactttgggaagccgaggtgggtggatcgcttgagtc
caggagtttgagaccagcctgggaacatggtgaaacactgtctctacaaaaaacacaaaaattagctgggtgtgttggtgcacgcctgaa
atcccaactactcaggaggttgagatggaaggatcacttgagcccagaaggtggaggttgctgtgagcagagatcacgccactgcactcc
atcctgggtcacagagcaacatcctatctcaatcaatcaatcaatcaaataagtggataaaactcatggtcagtataatgtcagctccat
ggaggtacttttttcctcttgttttgttctctgctgtgttctcagtgctgagaagaaggcctggcacatagttggtactcaataaagg
cttgtttcatgaataactgaatggtctcagcgttaggtaagcagcttgaggtcaggtttctttggctcccacatctttgtttttctgct TABLE 1-continued LIPA gene/SEC pre-mRNA sequence atatcactgtctcgggtacaggtgagtagaaaataaattctcacaggcagacacagacacatatatttatgaatttgtgtgtgtgagcct ttttatctatttaacttttattcagctttaaaaattttttattaaattttattttttaaagcagttttaagttcatagcaaaattgagtgg aaggtacagagatttcccatacacccctctgccccacactcccctgttatgaacatccctcacagagtggaattgtaattgttacagctg atgaacctacattcacacaaagtccgtagtttacattagggttcccttttttttttttttttgagactgagtctccctctgtcccctagg ctggagtgcagcagtgcaatcttggctcactgcaacctctgcctcccgggttcaagcaattctcctgcctcagcttcctgaatagctggg attacaggtgtggggcaccacacccagctaccttttttgtatttttagtagagacagggtttcgccatgttggccaggctagtctcgaac tactgacctcaagtgatccactcgcctcagcctcccaaagtgctgggattgcaggcatgaaccaccacacccggccactacagttcactc ttgatgttgtatattctatagttttggacaaatgtatgatggcatgtgtctacctctatagtatcatgcagagtagtcttactgccctga aaaatcctcttactctgtctatgaattccttcctcctcctaaccccctggcaaccaggatctttttactctctctatagttttgtctt ttccagcatgtcatatagaatgcagcctttacagatcttggtaatatgtatttaaggttcctctacatcttttgtggcttgatagctca tttccttttagggctgagtaatactccattgtctggatgtagcacagtttagttatgcattcatttactggagcacatcttggttgcttc taaattttggcaattatgagtaaaactactatagacatctgtatgcaggttttgtgtagatgtaagttttcaactcctttgggtaaaat accaaggaatgtgattgctggattatatggtaagagtatgtttagttttgtaagaaactgccaaacttttccagtgtggtgctaccagtt tgcatttccaccagcaatgaatgagagttcctgttcctccacatcctcttcagcagttggtgttttcagcgttttttggatgttgctcatt ctgatacgtgtatagtgatgtctcattatgtgtgatcttttctttccttttgtttattttgttaggaattattgtgagaaatgcaatta cgaaagcaaattgtaaaaacatttttataagaaaaaaattgtaaaaacatttttataatttcttaaaaatatattgatttttgttttgctg cttacataagtgtgtcttgttagtggacatgcaaaaaatggtccagtttcactgctaccttgccagtgctgttttaaaaaaattctttac taacattatatgtgagtacatcactatgtcaatctttcaatttatttctagttcattatttgcttatggatcttttacgaatgttctatt tagcaagatatcatatttgttttgaagcttggtgctactgcctcctaaacaatgaatgttttcagGTCCCAAACCAGTTGTCTTCCTGC AACATGGCTTGCTGGCAGATTCTAGTAACTGGGTCACAAACCTTGCCAACAGCAGCCTGGGCTTCATTCTTGCTGATGCTGGTTTTGACG TGTGGATGGGCAACAGCAGAGGAAATACCTGGTCTCGGAAACATAAGACACTCTCAGTTTCTCAGGATGAATTCTGGGCTTTCAGgtata tatgaattgataatggcatggatgtatttccttagtactcttaaagcagacaacaggcttccagcagaagaggtagataggtggtaactc tgaagttgtatgagaggggaagttagtgtcttttgaaaggttttaaatgttgctaggaatttaatgactagcagtaaggtaaattataag taaatgattacattaagatttacatttagttaggaattcttaagttacttcggcatttctggtggtgtgggtgctgctgggtaaacgtta ttccataactttcctccttttctccataaatatgtaatccagatgttcacttttcttcttccagaaattatccttcctccctcttcctt ctggctccaccagttaattgctgtatgacattggacatcttacataagcctcctgtgtctcggtttccttatttgtaaaatggagcgtaa taaacacctacctcataaggtcactgggggcttaaaggagagggtgcagagaaggaacctccacagaacctggcaccttgtatgaactgg ctaggggttggctcttctcctgccagtggcaacatgcgcatgcatataccccatacgcacacttgggttttggtctatgttttggtaccag gtattagagaaagtcagcagcactatagcagcctccgggcttgcttcccattttttaaaaccagaggcacctctaaggacatgaaacacaa gaatgagagcttttaacaaaaggcatatacaagaattggtttattgtcacgctatttgtaacaacgaaaacaggaaactacccaaatgc atgtcagcagtgaatggataaagtgttgtatatttatatagtagaataagaatgaacaacttacaattatatgcagcaaaaatggatta agccagatacaggagaatacacattgtataattctacttacagaaatatttaaaaacaggcgaaactaatttctggtgtgaaaaatgagg acaatagttacttttgggagacacaactggaagagagcccaaggggcttctgcagtcctgctggtgttgtttcctggactcactgctgg ttttcccagctgtgtttagtttgtgataactcatcaaactgcatactcagtatgtgtgtgctctattttatgtactatttcaatgaaaga gttcctttcttggattacagTTATGATGAGATGGCAAAATATGACCTACCAGCTTCCATTAACTTCATTCTGAATAAAACTGGCCAAGAA CAAGTGTATTATGTGGGTCATTCTCAAGGCACCACTATAGgtatgtatgtaaataagatcagaagttgatataaattcttcattacagag tttgtactttcttaaaagtgaaatataaaagatgttagttcaaattccatttatttttaaatgccaaacagaaataatgaataagata aggaatgttggtaacatttagtcttctatgaaaattcatgtatatggttgaaattgaagaaattaatgtaagccacaatatattacatgt tttcctagatgaagcaagataggggatgtgagagagtagaaaacaagtagtttctaagttcagagacttacataaagaaaacaagaaata TABLE 1-continued LIPA gene/SEC pre-mRNA sequence tactgccttctgaagttaagtggaatataactaactacaggtacatttggtttacaaaaaattttgaaaagttatatgcatttttaattta
tgctgattatataagtaatgcatgttcactgtagaaaaacagaagaacagaagatttagcaaaattaaagaaaataaaaattgcccataa
ttctagtcagcaagagttttttgtaattagggactaggaacctgtcctataatttatttaattctccctttttaatgtttactatgactaac
accttagtgttcccatcacatgctttccttacaatatattcctagaaggagccttactatatgaaaggtatgaatgttttgaagggtctc
aaaacatgtggttatattgccaggaaaaaaatggagttaggcatttttcttttatttatttcttctttcatgacttgcctgcttgggac
ctttgccccactgcttcctaaagtgacattctggggccaggtggcaagacgtcagagagggttgtattaattcgttttcatgccactact
aaagacatacccgagactgggcaatttataaagaaaaagaggtttaatggactcacagtttaatggattgtgagctagggaggccttaca
ataatgacggaagagcaaggaacatcttacatggtggcagacaagagagagtgagagccaagtgagggagtttccccttataaaaccatc
aaatctcaagagacttactcactaccacaagaacagtatgggggaaccgcctccgtgattcaattatctcccaccaggtccctcccaca
acacatggaattatgggaactacaattaaagatgagatttgggtgggaacacacccaaaccatatcaagggttaaaatatattttaaag
ctaggggattctaaatgtgtgagttcctttgaaatcattggtggtttatttcaacgtggtgtctgtaaattgttctttggggggagggca
tggggagataaaggtgatggggtgaggctcttggaaatagtctgttatttacattgtaaaaggaactgggaagattttctgattctccc
agactggatttcttccagtgcttatctaggttgagatttggagcaagcattaacaaatgcttgatttactagtttaaccaaattcagtgt
tagggcacacggaagttcagagtgccccatgtcaagtgttttggctcctgctggtggtattgtttgcgtgggtctcaggcctccgcgaga
gggcgtcgcgagtgacggcctttgtgttttctgagaaggaaatcccagatgatggaattcctgttttctgtcctttgttctcacagGTTT
TATAGCATTTTCACAGATCCCTGAGCTGGCTAAAAGGATTAAAATGTTTTTTGCCCTGGGTCCTGTGGCTTCCGTCGCCTTCTGTACTAG
CCCTATGGCCAAATTAGGACGATTACCAGATCATCTCATTAAGgtacttggaccccctcccatccctctcctctccccgcagatttcctcc
tgagatctgaagaaatggcaaggggagggataatctgtgccttcctccctgcgttttgatatcagtggagcagtgggcttttctttttc
cgtttaccccctccttccagacccaggggtggccggggacgcctgtcgtttcctgcacactggtgccacgtgtactcatggttagcatgtg
tcagtacagctctgcccacctcacagggagagcaaggagagtctgggagaaaataatttaagcatttgtggagttgcccttttatcccatg
aggtgagcctgtgcacagaggatgtaggagatgggagataggaaatgttcccaaaagcccatccctagctacactgagggtgacctaaca
acgctatcattattgtatttataatatggctcctaaacacagccagtagcttcatcagggctctgccctaaagctgtggcacccgaacc
tctgttcagggaggaaatagatttcatgaaaaagagttttaagctaggtaagaccagatgttctattatgcatgcattatatgtcttta
tgaaatatatgttcacacacacacatatgaaatcctgtatagaaatatatacatgaaatgaggtataacgtctctcatgggccatttaga
agacttaaataggaaagatggaatctcctaggcttaggcagtccttctgccttggcctctcaaagtgctgggattacaggcatgagctac
catgcctggccaataaaaaaatttttaaaaaacaaaataaaaaagcaagcgatgggctggatttggcctgctggccagtagcattgaatt
agatgggcacacctctggcagacattactgatcaatcacagccttgactgtttcttagaagtaaccaccgatccatcagagtcagatgaa
aattacttggggatggccctgggaggggtgatcattaaggcccttttcccactgtagaagtccgctgaaaacttatttgattttctgcctc
cttctcttcatttggagaatttaaatacacctctgtagtgtgtgattttttgctttggtaaacttgtgcaaaagcatcctgatttgatgtc
cactggttgccattctctcctgaggccattcgtgagacatttgggtacttgtctctgcttctgaggtgagtcacggagacttatgcacca
gagtgaaatgctgagatgttcttgggtttctttttattttgtagGACTTATTTGGAGACAAAGAATTTCTTCCCCAGAGTGCGTTTTTGA
AGTGGCTGGGTACCCACGTTTGCACTCATGTCATACTGAAGGAGCTCTGTGGAAATCTCTGTTTTCTTCTGTGTGGATTTAATGAGAGAA
ATTTAAATATGgtatgcatgtttatagtaagatttgatttttttttttatctgtgaatgtgcttatttgtgttgaatgatatgggagagg
tgggaatgacctcatcagaactctaaagagtcttcatttgagaggcacaagcatgaactttggccaatgcctagaatacggtaccacct
gctgccatcctcaggctgactgtggtcaccttcttatgttgtacctagatggagattattgaatgaggagatctgtcacaaattaagctg
taatattttataattactctagtgatttgtttcttttagaaatcattataagtataaacataaagatgggaacaatagacagtggggactc
caaaaggaaggagggagagggacaagggctgaagcctgttgagtactatagccaatattgagtactgtggttatgggatcaatagaagcc
cgcatctcagcatcatgcaatccaccccttgtaacaaacctgcacatggaccccccgaatctaaaatacacaaattttcaaaaattactat
aagtatttaaatttggaacggccatttacatacacataagtgtatgcttgcagtgtgtgtgtatttataaaagtacattttataaaatgt TABLE 1-continued LIPA gene/SEC pre-mRNA sequence aaacccatttttatttttataaaatataaaccccttggccaatactatgcccgtgtttctaaatatgtttgttagtttgtcatgtggcatttt gaaaaaagggttaaaatcctggaataaaggccctaaggaatttcagtgccattttttcttttgtctgataattaaagcaaggtgtgattg ttatatgaaatttgggaaattcaggaaagcatgaagaacaaaatgaaaatgccctgtaaacgaaacccacacagtcccgtgcttaccatg ttgttgcacctccttcatatggactttgtatgtggttgtatgtatttttataggggcagattttttagtcaaataattttttttctacctctc atctcacatacttgagattatggctctagttttttagtgctttgaagggcaaaatacaatgtttattatcaatgccacccttaatgctgttt tcattcttcattttcaatgtattttatttttgcagTCTAGAGTGGATGTATATACAACACATTCTCCTGCTGGAACTTCTGTGCAAAACATGT TACACTGGAGCCAGgtaggcattccaggagtgcatttgggggttcatgtaaaatcaacatcagaaaggtctgggcatgcaaacccttcca aatagaaagacaacctgcttacaaatctgatctggttttcttccccagagtcctgggttttttgtcatcgtgcttgtgttgcttttgatac ctgtggtggggcacactgtgttatacgtgggttcacaaacagctactgggggttgacattttttcttttccctcctctcccttcctcaagtc tcaggttaatatattctctccctttccttctcccccagctttcttttcctcctcctgtttcctccccttccatctgcttctcattgagtcc tagatttttttttatttctgtgttgcttcataaagagtgattttaagtccgtttttggagatagaaaccgctgtttcaacactaaccccctga tcacaatatgcttggaatagcagtgaataaactggagctaaaccaatgatagatgtgaatgggggcccctgacttttgaaatacagtttt gattattttatcatgtaaataagtcatgttcattctagaaaatttagaaactacatctagaaaaaaaattatcttaaaatgaaaataaaat cattctataaccctagacagagaggaaatgcatatccatagatattgaatgtctctgcattctattctatacctcttttcaaaaagatgc tgttaaagacatggatagaaatagtagatgtagaaatagattgattttttctcctgcttactgttttacagcttgcttttcttttttcacc tgacaatatgtcagggacttctttctacctcaggacataattttgtgccatttatttttcagctaacttcattttaatatgaaacaact caccatttaagccctaaaccaagacactgtaggtgtcttgaatagtaatttccaaacacctggcagtcactgcttgcatcagaatcacca aattgctttaaaaagtacactattaatiaaatcattgcattaaaaaagtaatgagagttggaattatagtggaattcttggattggctac catccaggcttataaaacaaatactcctgtgtcccaatcatttggactagagaatctgtacttttatttttttcgttttattttattttt tgagatggactctcactctgttgccaggctggagtgtagtggtgcgatcttggctcactgcaacctccgcctcccagcttcatgtgattc tcctgcctcagcctcccgagtcgttttatttttaaaaaaaaattttttattgaggtataagtgacatagaatatttaaagtatacaat ttgatatatttcagtgtttgtatacacctgtgaaaccatcaccataatcgacacagcaaatatatcatcatcctaaaaggtccctgctgc cccttttgtgataccctcccccatccctccctcaatcccactgatctgcttcctgtcattgtagcttagtttgcattttctagagcttgc atgagaacagtcatgcagtttatacttgttttgtctggcttcttccactcagaatacttgttttgaaattttcctatgttgtgtatgtc agtagttcattccttttatttctgaggatctgcatttttaaaaaatctgcctggtagattcttttgctccaccaggtttgggagcagac ctgttcgggacatcctgatactttcatctccttcttcagttgccccaggaactctaacagtgctatagttctcctttccctggggctcgt ctctaaggaactaggaagagcctggcctgaggctcctggtcctttatagtaactagaaggctgagagttaaatgtcagttcctcagggc agagtttgttgtggcctaaaagaggggcatctggaatgcaaatagttcatgacgtgctgaacagcacatgcttaccacttaaggaatgcc cccaaaccttcaaaaatcctcaaattcacaaagattgaggattttcgttcttggttcaggtctctgcttttctccttggtcacatttatg cttatagtcacttgttttcttcatatacccctgtcactagaattcccctacattttgaggatgcctaggacctcttacctaatggacatt ttcctaaaaggcccaatgtctgtcacctcatcagttattgcaccccagagatgatggagggtgactgagctggctggaggcagatcctg agctttcccaccagcttagtgactgccagcagcccacacacagtacacgccaggcctcagcaaagtacaaatggccaccagacctgggat gtcagaggcccttgggaatgttgaaaccaaggctgtcctaggccaactctattttatattacagacctgtgttgcttcacccttctgtgt cttgggcctccactgggcatggggtttgcagtagagacattggatcggctatcatctaggctactggtcttgttccagccctcttatcca gcagcttgccagggtcaaaggctgcagggtgagggccagagcactgctctgtgcccatttgtgacctggtgactttagattctaactac cctggaatatacctccagaatatttgcaaagcccagatttgctgtacaaggcagcctgggcctttgctcttctacccgctgtaccatctt ttgtcagtaaaatggttggttgcttttgtgcagccattgtatcggatcttcccctttggcttccctcctctgggctgttggccaggggctg ccactggtgcaggctgcaggctccaagaggcagtgcaggaaaaggcttctgtggaagctgggcaggcctggatgccgggcaggctggggc tagaattcaggtgtggcattagagggctcttatggtatgagtttgggggttgacctttaaaaggccatttttgtttacagtccattcagaagtt TABLE 1-continued LIPA gene/SEC pre-mRNA sequence tacttttttgtttaaataattaggattaacttgttaataaattccataccttgttctttagcgggattttaaatatagcatactcatctttccattctccttataaacctgatgaatttcggagctccccagagccaagacttgatattacttctcactttctcactggccctgcccagagcccaggtactctcacctgtttgaagaaggccatcccagtgtagttttccagtgttgttctgacctacctaaggtgctattaaaaatactggttcttgggcctgtctgagacctgtggagactctgaattcctagggctgtgaccctgggatctatgtttgagttaagtgccttagatgattacgatgtgctcttttttttttctttaaaggaaaaaacatacttttggtaggcttttaaagaacactgtaaaaggatattcagtataattttgttaaacatgtaatatgttttatgaaattttagaaaatacatgagtgaaagaaaaatgacttgtatgtctagcacccagcaatagccactattaatattttggtataatcttacagttttgtaatataatcatttccattacaaaagtcagatcatactacatctgcttttatgtaaattttcatttaaagaaatgccattatatttgttagatacaagttaagctgttgtattagagaccccaaaatacagctgctaaataaagagtttatttctttctcataataaagttcagagagaggtggcccagactgatgatagagggggttttggctgtgttccatgaggccatgcagggacccagttccctccatactatagctctgccatcctcggggtgttgtcctcttctgcctggttgcagcccggtcacctccatgtctcttccaactcacaggaaggcaggggagagggagctcagggcaagtgactttgtgcgaaggagatagcttagaagtgagcggtatggccatagcctggctgctcgcaggaggatgaggatgtggtttctatcttggcagccatgtacttagggaaagctttagggattctgttactgaaaggaagaaggcaagaatgggaatgggtggcagtctctgccataattaaaaatgcctttccgggtcagtaactaaagttttaaaatatttgtcataaagggcagtttctgttgcttgaattttattatcattttgttttttgcagtgatagttgttttgcagtcataaatcatctgtccttatatgttagagtgttttcttaggatgatacatttatagcagtagacttagtaagggagagggtaggcatagctttaagacttctaatacatattgtactttagaaaagttgaacccgtttacatttttattaccattcaagacctaaatataatttttaaatgtcattttaaaacggtttatcctaatactataggcatttcctcctgatcattatctacatatactctgtgatatgattatcacagaagtataaccttagtgtatatttggtttcattttttttccacttagtattatttatgagattatctgtaagccattttctgtttgtattttatttatttatgacagtggcatacccc ttgtgtatatttatgtaacatatttacccaaatatctattatttgaaatggtaagttttggccacaaggtggcgcccggtaaaaagaaatgcccagacattctcttcaaaactgcttttggtttatgtgaagtctgttcttatcaactgcatacaattctactgtttgatgtaataaaacacagagcgagatgatatactacaagggattgttacttattaaaattgggctttagcttatttccaggttttttgttactggaaatcatcttaatacttttcttttgaaatatcctttcaagtggatagcttgaagtcctaagtgacttagcacaaagtcaaatttagaacttcagtctgagctataggcaagtttcaccttttgtattctgtgctcacgctggtgcttcatatgaatgctgaaggacatgtgacaaagtgatgaactgctgtctgtgttcagtggcagaatagtttgcatcaatatattttcactgacaaagatggggaacagatgtaccaacaggtgctgtgaatccaaattttgttttgcttgttaaatatgccacaggtatttaatatcagtcatttgcaacggcaaaaacagatgccaaatatttctcctgtaacaatcccctatagtatatcatctcactctgtcttttattacatcaaacagtagaattgtatgcagttgattagaacagacttcacataaatcaaaagcagttttgacaaagaatgtctgagcatttcttttaccaggcgccaccttgtggccaaaacttaccatttcaaattcatttggcttgccaatttgtgtttaatttttgacatacatttaatttgagagtgtagaggaaatatggatttgcactattttgaattttaaaaataagtgacattttgctaatattttatattatactattttaaatatgaataaatgtaaatttcaatacaatttcaatttcatggctctagtatccctaactagttagaattgtgctggcatgcagtactacttggtgattatactgataccagtactcaagaaaagtgtttaatcaataccatcattaaaatttgactaatataactagacaagtagaatgggtaaatagaaaatatacagtcatccctcaagtatctttggggactggctgcagacatcatccccaaaccaaaattcacagatactcaagtcccttatataaaatgatgtagtatttgcatatagcctatgcatatcctttcatatgctttaaatcatctctagattacttatgatgcttaatacaatgtaaacgctatgtaagtaggtgttacactgttttaaaatttgtatttttattgttttattatcttttattgttttttttccaaatattttccatctgcaaaatatcacttggctgaatccacagatacaaactggatatggagggccaattgtatattataattatttttatctatatatatccatctctctctctctctctctattatatatatatatgtatatatatgtgagctacctatctgtctacctttatttcccaagtaaaatgactaactctttgaaaaagcttaggatgcaaatttcagcagaaaatgtcagcataaagttccgctagcaggagcaactgttgatctagtataattgacagcatatgtgcatagctgcttcttgtgtcaggtggtagctgcttaacaatcatacaatgagaaattgagtcattcagtaaagcaggacaaaaccatgccatctcatttaaaataatgccttggaaatgaagagtaaatctggatattggtataaagttgatttccgaggttgtggctagctccagcaacctatgatgttatctctaacttttggtg TABLE 1-continued LIPA gene/SEC pre-mRNA sequence tcagataactcttttccaaattatcttcttttagGCTGTTAAATTCCAAAAGTTTCAAGCCTTTGACTGGGGAAGCAGTGCCAAGAATT
ATTTTCATTACAACCAGgtaaagttttagtcttttcattaaagggggccctgaaaactcatcaagaaagccagcctggcctatcaggat
tctggccaggctcaggtgctgtgggaaatgtttgcaggagttgactagtgtttgttttccatcagtccattcagaacaatccaagctttg
tagctggtgttgtggactgggcctcctctctttgtccttttcccagctctaaataagaatcatcactgttatgcattactcagagtaatc
acgaacatagcctgtagagtcagacagtcctatgtctgttatctggtagctatggggccttggccagattacattgcttaagcctcttcc
ctgcactaataaaattagcattttttgagcatgctaaatgcactgaagtgtgaggcactttgctctgttttttaaatttaattcccagagc
atctctgtgatgtaaacgtgattatctctgacttaaacatgaggacagtgaggcttagagaatttctgtgacttgtcttacacccaaagg
gaagaagtaggagggcatgaccccaaactctttccagccactattgccttgagtgtactacctatggagtacaacaccttccttgccggg
gattaaacattcattttggtgcccagcctacggcagcagctccacagctagtggcgattataattagcattctctcattgggttagat
ttcttttttttgtgccggtaatggcaacttgaaaagatactcaaagagattttaaaaatttagtctgttagtcaaacttactagacaatgt
ttaatggagattgcgcttattgtgattttgaaaattaaaacaacaacaacaacgaggcttctctggttccttttcattgtagAGTTATC
CTCCCACATACAATGTGAAGGACATGCTTGTGCCGACTGCAGTCTGGAGCGGGGGTCACGACTGGCTTGCAGATGTCTACGACGTCAATA
TCTTACTGACTCAGATCACCAACTTGGTGTTCCATGAGAGCATTCCGGAATGGGAGCATCTTGACTTCATTTGGGGCCTGGATGCCCCTT
GGAGGCTTTATAATAAAATTATTAATCTAATGAGGAAATATCAGTGAAAGCTGGACTTGAGCTGTGTACCACCAAGTCAATGATTATGTC
ATGTGAAAATGTGTTTGCTTCATTTCTGTAAAACACTTGTTTTTCTTTCCCAGGTCTTTTGTTTTTTTATATCCAAGAAAATGATAACTT
TGAAGATGCCCAGTTCACTCTAGTTTCAATTAGAAACATACTAGCTATTTTTCTTTAATTAGGGCTGGAATAGGAAGCCAGTGTCTCAA
CCATAGTATTGTCTCTTTAAGTCTTTTAAATATCACTGATGTGAAAAAGGTCATTATATCCATTCTGTTTTTAAAATTTAAAATATATT
GACTTTTTGCCCTTCATAGGACAAAGTAATATATGTGTTGGAATTTTAAAATTGTGTTGTCATTGGTAAATCTGTCACTGACTTAAGCGA
GGTATAAAAGTACGCAGTTTTCATGTCCTTGCCTTAAAGAGCTCTCTAGTCTAACGGTCTTGTAGTTAGAGATCTAAATGACATTTTATC
ATGTTTTCCTGCAGCAGGTGCATAGTCAAATCCAGAAATATCACAGCTGTGCCAGTAATAAGGATGCTAACAATTAATTTTATCAAACCT
AACTGTGACAGCTGTGATTTGACACGTTTTAATTGCTCAGGTTAAATGAAATAGTTTTCCGGCGTCTTCAAAAACAAATTGCACTGATAA
AACAAAAACAAAAGTATGTTTTAAATGCTTTGAAGACTGATACACTCAACCATCTATATTCATGAGCTCTCAATTTCATGGCAGGCCATA
GTTCTACTTATCTGAGAAGCAAATCCCTGTGGAGACTATACCACTATTTTTTCTGAGATTAATGTACTCTTGGAGCCCGCTACTGTCGTT
ATTGATCACATCTGTGTGAAGCCAAAGCCCCGTGGTTGCCCATGAGAAGTGTCCTTGTTCATTTCACCCAAATGAAGTGTGAACGTGAT
GTTTTCGGATGCAAACTCAGCTCAGGGATTCATTTTGTGTCTTAGTTTTATATGCATCCTTATTTTTAATACACCTGCTTCACGTCCCTA
TGTTGGGAAGTCCATATTTGTCTGCTTTTCTTGCAGCATCATTTCCTTACAATACTGTCCGGTGGACAAAATGACAATTGATATGTTTTT
CTGATATAATTACTTTAGCTGCACTAACAGTACAATGCTTGTTAATGGTTAATATAGGCAGGGCGAATACTACTTTGTAACTTTTAAAGT
CTTAAACTTTTCAATAAAATTGAGTGAGACTTATAGGCCCAAAGAA

TABLE 2

LIPA SEC pre-mRNA target exon/intron sequences

| SEQ ID NO. | Target Exon/Intron | Sequence |
|---|---|---|
| 2 | Intron 8 | gtaggcattccaggagtgcatttgggttcatgtaaaatcaacatcagaaaggtctgggcatgcaaacc<br>ctttccaaatagaaagacaacctgcttacaaatctgatctggttttcttcccagagtcctgggtttt<br>gtcatcgtgcttgtgttgcttttgatacctgtggtggggcacactgtgttatacgtgggttcacaaaca<br>gctactggggttgacatttttcttttccctcctctcccttcctcaagtctcaggttaatatattctctc<br>cctttccttctccccagctttcttttcctcctcctgtttcctccctccatctgcttctcattgagtc<br>ctagatttttttatttctgtgttgcttcataaagagtgattttaagtccgttttggagatagaaaccg<br>ctgtttcaacactaacccctgatcacaatatgcttggaatagcagtgaataaactggagctaaaccaat<br>gatagatgtgaatgggggcccctgactttgaaatacagttttgattattttatcatgtaaataagtca<br>tgttcattctgaaaatttagaaactacatctagaaaaaaattatcttaaaatgaaaataaaatcattc<br>tataaccctagacagagaggaaatgcatatccatagatattgaatgtctctgcattctattctatacct<br>cttttcaaaagatgctgttaaagacatggatagaaatagtagatgtagaaatagattgattttttctcc<br>tgcttactgttttacagcttgcttttcttttttcacctgacaatatgtcagggacttcttttctacctca |

TABLE 2-continued

LIPA SEC pre-mRNA target exon/intron sequences

| SEQ ID NO. | Target Exon/Intron Sequence |
|---|---|
| | ggacataattttgtgccatttattttttcagctaacttcattttttaatatgaaacaactcaccatttaag |
| | ccctaaaccaagacactgtaggtgtcttgaatagtaatttccaaacacctggcagtcactgcttgcatc |
| | agaatcaccaaattgctttaaaaagtacactatttaataaatcattgcattaaaaaagtaatgagagtt |
| | ggaattatagtggaattcttggattggctaccatccaggcttataaaacaaatactcctgtgtcccaat |
| | catttggactagagaatctgtactttttattttttcgttttattttattttttttgagatggactctcact |
| | ctgttgccaggctggagtgtagtggtgcgatcttggctcactgcaacctccgcctcccagcttcatgtg |
| | attctcctgcctcagcctcccgagtcgttttattattttaaaaaaaaatttttttattgaggtataagtg |
| | acatagaatatttaaagtatacaatttgatatatttcagtgtttgtatacacctgtgaaaccatcacca |
| | taatcgacacagcaaatatatcatcatcctaaaaggtccctgctgcccctttgtgatacctcccccat |
| | ccctcccctcaatcccactgatctgcttcctgtcattgtagcttagtttgcattttctagagcttgcat |
| | gagaacagtcatgcagtttatacttgtttttgtctggcttcttccactcagaatacttgttttgaaatt |
| | ttcctatgttgtgtatgtcagtagttcattccttttttatttctgaggatctgcatttttaaaaaatctg |
| | cctggtagattcttttgctccaccaggtttgggagcagacctgttcgggacatcctgatactttcatct |
| | ccttcttcagttgccccaggaactctaacagtgctatagttctcctttccctggggctcgtctctaagg |
| | aactaggaagagcctggcctgaggctcctggtcctttatagtaactagaaggctgagagttaaatgtca |
| | gttcctcaggggcagagtttgtgtggcctaaaagaggggcatctggaatgcaaatagttcatgacgtg |
| | ctgaacagcacatgcttaccacttaaggaatgccccaaaccttcaaaaatcctcaaatttcacaaagat |
| | tgaggattttcgttcttggttcaggtctctgcttttctccttggtcacatttatgcttatagtcacttg |
| | ttttcttcatatacccttgtcactagaattcccctacatttttgaggatgcctaggacctcttacctaat |
| | ggacatttccctaaaaggcccaatgtctgtcacctcatcagttattgcacccccagagatgatggaggg |
| | tgactgagctggctggaggcagatcctgagctttcccaccagcttagtgactgccagcagcccacacac |
| | agtacacgccaggcctcagcaaagtacaaatggccaccagacctgggatgtcagaggcccttgggaatg |
| | ttgaaaccaaggctgtcctaggccaactctattttatattacagacctgtgttgcttcacccttctgtg |
| | tcttgggcctccactgggcatgggtttgcagtagagacatttggatcggctatcatctaggctactggt |
| | cttgttccagccctcttatccagcagcttgccagggtcaaaggctgcagggtgagggccagagcactgc |
| | tctgtgccccatttgtgacctggtgactttagattctaactaccctggaatatacctccagaatatttg |
| | caaagcccagatttgctgtacaaggcagcctgggcctttgctcttctacccgctgtaccatctttttgtc |
| | agtaaaatggttggttgctttgtgcagccattgtatcggatcttcccttttggctttccctcctctgggc |
| | tgttggccaggggctgccactggtgcaggctgcaggctccaagaggcagtgcaggaaaaggcttctgtg |
| | gaagctgggcaggcctggatgccgggcaggctggggctagaattcaggtgtggcattagagggctctta |
| | tggtatgagtttgggttgaccttaaaggccatttttgtttacagtccattcagaagtttacttttttgtt |
| | taaataattaggattaacttgttaataaaattccataccttgttctttagcgggatttttaaatatagcat |
| | actcatctttccattctccttttataaacctgatgaattttcggagctccccagagccaagacttgatatta |
| | cttctcacttttctcactggccctgcccagagcccaggtactctcacctgtttgaagaaggccatcccag |
| | tgtagttttccagtgttgttctgacctacctaaggtgctattaaaaatactggttcttgggcctgtctg |
| | agacctgtggagactctgaattcctagggctgtgaccctgggatctatgtttgagttaagtgccttaga |
| | tgattacgatgtgctcttttttttttcttttaaaggaaaaaacatacttttggtaggcttttaaagaaca |
| | ctgtaaaaaggatattcagtataattttttgttaaacatgtaatatgttttatgaaatttttagaaaatac |
| | atgagtgaaagaaaaatgacttgtatgtctagcacccagcaatagccactattaatatttttggtataat |
| | cttacagttttgtaatataatcatttccattacaaaagtcagatcatactacatctgcttttatgtaaa |
| | ttttcatttaaagaaatgccattatatttgttagatacaagttaagctgttgtattagagacccaaaa |
| | tacagctgctaaataaagagtttatttctttctcataataaagttcagagagaggtggcccagactgat |
| | gatagaggggggttttggctgtgttccatgaggccatgcagggacccagttccctccatactatagctct |
| | gccatcctcggggtgttgtcctcttctgcctggttgcagcccggtcacctccatgtctcttccaactca |
| | caggaaggcagggggagagggagctcagggcaagtgactttgtgcgaaggagatagcttagaagtgagcg |
| | gtatggccatagcctggctgctcgcaggaggatgaggatgtggtttctatcttggcagccatgtactta |
| | gggaaagctttagggattctgttactgaaaggaagaaggcaagaatgggaatgggtggcagtctctgcc |
| | ataattaaaaatgcctttccgggtcagtaactaaagtttttaaaatatttgtcataaagggcagtttctg |
| | ttgcttgaatttttattatcattttgtttttttgcagtgatagttgttttgcagtcataaatcatctgtcc |
| | ttatatgttagagtgttttcttaggatgatacatttatagcagtacttagtaaggagagggtaggc |
| | atagctttaagacttctaatacatattgtactttagaaaagttgaacccgtttacatttttattaccat |
| | tcaagacctaaatataattttttaaatgtcattttaaaacggtttatcctaatactataggcatttcctc |
| | ctgatcattatctacatatactctgtgatatgattatcacagaagtataaccttagtgtatatttggtt |
| | tcatttttttccacttagtattattttatgagattatctgtaagccattttctgttttgtattttatttat |
| | atttatgacagtggcataccccttgtgtatatttatgtaacatatttacccaaatatctattatttgaa |
| | atggtaagttttggccacaaggtggcgcccggtaaaaagaaatgcccagacattctcttcaaaactgct |
| | tttggtttatgtgaagtctgttcttcaactgcatacaattctactgtttgatgtaataaaacacaga |
| | gcgagatgatatactacaagggatttgttacttattaaaattgggcttttagcttatttttccaggttttttgt |
| | tactggaaatcatcttaatacttttctttttgaaatatccttttcaagtggatagcttgaagtcctaagtg |
| | acttagcacaaagtcaaatttagaacttcagtctgagctataggcaagtttcaccttttgtattctgtgc |
| | tcacgctggtgcttcatatgaatgctgaaggacatgtgacaaagtgatgaactgctgtctgtgttcagt |
| | ggcagaatagtttgcatcaatatattttcactgacaaagatggggaaacagatgtaccaacaggtgctgt |
| | gaatccaaattttgttttgcttgttaaaatatgccacaggtatttaatatcagtcatttgcaacggcaaa |
| | aacagatgccaaatatttctcctgtaacaatcccctatagtatatcatctcactctgtcttttattaca |
| | tcaaacagtagaattgtatgcagttgattagaacagacttcacatataaatcaaaagcagttttgacaaag |
| | aatgtctgagcatttcttttttaccaggcgccaccttgtggccaaaacttaccatttcaaattcatttgg |
| | cttgccaatttttgtgtttaatttttgacatacatttaatttgagagtgtagaggaaatatggattttgca |
| | ctattttgaattttaaaaaatgactttttgctaatattttatattatactattttaaatatgaata |
| | aatgtaaatttcaatacaatttcaatttcatggctctagtatccctaactagttagaattgtgctggca |
| | tgcagtactactggtgattatactgataccagtactcaagaaaaagtgtttaatcaataccatcatta |
| | aaatttgactaatataactagacaagtagaatgggtaaatagaaaatatacagtcatccctcaagtatc |
| | tttggggactggctgcagacatcatccccaaaccaaaattcacagatactcaagtcccttatataaaat |
| | gatgtagtatttgcatatagcctatgcatatcctttcatatgctttaaatcatctctagattacttatg |
| | atgcttaatacaatgtaaacgctatgtaagtaggtgttacactgttttaaaatttgtatttttttattgt |
| | tttattatctcttttattgttttttttccaaatattttccatctgcaaaatatcacttggctgaatccacag |

TABLE 2-continued

LIPA SEC pre-mRNA target exon/intron sequences

| SEQ ID NO. | Target Exon/Intron | Sequence |
|---|---|---|
| | | atacaaaactggatatggagggccaattgtatattataattattttatctatatatatccatctctctc<br>tctctctctctattatatatatatatgtatatatatgtagctacctatctgtctacctttatttc<br>ccaagtaaaatgactaactctttgaaaaagcttaggatgcaaatttcagcagaaaatgtcagcataaag<br>ttccgctagcaggagcaactgttgatctagtataattgacagcatatgtgcatagctgctttcttgtgt<br>caggtggtagctgcttaacaatcatacaatgagaaattgagtcattcagtaaagcaggacaaaaccatg<br>ccatctcatttaaaataatgccttggaaatgaagagtaaatctggatattggtataaagttgatttccg<br>aggttgtggctagctccagcaacctatgatgttatctctaactttggtgtcagataactcttttccaaa<br>ttatcttcttttttag |
| 3 | Intron 7 | gtatgcatgtttatagtaagatttgatttttttttttatctgtgaatgtgcttatttgtgttgaatgat<br>atgggagaggtgggaatgacctcatcagaactctaaagagtctttcatttgagaggcacaagcatgaac<br>tttggccaatgcctagaatacggtaccacctgctgcctccaggctgactgtggtcaccttcttatg<br>ttgtacctagatggagattattgaatgaggagatctgtcacaaattaagctgtaatatttataattact<br>ctagtgatttgtttcttttagaaatcattataagtataaacataaagatgggaacaatagacagtgggg<br>actccaaaaggaaggagggagagggacaagggctgaagcctgttgagtactatagccaatattgagtac<br>tgtggttatgggatcaatagaagcccgcatctcagcatcatgcaatccaccttgtaacaaacctgcac<br>atggacccccccgaatctaaaatacacaaattttcaaaaattactataagtatttaaatttggaacggcc<br>atttacatacacataagtgtatgcttgcagtgtgtgtgtatttataaaagtacattttataaaatgtaa<br>acccattttattttataaaatataaacccttggccaatactatgcccagtgccatttttcttttgtct<br>gataattaaagcaaggtgtgattgttatatgaaatttgggaaattcaggaaagcatgaagaacaaaatg<br>aaaatgccctgtaaacgaaacccacacagtcccgtgcttaccatgttgttgcacctccttcatatggac<br>tttgtatgtggttgtatgtattttttataggggcagattttttagtcaaataattttttttctacctctcatc<br>tcacatacttgagattatggctctagtttttagtgctttgaagggcaaaatacaatgtttattatcaat<br>gccaccttaatgctgttttcattcttcatttcaatgtatttattttgcag |
| 4 | Exon 8 | TCTAGAGTGGATGTATATACAACACATTCTCCTGCTGGAACTTCTGTGCAAAACATGTTACACTGGAGC<br>CAG |

TABLE 3

LIPA exon 8, intron 7 and intron 8 ASO macrowalk

| SEQ ID NO. | ASO ID NO. | Sequence 5'-3' | ASO Length (No. Nucleotides) | Internal ID/position | Target exon or intron |
|---|---|---|---|---|---|
| 5 | A-03331 | AAATGCACTCCTGGAATG | 18 | LIPA-IVS8+6 | Intron 8 |
| 6 | A-03332 | CAAATGCACTCCTGGAAT | 18 | LIPA-IVS8+7 | Intron 8 |
| 7 | A-03333 | CCAAATGCACTCCTGGAA | 18 | LIPA-IVS8+8 | Intron 8 |
| 8 | A-03334 | CCCAAATGCACTCCTGGA | 18 | LIPA-IVS8+9 | Intron 8 |
| 9 | A-03335 | CCCCAAATGCACTCCTGG | 18 | LIPA-IVS8+10 | Intron 8 |
| 10 | A-03336 | ACCCCAAATGCACTCCTG | 18 | LIPA-IVS8+11 | Intron 8 |
| 11 | A-03337 | CATGAACCCCAAATGCAC | 18 | LIPA-IVS8+16 | Intron 8 |
| 12 | A-03338 | TTTTACATGAACCCCAAA | 18 | LIPA-IVS8+21 | Intron 8 |
| 13 | A-03339 | GTTGATTTTACATGAACC | 18 | LIPA-IVS8+26 | Intron 8 |
| 14 | A-03340 | CTGATGTTGATTTTACAT | 18 | LIPA-IVS8+31 | Intron 8 |
| 15 | A-03341 | CCTTTCTGATGTTGATTT | 18 | LIPA-IVS8+36 | Intron 8 |
| 16 | A-03342 | CCAGACCTTTCTGATGTT | 18 | LIPA-IVS8+41 | Intron 8 |
| 17 | A-03343 | CATGCCCAGACCTTTCTG | 18 | LIPA-IVS8+46 | Intron 8 |
| 18 | A-03344 | GTTTGCATGCCCAGACCT | 18 | LIPA-IVS8+51 | Intron 8 |
| 19 | A-03345 | AAAGGGTTTGCATGCCCA | 18 | LIPA-IVS8+56 | Intron 8 |
| 20 | A-03346 | TTTGGAAAGGGTTTGCAT | 18 | LIPA-IVS8+61 | Intron 8 |
| 21 | A-03628 | ATTTGGAAAGGGTTTGCA | 18 | LIPA-IVS8+62 | Intron 8 |
| 22 | A-03629 | TATTTGGAAAGGGTTTGC | 18 | LIPA-IVS8+63 | Intron 8 |

TABLE 3-continued

LIPA exon 8, intron 7 and intron 8 ASO macrowalk

| SEQ ID NO. | ASO ID NO. | Sequence 5'-3' | ASO Length (No. Nucleotides) | Internal ID/position | Target exon or intron |
|---|---|---|---|---|---|
| 23 | A-03630 | CTATTTGGAAAGGGTTTG | 18 | LIPA-IVS8+64 | Intron 8 |
| 24 | A-03631 | TCTATTTGGAAAGGGTTT | 18 | LIPA-IVS8+65 | Intron 8 |
| 25 | A-03347 | TTCTATTTGGAAAGGGTT | 18 | LIPA-IVS8+66 | Intron 8 |
| 26 | A-03633 | TTTCTATTTGGAAAGGGT | 18 | LIPA-IVS8+67 | Intron 8 |
| 27 | A-03634 | CTTTCTATTTGGAAAGGG | 18 | LIPA-IVS8+68 | Intron 8 |
| 28 | A-03635 | TCTTTCTATTTGGAAAGG | 18 | LIPA-IVS8+69 | Intron 8 |
| 29 | A-03636 | GTCTTTCTATTTGGAAAG | 18 | LIPA-IVS8+70 | Intron 8 |
| 30 | A-03348 | TGTCTTTCTATTTGGAAA | 18 | LIPA-IVS8+71 | Intron 8 |
| 31 | A-03349 | CAGGTTGTCTTTCTATTT | 18 | LIPA-IVS8+76 | Intron 8 |
| 32 | A-03350 | GTAAGCAGGTTGTCTTTC | 18 | LIPA-IVS8+81 | Intron 8 |
| 33 | A-03351 | GATTTGTAAGCAGGTTGT | 18 | LIPA-IVS8+86 | Intron 8 |
| 34 | A-03680 | CCAAATGCACTCCTGGA | 17 | LIPA-IVS8+9 (17) | Intron 8 |
| 35 | A-03681 | CAAATGCACTCCTGGA | 16 | LIPA-IVS8+9 (16) | Intron 8 |
| 36 | A-03682 | CCCAAATGCACTCCTGG | 17 | LIPA-IVS8+10 (17) | Intron 8 |
| 37 | A-03683 | CCAAATGCACTCCTGG | 16 | LIPA-IVS8+10 (16) | Intron 8 |
| 38 | A-03684 | CCCAAATGCACTCCTG | 16 | LIPA-IVS8+11 (16) | Intron 8 |
| 39 | A-03603 | ACTAAAAACTAGAGCCAT | 18 | LIPA-IVS7-86 | Intron 7 |
| 40 | A-03604 | AAAGCACTAAAAACTAGA | 18 | LIPA-IVS7-81 | Intron 7 |
| 41 | A-03605 | CCTTCAAAGCACTAAAAA | 18 | LIPA-IVS7-76 | Intron 7 |
| 42 | A-03606 | TTTGCCCTTCAAAGCACT | 18 | LIPA-IVS7-71 | Intron 7 |
| 43 | A-03607 | TGTATTTTGCCCTTCAAA | 18 | LIPA-IVS7-66 | Intron 7 |
| 44 | A-03608 | AACATTGTATTTTGCCCT | 18 | LIPA-IVS7-61 | Intron 7 |
| 45 | A-03609 | TAATAAACATTGTATTTT | 18 | LIPA-IVS7-56 | Intron 7 |
| 46 | A-03610 | ATTGATAATAAACATTGT | 18 | LIPA-IVS7-51 | Intron 7 |
| 47 | A-03611 | GTGGCATTGATAATAAAC | 18 | LIPA-IVS7-46 | Intron 7 |
| 48 | A-03612 | TTAAGGTGGCATTGATAA | 18 | LIPA-IVS7-41 | Intron 7 |
| 49 | A-03613 | CAGCATTAAGGTGGCATT | 18 | LIPA-IVS7-36 | Intron 7 |
| 50 | A-03614 | GAAAACAGCATTAAGGTG | 18 | LIPA-IVS7-31 | Intron 7 |
| 51 | A-03615 | AGAATGAAAACAGCATTA | 18 | LIPA-IVS7-26 | Intron 7 |
| 52 | A-03616 | AATGAAGAATGAAAACAG | 18 | LIPA-IVS7-21 | Intron 7 |
| 53 | A-03617 | ATTGAAATGAAGAATGAA | 18 | LIPA-IVS7-16 | Intron 7 |
| 54 | A-03618 | TATATACATCCACTCTAG | 18 | LIPA-EX8+2 | Exon 8 |
| 55 | A-03619 | TGTTGTATATACATCCAC | 18 | LIPA-EX8+7 | Exon 8 |
| 56 | A-03620 | GAATGTGTTGTATATACA | 18 | LIPA-EX8+12 | Exon 8 |
| 57 | A-03621 | CAGGAGAATGTGTTGTAT | 18 | LIPA-EX8+17 | Exon 8 |

TABLE 3-continued

LIPA exon 8, intron 7 and intron 8 ASO macrowalk

| SEQ ID NO. | ASO ID NO. | Sequence 5'-3' | ASO Length (No. Nucleotides) | Internal ID/position | Target exon or intron |
|---|---|---|---|---|---|
| 58 | A-03622 | TCCAGCAGGAGAATGTGT | 18 | LIPA-EX8+22 | Exon 8 |
| 59 | A-03623 | GCACAGAAGTTCCAGCAG | 18 | LIPA-EX8-24 | Exon 8 |
| 60 | A-03624 | GTTTTGCACAGAAGTTCC | 18 | LIPA-EX8-19 | Exon 8 |
| 61 | A-03625 | AACATGTTTTGCACAGAA | 18 | LIPA-EX8-14 | Exon 8 |
| 62 | A-03626 | AGTGTAACATGTTTTGCA | 18 | LIPA-EX8-9 | Exon 8 |
| 63 | A-03627 | GCTCCAGTGTAACATGTT | 18 | LIPA-EX8-4 | Exon 8 |

Example 3: Design of ASO-Walk Targeting Intron 7 of LIPA

An ASO walk was designed to target intron 7 (Table 2, SEQ ID NO: 3) of LIPA (Table 1, SEQ ID NO: 1) using the method described herein (Table 3, SEQ ID NOs: 39-53), A region immediately upstream of the intron 7 3' splice site spanning nucleotides −16 to −100 was utilized to design ASOs to target intron 7 of LIPA SEC pre-mRNAs. Table 3 lists exemplary ASOs that were designed and their target sequences. From this design, 2'-MOE, PS backbone, 18-mer ASOs shifted by 5-nucleotide intervals were produced and will be utilized to target LIPA SEC pre-mRNAs to increase LAL protein production.

Example 4: Design of ASO-Walk Targeting Intron 8 of LIPA

Figure 3:
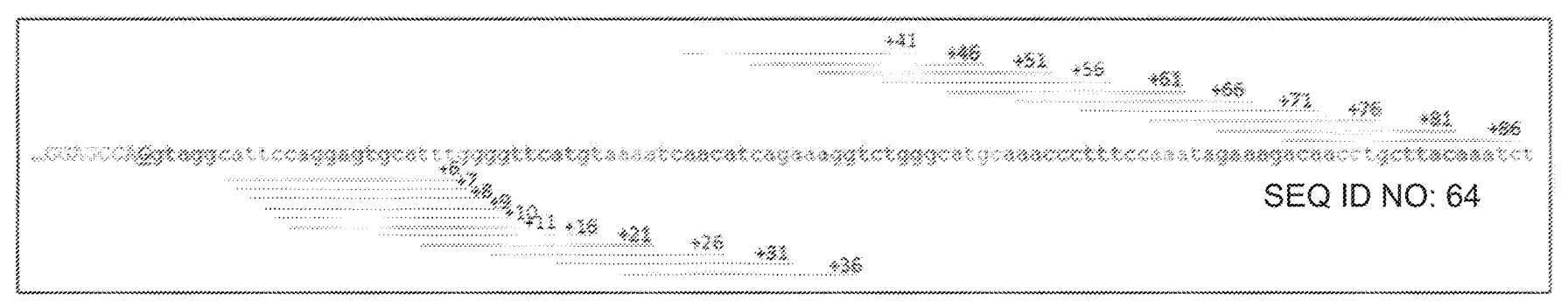
Figure 4A:
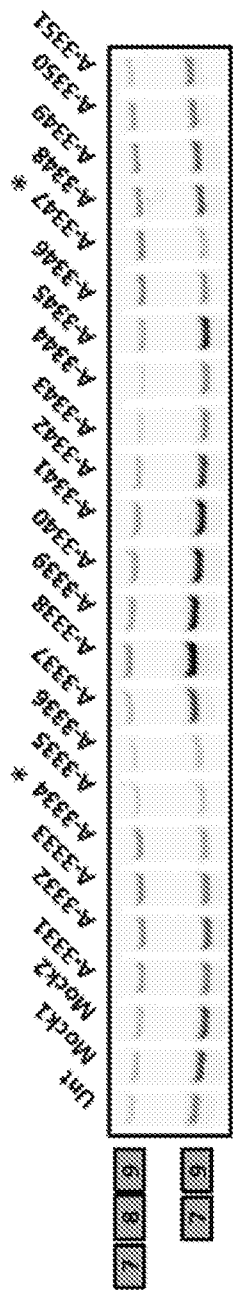
FIG. 4A depicts LIPA intron 8 5' splice site region ASO walk evaluated by Reverse Transcriptase-Polymerase Chain Reaction (RT-PCR). A representative PAGE shows SYBR-safe-stained RT-PCR products of LIPA, untreated (unt), mock-treated (Mock1, Mock2, electroporated), or treated with a 2'-MOE ASO targeting the intron 8 5' splice site region as described herein in the Examples and in the description of FIG. 3, at 120 nM concentration in CESD patient fibroblast carrying the c.894G>A mutation via electroporation. Two products corresponding to exon 8 inclusion (full-length, top band) and exon 8 skipping (bottom band) were quantified.
Figure 4B:
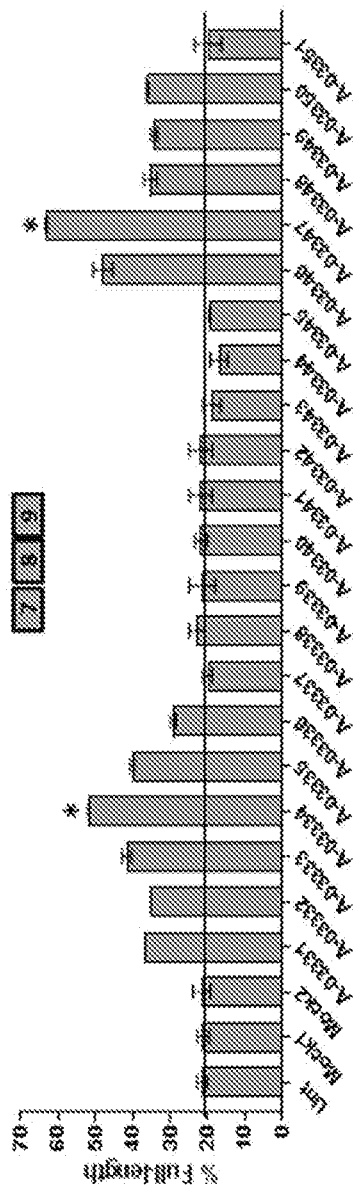
FIG. 4B depicts a graph plotting the percent full-length (exon 8 inclusion) from the data in FIG. 4A. The black line indicates no change with respect to untreated (Unt).

An ASO walk was designed to target intron 8 (FIG. 3; Table 2, SEQ ID NO: 2) of LIPA (Table 1, SEQ ID NO: 1) using the method described herein (Table 3, SEQ ID NOs: 1-38), A region immediately downstream of the intron 8 5' splice site spanning nucleotides +6 to +100 was utilized to design ASOs to target intron 8 of LIPA SEC pre-mRNAs. Table 3 lists exemplary ASOs that were designed and their target sequences. From this design, 2'-MOE, PS backbone, 18-mer ASOs shifted by 1-nucleotide intervals from +6 to +11 and 5-nucleotide intervals thereafter were produced and utilized to target LIPA SEC pre-mRNAs to increase LAL protein production (see FIG. 4A and FIG. 4B).

Example 5

A set of experiments were designed to demonstrate the dose-dependent ability of ASOs targeting LIPA SEC pre-mRNA to alter splicing of the transcript to increase retention of intron 8 in the mature mRNA product and thereby increase production of the full-length functional LAL protein in donor CESD cells carrying the c.894G>A mutation.

Figure 5B:
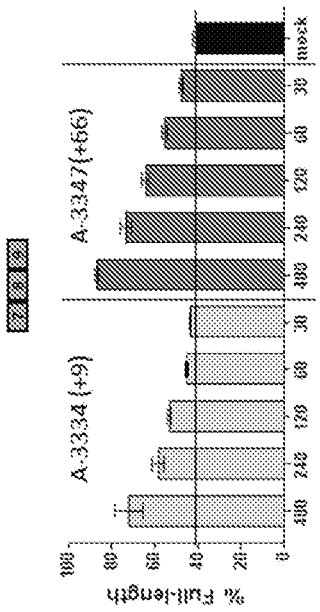
FIG. 5B depicts a graph plotting the percent full-length (exon 8 inclusion) from the data in FIG. 5A. The black line indicates no change with respect to mock.
Figure 5D:
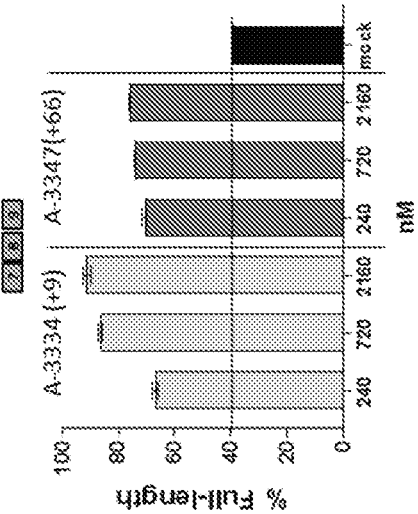
FIG. 5D depicts a graph plotting the percent full-length (exon 8 inclusion) from the data in FIG. 5C. The black line indicates no change with respect to mock.
Figure 5A:
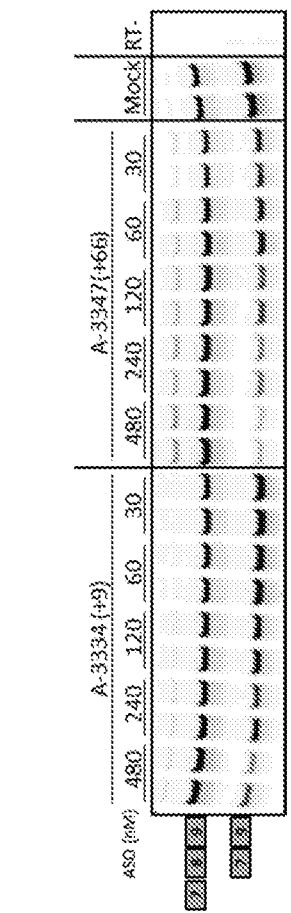
FIG. 5A depicts exemplary dose-dependent effect of selected ASOs in CESD patient fibroblast cells. A representative PAGE showing SYBR-safe-stained RT-PCR products of LIPA mock-treated (Mock, electroporated), or treated with A-3334 (+9) or A-3347 (+66) 2'-MOE ASOs targeting intron 8 at 30 nM, 60 nM, 120 nM, 240 nM, and 480 nM concentrations in CESD patient fibroblast carrying the c.894G>A mutation via electroporation is shown. Two products corresponding to exon 8 inclusion (full-length, top band) and exon 8 skipping (bottom band) were quantified.
Figure 5C:
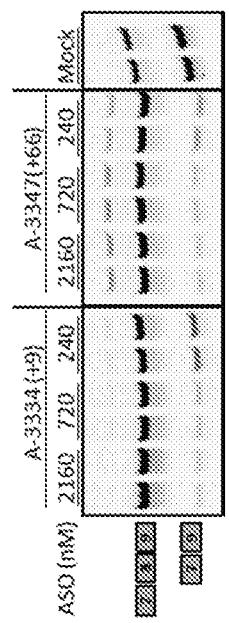
FIG. 5C depicts exemplary dose-dependent effect of selected ASOs in CESD patient fibroblast cells. A representative PAGE showing SYBR-safe-stained RT-PCR products of LIPA mock-treated (Mock), or treated with A-3334 (+9) or A-3347 (+66) 2'-MOE ASOs targeting intron 8 at 240 nM. 720 nM, and 2160 nM concentrations in CESD patient fibroblast carrying the c.894G>A mutation via electroporation is shown. Two products corresponding to exon 8 inclusion (full-length, top band) and exon 8 skipping (bottom band) were quantified.
Figure 6B:
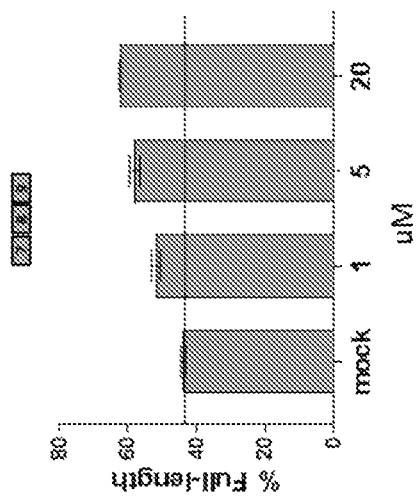
FIG. 6B depicts a graph plotting the percent full-length (exon 8 inclusion) from the data in FIG. 6A. The black line indicates no change with respect to mock.
Figure 6A:
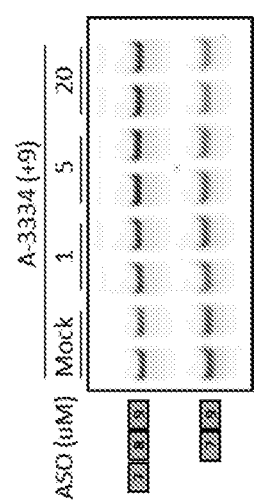
FIG. 6A depicts exemplary dose-dependent effect of selected ASO in CESD patient fibroblast cells. A representative PAGE showing SYBR-safe-stained RT-PCR products of LIPA mock-treated (Mock), or treated with A-3334 (+9) 2'-MOE ASO targeting intron 8 at 1-µM, 5-µM, and 20-µM concentrations in CESD patient fibroblast carrying the c.894G>A mutation via free-uptake is shown. Two products corresponding to exon 8 inclusion (full-length, top band) and exon 8 skipping (bottom band) were quantified.
Figure 8:
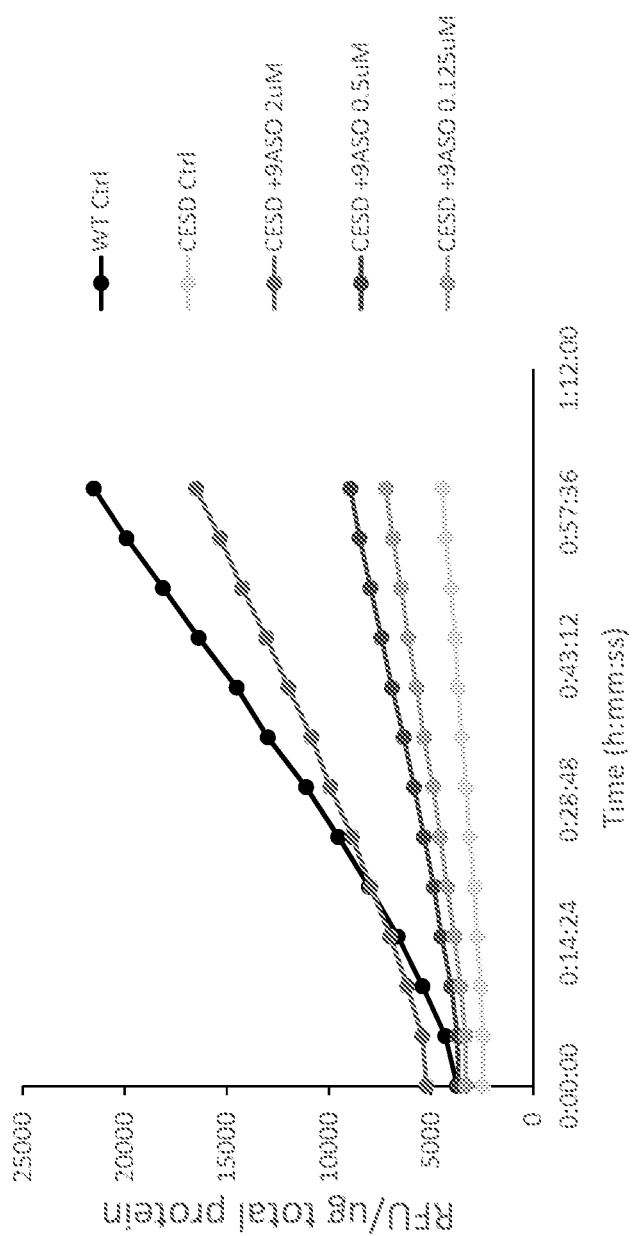
FIG. 8 depicts a graph plotting the kinetics of LAL activity measured from time 0 minutes to 60 minutes in 5-minute intervals from protein extracts of CESD patient fibroblast carrying the c.894G>A mock-treated (CESD Ctrl) or treated with A-3334 (+9) 2'-MOE ASO targeting intron 8 at 0.125-µM, 0.5-µM, and 2-µM concentrations via electroporation. Protein extract from a wild-type (WT Ctrl) fibroblast is included for comparison. Relative Fluorescence Unit (RFU) per microgram (ug) of protein is plotted.
Figure 10:
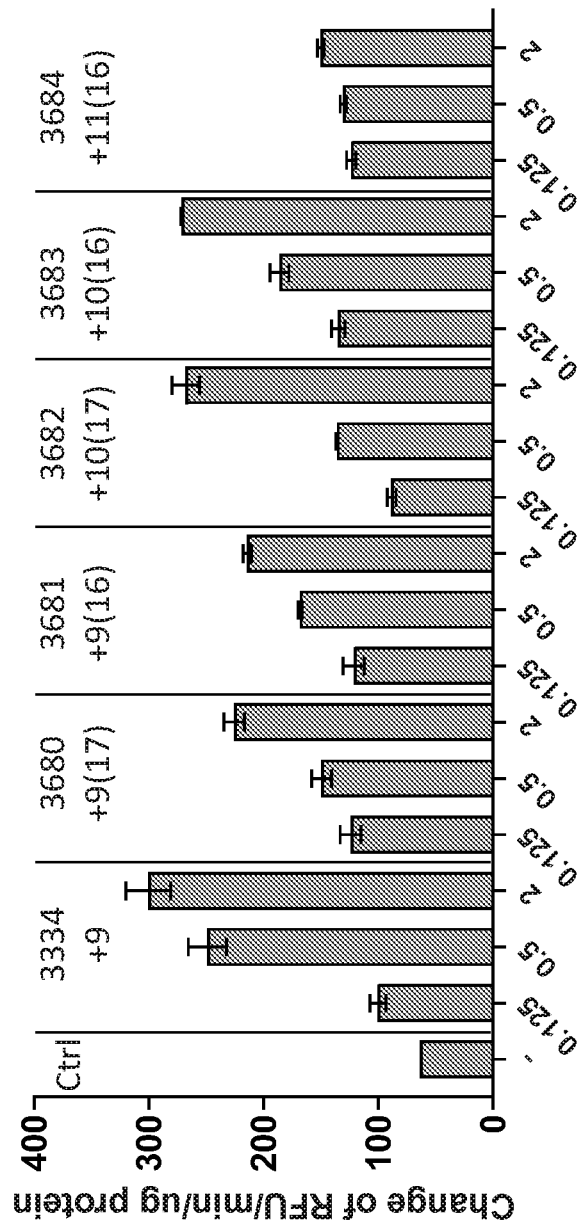
FIG. 10 depicts a graph plotting the change of LAL activity (slope of curve) measured from 30 minutes to 60 minutes from protein extracts of CESD patient fibroblast carrying the c.894G>A mock-treated (Ctrl), or treated with A-3334 (+9), A-3680) (+9(17)), A-3681 (+9(16)), A-3682 (+10(17)), A-3683 (+10(16)), A-3684 (+11(16)) 2'-MOE ASOs targeting intron 8 at 0.125 M, 0.5 M, and 2 M concentrations via electroporation. Change of RFU per minute per microgram (ug) of protein is plotted.

Cells were treated with a set of different 2'-MOE ASOs targeting intron 8 by electroporation (e.g., A-3334 (+9) in FIGS. 5, 7 & 9) or free uptake (e.g., A-3334 (+9) in FIG. 6) at a series of concentrations to show that treatment with increasing amounts of ASO leads to increasing retention of exon 8 in LIPA transcripts produced in CESD fibroblasts compared to untreated cells (e.g., FIG. 5A, 5C). Representative PAGE shows RT-PCR products for two products corresponding to exon 8 inclusion (full-length, top band) and exon 8 skipping (bottom band) and each were quantified and assessed as a percentage of full-length transcript (FIGS. 5, 6 & 9). Additional analysis was conducted to confirm that ASO treatment not only alters mRNA transcript generation but also results in dose-dependent increases in production of full-length functional LAL protein in CESD cells. Sodium dodecylsulfate-polyacrylamide gel electrophoresis (SDS-PAGE) shows lysosomal acid lipase (LAL) protein was produced at increasing levels in cells treated with increasing amounts of 2'-MOE ASO targeting intron 8 compared to mock-treated cells (−) from CESD patient fibroblast carrying the c.894G>A mutation (FIG. 7). A product corresponding to glycosylated full-length protein was quantified and normalized to Ponceau S-stained blot. The activity of LAL protein produced in ASO-treated CESD cells was confirmed using an enzymatic assay. The results demonstrate the protein expressed is functional and the amount of activity is proportional to the amount of LAL protein (FIGS. 8 & 10).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of modulating expression of a lysosomal acid lipase (LAL) protein encoded by an LIPA gene, by cells having a skippable-exon-containing pre-mRNA (SEC pre-mRNA), the SEC pre-mRNA comprising the skippable exon, an intron flanking the 5' splice site of the skippable exon, and an intron flanking the 3' splice site of the skippable exon, wherein the SEC pre-mRNA is transcribed from the LIPA gene in the cells and encodes the LAL protein, the method comprising contacting the cells with an antisense oligomer (ASO) complementary to a targeted portion of the SEC pre-mRNA encoding the LAL protein, whereby the skippable exon is retained in an mRNA processed from the SEC pre-mRNA encoding the LAL protein, thereby modulating the level of mRNA encoding LAL protein and modulating the expression of LAL protein in the cells, wherein the skippable exon is exon 8, and wherein the targeted portion of the SEC pre-mRNA is within (a) position +6 to position +28 in intron 8; or
(b) position +61 to position +98 in intron 8.

2. The method of claim 1, wherein a region +1 to +6 of the intron flanking the 5' splice site of the skippable exon or a region −3e to −1e of the skippable exon comprises at least one mutation.

3. The method of claim 2, wherein the at least one mutation comprises c.894G>A.

4. The method of claim 1, wherein the SEC pre-mRNA comprises a sequence with at least 80% sequence identity to SEQ ID NO: 1 or a complement thereof.

5. The method of claim 1, wherein the targeted portion of the SEC pre-mRNA comprises a sequence comprising at least 8 contiguous nucleotides of the sequence set forth in any one of SEQ ID NOs: 2-4 or complements thereof.

6. The method of claim 1, wherein the ASO comprises a sequence with at least 80% sequence identity to a sequence selected from the group consisting of SEQ ID NOs: 8, 25, 34-38, 5-7, 9-24, 26-33, 39-63, and complements thereof.

7. The method of claim 1, wherein the ASO comprises a sequence with at least 80% sequence identity to a sequence selected from the group consisting of SEQ ID NOs: 8, 25, 34-38, and complements thereof.

8. The method of claim 1, wherein the SEC pre-mRNA is a partially spliced pre-mRNA of a full-length pre-mRNA or is a partially spliced pre-mRNA of a wild-type pre-mRNA.

9. The method of claim 1, wherein
(a) the mRNA encoding the LAL protein is a full-length mature mRNA or a wild-type mature mRNA; or
(b) the LAL protein produced is a full-length protein or a wild-type protein.

10. The method of claim 1, wherein the ASO comprises a backbone modification, a modified sugar moiety, or a combination thereof.

11. The method of claim 1, wherein the ASO comprises a phosphorothioate linkage, a phosphorodiamidate linkage, a phosphorodiamidate morpholino, a locked nucleic acid, a peptide nucleic acid, a 2'-O-methyl moiety, a 2'-Fluoro moiety, or a 2'-O-methoxyethyl moiety.

12. The method of claim 1, wherein the ASO is from 8 to 50 nucleobases in length.

13. The method of claim 1, wherein the ASO is administered by intrathecal injection, intracerebroventricular injection, intraperitoneal injection, intramuscular injection, subcutaneous injection, or intravenous injection.

14. The method of claim 1, wherein a composition comprising the ASO is administered to a subject in need thereof.

15. The method of claim 14, wherein the subject has a deficient amount of the LAL protein.

16. The method of claim 15, wherein the subject has a disease or a condition, and wherein the disease or condition is an autosomal recessive disease or condition.

17. The method of claim 14, wherein the subject has Cholesteryl Ester Storage Disease (CESD).

18. The method of claim 14, wherein the subject has a first allele encoding the LAL protein and is carrying a mutation, and (a) a second allele from which the LAL protein is not produced, or (b) a second allele encoding a nonfunctional LAL protein.

* * * * *